(12) United States Patent
Liu et al.

(10) Patent No.: US 8,865,701 B2
(45) Date of Patent: Oct. 21, 2014

(54) SPIROPYRROLIDINE BETA-SECRETASE INHIBITORS FOR THE TREATMENT OF ALZHEIMER'S DISEASE

(75) Inventors: Kun Liu, Edison, NJ (US); Shawn J. Stachel, Perkasie, PA (US); Craig A. Coburn, Royersford, PA (US); Thomas G. Steele, Schwenksville, PA (US); Richard Soll, Waigaoqiao Free Trade Zone (CN); Hao Wu, Waigaoqiao Free Trade Zone (CN); Xuanjin Peng, Waigaoqiao Free Trade Zone (CN); Yaxian Cai, Waigaoqiao Free Trade Zone (CN); Xiaoxiang Du, Waigaoqiao Free Trade Zone (CN); Jian Li, Waigaoqiao Free Trade Zone (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 8 days.

(21) Appl. No.: 13/201,570

(22) PCT Filed: Feb. 20, 2010

(86) PCT No.: PCT/CN2010/070697
§ 371 (c)(1),
(2), (4) Date: Aug. 15, 2011

(87) PCT Pub. No.: WO2010/094242
PCT Pub. Date: Aug. 26, 2010

(65) Prior Publication Data
US 2011/0306595 A1  Dec. 15, 2011

Related U.S. Application Data

(60) Provisional application No. 61/208,172, filed on Feb. 20, 2009.

(51) Int. Cl.
*A61K 31/55* (2006.01)
*C07D 513/20* (2006.01)
*A61K 31/438* (2006.01)
*A61K 31/445* (2006.01)
*A61P 25/28* (2006.01)
*C07D 405/14* (2006.01)
*C07D 413/14* (2006.01)
*C07D 495/10* (2006.01)
*C07D 491/20* (2006.01)
*C07D 209/96* (2006.01)
*C07D 491/10* (2006.01)
*C07D 471/20* (2006.01)
*C07D 513/10* (2006.01)
*C07D 471/10* (2006.01)

(52) U.S. Cl.
CPC .......... *C07D 491/10* (2013.01); *C07D 495/10* (2013.01); *C07D 491/20* (2013.01); *C07D 209/96* (2013.01); *C07D 471/20* (2013.01); *C07D 513/10* (2013.01); *C07D 513/20* (2013.01); *C07D 471/10* (2013.01)
USPC ......... 514/212.02; 514/278; 540/543; 543/18

(58) Field of Classification Search
USPC ................. 514/212.02, 278; 546/18; 540/543
See application file for complete search history.

(56) References Cited

U.S. PATENT DOCUMENTS

| 6,949,546 B2 | 9/2005 | Ko et al. |
| 2006/0287287 A1 | 12/2006 | Gerritz et al. |
| 2007/0088036 A1 | 4/2007 | Zhang et al. |
| 2007/0142634 A1 | 6/2007 | Barrow et al. |
| 2007/0232679 A1 | 10/2007 | Boy et al. |
| 2010/0280009 A1 | 11/2010 | Stachel et al. |

FOREIGN PATENT DOCUMENTS

| WO | WO2007/092681 | 8/2007 |
| WO | WO2009/078932 | 12/2008 |

OTHER PUBLICATIONS

PCT International Search report for PCT/CN2010/070697; mailed on May 27, 2010, 5 pages.
U.S. Appl. No. 12/747,605 filed on Dec. 10, 2008.
PCT International Search Report dated May 27, 2010 for related International Application No. PCT/US2010/070697; 4 pages.
Written Opinion of the PCT International Search Report dated Sep. 2, 2010 for related International Application No. PCT/US2010/070697; 3 pages.
Supplementary European Search Report for EP 10743423 dated Dec. 4, 2012; 2 pages.
Silvestri, R; "Boom in the development of non-peptidic beta-secretase (BACE1) inhibitors for the treatment of Alzheimer's disease"; Medicinal Research Reviews; vol. 29, No. 2., Mar. 1, 2009; pp. 295-338.

*Primary Examiner* — San-Ming Hui
*Assistant Examiner* — Kathrien Cruz
(74) *Attorney, Agent, or Firm* — John C. Todaro; Keith D. MacMillan

(57) ABSTRACT

The present invention is directed to spiropyrrolidine compounds of formula (I) which are inhibitors of the beta-secretase enzyme and that are useful in the treatment of diseases in which the beta-secretase enzyme is involved, such as Alzheimer's disease. The invention is also directed to pharmaceutical compositions comprising these compounds and the use of these compounds and compositions in the treatment of such diseases in which the beta-secretase enzyme is involved.

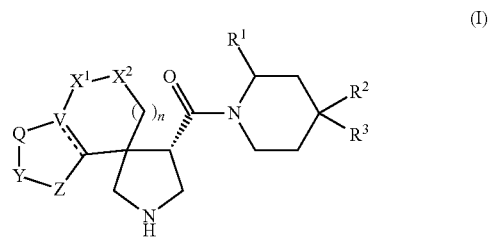

8 Claims, No Drawings

SPIROPYRROLIDINE BETA-SECRETASE INHIBITORS FOR THE TREATMENT OF ALZHEIMER'S DISEASE

FIELD OF THE INVENTION

The invention is directed to spiropyrrolidine compounds which are useful as inhibitors of the beta secretase enzyme, and are useful in the treatment of diseases in which the beta secretase enzyme is involved, such as Alzheimer's Disease.

BACKGROUND OF THE INVENTION

Alzheimer's disease is characterized by the deposition of amyloid in the brain in the form of extra-cellular plaques and intra-cellular neurofibrillary tangles. The rate of amyloid accumulation is a function of the rates of formation, aggregation and egress from the brain. It is generally accepted that the main constituent of amyloid plaques is the 4 kD amyloid protein ($\beta$A4, also referred to as A$\beta$, $\beta$-protein and $\beta$AP) which is a proteolytic product of a precursor protein of much larger size. The amyloid precursor protein (APP or A$\beta$PP) has a receptor-like structure with a large ectodomain, a membrane spanning region and a short cytoplasmic tail. The A$\beta$ domain encompasses parts of both extra-cellular and transmembrane domains of APP, thus its release implies the existence of two distinct proteolytic events to generate its $NH_2$- and COOH-termini. At least two secretory mechanisms exist which release APP from the membrane and generate soluble, COOH-truncated forms of APP ($APP_S$). Proteases that release APP and its fragments from the membrane are termed "secretases." Most $APP_S$ is released by a putative $\alpha$-secretase which cleaves within the A$\beta$ protein to release $\alpha$-$APP_S$ and precludes the release of intact A$\beta$. A minor portion of $APP_S$ is released by a $\beta$-secretase ("$\beta$-secretase"), which cleaves near the $NH_2$-terminus of APP and produces COOH-terminal fragments (CTFs) which contain the whole A$\beta$ domain.

Thus, the activity of $\beta$-secretase or $\beta$-site amyloid precursor protein-cleaving enzyme ("BACE") leads to the cleavage of APP, production of A$\beta$, and accumulation of $\beta$-amyloid plaques in the brain, which is characteristic of Alzheimer's disease (see R. N. Rosenberg, *Arch. Neurol.*, vol. 59, September 2002, pp. 1367-1368; H. Fukumoto et al, *Arch. Neurol.*, vol. 59, September 2002, pp. 1381-1389; J. T. Huse et al, *J. Biol. Chem.*, vol 277, No. 18, issue of May 3, 2002, pp. 16278-16284; K. C. Chen and W. J. Howe, *Biochem. Biophys. Res. Comm*, vol. 292, pp 702-708, 2002). Therefore, therapeutic agents that can inhibit $\beta$-secretase or BACE may be useful for the treatment of Alzheimer's disease.

The compounds of the present invention are useful for treating Alzheimer's disease by inhibiting the activity of $\beta$-secretase or BACE, thus preventing the formation of insoluble A$\beta$ and arresting the production of A$\beta$.

SUMMARY OF THE INVENTION

The present invention is directed to spiropyrrolidine compounds of general formula (I)

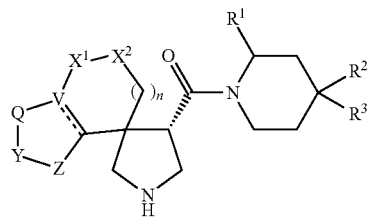

and pharmaceutically acceptable salts thereof, which are useful as inhibitors of the $\beta$-secretase enzyme.

The invention is also directed to pharmaceutical compositions which include a therapeutically effective amount of a compound of formula (I), or pharmaceutically acceptable salts thereof, and a pharmaceutically acceptable carrier. The invention is also directed to methods of treating mammals for diseases in which the $\beta$-secretase enzyme is involved, such as Alzheimer's disease, and the use of the compounds and pharmaceutical compositions of the invention in the treatment of such diseases.

DETAILED DESCRIPTION OF THE INVENTION

In one embodiment, the present invention is directed to spiropyrrolidine compounds represented by general formula (I)

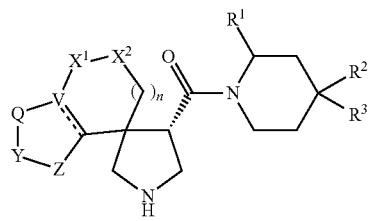

and pharmaceutically acceptable salts thereof, wherein:
V is selected from the group consisting of
  (1) C, or
  (2) N, and the dotted line leading to V represents an optional double bond, and is present when V is C and is absent when V is N;
or V is selected from the group consisting of
  (1) C, or
  (2) N, and the real line and optional dotted line leading to V represent a single bond or an optional double bond, and represent a single bond when V is N;
Q is selected from the group consisting of
  (1) =$CR^{10}$—,
  (2) =N—,
  (3) —(N→O)—,
  (4) —O—, or
  (5) =S—;
Y is selected from the group consisting of
  (1) =$CR^{10}$—,
  (2) —$CR^{10}$=,
  (3) =$CR^{10}$—$CR^{11}$=,
  (4) =$CR^{10}$—N=, or
  (5) =N—$CR^{10}$=;
Z is selected from the group consisting of
  (1) =$CR^{10}$—,
  (2) —N—,
  (3) —O—, or
  (4) =S—;

provided that Q, Y and Z together with V and the neighboring C atom form a fused aromatic 5- or 6-membered ring;

$X^1$-$X^2$ is selected from the group consisting of
(1) —$CR^{10}R^{11}$—$CR^{12}R^{13}$,
(2) —$CR^{10}R^{11}$—O—,
(3) —O—$CR^{10}R^{11}$—,
(4) —$CR^{10}R^{11}$—$NR^{12}$—,
(5) —$NR^{12}$—$CR^{10}R^{11}$—,
(6) —$CR^{10}R^{11}$—$S(=O)mR^{12}$—,
(7) —$S(=O)mR^{12}$—, $CR^{10}R^{11}$—,
(8) —$CR^{10}R^{11}$—$CR^{12}R^{13}$—O—,
(9) —$CR^{10}R^{11}$—$CR^{12}R^{13}$—,
(10) —$CR^{10}R^{11}$—O—$CR^{12}R^{13}$,
(11) —$CR^{10}R^{11}$—$CR^{12}R^{13}NR^{14}$—, or
(12) —O—$CR^{10}R^{11}$—$CR^{12}R^{13}$—, or
(13) —$S(=O)pR^{12}$—$CR^{10}R^{11}$—;

$R^1$ is selected from the group consisting of
(1) hydrogen
(2) $C_{1-6}$alkyl,
(3) $C_{2-6}$alkenyl,
(4) —$C_{3-9}$ cycloalkyl,
(5) —$C_{6-10}$aryl,
(6) heteroaryl group having from 5 to 12 ring atoms, wherein at least one ring atom is a heteroatom selected from the group consisting of nitrogen, sulfur or oxygen,
(7) a heterocyclic group having 4 to 8 ring atoms, wherein at least one ring atom is a heteroatom selected from the group consisting of nitrogen, sulfur or oxygen,
wherein said alkyl, alkenyl, aryl, cycloalkyl, heterocyclic or heteroaryl $R^1$ moiety is optionally substituted with one or more
(a) halo,
(b) —OH,
(c) —CN,
(d) —$C_{1-6}$ alkyl,
(e) —$C_{3-8}$ cycloalkyl,
(f) —O—$C_{1-6}$ alkyl,
(g) —O—$CH_2$—$C_{6-10}$aryl,
(h) —$C_{6-10}$aryl,
(i) heteroaryl group having from 5 to 12 ring atoms, wherein at least one ring atom is a heteroatom selected from the group consisting of nitrogen, sulfur or oxygen,
(j) oxo,
(k) a heterocyclic group having 4 to 8 ring atoms, wherein at least one ring atom is a heteroatom selected from the group consisting of nitrogen, sulfur or oxygen,
(l) —O—$CH_2$—$C_{3-8}$ cycloalkyl,
(m) —C(=O)—$C_{1-6}$ alkyl, or
(n) —$NR^{5A}R^{5B}$, $R^2$ and $R^3$ are independently selected from the group consisting of:
(1) hydrogen,
(2) OH,
(3) —$C_{1-6}$ alkyl,
(4) —CN,
(5) —$C_{6-10}$ aryl, or
(6) heteroaryl group having from 5 to 12 ring atoms, wherein at least one ring atom is a heteroatom selected from the group consisting of nitrogen, sulfur or oxygen,
wherein said alkyl, aryl or heteroaryl $R^2$ or $R^3$ moiety is optionally substituted with one or more
(a) halo,
(b) —$C_{1-6}$ alkyl, wherein said alkyl is optionally substituted with one or more halogen, and
(c) —O—$C_{1-6}$ alkyl, or $R^2$ and $R^3$ are linked together to form cyclic group of 4-10 ring carbon atoms, wherein one or two of the ring carbon atoms is replaced by an oxygen, nitrogen or sulfur;

$R^{5A}$ and $R^{5B}$ are independently selected from the group consisting of
(1) hydrogen,
(2) —$C_{1-6}$ alkyl,
(3) —C(=O)—$(O)_m$—$C_{1-6}$ alkyl,
(4) —C(=O)—$(O)_m$—$C_{6-10}$ aryl,
(5) —$SO_2$—$C_{3-8}$ cycloalkyl,
(6) —$SO_2$—$C_{1-6}$ alkyl,
(4) —C(=O)—$NR^{6A}R^{6B}$, wherein $R^{6A}$ and $R^{6B}$ are selected from the group consisting of wherein the alkyl, cycloalkyl or aryl moiety is optionally substituted with one or more
(a) halogen,
(b) hydroxyl,
(c) —O—$C_{1-6}$ alkyl, or
(d) —C(=O)—$(O)_m$—$C_{1-6}$ alkyl,
or $R^{6A}$ and $R^{6B}$ are linked together with the nitrogen to which they are attached to form a 4-6 membered carbocyclic ring, wherein one or two of the ring carbon atoms is optionally replaced by a nitrogen, oxygen or sulfur, and the ring is optionally substituted with one or more
(a) halogen,
(b) hydroxyl,
(c) $C_{1-6}$ alkyl,
(d) —O—$C_{1-6}$ alkyl,
(e) —C(=O)—$(O)_m$—$C_{1-6}$ alkyl, or
(f) —$SO_2$—$C_{1-6}$ alkyl;

$R^{10}$, $R^{11}$, $R^{12}$, $R^{13}$ and $R^{14}$ are independently selected from the group consisting of:
(1) hydrogen,
(2) —$C_{1-6}$ alkyl,
(3) hydroxyl,
(4) —$(CH_2)_m$ $C_{6-10}$aryl
(5) —$C_{2-6}$alkenyl,
(6) —O—$C_{1-6}$alkyl,
(7) halogen,
(8) —$SO_2$—$C_{1-6}$alkyl,
(9) —$NR^{5A}R^{5B}$,
(10) —$C_{3-8}$ cycloalkyl,
(11) —C(=O)—$(O)_m$—$C_{1-6}$ alkyl,
(12) —C(=O)—$(O)_m$—$C_{6-10}$ aryl,
(13) —C(=O)—NH—$C_{1-6}$ alkyl,
(14) —$S(=O)_2$—$C_{6-10}$ aryl,
wherein said alkyl, cycloalkyl, alkenyl or aryl moiety is optionally substituted with one or more
(a) halo,
(b) hydroxyl,
(c) —$C_{1-6}$ alkyl,
(d) —$NR^{5A}R^{5B}$,
(e) —O—$C_{1-6}$ alkyl, and
(f) —$C_{6-10}$aryl,
wherein said wherein said alky or aryl is optionally substituted with one or more halo,
or any $R^{10}$ and $R^{11}$, or any $R^{12}$ and $R^{13}$, on identical carbon ring atoms, are linked together to form an oxo group,
or any $R^{10}$ and $R^{11}$, or any $R^{12}$ and $R^{13}$, on identical carbon ring atoms, are linked together to form an aromatic or non-aromatic spirocyclic group of 5-10 ring carbon atoms, wherein one or two of the ring carbon atoms is replaced by an oxygen, nitrogen or sulfur,
or any $R^{10}$ and $R^{11}$, or any $R^{12}$ and $R^{13}$, on adjacent carbon ring atoms, are linked together to form to form a fused aromatic or non-aromatic cyclic group of 5-10 ring carbon atoms, wherein one or two of the ring carbon atoms is replaced by an oxygen, nitrogen or sulfur, m is 0 or 1;
n is 0 or 1;
p is 0, 1 or 2;
and pharmaceutically acceptable salts thereof.

In particular embodiments of the compounds of formula (I), V is C and the dotted line leading to V represents a double bond. In other embodiments of the compounds of formula (I), V is n and the dotted line leading to V is absent.

In particular embodiments of the compounds of formula (I), -Q-Y—Z— together form the group —CR$^{10}$=CR$^{10}$—CR$^{11}$=CR$^{10}$—, thereby forming a fused phenyl ring.

In other embodiments of the compounds of formula (I), -Q-Y—Z— together forms the groups —N=CR$^{10}$—CR$^{11}$=CR$^{10}$— or —CR$^{10}$=CR$^{10}$—CR$^{11}$=N—, thereby forming a fused pyridyl ring.

In other embodiments of the compounds of formula (I), -Q-Y—Z— together forms the group —N=CR$^{10}$—CR$^{11}$=N— or —N=CR$^{10}$—N=CR$^{11}$—, thereby forming a fused pyrimidinyl ring.

In other embodiments of the compounds of formula (I), -Q-Y—Z— together forms the group —NH—CR$^{10}$=CR$^{10}$—, —S—CR$^{10}$=CR$^{10}$—, —O—CR$^{10}$=CR$^{10}$—, —N=CR$^{10}$—S—, —CR$^{10}$=CR$^{10}$—S— or —CR$^{10}$=CR$^{10}$—O—, thereby forming a five-membered heteroaryl ring.

In particular embodiments of the compounds of formula (I), $X^1$-$X^2$ is —CR$^{10}$R$^{11}$—CR$^{12}$CR$^{13}$— and n is 0 or 1.

In other embodiments $X^1$-$X^2$ is —NR$^{12}$—CR$^{10}$R$^{11}$— or CR$^{10}$R$^{11}$—NR$^{12}$— and n is 1.

In other embodiments, $X^1$-$X^2$ is —S(=O)pR$^{12}$—CR$^{10}$R$^{11}$— and n is 1.

In other embodiments, $X^1$-$X^2$ is —CR$^{10}$R$^{11}$—O— or —O—CR$^{10}$R$^{11}$—, and n is 1.

In other embodiments, $X^1$-$X^2$ is one of —CR$^{10}$R$^{11}$—NR$^{14}$CR$^{12}$R$^{13}$—, —CR$^{10}$R$^{11}$—O—CR$^{12}$CR$^{13}$—, —CR$^{10}$R$^{11}$—CR$^{14}$CR$^{12}$NR$^{13}$—, or —O—CR$^{10}$R$^{11}$—CR$^{12}$CR$^{13}$—.

In particular embodiments of the compounds of formula (I), $R^1$ is selected from the group consisting of
(1) hydrogen
(2) C$_{1-6}$alkyl,
(3) C$_{3-9}$ cycloalkyl, or
(4) phenyl,
wherein said alkyl, cycloalkyl or phenyl $R^1$ moiety is optionally substituted with one or more
(a) halo,
(b) —OH,
(c) —CN,
(d) —C$_{1-6}$ alkyl
(e) —C$_{3-6}$ cycloalkyl, or
(f) —O—C$_{1-6}$ alkyl.

In particular embodiments, $R^1$ is hydrogen, phenyl (optionally substituted with halogen), or cyclohexyl.

In particular embodiments of the compounds of formula (I), $R^2$ is hydrogen and $R^3$ is selected from the group consisting of:
(1) hydrogen,
(2) C$_{6-10}$aryl (for example, phenyl), or
(3) heteroaryl,
wherein said aryl or heteroaryl $R^3$ moiety is optionally substituted with one or more
(a) halo,
(b) —C$_{1-6}$ alkyl, wherein said alkyl is optionally substituted with one or more halogen, and
(c) —O—C$_{1-6}$ alkyl.

In particular embodiments, $R^2$ is hydrogen and $R^3$ is hydrogen or unsubstituted phenyl.

In other embodiments, $R^2$ and $R^3$ are linked together to form cyclic group of 4-10 ring carbon atoms, wherein one or two of the ring carbon atoms is replaced by an oxygen, nitrogen or sulfur.

The invention is also directed to methods of treating mammals for diseases in which the β-secretase enzyme is involved, such as Alzheimer's disease, by administering a therapeutically effective amount of a compound of any of the embodiments of formula (I).

The invention is also directed to pharmaceutical compositions which include an effective amount of a compound of any of the embodiments of formula (I) or pharmaceutically acceptable salts thereof, and a pharmaceutically acceptable carrier.

The invention is further directed to a method for the manufacture of a medicament or a composition for inhibiting β-secretase enzyme activity in humans and animals comprising combining a compound of any of the embodiments of formula (I) or a pharmaceutically acceptable salt thereof, with a pharmaceutical carrier or diluent.

In one embodiment, the invention is directed to methods of inhibiting BACE1 enzyme activity, by administering a therapeutically effective amount of a compound of any of the embodiments of formula (I).

In another embodiment, the invention is directed to methods of inhibiting BACE2 enzyme activity, by administering a therapeutically effective amount of a compound of any of the embodiments of formula (I).

The invention is also directed to a method for the manufacture of a medicament or a composition for treating Alzheimer's Disease in humans, comprising combining a compound of any of the embodiments of formula (I) or a pharmaceutically acceptable salt thereof, with a pharmaceutical carrier or diluent.

In some embodiments, the compound of formula (I) is a compound of formula (II)

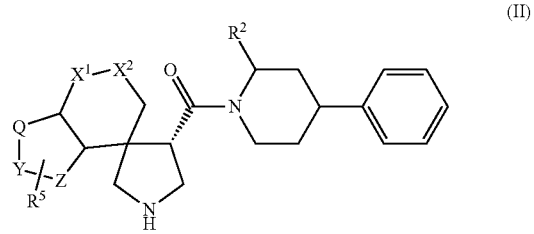

and pharmaceutically acceptable salts thereof, wherein $R^2$, $R^5$, $X^1$, $X^2$, Q, Y and Z are as defined above.

In particular embodiments of the compounds of formula (II), -Q-Y—Z— together form the group —CR$^{10}$=CR$^{10}$—CR$^{11}$=CR$^{10}$—, thereby forming a fused phenyl ring.

In other embodiments of the compounds of formula (II), -Q-Y—Z— together forms the groups —N=CR$^{10}$—CR$^{11}$=CR$^{10}$— or —CR$^{10}$=CR$^{10}$—CR$^{11}$=N—, thereby forming a fused pyridyl ring.

In other embodiments of the compounds of formula (II), -Q-Y—Z— together forms a the group —N=CR$^{10}$—CR$^{11}$=N— or —N=CR$^{10}$—N=CR$^{11}$, thereby forming a fused pyrimidinyl ring.

In other embodiments of the compounds of formula (II), -Q-Y—Z— together forms the group —NH—CR$^{10}$=CR$^{10}$—, —S—CR$^{10}$=CR$^{10}$—, —O—CR$^{10}$═CR$^{10}$—, —N═CR$^{10}$—S—, —CR$^{10}$═CR$^{10}$—S— or —CR$^{10}$═CR$^{10}$—O—, thereby forming a five-membered heteroaryl ring.

In particular embodiments of the compounds of formula (II), X$^1$-X$^2$ is —CR$^{10}$R$^{11}$—CR$^{12}$CR$^{13}$— and n is 0 or 1.

In other embodiments of the compounds of formula (II), X$^1$-X$^2$ is —NR$^{12}$—CR$^{10}$R$^{11}$— or CR$^{10}$R$^{11}$— and n is 1.

In other embodiments of the compounds of formula (II), X$^1$-X$^2$ is —S(═O)pR$^{12}$—CR$^{10}$R$^{11}$— and n is 1.

In other embodiments of the compounds of formula (II), X$^1$-X$^2$ is —CR$^{10}$R$^{11}$—O— or —O—CR$^{10}$R$^{11}$—, and n is 0 or 1.

In other embodiments of the compounds of formula (II), X$^1$-X$^2$ is one of —CR$^{10}$R$^{11}$—NR$^{14}$CR$^{12}$R$^{13}$—, —CR$^{10}$R$^{11}$—O—CR$^{12}$CR$^{13}$—, —CR$^{10}$R$^{11}$—CR$^{14}$CR$^{12}$NR$^{13}$—, or —O—CR$^{10}$R$^{11}$—CR$^{12}$CR$^{13}$—.

In particular embodiments of the compounds of formula (II), R$^2$ is hydrogen and R$^3$ is selected from the group consisting of:
(1) hydrogen,
(2) aryl (for example, phenyl), or
(3) heteroaryl,
  wherein said aryl or heteroaryl R$^3$ moiety is optionally substituted with one or more
  (a) halo,
  (b) —C$_{1-6}$ alkyl, wherein said alkyl is optionally substituted with one or more halogen, and
  (c) —O—C$_{1-6}$ alkyl.

In particular embodiments of the compounds of formula (II), R$^2$ is hydrogen and R$^3$ is hydrogen or unsubstituted phenyl.

In some embodiments, the compound of formula (I) is a compound of formula (III)

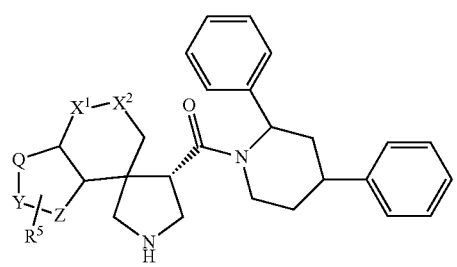

(III)

and pharmaceutically acceptable salts thereof, wherein R$^2$, R$^5$, X$^1$, X$^2$, Q, Y and Z are as defined above.

In particular embodiments of the compounds of formula (III), -Q-Y—Z— together form the group —CR$^{10}$═CR$^{10}$—CR$^{11}$═CR$^{10}$—, thereby forming a fused phenyl ring.

In other embodiments of the compounds of formula (III), -Q-Y—Z— together forms the groups —N═CR$^{10}$—CR$^{11}$═CR$^{10}$— or —CR$^{10}$═CR$^{11}$═N—, thereby forming a fused pyridyl ring.

In other embodiments of the compounds of formula (III), -Q-Y—Z— together forms the group —N═CR$^{10}$—CR$^{11}$═N— or —N═CR$^{10}$—N═CR$^{11}$—, thereby forming a fused pyrimidinyl ring.

In other embodiments of the compounds of formula (III), -Q-Y—Z— together forms the group —NH—CR$^{10}$═CR$^{10}$—, —S—CR$^{10}$═CR$^{10}$—, —O—CR$^{10}$═CR$^{10}$—, —N═CR$^{10}$—S—, —CR$^{10}$═CR$^{10}$—S— or —CR$^{10}$═CR$^{10}$—O—, thereby forming a five-membered heteroaryl ring.

In particular embodiments of the compounds of formula (III), X$^1$-X$^2$ is —CR$^{10}$R$^{11}$—CR$^{12}$CR$^{13}$— and n is 0 or 1

In other embodiments of the compounds of formula (III), X$^1$-X$^2$ is NR$^{12}$—CR$^{10}$R$^{11}$— or —CR$^{10}$R$^{11}$—NR$^{12}$— and n is 1.

In other embodiments of the compounds of formula (III), X$^1$-X$^2$ is —S(═O)pR$^{12}$—CR$^{10}$R$^{11}$— and n is 1.

In other embodiments of the compounds of formula (III), X$^1$-X$^2$ is —CR$^{10}$R$^{11}$—O— or —O—CR$^{10}$R$^{11}$—, and n is 1.

In other embodiments of the compounds of formula (III), X$^1$-X$^2$ is one of —CR$^{10}$R$^{11}$—NR$^{14}$CR$^{12}$R$^{13}$—, —CR$^{10}$R$^{11}$—O—CR$^{12}$CR$^{13}$—, —CR$^{10}$R$^{11}$—CR$^{14}$CR$^{12}$NR$^{13}$—, or —O—CR$^{10}$R$^{11}$—CR$^{12}$CR$^{13}$—.

In some embodiments, the compound of formula (I) is a compound of formula (IV)

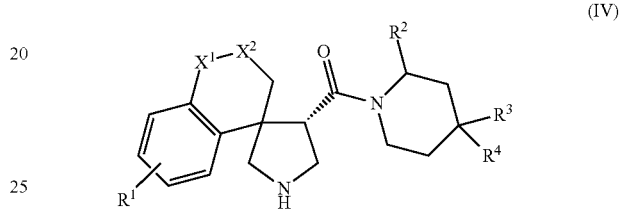

(IV)

and pharmaceutically acceptable salts thereof, wherein R$^2$, R$^3$, R$^4$, R$^5$, X$^1$ and X$^2$ are as defined above.

In particular embodiments of the compounds of formula (IV), X$^1$-X$^2$ is —CR$^{10}$R$^{11}$—CR$^{12}$CR$^{13}$— and n is 0 or 1.

In other embodiments of the compounds of formula (IV), X$^1$-X$^2$ is NR$^{12}$—CR$^{10}$R$^{11}$— or —CR$^{10}$R$^{11}$—NR$^{12}$— and n is 1.

In other embodiments of the compounds of formula (IV), X$^1$-X$^2$ is —S(═O)pR$^{12}$—CR$^{10}$R$^{11}$— and n is 1.

In other embodiments of the compounds of formula (IV), X$^1$-X$^2$ is cR$^{10}$R$^{11}$—O— or —O—CR$^{10}$R$^{11}$— and n is 1 or 2.

In other embodiments of the compounds of formula (IV), X$^1$-X$^2$ is one of —CR$^{10}$R$^{11}$—NR$^{14}$CR$^{12}$R$^{13}$—, —CR$^{10}$R$^{11}$—O—CR$^{12}$CR$^{13}$—, —CR$^{10}$R$^{11}$—CR$^{14}$CR$^{12}$NR$^{13}$—, or —O—CR$^{10}$R$^{11}$—CR$^{12}$CR$^{13}$—.

In particular embodiments of the compounds of formula (IV), R$^1$ is selected from the group consisting of
(1) hydrogen
(2) C$_{1-6}$alkyl,
(3) C$_{3-6}$ cycloalkyl, or
(4) phenyl,
  wherein said alkyl, cycloalkyl or phenyl R$^1$ moiety is optionally substituted with one or more
  (a) halo,
  (b) —OH,
  (c) —CN,
  (d) —C$_{1-6}$ alkyl
  (e) —C$_{3-6}$ cycloalkyl, or
  (f) —O—C$_{1-6}$ alkyl.

In particular embodiments of the compounds of formula (IV), R$^1$ is hydrogen, phenyl (optionally substituted with halogen), or cyclohexyl.

In particular embodiments of the compounds of formula (IV), R$^2$ is hydrogen and R$^3$ is selected from the group consisting of:
(1) hydrogen,
(2) aryl (for example, phenyl), or
(3) heteroaryl,
  wherein said aryl or heteroaryl R$^3$ moiety is optionally substituted with one or more (a) halo,
(b) —$C_{1-6}$ alkyl, wherein said alkyl is optionally substituted with one or more halogen, and
(c) —O—$C_{1-6}$ alkyl.

In particular embodiments of the compounds of formula (IV), $R^2$ is hydrogen and $R^3$ is hydrogen or unsubstituted phenyl.

In other embodiments of the compounds of formula (IV), $R^2$ and $R^3$ are linked together to form cyclic group of 4-10 ring carbon atoms, wherein one or two of the ring carbon atoms is replaced by an oxygen, nitrogen or sulfur.

In some embodiments, the compound of formula (I) is a compound of formula (V)

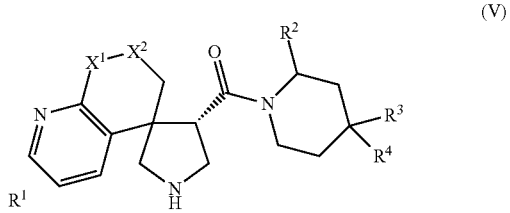

(V)

and pharmaceutically acceptable salts thereof, wherein $R^2$, $R^3$, $R^4$, $R^5$, $X^1$ and $X^2$ are as defined above.

In particular embodiments of the compounds of formula (V), $X^1$-$X^2$ is —$CR^{10}R^{11}$—$CR^{12}CR^{13}$— and n is 0 or 1

In other embodiments of the compounds of formula (V), $X^1$-$X^2$ is $NR^{12}$—$CR^{10}R^{11}$— or —$CR^{10}R^{11}$—$NR^{12}$— and n is 1.

In other embodiments of the compounds of formula (V), $X^1$-$X^2$ is —$S(=O)pR^{12}$—$CR^{10}R^{11}$— and n is 1.

In other embodiments of the compounds of formula (V), $X^1$-$X^2$ is —$CR^{10}R^{11}$—O— or —O—$CR^{10}R^{11}$—, and n is 1.

In other embodiments of the compounds of formula (V), $X^1$-$X^2$ is one of —$CR^{10}R^{11}$—$NR^{14}CR^{12}R^{13}$—, —$CR^{10}R^{11}$—O—$CR^{14}CR^{12}NR^{13}$—, or —O—$CR^{10}R^{11}$—$CR^{12}CR^{13}$—.

In particular embodiments of the compounds of formula (V), $R^1$ is selected from the group consisting of
(1) hydrogen
(2) $C_{1-6}$alkyl,
(3) $C_{3-6}$ cycloalkyl, or
(4) phenyl,
wherein said alkyl, cycloalkyl or phenyl $R^1$ moiety is optionally substituted with one or more
(a) halo,
(b) —OH,
(c) —CN,
(d) —$C_{1-6}$ alkyl
(e) —$C_{3-6}$ cycloalkyl, or
(f) —O—$C_{1-6}$ alkyl.

In particular embodiments of the compounds of formula (V), $R^1$ is hydrogen, phenyl (optionally substituted with halogen), or cyclohexyl.

In particular embodiments of the compounds of formula (V), $R^2$ is hydrogen and $R^3$ is selected from the group consisting of:
(1) hydrogen,
(2) aryl (for example, phenyl), or
(3) heteroaryl,
wherein said aryl or heteroaryl $R^3$ moiety is optionally substituted with one or more (a) halo,
(b) —$C_{1-6}$ alkyl, wherein said alkyl is optionally substituted with one or more halogen, and
(c) —O—$C_{1-6}$ alkyl.

In particular embodiments of the compounds of formula (V), $R^2$ is hydrogen and $R^3$ is hydrogen or unsubstituted phenyl.

In other embodiments of the compounds of formula (V), $R^2$ and $R^3$ are linked together to form cyclic group of 4-10 ring carbon atoms, wherein one or two of the ring carbon atoms is replaced by an oxygen, nitrogen or sulfur.

The invention is also directed to methods of treating mammals for diseases in which the β-secretase enzyme is involved, such as Alzheimer's disease, by administering a therapeutically effective amount of a compound of any of the embodiments of formulas (II) to (V).

The invention is also directed to pharmaceutical compositions which include an effective amount of a compound of any of the embodiments of formulas (II) to (V) or pharmaceutically acceptable salts thereof, and a pharmaceutically acceptable carrier.

The invention is further directed to a method for the manufacture of a medicament or a composition for inhibiting β-secretase enzyme activity in humans and animals comprising combining a compound of any of the embodiments of formulas (II) to (V) or a pharmaceutically acceptable salt thereof, with a pharmaceutical carrier or diluent.

In one embodiment, the invention is directed to methods of inhibiting BACE1 enzyme activity, by administering a therapeutically effective amount of a compound of any of the embodiments of formulas (II) to (V).

In another embodiment, the invention is directed to methods of inhibiting BACE2 enzyme activity, by administering a therapeutically effective amount of a compound of any of the embodiments of formulas (II) to (V).

The invention is also directed to a method for the manufacture of a medicament or a composition for treating Alzheimer's Disease in humans, comprising combining a compound of any of the embodiments of formulas (II) to (V) or a pharmaceutically acceptable salt thereof, with a pharmaceutical carrier or diluent.

In another embodiment, the invention is directed to compounds of Examples 1—as described herein, or pharmaceutically acceptable salts thereof.

As used herein, the definitions of each of Q-Y—Z should read from left to right, so that when Q is =$CR^{10}$—, Y is =$CR^{10}$—$CR^{11}$= and Z is =$CR^{10}$—, the formula (I) ring structure should appear as follows:

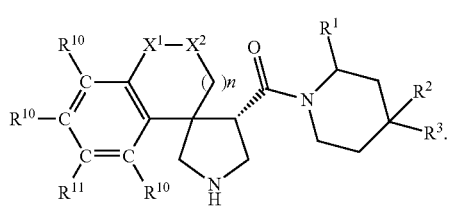

As used herein, the definitions of $X^1$-$X^2$ are read from left to right, so that when $X^1$-$X^2$ is —$CR^{10}R^{11}$=$CR^{12}CR^{13}$—, the formula (I) ring structure should appear as follows:

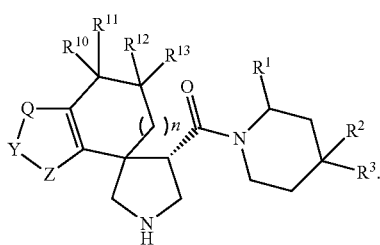

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Suitable alkyl groups for use in the invention are $C_{1-6}$ alkyl groups, having from one to six carbon atoms. Exemplary alkyl groups include methyl, ethyl, n-propyl, isopropyl, n-butyl, isobutyl, tert-butyl, pentyl, hexyl, and the like.

The term "$C_0$ alkyl," for example in the term "—$C_0$alkyl-$C_{6-12}$ aryl", refers to a bond.

As used herein, the term "alkenyl," by itself or as part of another substituent, means a straight or branched chain hydrocarbon radical having a single carbon-carbon double bond and the number of carbon atoms designated (e.g., $C_{2-10}$ alkenyl means an alkenyl group having from two to ten carbon atoms). Suitable alkenyl groups for use in the invention are $C_{2-6}$ alkenyl groups, having from two to six carbon atoms. Exemplary alkenyl groups include ethenyl and propenyl.

Suitable cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantly and norbornyl. Exemplary fused cycloalkyl groups include decahydronaphthalene.

As used herein, the term "heterocyclic," by itself or as part of another substituent, means a cycloalkyl group as defined above, in which one or more of the ring carbon atoms is replaced with a heteroatom (such as N, S or O). Suitable non-aromatic heterocyclic groups for use in the invention include piperidinyl, piperazinyl, morpholinyl, tetrahydropyranyl, tetrahydrofuranyl, pyrrolidinyl, pyrazolidinyl and imidazolildinyl. In certain embodiments, heterocyclic groups for use in the invention have four to eight ring atoms and a single nitrogen or oxygen heteroatom.

When a heterocyclic group as defined herein is substituted, the substituent may be bonded to a ring carbon atom of the heterocyclic group, or to a ring heteroatom (i.e., a nitrogen, oxygen or sulfur), which has a valence which permits substitution. Similarly, when a heterocyclic group is defined as a substituent herein, the point of attachment may be at a ring carbon atom of the heterocyclic group, or on a ring heteroatom (i.e., a nitrogen, oxygen or sulfur), which has a valence which permits attachment.

As used herein, the term "aryl," by itself or as part of another substituent, means an aromatic or cyclic radical having the number of carbon atoms designated (e.g., $C_{6-10}$ aryl means an aryl group having from six to ten carbons atoms). The term "aryl" includes multiple ring systems (such as fused ring systems) as well as single ring systems, and includes multiple ring systems wherein part of the molecule is aromatic and part is non-aromatic. A suitable single ring aryl group for use in the invention is phenyl. Suitable fused ring aryl groups include naphthyl, tetrahydronaphthyl and indanyl.

The term "halo" or "halogen" includes fluoro, chloro, bromo and iodo.

As used herein, the term "heteroaryl," by itself or as part of another substituent, means an aromatic cyclic group having at least one ring heteroatom (O, N or S). The term "heteroaryl" includes multiple ring systems as well as single ring systems. Exemplary heteroaryl groups have from 5 to 12 ring atoms. Exemplary heteroaryl groups include pyrazinyl, pyrazolyl, pyridazinyl, pyridyl, pyrimidinyl, pyrrolyl, tetrazolyl, furanyl, imidazolyl, indazolyl, triazinyl, pyranyl, thiazolyl, thienyl, triazolyl, oxazolyl, isoxazolyl, thiazolyl, oxadiazolyl, indolyl, quinolinyl, isoquinolinyl, benzimidazolyl, benzofuranyl, indynyl and benzoxazolyl.

When a heteroaryl group as defined herein is substituted, the substituent may be bonded to a ring carbon atom of the heteroaryl group, or on a ring heteroatom (i.e., a nitrogen, oxygen or sulfur), which has a valence which permits substitution. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment.

As used herein, the term "beta-secretase" or "β-secretase" refers to an enzyme that is sometimes known in the literature as "BACE", "BACE1" (see, e.g., Vassar et al., 1999, *Science* 286:735-741), or "BACE2" (see, e.g., Farzan et al., 2000, *PNAS* 97:9712-9717). BACE1 is a 501 amino acid membrane-bound aspartic protease. BACE1 has all the known functional properties and characteristics of β-secretase. BACE2, also called Asp-1 or memapsin-1, is a second member of the BACE family of membrane-bound aspartic proteases. See Roggo, *Current Topics in Medicinal Chemistry*, 2002, 2:359-370, for a further discussion of the differences between BACE1 and BACE2.

The compounds of the invention are inhibitors of both the BACE1 and BACE2 enzyme.

The compounds of formula (I) have at least one asymmetric center. Additional asymmetric centers may be present depending upon the nature of the various substituents on the molecule.

Compounds with asymmetric centers give rise to enantiomers (optical isomers), diastereomers (configurational isomers) or both. All of the possible enantiomers and diastereomers in mixtures (as pure or partially purified compounds) are included within the scope of formula (I)

Compounds described herein may contain one or more double bonds, and may thus give rise to cis/trans isomers as well as other configurational isomers. The compounds of formula (I) include all such possible isomers as well as mixtures of such isomers.

Formula (I) is shown above without a definite stereochemistry at certain positions. Figure (I) as depicted includes all stereoisomers of formula (I) and pharmaceutically acceptable salts thereof.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

The term "substantially pure" means that the isolated material is at least 90% pure, as assayed by analytical techniques known in the art. In one embodiment, the isolated material is at least 95% pure. In another embodiment, the isolated material is at least 99% pure.

The term "pharmaceutically acceptable salts" refers to salts prepared from pharmaceutically acceptable non-toxic bases or acids including inorganic or organic bases and inorganic or organic acids. The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like. Particular salts are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular salts are the citric, hydrobromic, hydrochloric, trifluoroacetic, maleic, phosphoric, sulfuric, fumaric, and tartaric acids.

The present invention is directed to the use of the compounds of formulas (I) to (III) disclosed herein as inhibitors of β-secretase enzyme activity or β-site amyloid precursor protein-cleaving enzyme ("BACE") activity, in a patient or subject such as a mammal in need of such inhibition, comprising the administration of an effective amount of the compound. The terms "-secretase enzyme," "β-site amyloid precursor protein-cleaving enzyme," and "BACE" are used interchangeably in this specification. In addition to humans, a variety of other mammals can be treated according to the method of the present invention.

The compounds of the present invention have utility in treating, ameliorating, controlling or reducing the risk of Alzheimer's disease. For example, the compounds may be useful for the prevention of dementia of the Alzheimer's type, as well as for the treatment of early stage, intermediate stage or late stage dementia of the Alzheimer's type. The compounds may also be useful in treating, ameliorating, controlling or reducing the risk of diseases mediated by abnormal cleavage of amyloid precursor protein (also referred to as APP), and other conditions that may be treated or prevented by inhibition of β-secretase. Such conditions include mild cognitive impairment, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes and atherosclerosis.

The subject or patient to whom the compounds of the present invention is administered is generally a human being, male or female, in whom inhibition of β-secretase enzyme activity is desired, but may also encompass other mammals, such as dogs, cats, mice, rats, cattle, horses, sheep, rabbits, monkeys, chimpanzees or other apes or primates, for which inhibition of β-secretase enzyme activity or treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients.

Examples of combinations of the compounds of the present invention with other drugs in either unit dose or kit form include combinations with anti-Alzheimer's agents, for example other beta-secretase inhibitors or gamma-secretase inhibitors; glycine transport inhibitors, tau phosphorylation inhibitors; blockers of Aβ oligomer formation; p25/CDK5 inhibitors; HMG-CoA reductase inhibitors; PPAR gamma agonists, such as pioglitazone and rosiglitazone; NK1/NK3 receptor antagonists; NSAID's including ibuprofen; vitamin E; anti-amyloid antibodies, including anti-amyloid humanized monoclonal antibodies; COX-2 inhibitors; anti-inflammatory compounds, such as (R)-flurbiprofen; CB-1 receptor antagonists or CB-1 receptor inverse agonists; antibiotics such as doxycycline and rifampin; N-methyl-D-aspartate (NMDA) receptor antagonists, such as memantine and neramexane; NR2B antagonists; androgen receptor modulators; acetylcholinesterase inhibitors such as galantamine, rivastigmine, donepezil, and tacrine; mGluR5 modulators; growth hormone secretagogues such as ibutamoren, ibutamoren mesylate, and capromorelin; histamine $H_3$ antagonists; AMPA agonists; PDE IV inhibitors; $GABA_A$ inverse agonists; $GABA_A$ α5 receptor ligands; $GABA_B$ receptor ligands; potassium channel blockers; neuronal nicotinic agonists; P-450 inhibitors, such as ritonavir; or other drugs that affect receptors or enzymes that either increase the efficacy, safety, convenience, or reduce unwanted side effects or toxicity of the compounds of the present invention. The foregoing list of combinations is illustrative only and not intended to be limiting in any way.

In the pharmaceutical composition the active compound, which is a compound of the invention, is included in an amount sufficient to produce the desired effect upon the process or condition of diseases. Accordingly, the pharmaceutical compositions of the present invention encompass any composition made by admixing a compound of the invention and a pharmaceutically acceptable carrier.

The carrier may take a wide variety of forms depending on the form of preparation desired for administration, e.g., oral or parenteral (including intravenous). Thus, the pharmaceutical compositions of the invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, may also be administered by controlled release means and/or delivery devices.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain a compound of the invention in admixture with nontoxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing a composition of this invention may be prepared by compression or molding, optionally with one or more accessory ingredients or adjuvants. Compressed tablets may be prepared by compressing, in a suitable machine, a compound of the invention in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. In certain embodiments, each tablet contains from about 0.1 mg to about 500 mg of the active ingredient and each cachet or capsule contains from about 0.1 mg to about 500 mg of the compound of the invention.

Compositions for oral use may also be presented as hard gelatin capsules wherein the compound of the invention is mixed with an inert solid diluent, for example, calcium carbonate, calcium phosphate or kaolin, or as soft gelatin capsules wherein the compound of the invention is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the compound of the invention in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage, and should be preserved against the contaminating action of microorganisms such as bacteria and fungi.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment is prepared by mixing hydrophilic material and water, together with about 5 wt % to about 10 wt % of the compound of the invention, to produce a cream or ointment having a desired consistency.

Pharmaceutical compositions of this invention can also be in a form suitable for rectal administration wherein the carrier is a solid. Suitable carriers include cocoa butter and other materials commonly used in the art.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise-undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant. By "pharmaceutically acceptable" it is meant the carrier, diluent or excipient must be compatible with the other ingredients of the formulation and not deleterious to the recipient thereof.

Optional" or "optionally" means that the subsequently described event, circumstance, feature, or element may, but need not, occur, and that the description includes instances where the event or circumstance occurs and instances in which it does not. For example, "heterocyclo group optionally mono- or di-substituted with an alkyl group" means that the alkyl may, but need not, be present, and the description includes situations where the heterocyclo group is mono- or disubstituted with an alkyl group and situations where the heterocyclo group is not substituted with the alkyl group.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician.

As used herein, the term "treatment" or "treating" means any administration of a compound of the invention to obtain a desired pharmacologic and/or physiologic effect. The effect may be prophylactic in terms of completely or partially preventing a disease or symptom thereof, and/or may be therapeutic in terms of a partial or complete cure for a disease and/or adverse affect attributable to the disease. Treatment includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology).

The terms "individual," "subject," and "patient," used interchangeably herein, refer to a mammal, including, but not limited to, murines, simians, humans, mammalian farm animals, mammalian sport animals, and mammalian pets.

The compositions containing compounds of the invention may conveniently be presented in unit dosage form and may be prepared by any of the methods well known in the art of pharmacy.

The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The compositions containing compounds of the invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating, ameliorating, controlling or reducing the risk of Alzheimer's disease or other diseases for which compounds of the invention are indicated, generally satisfactory results are obtained when the compounds of the invention are administered at a daily dosage of from about 0.1 mg to about 100 mg per kg of animal body weight. For example, the compounds may be given as a single daily dose or in divided doses two to six times a day, or in sustained release form. The total daily dosage is from about 1.0 mg to about 2000 mg (for example, from about 0.1 mg to about 20 mg per kg of body weight). In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, for example once or twice per day.

The amount of the compound of the invention that may be combined with the carrier materials to produce a single dosage form will vary depending upon the host treated and the particular mode of administration. For example, a formulation intended for the oral administration to humans may conveniently contain from about 0.005 mg to about 2.5 g of a compound of the invention, compounded with an appropriate and convenient amount of carrier material. Unit dosage forms will generally contain between from about 0.005 mg to about 1000 mg of the compound of the invention, typically 0.005 mg, 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg, administered once, twice or three times a day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the invention may be prepared according to the following reaction Schemes, in which variables are as defined before or are derived, using readily available starting materials, from reagents and conventional synthetic procedures. It is also possible to use variants which are themselves known to those of ordinary skill in organic synthesis art, but are not mentioned in greater detail.

The present invention also provides a method for the synthesis of compounds useful as intermediates in the preparation of compounds of the invention.

Generic scheme I outlines a method for preparing compounds having different combination of 4-spiro fused aryl and amide substituents on the pyrrolidine ring. In this method, the appropriate cyclic ketone A is reacted with triethylphosphonoacetate to yield upon isolation the desired E-stereoisomer B which undergoes dipolar cycloaddition upon treatment with benzyl-N-(methoxymethyl)-trimethylsilylmethyl amine as an azomethine ylide precursor to provide the trans pyrrolidine C. The ester is hydrolyzed and coupled under standard conditions with a suitable amine E. Removal of the benzyl amine by either hydrogenation or other chemical methods such as a-chloroethyl chloroformate yields the target products F.

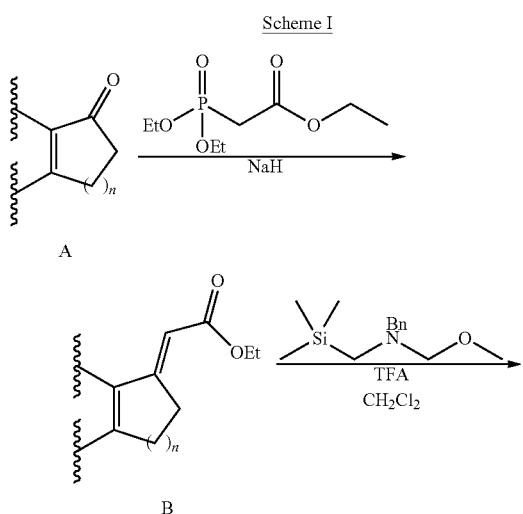

Scheme I

A

B

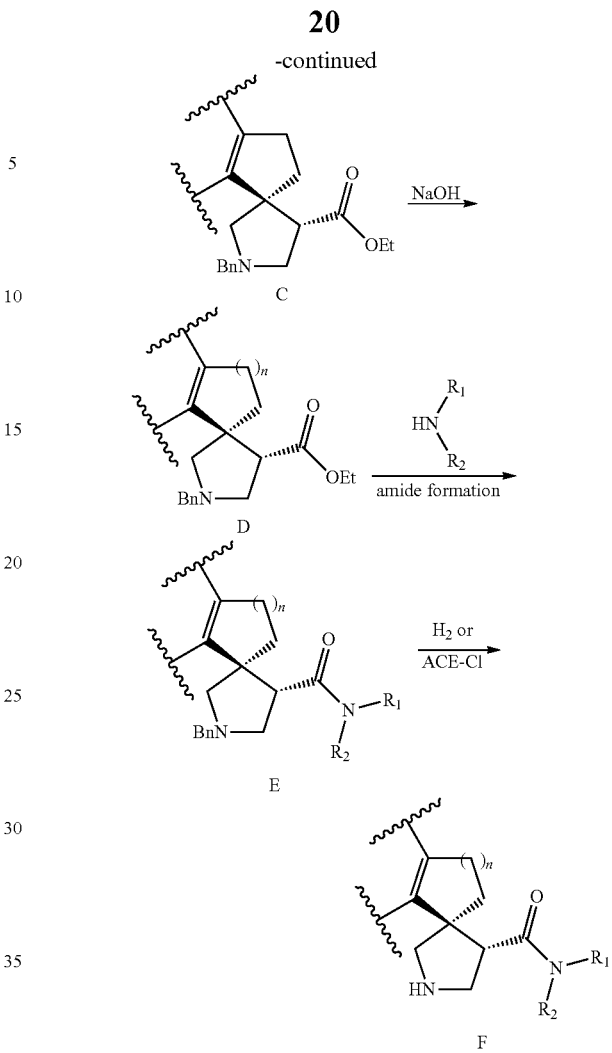

C

D

E

F

Generic Scheme II outlines a method for preparing 4-spiro-fused compounds that have a spiro ring substitution that is not compatible with hydrogenation conditions. In this method, the appropriate ketone is reacted with triethylphosphonoacetate to yield upon isolation the desired E-stereoisomer Bb which undergoes dipolar cycloaddition upon treatment with benzyl-N-(methoxymethyl)-trimethylsilylmethyl amine as an azomethine ylide precursor to provide the trans pyrrolidine Cc. The benzyl protecting group is then exchanged for a t-butoxycarbonyl by sequential treatment with 1-chloroethyl chloroformate, then methanol, and finally BOC anhydride to provide the BOC-protected pyrrolidine Dd. The ester is hydrolyzed and coupled under standard conditions with a suitable amine. TFA mediated deprotection of the t-butyl carbamate yields the desired product Ff.

Scheme II

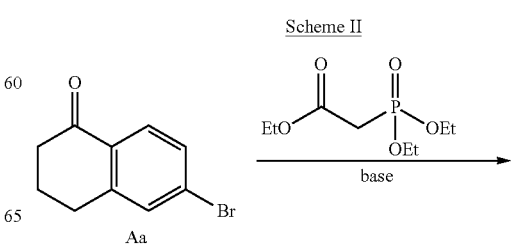

Aa

-continued

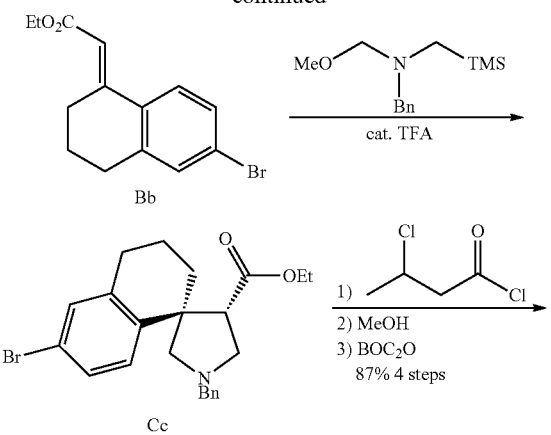

Intermediate I:
(2S,4R)-2-cyclohexyl-4-phenylpiperidine

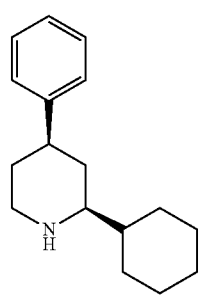 [SMILES: c1ccc([C@@H]2CCN[C@H](C3CCCCC3)C2)cc1]

Step 1: Benzyl 2-cyclohexyl-4-oxo-3,4-dihydropyridine-1(2H)-carboxylate

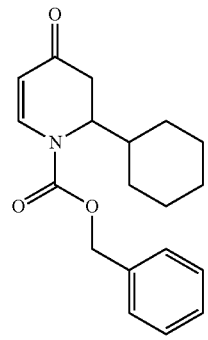 [SMILES: O=C1C=CN(C(=O)OCc2ccccc2)C(C2CCCCC2)C1]

4-methoxypyridine (17.56 ml, 173 mmol) in THF (577 ml) at −30° C. was added benzyl chloroformate (24.70 ml, 173 mmol) dropwise. Stirred at −30° C. for 30 minutes and then added cyclohexylmagnesium chloride (200 ml, 260 mmol). Stirred for 30 minutes at −30° C. and quenched with 1N HCl. Extracted 3 times with diethyl ether. The combined organic fractions were combined, dried ($Na_2SO_4$), filtered and the solvent was evaporated under reduced pressure. Purified on silica gel 30% EtOAc/Hexanes affording 35.25 g.

$^1$H NMR (CDCl$_3$) δ 7.83 (br s, 1H), 7.42-7.36 (m, 5H), 5.34-5.24 (m, 3H), 4.38 (br s, 1H), 2.80-2.72 (m, 1H), 2.66-2.58 (m, 1H), 1.77-1.42 (m, 6H), 1.17-0.91 (m, 5H).

Step 2: Benzyl 2-cyclohexyl-4-oxopiperidine-1-carboxylate

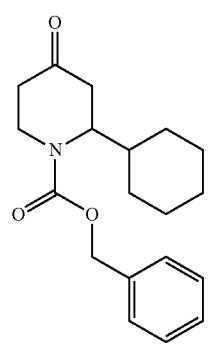 [SMILES: O=C1CCN(C(=O)OCc2ccccc2)C(C2CCCCC2)C1]

Benzyl 2-cyclohexyl-4-oxo-3,4-dihydropyridine-1(2H)-carboxylate (35.25 g, 112 mmol) was dissolved in AcOH (450 ml) and added zinc dust (22.07 g, 337 mmol). The solution stirred at room temperature for 12 hours. The solution was filtered through celite and washed with EtOAc. The solvent was evaporated under reduced pressure and the product was purified by column chromatography on silica gel 30% EtOAc/Hexanes.

¹H NMR (CDCl₃) δ 7.40-7.31 (m, 5H), 5.22-5.14 (m, 2H), 4.54-4.21 (m, 2H), 3.19-3.08 (m, 1H), 2.62-2.43 (m, 3H), 2.35-2.27 (m, 1H), 1.82-1.53 (m, 6H), 1.42-0.80 (m, 5H).

Step 3: Benzyl 2-cyclohexyl-4-hydroxy-4-phenylpiperidine-1-carboxylate

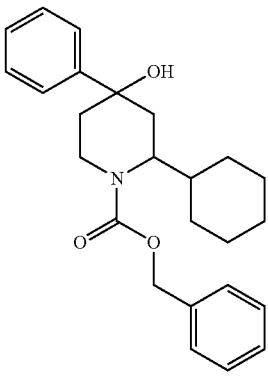 [SMILES: O=C(OCc1ccccc1)N1CCC(O)(c2ccccc2)CC1C1CCCCC1]

Benzyl 2-cyclohexyl-4-oxopiperidine-1-carboxylate in THF (155 ml) was cooled to 0° C. and added phenylmagnesium bromide (22.08 ml, 61.8 mmol). The ice bath was removed and the solution stirred at room temperature for 14 hours. Quenched the reaction with 1N HCl and concentrated. Extracted three times with EtOAc and washed twice with water. The organics were dried, concentrated, and purified on silica gel 30% EtOAc.

¹H NMR (CDCl₃) δ 7.47-7.43 (m, 2H), 7.38-7.24 (m, 8H), 5.16 (s, 2H), 4.25-3.92 (m, 2H), 3.40-3.27 (m, 1H), 2.38-2.27 (m, 1H), 2.15-2.04 (m, 1H), 1.92-1.84 (m, 2H), 1.79-1.62 (m, 5H), 1.33-1.08 (m, 4H), 0.98-0.82 (m, 3H).

Step 4: Benzyl 2-cyclohexyl-4-phenyl-3,6-dihydropyridine-1(2H)-carboxylate

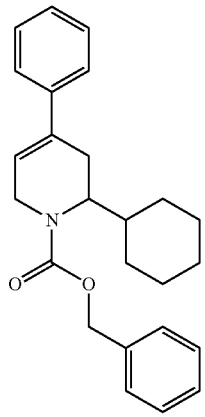 [SMILES: O=C(OCc1ccccc1)N1CC=C(c2ccccc2)CC1C1CCCCC1]

A solution of BF₃.OEt₂ (4.93 ml, 38.9 mmol) in CH₂Cl₂ (30 ml) was added to a stirred solution of benzyl 2-cyclohexyl-4-hydroxy-4-phenylpiperidine-1-carboxylate (5 g, 12.71 mmol) in CH₂Cl₂ (244 ml) at 0° C. The mixture was stirred at room temperature for 15 minutes. Saturated sodium bicarbonate (100 ml) was added after 15 minutes. Extracted twice with CH₂Cl₂ and the combined organics were dried and concentrated. The crude product was not purified.

¹H NMR (CDCl₃) δ 7.40-7.22 (m, 10H), 6.21-5.93 (m, 1H), 5.22-5.16 (m, 2H), 4.58-4.10 (m, 2H), 3.74-3.05 (m, 1H), 2.67-2.32 (m, 2H), 1.88-1.55 (m, 6H), 1.27-0.90 (m, 5H).

Step 5: 2-cyclohexyl-4-phenylpiperidine

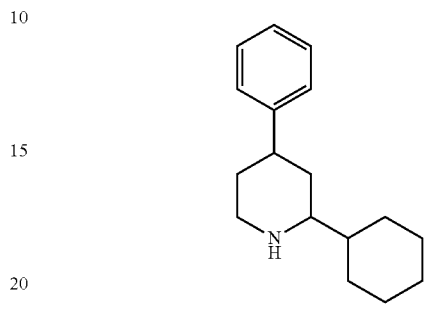

Benzyl 2-cyclohexyl-4-phenyl-3,6-dihydropyridine-1 (2H)-carboxylate (4.7 g, 12.52 mmol) in EtOH (25 ml) was added Pd/C (1.18 g, 0.554 mmol) and hydrogenated with a balloon for 10 hours. Filter through celite and concentrate. The crude piperidine was not purified. LRMS (M+H)=217.10

Step 6: Benzyl 2-cyclohexyl-4-phenylpiperidine-1-carboxylate

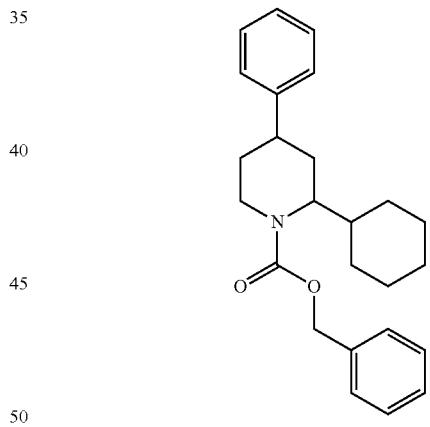

2-cyclohexyl-4-phenylpiperidine (2.85 g, 11.71 mmol) in CH₂Cl₂ (58.5 ml) was added benzyl chloroformate (2.507 ml, 17.56 mmol) and triethylamine (2.45 ml, 17.56 mmol). The reaction was stirred at room temperature for 2 hours. Added water and extracted 3 times with CH₂Cl₂. The combined organics were dried, concentrated, and purified on silica gel 20% EtOAc/Hexanes. Separated cis and trans on the AD column, 20% IPA/Hexanes w/DEA. Peak 1 corresponds to the cis racemic mixture with one trans diastereomer and peak2 is a single trans diastereomer. Obtained 2.5 g racemic cis/trans peak1. Resolved on the OJ column 20% EtOH/Hexanes w/DEA: Peak 1: 0.68 g pure cis undesired, peak 2 1.75 g cis/trans mixture.

¹H NMR (CDCl₃) δ 7.39-7.27 (m, 7H), 7.22-7.17 (m, 3H), 5.22-5.14 (m, 2H), 4.04-3.97 (m, 1H), 3.90-3.83 (m, 1H), 3.18-3.09 (m, 1H), 2.72-2.61 (m, 1H), 2.23-2.12 (m, 1H), 1.97-1.90 (m, 1H), 1.74-1.55 (m, 8H), 1.18-0.96 (m, 5H). LRMS (M+H)=378.99

Step 7: (2S,4R)-2-cyclohexyl-4-phenylpiperidine

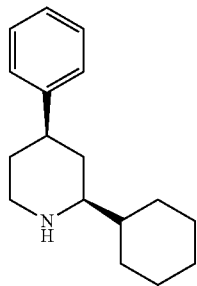 [SMILES: c1ccc([C@@H]2CCN[C@H](C3CCCCC3)C2)cc1]

Benzyl 2-cyclohexyl-4-phenylpiperidine-1-carboxylate (1.05 g, 2.78 mmol) in EtOH (50 ml) was added Pd/C (0.5 g, 0.235 mmol) and hydrogenated with a balloon overnight. Filtered through celite and concentrated. The trans isomer was removed on the chiral OD column 20% IPA/Hexanes w/DEA affording the single cis diastereomer.

$^1$H NMR (CDCl$_3$) δ 7.26-7.18 (m, 5H), 3.29-3.23 (m, 1H), 2.82-2.74 (m, 1H), 2.65-2.55 (m, 1H), 2.46-2.39 (m, 1H), 1.93-1.87 (m, 2H), 1.85-1.70 (m, 5H), 1.66-1.53 (m, 2H), 1.38-0.97 (m, 7H).
LRMS (M+H)=244.05

Intermediate II: (2S,4R)-2-(3,3-Difluorocyclohexyl)-4-phenylpiperidine

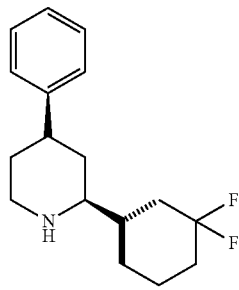

Step 1: 3-Oxocyclohex-1-en-1-yl trifluoromethanesulfonate

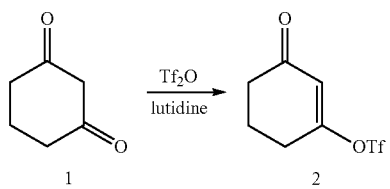 [SMILES: "Tf2O" ; O=C1CCCC(=O)C1 ; O=C1C=C(OS(=O)(=O)C(F)(F)F)CCC1]

To a solution of 1 (50 g, 0.48 mmol) and 1,6-lutidine (103 g, 0.96 mmol) in 1 L of dry DCM was added Tf$_2$O (144 ml, 0.72 mmol) dropwise slowly at 0° C. The reaction mixture was stirred at 0° C. for 30 min, warmed to room temperature, stirred for 1 hour, and quenched with HCl (2.0 N). The mixture was partitioned between DCM and diluted aqueous HCl. The organic layer was washed with water and brine, dried over anhydrous sodium sulfate, filtered, and concentrated in vacuo. Purification on silica gel afforded 2 as brown liquid (99 g, 85%).

Step 2: 3-(4,4,5,5-tetramethyl-1,3,2-dioxaborolan-2-yl)cyclohex-2-en-1-one

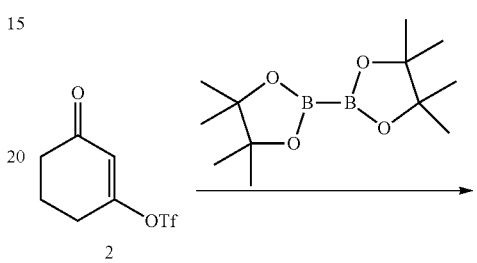

To a solution of 2 (55 g, 0.227 mol) and bis-pinacolatodiboron (55.5 g, 0.250 mol) in 600 ml of dry dioxane was added K$_2$CO$_3$ (47 g, 0.341 mol), followed by Pd(PPh$_3$)Cl$_2$ (2.9 g, 6.8 mmol), PPh$_3$ (3.6 g, 13.6 mmol) under nitrogen. The mixture was refluxed for 4 hour, cooled to room temperature, and filtered. The filtrate was used in the next step directly.

Step 3: 3-(4-Phenylpyridin-2-yl)cyclohex-2-en-1-one

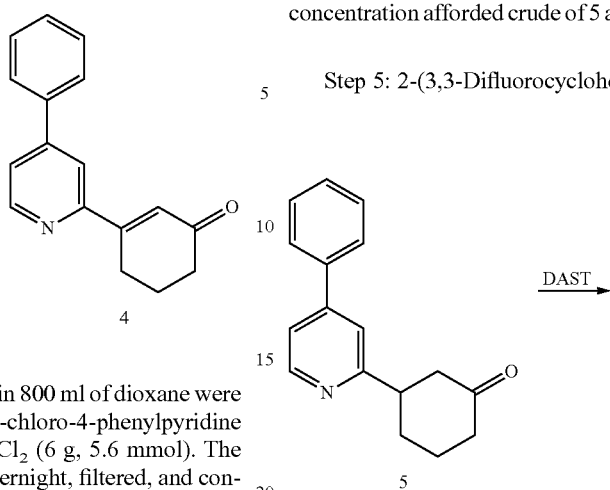

To a solution 3 (prepared above) in 800 ml of dioxane were added K₃PO₄ (118 g, 0.561 mol), 2-chloro-4-phenylpyridine (35.5 g, 0.187 mol), and Pd(dppf)Cl₂ (6 g, 5.6 mmol). The suspension was stirred at 80° C. overnight, filtered, and concentrated in vacuo. Purification on silica gel afforded 4 as a yellow solid (30 g, 64%).

Step 4: 3-(4-Phenylpyridin-2-yl)cyclohexanone

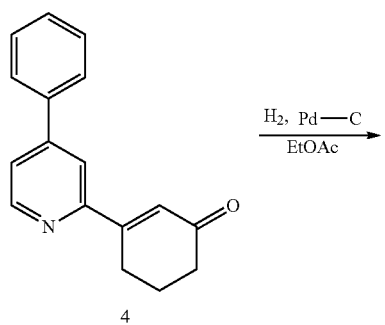

A suspension of 4 (30 g, 0.12 mol) and 2 g of Pd—C in 500 ml of ethyl acetate was hydrogenated under 20 psi of pressure of hydrogen at room temperature overnight. Filtration and concentration afforded crude of 5 as a brown oil (30 g, 100%).

Step 5: 2-(3,3-Difluorocyclohexyl)-4-phenylpyridine

To a solution of DAST (213 g, 1.325 mol) in 500 ml of dry DCM was added a solution of 5 (52 g, 0.207 mmol) in 500 ml of DCM at −70° C. After 1 hour, the reaction mixture was warmed to room temperature slowly, and stirred overnight. The reaction was quenched by adding water slowly at 0° C., neutralized with bicarbonate to pH=7-8, and extracted with DCM. The combined organic layers were washed with water and brine, dried over anhydrous sodium sulfate, filtered, and concentrated in vacuo. Purification on silica gel afforded 6 as a yellow liquid (18 g, 32%).

Step 6: 2-(3,3-Difluorocyclohexyl)-1-methyl-4-phenylpyridinium iodide

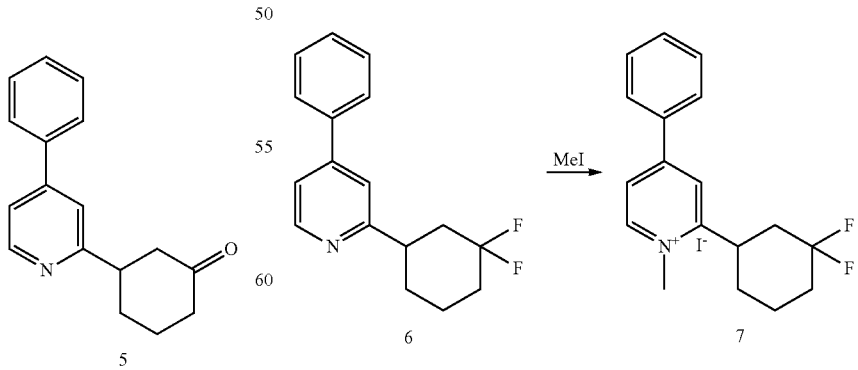

A mixture of 6 (18 g, 66 mmol) and CH₃I (105 ml, 198 mmol) in CH₃COCH₃ (150 ml) in a retort was stirred at 90 degree for 2 days. After cooled to room temperature, the mixture was filtered. The filtered cake was washed with ethyl acetate to give 7 as a yellow solid (23 g, 85%).

Step 7: 2-(3,3-Difluorocyclohexyl)-1-methyl-4-phenylpiperidine

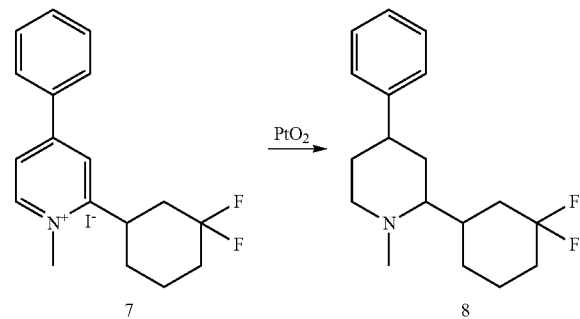 [SMILES: C[n+]1ccc(-c2ccccc2)cc1C1CCCC(F)(F)C1 ; [I-] ; "PtO2" ; CN1CCC(c2ccccc2)CC1C1CCCC(F)(F)C1]

The suspension of 7 (1.3 g, 3.1 mmol) and PtO$_2$ (0.26 g) in 50 ml of MeOH was stirred under 1 atmosphere of hydrogen at room temperature overnight, and then filtered. The PtO$_2$ (0.13 g) was added again and the stirring was continued overnight more. After filtered and concentrated, the residue was dissolved in EA and washed with sat. bicarbonate sodium, water, brine, dried over sodium sulfate anhydrous. After filtered and concentrated, 8 (780 mg, 85%) was obtained as a brown oil.

Step 8: 2-(3,3-Difluorocyclohexyl)-4-phenylpiperidine-1-carbonitrile

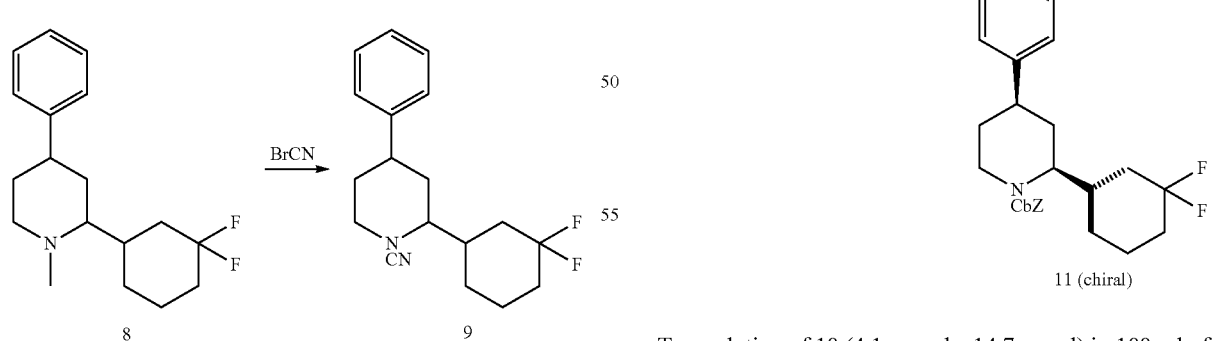

To a solution of 8 (780 mg, 2.7 mmol) in 30 ml of CHCl$_3$ was added K$_2$CO$_3$ (1.3 g, 8.2 mmol) under nitrogen, followed by BrCN (430 mg, 4.1 mmol). The suspension was refluxed overnight. After cooled to room temperature, the reaction mixture was partitioned between DCM and water. The organic layer was washed with brine, dried over anhydrous sodium sulfate, filtered, and concentrated in vacuo. Purification on silica gel afforded 9 as off-white solid (480 mg, 56%).

Step 9: 2-(3,3-Difluorocyclohexyl)-4-phenylpiperidine

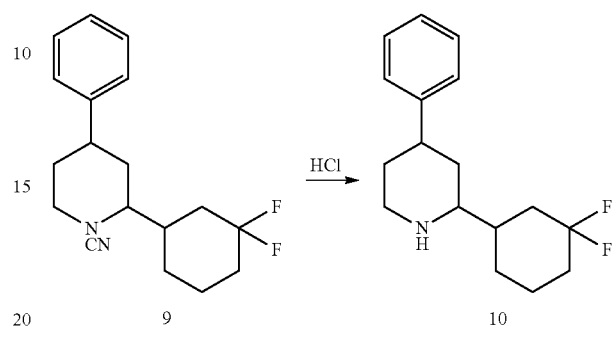

The suspension of 9 (480 mg, 1.6 mmol) in 30 ml of diluted aqueous HCl (1N) was refluxed overnight, and concentrated in vacuo. The residue was dissolved in ethyl acetate, washed with saturated aqueous NaHCO$_3$, water, brine, dried over sodium sulfate, filtered, and concentrated in vacuo to give 10 as a colorless oil (400 mg, 91%).

Step 10: Benzyl (2S,4R)-2-(3,3-difluorocyclohexyl)-4-phenylpiperidine-1-carboxylate

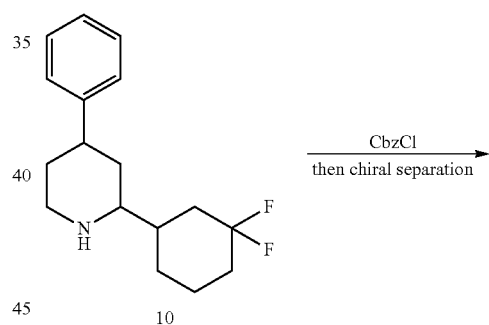

To a solution of 10 (4.1 g crude, 14.7 mmol) in 100 ml of THF and 50 ml of water was added sodium carbonate (3.9 g, 36.7 mmol), followed by CbzCl (5 g, 29.4 mmol) at room temperature. The reaction mixture was stirred at room temperature overnight, diluted with ethyl acetate, washed with water, brine, dried over anhydrous sodium sulfate, filtered, and concentrated in vacuo. Purification on silica gel afforded benzyl 2-(3,3-difluorocyclohexyl)-4-phenylpiperidine-1- carboxylate as a mixture of 4 isomers (2.3 g, 38%). Chiral SFC separation afforded 500 mg of benzyl (2S,4R)-2-(3,3-difluorocyclohexyl)-4-phenylpiperidine-1-carboxylate 11.

Step 11: (2S,4R)-2-(3,3-difluorocyclohexyl)-4-phenylpiperidine

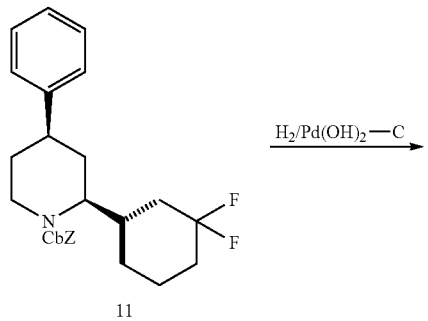

A suspension of 11 (500 mg, 1.2 mmol) and Pd(OH)$_2$ (0.2 g) in 10 ml of EtOH was hydrogenated under 1 atmosphere of hydrogen at room temperature overnight. Filtration and concentration afforded (2S,4R)-2-(3,3-difluorocyclohexyl)-4-phenylpiperidine as a colorless oil (330 mg, 98%).

Alternative Procedures for the Preparation of Intermediate II

Step 1: tert-Butyl 2-(3-oxocyclohexyl)-4-phenylpiperidine-1-carboxylate

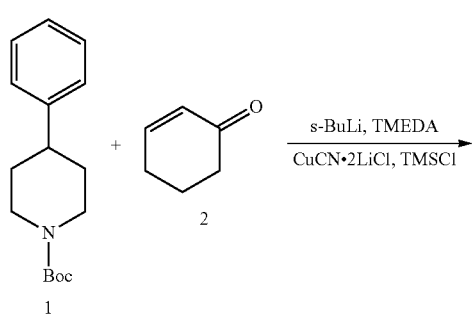

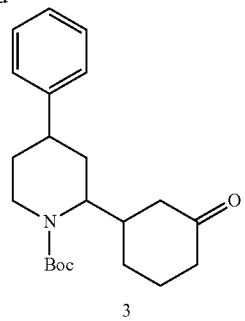

To a solution of compound 1 (10.8 g, 41.2 mmol) in Et$_2$O (150 mL) at −78° C. was added TMEDA (6.2 mL, 41.2 mmol), followed by sec-BuLi (41.4 mL, 1.3 eq, 53.8 mmol). The mixture was stirred at −78° C. for 2 h before a solution of CuCN.2LiCl (3.6 g, 20.6 mmol) in THF (41.2 mL) was added. The reaction mixture was allowed to stir at −50° C. for 1 h before a solution of compound 2 (4 g, 41.2 mmol) in TMSCl (26 mL, 206 mmol) was added. The reaction mixture was stirred at −50° C. for 30 min and then was allowed to stir at room temperature overnight. The reaction mixture was quenched with H$_2$O, stirred at room temperature briefly, diluted with EA, and filtered through Celite. The organic phase was separated, and the aqueous phase was extracted with EA (40 mL×4). The combined organic phases were washed with saturated NH4Cl (aq.), 5% NaHCO$_3$ (aq.), brine, and dried over a mixture of anhydrous Na$_2$SO$_4$ and K$_2$CO$_3$. Evaporation of the solvent in vacuo afforded the crude product which was purified by column chromatography to give 6.8 g of compound 3 in 46% yields.

$^1$H NMR (400 MHz, CDCl$_3$): δ 7.34 (t, J=7.2 Hz, 2H), 7.23 (t, J=7.2 Hz, 3H), 4.31~4.35 (m, 1H), 4.15~4.20 (m, 1H), 2.75~3.0 (m, 2H), 2.25~2.53 (m, 4H), 1.60~2.25 (m, 8H), 1.25~1.59 (m, 10H). LRMS (M+Na$^+$): 380.

Step 2: 3-(4-Phenylpiperidin-2-yl)cyclohexanone

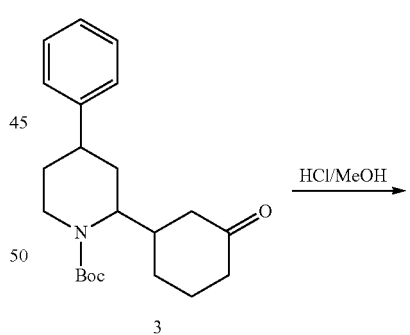

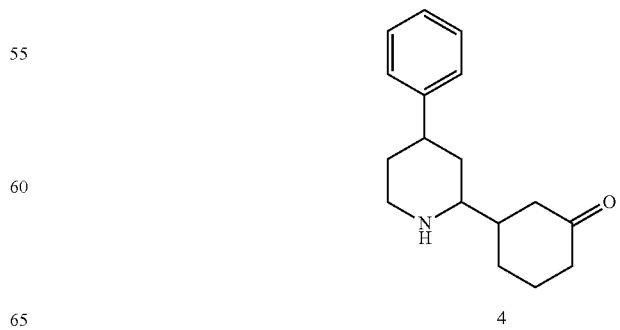

To a solution of 3 (6.27 g, 17.6 mmol) in MeOH (20 mL) was added HCl/MeOH (2 M, 40 mL). After 2 hours, the reaction mixture was concentrated to give 5.1 g of compound 4 as HCl salt in 100% yields.

LRMS (M+H⁺): 258.

Step 3: Benzyl 2-(3-oxocyclohexyl)-4-phenylpiperidine-1-carboxylate

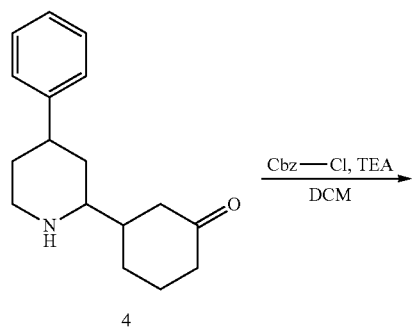

4

To a solution of compound 4 (5.1 g, 17.6 mmol) in DCM (50 mL) were added Et₃N (5.3 g, 52.7 mmol) and CbzCl (4.5 g, 26.3 mmol) at 0° C. The mixture was allowed to stir at room temperature for 2 h, and quenched with H₂O, extracted with DCM (20 mL×3). The combined organics were washed with brine, dried over Na₂SO₄ and concentrated. The residue was purified by column chromatography to give 5.56 g of compound 5 in 81% yields.

¹H NMR (400 MHz, CDCl₃): δ 7.28~7.39 (m, 7H), 7.15~7.23 (m, 3H), 5.13~5.19 (m, 2H), 3.95~4.45 (m, 2H), 2.60~3.20 (m, 2H), 1.59~2.41 (m, 13H). LRMS (M+H⁺): 392.

Step 4: Benzyl (2S,4R)-2-(3,3-difluorocyclohexyl)-4-phenylpiperidine-1-carboxylate

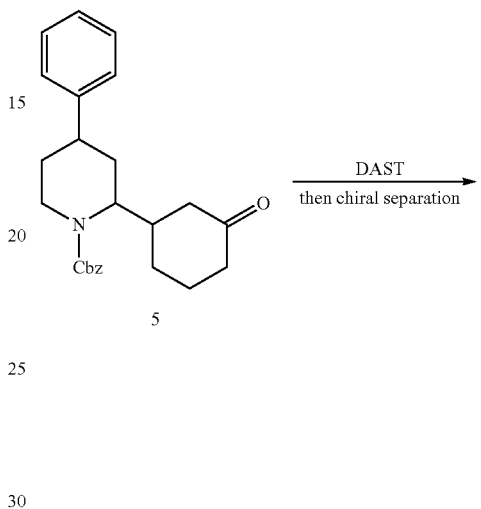

5

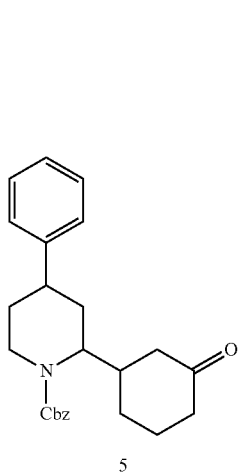

5

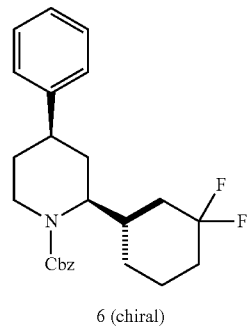

6 (chiral)

To a solution of compound 5 (5.56 g, 14.2 mmol) in DCM (70 mL) was added dropwise DAST (4 eq, 56.8 mmol) at 0° C. The reaction mixture was stirred at room temperature for 12 h, poured slowly onto ice-water, extracted with DCM (20 mL×3). The combined organics were washed with NaHCO₃ (aq.) and brine, dried over Na₂SO₄, filtered, and concentrated. The residue was purified by p-HPLC to give 3.64 g of benzyl 2-(3,3-difluorocyclohexyl)-4-phenylpiperidine-1-carboxylate in 62% yields as a mixture of 4 isomers.

LRMS (M+H⁺): 414.

The mixture was resolved by SFC column to give benzyl (2S,4R)-2-(3,3-difluorocyclohexyl)-4-phenylpiperidine-1-carboxylate 6. (Column: Chiralcel OJ-H 250*4.6 mm I.D., Sum; Mobile phase: methanol (0.05% DEA) in CO$_2$ from 5% to 40%; Flow rate: 2.5 mL/min; Wavelength: 220 nm).

Step 5: (2S,4R)-2-(3,3-difluorocyclohexyl)-4-phenylpiperidine

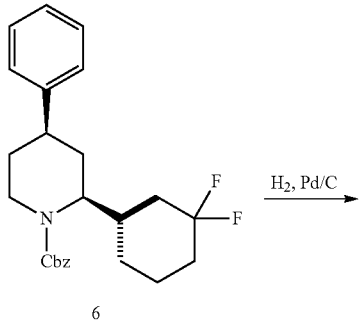

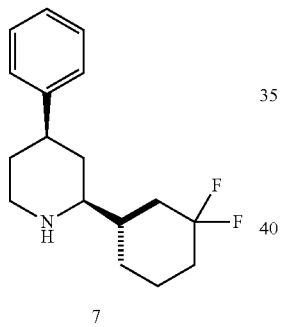

A mixture of compound 6 (130 mg, 0.31 mmol) and Pd(OH)$_2$ (70 mg) in MeOH (20 mL) was stirred at 50° C. under H$_2$ (50 psi) for 4 hours. The mixture was filtrated and the filtrate was concentrated to give 80 mg of (2S,4R)-2-(3,3-difluorocyclohexyl)-4-phenylpiperidine 7 in 92% yields. LRMS (M+H$^+$): 280.

Intermediate III:
4-phenyl-2-(2,2,2-trifluoroethyl)piperidine

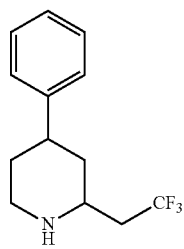 [SMILES: FC(F)(F)CC1CC(c2ccccc2)CCN1]

Step 1: 2-Chloro-4-phenylpyridine

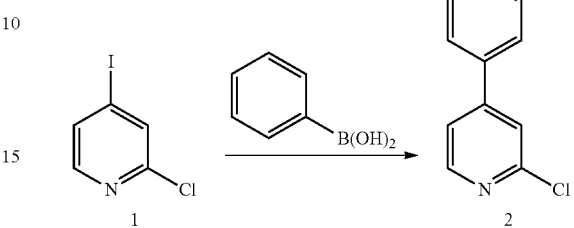

To a mixture of 1 (57.36 g, 0.24 mol) in THF/H$_2$O (400 mL/100 mL) were added phenylboric acid (24.2 g, 0.2 mol) and K$_2$CO$_3$ (82.8 g, 0.6 mol). PdCl$_2$(dppf) (2 g) was then added after being charged with N$_2$ three times. The resulting mixture was refluxed for 2 hrs, cooled, and partitioned between a.q. NH$_4$Cl and EtOAc. The aqueous layer was washed with EtOAc. The combined organic layers were washed with water, brine and dried over Na$_2$SO$_4$. The solvent was removed in vacuo and the residue was purified by silica gel column (PE:EA=10:1) to afford 32 g of 2 (yield 84%).

Step 2: Methyl 4-phenylpyridine-2-carboxylate

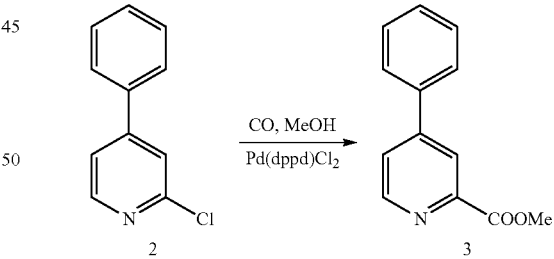

To a solution of 2 (2 g, 0.01 mol) in MeOH (100 mL) were added TEA (5.33 g, 0.05 mol) and PdCl$_2$(dppf) (0.5 g). The reaction mixture was stirred overnight at 70° C. under 4 MPa CO. The suspension was filtered through a pad of celite and washed with MeOH. The combined filtrates were concentrated in vacuo. Purification on silica gel (PE:EA=10:1) afforded 1.5 g of 3 (yield 71%).

¹H-NMR (400 MHz, CDCl₃) δ 8.72 (d, 1H), 8.31 (m, 1H), 7.63 (m, 3H), 7.42 (m, 3H), 3.95 (s, 3H)

Step 3: (4-Phenylpyridin-2-yl)methanol

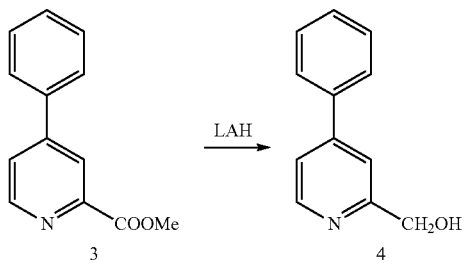 [SMILES: COC(=O)c1cc(-c2ccccc2)ccn1 ; OCc1cc(-c2ccccc2)ccn1]

To a solution of 3 (1.5 g, 7 mmol) in THF (20 mL) was added LiAlH4 (0.32 g, 8.4 mmol). The reaction mixture was stirred at room temperature for 30 minutes, quenched by adding 15% NaOH aqueous solution, and filtered through silica gel. The filtrate was concentrated to give the crude product, which was used directly in the next step without further purification.

Step 4: 4-Phenylpyridine-2-carbaldehyde

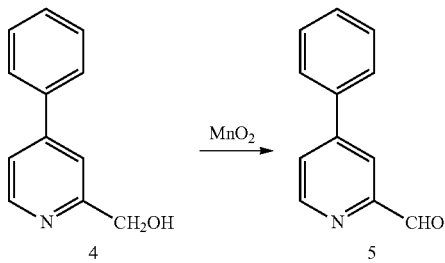 [SMILES: OCc1cc(-c2ccccc2)ccn1 ; "MnO2" ; O=Cc1cc(-c2ccccc2)ccn1]

To a solution of 4 (1.4 g, 7 mmol) in CH₂Cl₂ (100 mL) was added MnO₂ (1.8 g, 21 mmol). The mixture was refluxed overnight, cooled, and filtered through silica gel. The filtrate was concentrated in vacuo. Purification on silica gel (PE:EA=10:1) afforded 1.1 g of 5 (yield 78%).

¹H-NMR (400 MHz, CDCl₃) δ 10.14 (s, 1H), 8.82 (d, 1H), 8.18 (m, 1H), 7.64 (m, 3H), 7.45 (m, 3H)

Step 5: 2,2,2-Trifluoro-1-(4-phenylpyridin-2-yl)ethanol

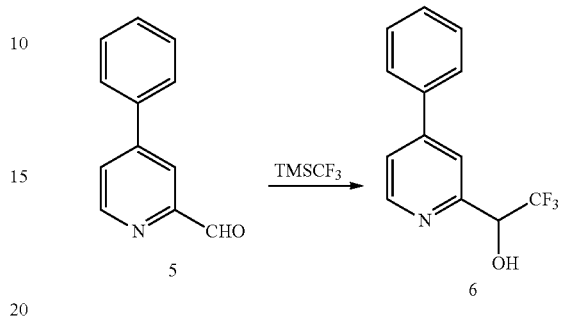

To the solution of TMSCF₃ (245 mg, 2.5 mmol) in THF (50 mL) were added 5 (366 mg, 2 mmol) and TBAT (cat). The reaction mixture was stirred at room temperature for 1 hr before 1.0 N HCl (5 mL) was added. After 1 hr, the reaction mixture was partitioned between aqueous NaHCO₃ and EtOAc. The aqueous layer was washed with EtOAc. The combined organic layers were washed with water and brine, dried over Na₂SO₄, filtered, and concentrated in vacuo. The crude product thus obtained was used directly in the next step without further purification.

¹H-NMR (400 MHz, CDCl₃) δ 8.62 (d, 1H), 7.25-7.61 (m, 8H), 5.05 (m, 1H),

Step 6: 4-Phenyl-2-(2,2,2-trifluoroethyl)pyridine

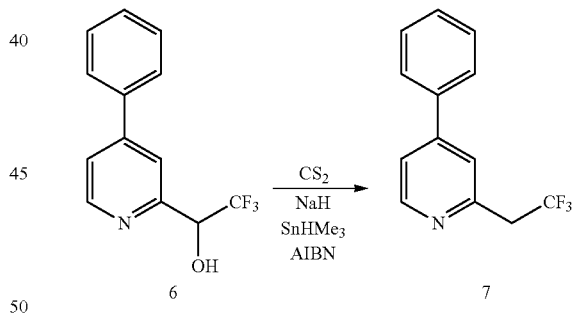

A mixture of 6 (647 mg, 2.9 mmol), NaH (232 mg, 5.8 mmol, 60% in mineral oil), imidazole (26 mg, 0.3 mmol) in THF (30 mL) was stirred for a half an hour at room temperature before CS₂ (2 mL, 33.3 mmol) was introduced. After stirring for 1 h, iodomethane (0.3 mL, 4.8 mmol) was added. The resultant reaction mixture was stirred for another hour, poured into water (30 mL), extracted with EtOAc two times. The combined organic layers were washed with water and brine, dried over Na2SO4, filtered, and concentrated in vacuo to give a yellow oil. The residue was dissolved in toluene (30 mL), to which catalytic AIBN (100 mg) was added. The reaction mixture was refluxed under N₂ while a solution of Bu₃SnH (3 mL, 11 mmol) in toluene (3 mL) was added slowly over 30 minutes. After refluxing overnight, the reaction mixture was cooled, partitioned between saturated NaHCO₃ aqueous solution and EtOAc. The combined organic layers were washed with water and brine, dried over Na$_2$SO$_4$. The solvent was removed in vacuo and the residue was purified by silica gel column (PE:EA=20:1) to afford 0.32 g of 7 (yield 53%).

Step 7: 4-phenyl-2-(2,2,2-trifluoroethyl)piperidine

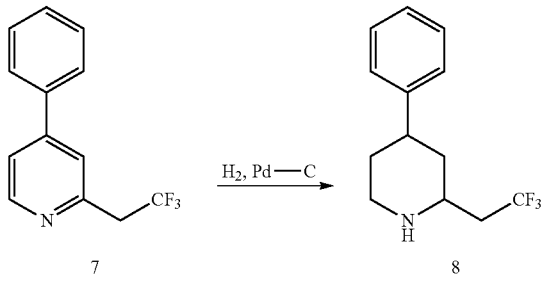

To a solution of 7 (300 mg, 1.23 mmol) in acetic acid (10 mL) was added Pd/C (100 mg). The reaction mixture was hydrogenated at 80° C. for 2 hrs. LC-MS showed the starting material was consumed. The suspension was filtered through a pad of celite and washed with methanol. The combined filtrates were concentrated in vacuo. The residue was partition between aqueous NaHCO$_3$ and EtOAc. The separated aqueous layer was washed with EtOAc. The combined organic layers were washed with water, brine and dried over Na$_2$SO$_4$. The solvent was removed in vacuo to afford 4-phenyl-2-(2,2,2-trifluoroethyl)piperidine 8.

Intermediate A to YY are depicted below in Table 1. Intermediates A to YY are either commercially available, or are taught in the literature.

TABLE 1

| INTERMEDIATE | STRUCTURE | SOURCE |
|---|---|---|
| A | (indan-1-one) | Commercially available |
| B | (tetralone) | Commercially available |
| C | (chroman-4-one) | Commercially available |
| D | (4,4-dimethyl-tetralone) | Commercially available |
| E | (7-bromo-tetralone) | Commercially available |
| F | (6-bromo-tetralone) | Commercially available |
| G | (6-methoxy-tetralone) | Commercially available |
| H | (6-chloro-tetralone) | Commercially available |
| I | (N-Boc-quinolinone) | Organic Letters (2005), 7(23), 5167-5170 |
| J | (6-hydroxy-tetralone) | Synlett (2007), (11), 1699-1702 |
| K | (5-bromo-tetralone) | Commercially available |
| L | (6-fluoro-tetralone) | US 2005043309 |
| M | (pyridine-fused cyclohexanone) | J Heterocyclic Chemistry (2000), 37(1), 41-46 |

TABLE 1-continued

| INTERMEDIATE | STRUCTURE | SOURCE |
|---|---|---|
| N | 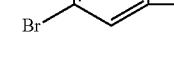 | Commercially available |
| O | 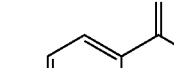 | Commercially available |
| P | 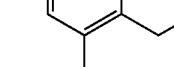 | Synthesis 1983, 11, 902-903 |
| Q | 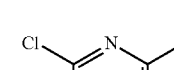 | Synthesis 1983, 11, 902-903 |
| R | 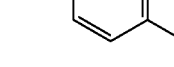 | Commercially available |
| S | 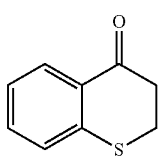 [SMILES: O=C1CCSc2ccccc21] | Commercially available |
| T | 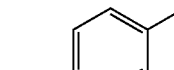 | J. Med. Chem., 1974, 17(9), 1020-1023 |
| U | 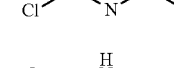 | J. Org. Chem., (1985), 50(12), 2128-2133 |
| V | 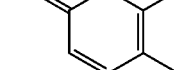 | Commercially available |
| W | 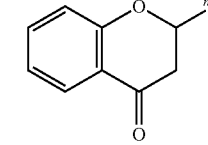 | Bulletin Chem Soc Japan (1999), 72(2), 303-311 |
| X | 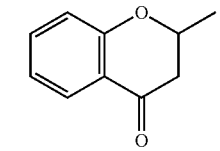 | Chem Communications (2007), 44: 4686-4688 |
| Y | 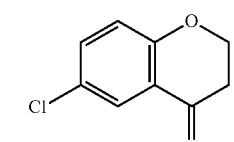 | Commercially available |
| Z | 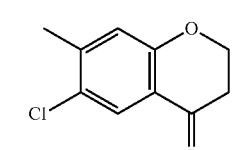 | Commercially available |
| AA | 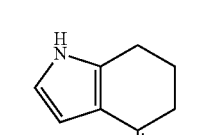 | Heterocycles (1986), 24(9); 2011-2618. |
| BB | 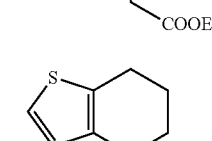 | Indian Journmal of Chem., Section B: Organic Chemistry (1985), 24B(6), 659-661. |
| CC | 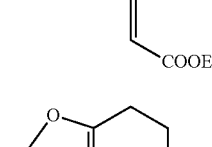 | J. Labelled Compounds and Radiopharmaceuticals (1990), 28(1), 15-24. |
| DD | 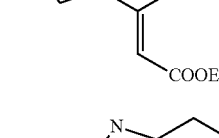 | WO 2005/005438 |
| EE | 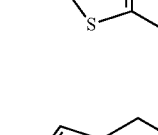 | J. Heterocyclic Chem. (1975), 9(1), 44-48. |

TABLE 1-continued

| INTERMEDIATE | STRUCTURE | SOURCE |
|---|---|---|
| FF | 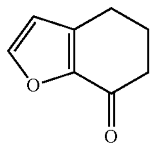 | *Tetrahedron Letters* (1986), 27(10), 1127-1130. |
| GG | 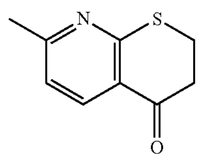 | *Eur. J. Med. Chem.* (2000), 39(9), 815-823. |
| HH | 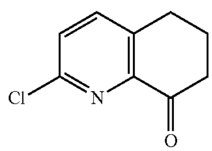 [SMILES: O=C1CCCc2ccc(Cl)nc21] | *J. Org. Chem.* (1990), 55(16), 4789-4791. |
| II | 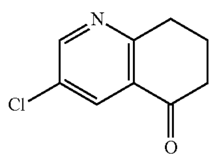 [SMILES: O=C1CCCc2ncc(Cl)cc21] | U.S. Pat. No. 4,952,694 |
| JJ | 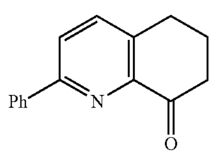 | *J. Chem. Soc. Perkin Trans.* (1985), (2), 213-219. |
| KK | 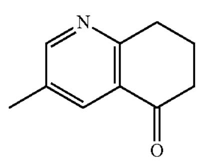 | U.S. Pat. No. 3,998,331 |
| LL | 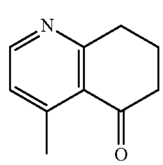 | *Arch. Pharma.* (1985), 318(10), 871-878. |
| MM | 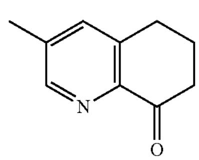 | *J. Med Chem.* (1977), 20(5), 718-721. |
| NN | 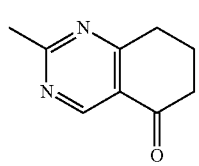 | *J. Heterocyclic Chem.*, 1983, 649. |
| OO | 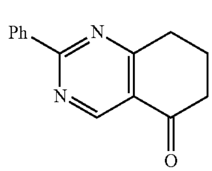 [SMILES: O=C1CCCc2nc(-c3ccccc3)ncc21] | WO 2006/047017 |
| PP | | *Heterocycles*, 1997, 129. |
| QQ | | *J. Am. Chem. Soc.* (1985), 107(17), 4998-4999. |
| RR | | *J. Am. Chem. Soc.* (1985), 107(17), 4998-4999. |
| SS | | *Heterocycles* (1995), 41(1), 29-36. |
| TT | | *J. Prak. Chemie* (1999), 341(5), 487-491. |
| UU | | *J. Med. Chem.* (1990), 33(11), 3028-3034.. |
| VV | | Commercially available |
| WW | | WO 98/00134 |
| XX | | Commercially available |

TABLE 1-continued

| INTERMEDIATE | STRUCTURE | SOURCE |
|---|---|---|
| YY | 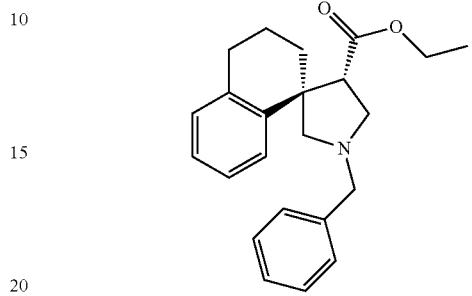 | J. Org. Chem. (2002), 67(11), 3972-3974. |

EXAMPLE 1

4'-[(4-phenylpiperidin-1-yl)carbonyl]-3,4-dihydro-2H-spiro[naphthalene-1,3'-pyrrolidine]

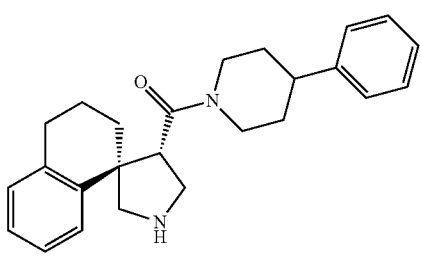 [SMILES: O=C([C@@H]1CNC[C@]12CCCc1ccccc12)N1CCC(c2ccccc2)CC1]

Step 1: Ethyl(2E)-3,4-dihydronaphthalen-1(2H)-ylideneacetate

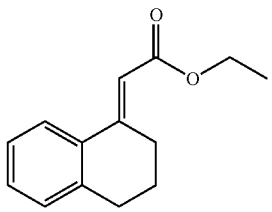 [SMILES: CCOC(=O)/C=C1\CCCc2ccccc21]

Sodium hydride (2.160 g, 54.0 mmol) in THF (150 ml) was added triethyl phosphonoacetate (10.81 ml, 54.0 mmol) dropwise. Stir at room temperature for 1 hour, added a-tetralone (3.99 ml, 30 mmol) and heated overnight at 70° C. The next day the solution was cooled to room temperature and quenched with 1N HCl. Extracted three times with EtOAc and washed the combined organics with brine. The organics were dried over sodium sulfate, concentrated, and purified on silica gel 10% EtOAc/Hex.

$^1$H NMR (CDCl$_3$) δ 7.65 (d, J=7.9 Hz, 1H), 7.27-7.13 (m, 3H), 6.33 (t, J=1.8 Hz, 1H), 4.20 (q, J=7.1 Hz, 2H), 3.22-3.17 (m, 2H), 2.80 (t, J=6.2 Hz, 2H), 1.88-1.83 (m, 2H), 1.32 (t, J=7.1 Hz, 3H). LRMS (M+H)=217.10

Step 2: Ethyl 1'-benzyl-3,4-dihydro-2H-spiro[naphthalene-1,3'-pyrrolidine]-4'-carboxylate

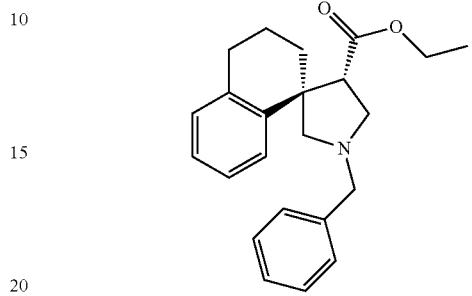

N-benzyl-N-(methoxymethyl)-N-trimethylsilylmethylamine (2.112 ml, 8.26 mmol) and ethyl(2E)-3,4-dihydronaphthalen-1(2H)-ylideneacetate (1.785 g, 8.26 mmol) in CH$_2$Cl$_2$ (33.3 ml) at 0° C. was added TFA (0.064 ml, 0.826 mmol) dropwise. Removed the ice bath and stirred at room temperature for 4 hours. Dilute with CH$_2$Cl$_2$ and wash twice with saturated NaHCO$_3$. The organics were dried over sodium sulfate, concentrated, and purified on silica gel 20% EtOAc/Hex.

$^1$H NMR (CDCl$_3$) δ 7.76-7.68 (m, 1H), 7.41-7.18 (m, 6H), 7.15-7.09 (m, 1H), 7.06-6.98 (m, 1H), 4.12-4.03 (m, 2H), 3.75-3.63 (m, 2H), 3.42-3.36 (m, 1H), 3.20-3.10 (m, 1H), 3.07-2.90 (m, 2H), 2.78-2.67 (m, 2H), 2.63-2.57 (m, 1H), 1.89-1.81 (m, 2H), 1.69-1.62 (m, 2H), 1.20-1.09 (m, 3H).

LRMS (M+H)=350.20

Step 3: 1'-benzyl-3,4-dihydro-2H-spiro[naphthalene-1,3'-pyrrolidine]-4'-carboxylic acid

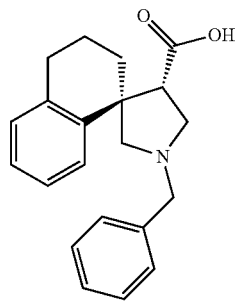 [SMILES: O=C(O)[C@@H]1CN(Cc2ccccc2)C[C@]12CCCc1ccccc12]

Ethyl 1'-benzyl-3,4-dihydro-2H-spiro[naphthalene-1,3'-pyrrolidine]-4'-carboxylate (1.1 g, 3.15 mmol) in THF/MeOH/H2O (41 ml) was added 2N sodium hydroxide (4.72 ml, 9.44 mmol). Stir overnight at 50° C. Cooled to room temperature and acidified to pH1-2 with 0.5N HCl and extracted with EtOAc. The organic layer was dried and concentrated. The crude acid was not purified.

¹H NMR (CDCl₃) δ 7.36-7.22 (m, 6H), 7.11-6.92 (m, 3H), 3.73-3.65 (m, 2H), 3.18-3.11 (m, 2H), 3.00-2.49 (m, 6H), 1.89-1.55 (m, 3H). LRMS (M+H)=322.08

Step 4: N-benzyl-4'-[(4-phenylpiperidin-1-yl)carbonyl]-3,4-dihydro-2H-spiro[naphthalene-1,3'-pyrrolidine]

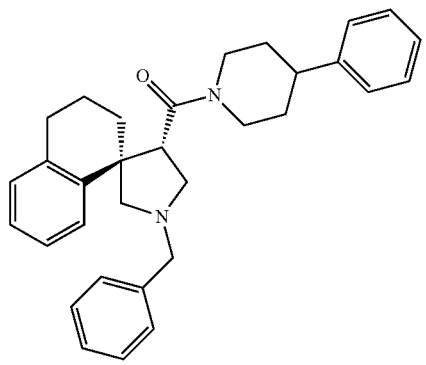 [SMILES: O=C([C@@H]1CN(Cc2ccccc2)C[C@]12CCCc1ccccc12)N1CCC(c2ccccc2)CC1]

N-benzyl-3,4-dihydro-2H-spiro[naphthalene-1,3'-pyrrolidine]-4'-carboxylic acid (0.1 g, 0.311 mmol) in CH₂Cl₂ (4 ml) was added oxalyl chloride (0.187 ml, 0.373 mmol) followed by 2 drops of DMF. Stirred at room temperature for 30 minutes and concentrated. Dissolve in THF (5 mL) and added 4-phenylpiperidine (0.050 g, 0.311 mmol) and triethylamine (0.173 ml, 1.245 mmol).

The solution was stirred for 2 hours then concentrated, taken up in CH₂Cl₂ and washed with water. The crude product was not purified.

¹H NMR (CDCl₃) δ 7.86-7.78 (m, 1H), 7.40-7.35 (m, 2H), 7.31-7.16 (m, 7H), 7.10-7.03 (m, 3H), 7.00-6.95 (m, 1H), 4.88-4.73 (m, 1H), 3.72-3.55 (m, 4H), 3.29-3.08 (m, 5H), 2.76-2.69 (m, 3H), 2.60-2.39 (m, 4H), 2.10-2.02 (m, 1H), 1.80-1.60 (m, 4H). LRMS (M+H)=465.22

Step 5: 4'-[(4-phenylpiperidin-1-yl)carbonyl]-3,4-dihydro-2H-spiro[naphthalene-1,3'-pyrrolidine]

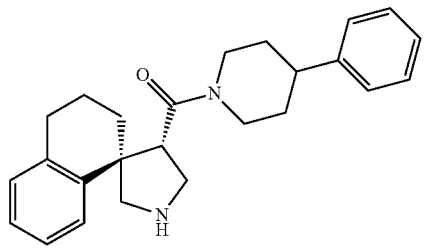 [SMILES: O=C([C@@H]1CNC[C@]12CCCc1ccccc12)N1CCC(c2ccccc2)CC1]

N-benzyl-4'-[(4-phenylpiperidin-1-yl)carbonyl]-3,4-dihydro-2H-spiro[naphthalene-1,3'-pyrrolidine] (0.15 g, 0.323 mmol) in EtOH (20 ml) was added Pearlman's Catalyst (0.075 g, 0.107 mmol) and hydrogenated with a balloon for 2 hours. Filtered through celite and concentrated.

The product was purified on the Waters Prep HPLC. The desired fractions were free based with NaHCO₃ and extracted 2× with EtOAc.

¹H NMR (CD₃OD) δ 7.67-7.54 (m, 1H), 7.30-7.08 (m, 6H), 6.96-6.91 (m, 2H), 4.66-4.57 (m, 1H), 4.17-3.98 (m, 2H), 3.72-3.64 (m, 1H), 3.58-3.50 (m, 3H), 2.91-2.73 (m, 3H), 2.65-2.39 (m, 2H), 2.19-2.12 (m, 1H), 2.00-1.60 (m, 5H), 1.53-1.47 (m, 1H), 1.40-1.05 (m, 2H). LRMS (M+H) =375.13

EXAMPLE 2

[(1R,4'S)-6-methyl-3,4-dihydro-2H-spiro[naphthalene-1,3'-pyrrolidin]-4'-yl](4-phenylpiperidin-1-yl)methanone

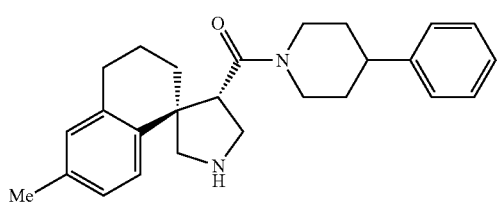 [SMILES: Cc1ccc2c(c1)CCC[C@]21CNC[C@H]1C(=O)N1CCC(c2ccccc2)CC1]

Step 1: 6-bromo-3,4-dihydronaphthalen-1(2H)-one

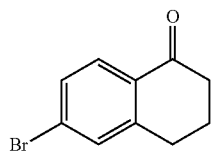

To a suspension of 6-amino-3,4-dihydro-2H-naphthalen-1-one (20.5 g, 127 mmol) in 25% HBr (aq) (1017 ml) at 0° C. was added a solution of sodium nitrite (10.53 g, 153 mmol) in water (50 ml) dropwise at a rate as to maintain the temperature below 3°. The cooled reaction mixture was then added to a cooled solution of copper(I) bromide (18.79 g, 131 mmol) in HBr (98 ml, 865 mmol). When the addition was done, the reaction mixture was stirred at 0° C. for 1 h, then warmed to rt. Water (380 mL) was added and the product was extracted with a mixture of Et₂O/EtOAc (8:2, 3×). The organic layer was dried over Na₂SO₄, filtered, and concentrated in vacuo to give a dark brown crude oil. The crude was purified by distillation (3 mm Hg) to give 16.415 g of 6-bromo-3,4-dihydro-2H-naphthalen-1-one.

¹H NMR (CDCl₃): δ 7.89 (d, J=8.6 Hz, 1H); 7.44 (d, J=6.8 Hz, 2H); 2.94 (t, J=6.1 Hz, 2H); 2.65 (t, J=6.5 Hz, 2H); 2.14 (t, J=6.4 Hz, 2H). LRMS (M+H)=226.8

Step 2: Ethyl (2E)-(6-bromo-3,4-dihydronaphthalen-1(2H)-ylidene)ethanoate

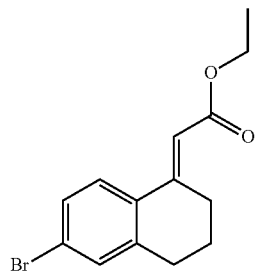 [SMILES: CCOC(=O)/C=C1\CCCc2cc(Br)ccc21]

To a suspension of NaH (2.73 g, 68.4 mmol in THF (190 ml) at room temperature was added triethyl phosphonoacetate (31.3 ml, 157 mmol) dropwise. The resulting solution was stirred at room temperature for 1 h. Then 6-bromo-3,4-dihydronaphthalen-1(2H)-one (19.5839 g, 87 mmol) was added in one portion and the reaction mixture stirred overnight. The reaction mixture was quenched with 1N HCl to pH~1. The mixture was extracted three times with EtOAc. The combined organic layers were dried over $Na_2SO_4$, filtered, and concentrated in vacuo to give an orange crude oil. The crude was purified on silica gel (8% EtOAc/hexanes) affording 6.7 g of Ethyl (2E)-(6-bromo-3,4-dihydronaphthalen-1(2H)-ylidene)ethanoate.

$^1$H NMR (CDCl$_3$): δ 7.53-7.46 (m, 1H); 7.32 (d, J=6.6 Hz, 2H); 6.30 (s, 1H); 4.20 (q, J=7.1 Hz, 2H); 3.19-3.12 (m, 2H); 2.77 (t, J=6.2 Hz, 2H); 1.84 (p, J=6.3 Hz, 2H); 1.31 (t, J=7.1 Hz, 3H). LRMS (M+H)=296.74

Step 3: Ethyl (1R,4'S)-1'-benzyl-6-bromo-3,4-dihydro-2H-spiro[naphthalene-1,3'-pyrrolidine]-4'-carboxylate

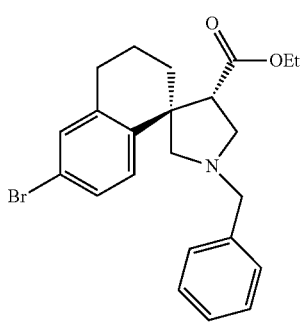 [SMILES: CCOC(=O)[C@@H]1CN(Cc2ccccc2)C[C@]12CCCc1cc(Br)ccc12]

To a solution of N-(methoxymethyl)-N-(trimethylsilylmethyl)benzylamine (6.85 ml, 26.8 mmol) and [6-Bromo-3,4-dihydro-2H-naphthalen-(E)-ylidene]-acetic acid ethyl ester (7.9 g, 26.8 mmol) in CH$_2$Cl$_2$ (14.33 ml) at 0° C. was added TFA (0.206 ml, 2.68 mmol) dropwise. The ice bath was removed and the reaction mixture was stirred at room temperature. The process of the reaction was followed by LC/MS. N-(methoxymethyl)-N-(trimethylsilylmethyl)benzylamine (6.85 ml, 26.8 mmol) was added after every 2 h and stirred at room temperature till LC/MS showed no SM. The solution was diluted with CH$_2$Cl$_2$, washed three times with saturated aqueous NaHCO$_3$, dried, filtered, concentrated, and purified on silica gel (10% EtOAc/hexanes) affording 8.85 g of ethyl (1R,4'S)-1'-benzyl-6-bromo-3,4-dihydro-2H-spiro[naphthalene-1,3'-pyrrolidine]-4'-carboxylate.

$^1$H NMR (CDCl$_3$): δ 7.59 (d, J=8.5 Hz, 1H); 7.33-7.22 (m, 5H); 7.22-7.15 (m, 1H); 7.13 (s, 1H); 4.04 (q, J=7.1 Hz, 2H); 3.72-3.58 (m, 2H); 3.33-3.23 (m, 1H); 3.17-3.07 (m, 1H); 2.98-2.88 (m, 1H); 2.86 (d, J=9.2 Hz, 1H); 2.74-2.53 (m, 2H); 2.51 (d, J=9.2 Hz, 1H); 1.81-1.75 (m, 2H); 1.74-1.53 (m, 2H); 1.13 (t, J=7.1 Hz, 3H). LRMS (M+H)=429.72

Step 4: 1'-tert-butyl 4'-ethyl (1R,4'S)-6-bromo-3,4-dihydro-1'H,2H-spiro[naphthalene-1,3'-pyrrolidine]-1',4'-dicarboxylate

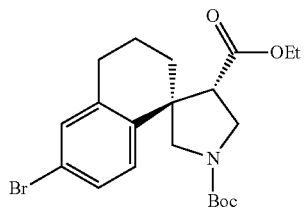 [SMILES: CCOC(=O)[C@@H]1CN(C(=O)OC(C)(C)C)C[C@]12CCCc1cc(Br)ccc12]

To a solution of ethyl (1R,4'S)-1'-benzyl-6-bromo-3,4-dihydro-2H-spiro[naphthalene-1,3'-pyrrolidine]-4'-carboxylate (8.85 g, 20.66 mmol) at 0° C. was added 1-chloroethyl chloroformate (2.68 ml, 24.79 mmol) dropwise. The reaction mixture was stirred at 0° C. for 15 minutes, warmed to room temperature then heated to 40° C. for 2 hours. The reaction was cooled to room temperature concentrated in vacuo. The residue was dissolved in MeOH (275 ml) and heated to reflux for 1 hour. The crude amine was cooled to room temperature, concentrated in vacuo, and reconstituted in THF (207 ml). Boc$_2$O (4.96 g, 22.73 mmol) was added to the solution followed by DIPEA (7.22 ml, 41.3 mmol). The reaction mixture was stirred at room temperature overnight. The solution concentrated, dissolved in CH$_2$Cl$_2$ and washed with water. The organic was dried, filtered, concentrated, and purified on silica gel (15% EtOAc/hexanes) affording 7.1 g of 1'-tert-butyl 4'-ethyl (1R,4'S)-6-bromo-3,4-dihydro-1'H,2H-spiro[naphthalene-1,3'-pyrrolidine]-1',4'-dicarboxylate.

$^1$H NMR (CDCl$_3$): δ 7.31 (dd, J=8.5, 2.1 Hz, 1H); 7.26-7.18 (m, 2H); 4.14-4.05 (m, 2H); 3.95 (ddd, J=15.1, 10.8, 7.1 Hz, 1H); 3.81-3.68 (m, 3H); 3.61 (d, J=11.1 Hz, 1H); 3.47-3.32 (m, 2H); 2.75-2.68 (m, 2H); 1.91-1.77 (m, 2H); 1.76-1.57 (m, 2H); 1.48 (d, J=12.1 Hz, 9H); 1.05 (dt, J=14.7, 7.1 Hz, 3H). LRMS (M+H)=439.74

Step 5: (1R,4'S)-6-bromo-1'-(tert-butoxycarbonyl)-3,4-dihydro-2H-spiro[naphthalene-1,3'-pyrrolidine]-4'-carboxylic acid

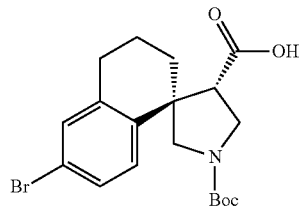

To a solution of 1'-tert-butyl 4'-ethyl (1R,4'S)-6-bromo-3,4-dihydro-1'H,2H-spiro[naphthalene-1,3'-pyrrolidine]-1',4'- dicarboxylate (7.1 g, 16.20 mmol) in THF/MeOH/H2O (3:1: 1, 40.5 ml) at room temperature was added sodium hydroxide (3M, 16.20 ml, 48.6 mmol) in one portion. The reaction mixture was heated to 55° C. and stirred for 2 hours. The solution was cooled to room temperature, neutralized with 2N HCl, and concentrated to dryness. The residue was diluted with MeOH/chloroform (1:9) and filtered to remove the salt. The filtrate was concentrated to give 6.55 g of crude (1R,4'S)-6-bromo-1'-(tert-butoxycarbonyl)-3,4-dihydro-2H-spiro[naphthalene-1,3'-pyrrolidine]-4'-carboxylic acid. The crude was not purified.

$^1$H NMR (399 MHz, CD 30D): δ 7.42-7.28 (m, 3H); 3.76-3.57 (m, 5H); 2.80-2.74 (m, 3H); 1.93 (s, 1H); 1.79-1.68 (m, 4H); 1.48 (d, J=13.4 Hz, 9H). LRMS (M+H)=411.72

Step 6: tert-butyl (1R,4'S)-6-bromo-4'-[(4-phenylpiperidin-1-yl)carbonyl]-3,4-dihydro-1'H,2H-spiro[naphthalene-1,3'-pyrrolidine]-1'-carboxylate

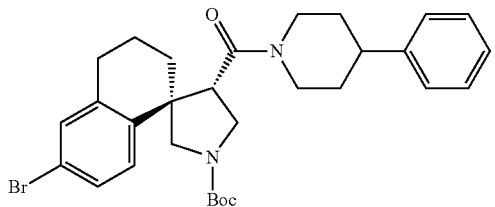 [SMILES: CC(C)(C)OC(=O)N1C[C@@H](C(=O)N2CCC(c3ccccc3)CC2)[C@@]2(CCCc3cc(Br)ccc32)C1]

To a solution of (1R,4'S)-6-bromo-1'-(tert-butoxycarbonyl)-3,4-dihydro-2H-spiro[naphthalene-1,3'-pyrrolidine]-4'-carboxylic acid (1.5 g, 3.66 mmol), 4-phenylpiperidine (0.589 g, 3.66 mmol), and BOP (2.425 g, 5.48 mmol) in CH$_2$Cl$_2$ (73 ml) at room temperature was added DIPEA (0.207 ml, 1.187 mmol) in one portion. The reaction mixture was stirred for 15 hours. The solution was diluted with CH$_2$Cl$_2$, washed with water (1×), brine (1×), dried, filtered, concentrated, and purified on silica gel (10%-50% EtOAc/hexanes) affording 1.3 g tert-butyl (1R,4'S)-6-bromo-4'-[(4-phenylpiperidin-1-yl)carbonyl]-3,4-dihydro-1'H,2H-spiro[naphthalene-1,3'-pyrrolidine]-1'-carboxylate.

$^1$H NMR (CDCl$_3$): δ 7.31 (t, J=14.4 Hz, 5H); 7.24-7.16 (m, 1H); 7.12 (s, 1H); 6.98 (d, J=7.2 Hz, 1H); 4.73 (d, J=13.1 Hz, 1H); 4.07 (d, J=10.2 Hz, 1H); 3.71 (d, J=13.9 Hz, 2H); 3.67-3.51 (m, 3H); 2.73 (s, 2H); 2.52 (s, 2H); 1.83 (d, J=13.6 Hz, 1H); 1.72 (s, 4H); 1.47 (d, J=7.8 Hz, 9H); 1.17 (t, J=12.9 Hz, 1H). LRMS (M+H)=554.87

Step 7: [(1R,4'S)-6-methyl-3,4-dihydro-2H-spiro[naphthalene-1,3'-pyrrolidin]-4'-yl](4-phenylpiperidin-1-yl)methanone

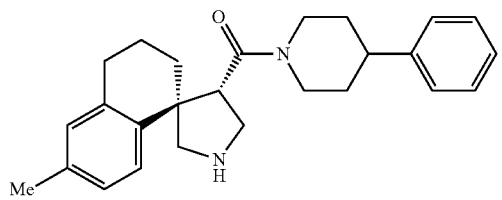 [SMILES: Cc1ccc2c(c1)CCC[C@]21CNC[C@H]1C(=O)N1CCC(c2ccccc2)CC1]

To a microwave tube equipped with a stir bar was added Pd(Ph$_3$P)$_4$ (94 mg, 0.081 mmol) and potassium carbonate (164 mg, 1.185 mmol). The tube was flushed with argon. Then trimethylboroxine (0.028 ml, 0.203 mmol) was added followed by tert-butyl (1R,4'S)-6-bromo-4'-[(4-phenylpiperidin-1-yl)carbonyl]-3,4-dihydro-1'H,2H-spiro[naphthalene-1,3'-pyrrolidine]-1'-carboxylate (100 mg, 0.181 mmol) in DMF (0.9 ml). The reaction mixture was heated to 105° C. under N$_2$ for 15 hours. The mixture was cooled to room temperature, and filtered through Celite. The wet cake was washed several times with EtOAc. The combined organics were washed once with water and brine, dried, filtered, concentrated. The crude was dissolved in CH$_2$Cl$_2$ (20 ml). QuadraPure TU (1 g) was added and the mixture was stirred at 35° C. for 16 hours. The mixture was filtered through Celite and the wet cake was washed several times with CH$_2$Cl$_2$. The combined organics were concentrated and purified by reverse phase HPLC. The desired fractions were free based with 1N NaOH and extracted three times with CH$_2$Cl$_2$. The residue was dissolved in CH$_2$Cl$_2$. TFA was added and the reaction was stirred at room temperature for 1 hour. The solution was concentrated, basified with 1N NaOH, and extracted three times with CH$_2$Cl$_2$. The combined organics were dried, filtered, and concentrated to give the free amine.

$^1$H NMR (399 MHz, CDCl$_3$): δ 7.36 (d, J=8.1 Hz, 1H); 7.21 (t, J=7.9 Hz, 3H); 7.12 (d, J=7.5 Hz, 1H); 7.04 (d, J=7.2 Hz, 2H); 6.88 (s, 1H); 4.78 (t, J=15.1 Hz, 1H); 3.81 (dd, J=11.7, 5.6 Hz, 1H); 3.67-3.58 (m, 1H); 3.51-3.25 (m, 2H); 3.27-3.13 (m, 1H); 3.05 (d, J=12.0 Hz, 1H); 2.76-2.68 (m, 2H); 2.65-2.49 (m, 4H); 2.26 (d, J=20.3 Hz, 3H); 1.95-1.53 (m, 6H); 1.43 (td, J=12.7, 4.1 Hz, 1H); 1.14 (s, 1H). LRMS (M+H)=388.90

EXAMPLE 3

[(4R,4'S)-8-methoxy-2,3-dihydrospiro[chromene-4,3'-pyrrolidin]-4'-yl][(2S,4R)-2-(3,3-difluorocyclohexyl)-4-phenylpiperidin-1-yl]methanone

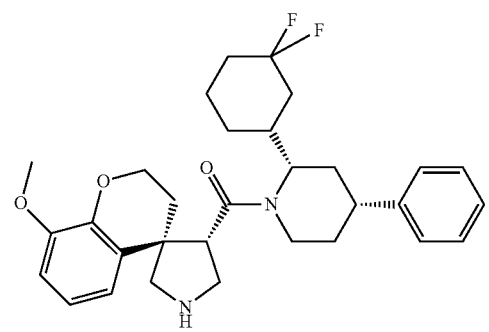 [SMILES: COc1cccc2c1OCC[C@]21CNC[C@H]1C(=O)N1CC[C@@H](c2ccccc2)C[C@H]1C1CCCC(F)(F)C1]

Step 1: 1-Methoxy-2-(methoxymethoxy)benzene

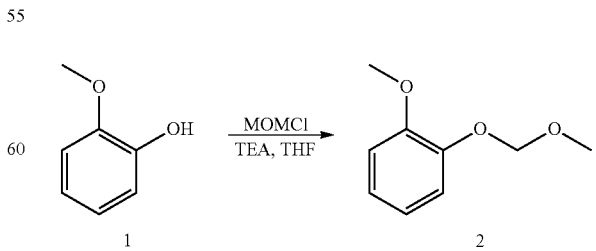

To a mixture of compound 1 (50 g, 0.4 mol) in DCM (500 mL) were added MOMCl (38.64 g, 0.48 mol) and DIEA (77.4 g, 0.6 mol) at 0° C. The mixture was stirred at room temperature overnight, diluted with EtOAc, and washed with 1N HCl solution. The organic layer were washed with brine, dried over $Na_2SO_4$, filtered, and concentrated in vacuo. Purification on silica gel (PE:EA=20:1) gave 64 g of compound 2 in 99% yields.

$^1$H NMR $CDCl_3$ (400 MHz, $CDCl_3$): δ 7.12 (d, J=8.0 Hz, 1H), 6.95 (d, J=8.0 Hz, 1H), 6.82 (t, J=8.0 Hz, 2H), 5.21 (s, 2H), 3.86 (s, 3H), 3.5 (s, 3H).

Step 2:
1-Iodo-3-methoxy-2-(methoxymethoxy)benzene

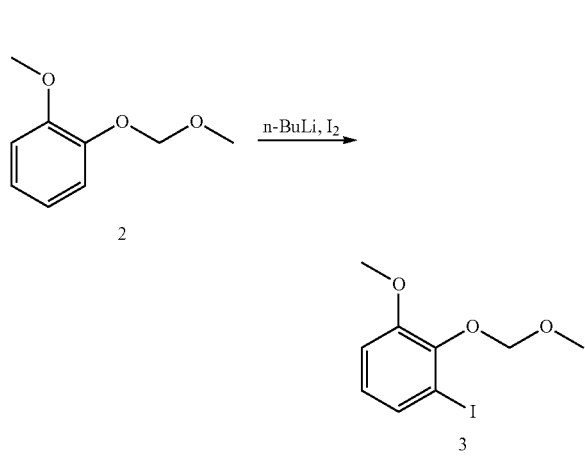

To a mixture of compound 2 (48 g, 0.29 mol) in THF (600 mL) was added n-BuLi (197 mL, 1.6 M) at −78° C. After 2 h, a solution of $I_2$ (40 g, 0.16 mol) in THF (200 mL) was added dropwise at −50° C. The reaction mixture was stirred at room temperature overnight, quenched by $NH_4Cl$ and $Na_2S_2O_5$ solutions at 0° C., and extracted with EA. The combined extracts were washed with brine, dried over $Na_2SO_4$ and then purified on silica gel (PE:EA=60:1) to give 64 g of compound 3 in 50% yields.

$^1$H NMR (400 MHz, $CDCl_3$): δ 7.28~7.36 (m, 1H), 7.06~7.12 (m, 1H), 6.68~6.76 (m, 1H), 5.16 (s, 2H), 3.82 (s, 3H), 3.46 (s, 3H).

Step 3: 2-Iodo-6-methoxyphenol

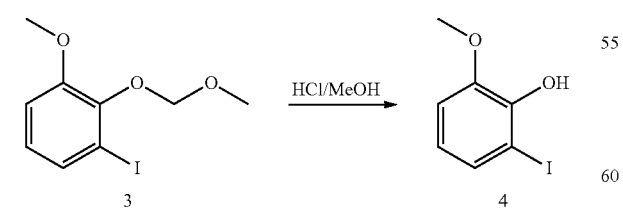

To a mixture of compound 3 (52 g, 0.18 mol) in MeOH (400 mL) was added HCl/MeOH (100 mL, 2 M) at 0° C. The reaction mixture was stirred at RT for 4 h, then concentrated to give 42 g of compound 4 in 95% yields.

$^1$H NMR (400 MHz, $CDCl_3$): δ 7.12 (d, J=8.0 Hz, 1H), 6.70 (d, J=8.0 Hz, 1H), 6.65 (t, J=8.0 Hz, 1H), 4.46 (s, 1H), 3.75 (s, 3H).

Step 4: 3-(2-Iodo-6-methoxyphenoxy)propan-1-ol

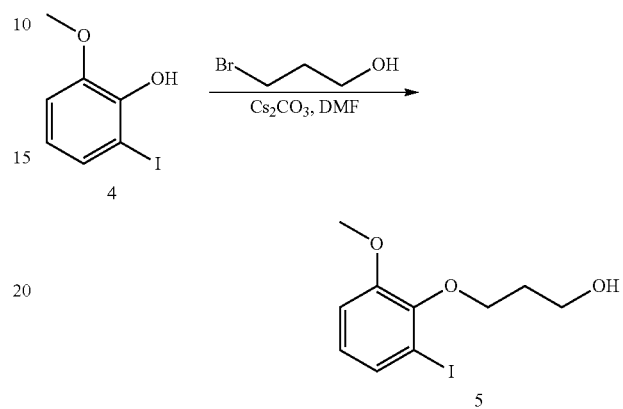

A mixture of compound 4 (40 g, 0.16 mol), $Br(CH_2)_3OH$ (33.3 g, 0.24 mol) and $Cs_2CO_3$ (104.3 g, 0.32 mol) in DMF (200 mL) was stirred at room temperature overnight, then diluted with water. The resulting mixture was extracted with EA. The combined extracts were washed with brine, dried over $Na_2SO_4$ and then purified on silica gel (PE:EA=30:1) to give 48 g of compound 5 in 60% yields.

$^1$H NMR (400 MHz, $CDCl_3$): δ 7.20~7.23 (m, 1H), 6.75~6.78 (m, 1H), 6.68~6.72 (m, 1H), 3.98~4.01 (m, 2H), 3.80~3.83 (m, 2H), 3.40~3.44 (m, 2H), 1.90~1.93 (m, 3H).

Step 5: 3-(2-Iodo-6-methoxyphenoxy)propanal

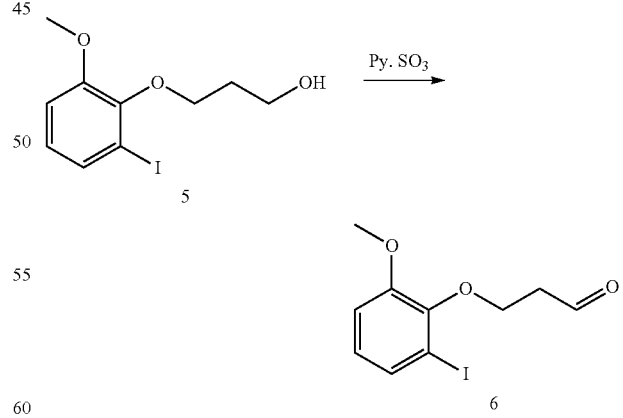

To a solution of compound 5 (48 g, 0.16 mol) in DCM (500 mL) at 0° C. were added $Py.SO_3$ (50.9 g, 0.32 mol), DIEA (51.6 g, 0.4 mol) and DMSO (18.72 g, 0.24 mol). The mixture was stirred at 0° C. for 1 h and then quenched by water, extracted with EA. The combined extracts were dried over Na₂SO₄ and filtered. The filtrate was concentrated to give 48 g of compound 6. It was used directly in the next step without further purification.

Step 6: Ethyl (2E)-5-(2-iodo-6-methoxyphenoxy)pent-2-enoate

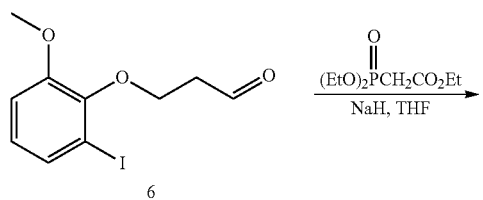

To a solution of ethyl 2-(diethoxyphosphoryl)acetate (62.7 g, 0.28 mol) in THF (500 mL) at 0° C. was added NaH (6.77 g, 0.28 mol). After stirring for 1 h, a solution of compound 6 (48 g, 0.16 mol) in THF was added dropwise. The mixture was stirred at room temperature overnight, quenched with water, and extracted with EA. The combined extracts were dried over Na₂SO₄ and filtered. The filtrate was concentrated and purified on silica gel (PE:EA=30:1) to give 13 g of compound 7 in 30% yields.

¹H NMR (400 MHz, CDCl₃): δ 7.25~7.28 (m, 1H), 7.03~7.07 (m, 1H), 6.78~6.82 (m, 1H), 6.70~6.75 (m, 1H), 5.9~5.97 (m, 1H), 4.10~4.15 (m, 2H), 4.00~4.05 (m, 2H), 3.75~3.78 (m, 3H), 2.64~2.70 (m, 2H), 1.53 (s, 3H). LRMS (M+H⁺): 377.

Step 7: Ethyl (2E)-(8-methoxy-2,3-dihydro-4H-chromen-4-ylidene)ethanoate

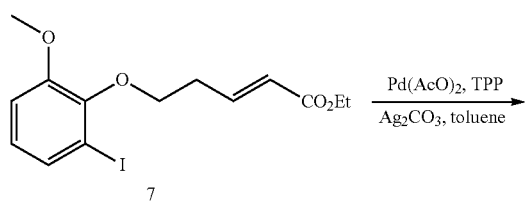

A mixture of compound 7 (12 g, 0.032 mol), Ag₂CO₃ (17.6 g, 0.064 mmol), Pd(AcO)₂ (2.5 g, 0.016 mmol) and PPh₃ (8.416 g, 0.032 mmol) in toluene (200 mL) was refluxed overnight, filtered, and concentrated in vacuo. Purification on silica gel (PE:EA=30:1) gave 3 g of compound 8 in 39% yields.

¹H NMR (400 MHz, CDCl₃): δ 7.09~7.11 (m, 1H), 6.76~6.82 (m, 1H), 6.28 (s, 1H), 4.22~4.24 (m, 2H), 4.10~4.13 (m, 2H), 3.81 (s, 3H), 3.33 (s, 3H), 1.24~1.26 (m, 3H). LRMS (M+H⁺): 249.

Step 8: Ethyl (1R,4'S)-8-methoxy-1'-benzyl-2,3-dihydrospiro[chromene-4,3'-pyrrolidine]-4'-carboxylate

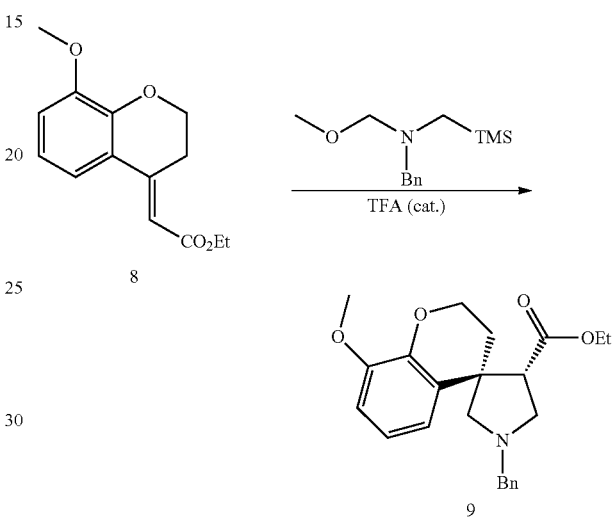

To a mixture of compound 8 (3 g, 12 mmol) and N-benzyl-N-(methoxymethyl)-N-trimethylsilylmethylamine (8.5 g, 36 mmol) in DCM (5 mL) at 0° C. was added TFA (0.136 g, 1 M in DCM). The mixture was stirred at room temperature overnight, and washed with NaHCO₃ solution. The organic layer was dried over Na₂SO₄, filtered, and concentrated in vacuo. Purification on silica gel (PE:EA=50:1 to 10:1) gave 4.5 g of compound 9 in 99% yields.

¹H (400 MHz, CDCl₃): δ 7.20~7.22 (m, 5H), 6.86~6.88 (m, 1H), 6.70~6.74 (m, 1H), 6.61~6.64 (m, 1H), 4.50~4.53 (m, 2H), 4.00~4.03 (m, 2H), 3.84 (s, 3H), 3.69 (s, 2H), 3.32 (s, 2H), 2.95 (t, J=12.0 Hz, 2H), 2.61 (d, J=8.0 Hz, 1H), 1.90 (s, 2H), 1.10~1.14 (m, 3H).

LRMS (M+H⁺): 382

Step 9: 1'-tert-Butyl 4'-ethyl (4R,4'S)-8-methoxy-1'-benzyl-2,3-dihydrospiro[chromene-4,3'-pyrrolidine]-1',4'-dicarboxylate

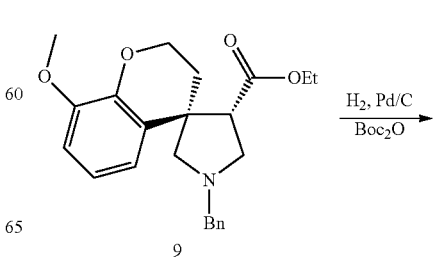

-continued

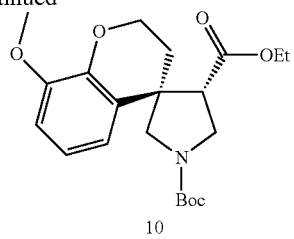

To a mixture of compound 9 (4.5 g, 11.8 mmol) in EtOH (400 mL) was added Pd/C (450 mg) and Boc₂O (10 g, 70.8 mmol). The mixture was stirred at 50° C. under H₂ (50 Psi) overnight, and then filtered. The filtrate was purified on silica gel to give 4.5 g of compound 10 in 95% yields.

$^1$H (400 MHz, CDCl$_3$): δ 6.86 (d, J=8.0 Hz, 2H), 6.74 (d, J=8.0 Hz, 1H), 4.10~4.14 (m, 2H), 3.90~4.93 (m, 2H), 3.85 (s, 3H), 3.6~3.64 (m, 2H), 3.4~3.5 (m, 2H), 2.82~2.85 (m, 1H), 1.80~1.85 (m, 2H), 1.43 (s, 9H), 1.00~1.03 (m, 3H). LRMS (M+H⁺): 391

Step 10: (1R,4'S)-8-Methoxy-1'-(tert-butoxycarbonyl)-2,3-dihydrospiro[chromene-4,3'-pyrrolidine]-4'-carboxylic acid

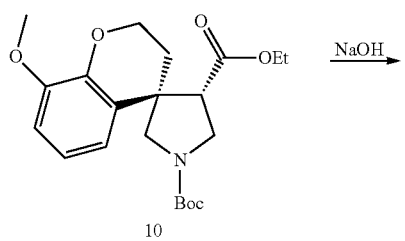

A mixture of compound 10 (1 g, 2.56 mmol) in NaOH/MeOH (20 mL, 2 M) was stirred at room temperature for 3 h. The mixture was acidified to pH 2~3 with 2M HCl and extracted to times with CH₂Cl₂. The combined organic layers were dried over Na₂SO₄ and concentrated to give 0.85 g of compound 11 in 91% yields.

LRMS (M+H⁺): 364.

Step 11: [(4R,4'S)-8-methoxy-1'-(tert-butoxycarbonyl)-2,3-dihydrospiro[chromene-4,3'-pyrrolidin]-4'-yl][(2S,4R)-2-(3,3-difluorocyclohexyl)-4-phenylpiperidin-1-yl]methanone

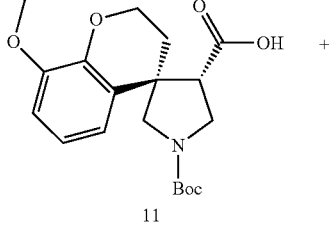

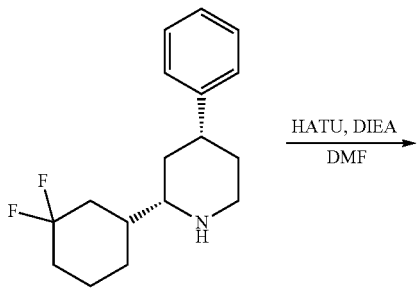

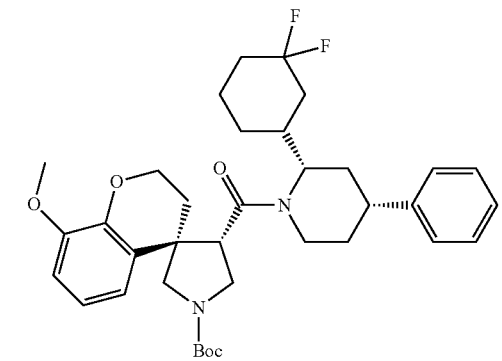

A solution of compound 11 (100 mg, 0.275 mmol), (2S, 4R)-2-(3,3-difluorocyclohexyl)-4-phenylpiperidine (77 mg, 0.275 mmol), HATU (171 mg, 0.45 mmol) and DIEA (71 mg, 0.6 mmol) in DMF were stirred at room temperature overnight, diluted with EA, and washed with water. The organic layer was dried over Na₂SO₄, filtered, and concentrated in vacuo. Purification on silica gel gave 70 mg of compound 12 in 41% yields.

LRMS (M+H⁺): 625.

Step 12: [(4R,4'S)-8-methoxy-2,3-dihydrospiro[chromene-4,3'-pyrrolidin]-4'-yl][(2S,4R)-2-(3,3-difluorocyclohexyl)-4-phenylpiperidin-1-yl]methanone

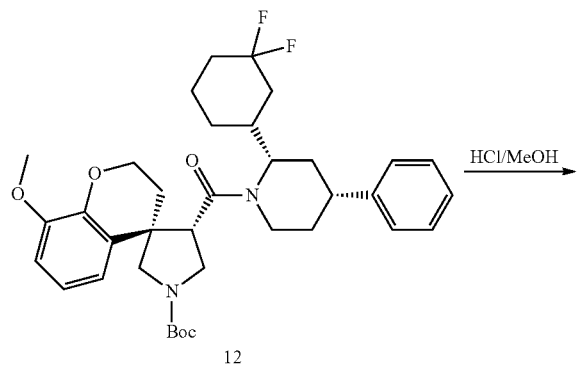

To a solution of compound 12 (70 mg) in 2 mL of MeOH was added a solution of HCl/MeOH (2 mL, 2 M). After 2 h at room temperature, the mixture was concentrated in vacuo to give [(4R,4'S)-8-methoxy-2,3-dihydrospiro[chromene-4,3'-pyrrolidin]-4'-yl][(2S,4R)-2-(3,3-difluorocyclohexyl)-4-phenylpiperidin-1-yl]methanone as HCl salts.

1H NMR (400 MHz, methanol-$d_4$) δ 7.08 (d, J=7.6 Hz, 1H, Ar—H), 6.99 (t, J=7.2 Hz, 2H, Ar—H), 6.89 (d, J=7.2 Hz, 1H, Ar—H), 6.76 (d, J=7.2 Hz, 1H, Ar—H), 6.74 (m, 1H, Ar—H), 6.73 (d, J=8.0 Hz, 1H, Ar—H), 4.08 (m, 3H, CH), 3.77 (m, 2H, CH), 3.58 (m, 2H, CH), 3.45 (s, 3H, OCH$_3$), 3.26 (m, 2H, CH), 2.93 (m, 1H, CH), 2.25 (m, 1H, CH), 1.89 (m, 2H, CH), 1.77 (m, 4H, CH), 1.60 (m, 1H, CH), 1.52 (m, 1H, CH), 1.44 (m, 4H, CH), 1.31 (m, 1H, CH), 0.91 (m, 3H, CH), 0.10 (m, 1H, CH). LRMS (M+H$^+$): 525.

EXAMPLES 4-137

The following compounds were prepared similar to Examples 1 and 2 using the starting materials and methods described herein, and applying the knowledge of one of skilled in the art.

TABLE 2

| Ex | Scheme | Product | Name | Parent MW |
|----|--------|---------|------|-----------|
| 4 | 1 | | (1R,4'S)-2,3-dihydrospiro[indene-1,3'-pyrrolidin]-4'-yl(4-phenylpiperidin-1-yl)methanone | 360.504 |
| 5 | 1 | | (1R,4'S)-2,3-dihydrospiro[indene-1,3'-pyrrolidin]-4'-yl[(2S,4R)-4-phenyl-2-(propan-2-yl)piperidin-1-yl]methanone | 402.585 |
| 6 | 1 | | (1R,4'S)-3,4-dihydro-2H-spiro[naphthalene-1,3'-pyrrolidin]-4'-yl(4-phenylpiperidin-1-yl)methanone | 374.531 |

TABLE 2-continued

| Ex | Scheme | Product | Name | Parent MW |
|---|---|---|---|---|
| 7 | 1 | | (1R,4'S)-3,4-dihydro-2H-spiro[naphthalene-1,3'-pyrrolidin]-4'-yl[(2S,4R)-4-phenyl-2-(propan-2-yl)piperidin-1-yl]methanone | 416.612 |
| 8 | 1 | | (4R,4'S)-2,3-dihydrospiro[chromene-4,3'-pyrrolidin]-4'-yl(4-phenylpiperidin-1-yl)methanone | 376.503 |
| 9 | 1 | | (1R,4'S)-3,4-dihydro-2H-spiro[naphthalene-1,3'-pyrrolidin]-4'-yl[(2S,4R)-2,4-diphenylpiperidin-1-yl]methanone | 450.629 |
| 10 | 1 | | (1S,4'S)-3,4-dihydro-2H-spiro[naphthalene-1,3'-pyrrolidin]-4'-yl[2-(2-methoxypropan-2-yl)piperidin-1-yl]methanone | 370.54 |
| 11 | 1 | | [(1R,4'S)-4,4-dimethyl-3,4-dihydro-2H-spiro[naphthalene-1,3'-pyrrolidin]-4'-yl](4-phenylpiperidin-1-yl)methanone | 402.585 |

TABLE 2-continued

| Ex | Scheme | Product | Name | Parent MW |
|---|---|---|---|---|
| 12 | 1 | | [(2S,4R)-2-cyclohexyl-4-phenylpiperidin-1-yl][(1R,4'S)-3,4-dihydro-2H-spiro[naphthalene-1,3'-pyrrolidin]-4'-yl]methanone | 456.677 |
| 13 | 1 | | [(2R,4S)-2-cyclohexyl-4-phenylpiperidin-1-yl][(1R,4'S)-3,4-dihydro-2H-spiro[naphthalene-1,3'-pyrrolidin]-4'-yl]methanone | 456.677 |
| 14 | 2 | | [(1R,4'S)-7-bromo-3,4-dihydro-2H-spiro[naphthalene-1,3'-pyrrolidin]-4'-yl](4-phenylpiperidin-1-yl)methanone | 453.427 |
| 15 | 1 | | (1S,4'S)-3,4-dihydro-2H-spiro[naphthalene-1,3'-pyrrolidin]-4'-yl[2-(3-methoxypentan-3-yl)piperidin-1-yl]methanone | 398.594 |
| 16 | 1 | | [(2S,4R)-2-cyclohexyl-4-phenylpiperidin-1-yl][(1R,4'S)-2,3-dihydrospiro[indene-1,3'-pyrrolidin]-4'-yl]methanone | 442.65 |

TABLE 2-continued

| Ex | Scheme | Product | Name | Parent MW |
|---|---|---|---|---|
| 17 | 2 | | [(1R,4'S)-6-bromo-3,4-dihydro-2H-spiro[naphthalene-1,3'-pyrrolidin]-4'-yl](4-phenylpiperidin-1-yl)methanone | 453.427 |
| 18 | 1 | | [(1R,4'S)-6-methoxy-3,4-dihydro-2H-spiro[naphthalene-1,3'-pyrrolidin]-4'-yl](4-phenylpiperidin-1-yl)methanone | 404.557 |
| 19 | 2 | | [(1R,4'S)-6-chloro-3,4-dihydro-2H-spiro[naphthalene-1,3'-pyrrolidin]-4'-yl](4-phenylpiperidin-1-yl)methanone | 408.976 |
| 20 | 2 | | [(1R,4'S)-6-bromo-3,4-dihydro-2H-spiro[naphthalene-1,3'-pyrrolidin]-4'-yl](1'H-spiro[indene-1,4'-piperidin]-1'-yl)methanone | 477.449 |
| 21 | 1 | | (1R,4'S)-2,3-dihydrospiro[indene-1,3'-pyrrolidin]-4'-yl[(2S,4R)-2,4-diphenylpiperidin-1-yl]methanone | 436.602 |
| 22 | 2 | | [(1R,4'S)-6-bromo-3,4-dihydro-2H-spiro[naphthalene-1,3'-pyrrolidin]-4'-yl][(2S,4R)-2,4-diphenylpiperidin-1-yl]methanone | 529.525 |

TABLE 2-continued

| Ex | Scheme | Product | Name | Parent MW |
|---|---|---|---|---|
| 23 | 1 | | (1S,4'S)-3,4-dihydro-2H-spiro[naphthalene-1,3'-pyrrolidin]-4'-yl(4-phenylpiperidin-1-yl)methanone | 374.531 |
| 24 | 1 | | (3R,4S)-2',3'-dihydro-1'H-spiro[pyrrolidine-3,4'-quinolin]-4-yl(4-phenylpiperidin-1-yl)methanone | 375.518 |
| 25 | 2 | | [(1R,4'S)-6-bromo-3,4-dihydro-2H-spiro[naphthalene-1,3'-pyrrolidin]-4'-yl][(2S,4R)-4-phenyl-2-(propan-2-yl)piperidin-1-yl]methanone | 495.508 |
| 26 | 1 | | [(1R,4'S)-6-hydroxy-3,4-dihydro-2H-spiro[naphthalene-1,3'-pyrrolidin]-4'-yl](4-phenylpiperidin-1-yl)methanone | 390.53 |
| 27 | 2 | | [(1R,4'S)-5-bromo-3,4-dihydro-2H-spiro[naphthalene-1,3'-pyrrolidin]-4'-yl](4-phenylpiperidin-1-yl)methanone | 453.427 |
| 28 | 1 | | [(1R,4'S)-6-fluoro-3,4-dihydro-2H-spiro[naphthalene-1,3'-pyrrolidin]-4'-yl](4-phenylpiperidin-1-yl)methanone | 392.521 |
| 29 | 1 | | (3R,4S)-7',8'-dihydro-6'H-spiro[pyrrolidine-3,5'-quinolin]-4-yl(4-phenylpiperidin-1-yl)methanone | 375.518 |
| 30 | 2 | | [(1R,4'S)-5-bromo-2,3-dihydrospiro[indene-1,3'-pyrrolidin]-4'-yl](4-phenylpiperidin-1-yl)methanone | 439.4 |

TABLE 2-continued

| Ex | Scheme | Product | Name | Parent MW |
|---|---|---|---|---|
| 31 | 2 | | (4-phenylpiperidin-1-yl)[(1R,4'S)-5-(propan-2-yl)-3,4-dihydro-2H-spiro[naphthalene-1,3'-pyrrolidin]-4'-yl] methanone | 416.612 |
| 32 | 2 | | [(1R,4'S)-6-bromo-3,4-dihydro-2H-spiro[naphthalene-1,3'-pyrrolidin]-4'-yl][(2S,4R)-2-cyclohexyl-4-phenylpiperidin-1-yl] methanone | 535.573 |
| 33 | 2 | | [(1R,4'S)-6-bromo-3,4-dihydro-2H-spiro[naphthalene-1,3'-pyrrolidin]-4'-yl][(2R,4S)-2-cyclohexyl-4-phenylpiperidin-1-yl] methanone | 535.573 |
| 34 | 1 | | [(3R,4S)-1'-(methylsulfonyl)-2',3'-dihydro-1'H-spiro[pyrrolidine-3,4'-quinolin]-4-yl](4-phenylpiperidin-1-yl) methanone | 453.608 |
| 35 | 2 | | [(3R,4S)-2'-chloro-7',8'-dihydro-6'H-spiro[pyrrolidine-3,5'-quinolin]-4-yl](4-phenylpiperidin-1-yl) methanone | 409.963 |

TABLE 2-continued

| Ex | Scheme | Product | Name | Parent MW |
|---|---|---|---|---|
| 36 | 2 | | [(3R,4S)-2'-chloro-7',8'-dihydro-6'H-spiro[pyrrolidine-3,5'-quinolin]-4-yl][(2S,4R)-4-phenyl-2-(propan-2-yl)piperidin-1-yl]methanone | 452.045 |
| 37 | 2 | | [(3R,4S)-2'-bromo-7',8'-dihydro-6'H-spiro[pyrrolidine-3,5'-quinolin]-4-yl](4-phenylpiperidin-1-yl)methanone | 454.414 |
| 38 | 1 | | (3R,4S)-2',3'-dihydrospiro[pyrrolidine-3,4'-thiochromen]-4-yl(4-phenylpiperidin-1-yl)methanone | 392.568 |
| 39 | 2 | | [(3R,4S)-2'-(dimethylamino)-7',8'-dihydro-6'H-spiro[pyrrolidine-3,5'-quinolin]-4-yl](4-phenylpiperidin-1-yl)methanone | 418.587 |
| 40 | 2 | | [(3R,4S)-2'-(methylamino)-7',8'-dihydro-6'H-spiro[pyrrolidine-3,5'-quinolin]-4-yl](4-phenylpiperidin-1-yl)methanone | 404.56 |
| 41 | 2 | | [(1R,4'S)-6-ethenyl-3,4-dihydro-2H-spiro[naphthalene-1,3'-pyrrolidin]-4'-yl](4-phenylpiperidin-1-yl)methanone | 400.569 |
| 42 | 2 | | [(1R,4'S)-5-amino-2,3-dihydrospiro[indene-1,3'-pyrrolidin]-4'-yl](4-phenylpiperidin-1-yl)methanone | 375.518 |

TABLE 2-continued

| Ex | Scheme | Product | Name | Parent MW |
|---|---|---|---|---|
| 43 | 2 | 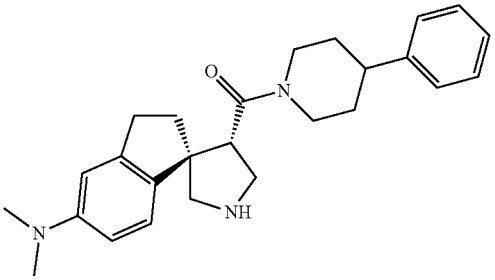 [SMILES: CN(C)c1ccc2c(c1)CC[C@]21CNC[C@H]1C(=O)N1CCC(c2ccccc2)CC1] | [(1R,4'S)-5-(dimethylamino)-2,3-dihydrospiro[indene-1,3'-pyrrolidin]-4'-yl](4-phenylpiperidin-1-yl)methanone | 403.572 |
| 44 | 2 | 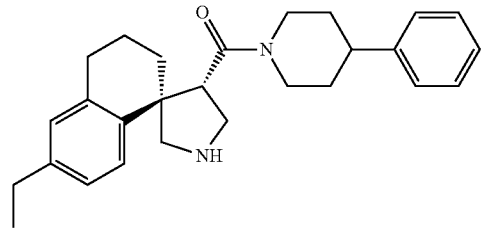 [SMILES: CCc1ccc2c(c1)CCC[C@]21CNC[C@H]1C(=O)N1CCC(c2ccccc2)CC1] | [(1R,4'S)-6-ethyl-3,4-dihydro-2H-spiro[naphthalene-1,3'-pyrrolidin]-4'-yl](4-phenylpiperidin-1-yl)methanone | 402.585 |
| 45 | 1 | 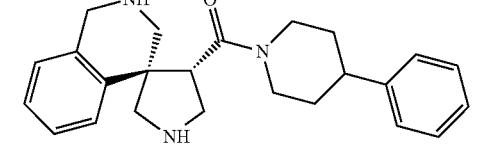 | (4S,4'S)-2,3-dihydro-1H-spiro[isoquinoline-4,3'-pyrrolidin]-4'-yl(4-phenylpiperidin-1-yl)methanone | 375.518 |
| 46 | 2 | 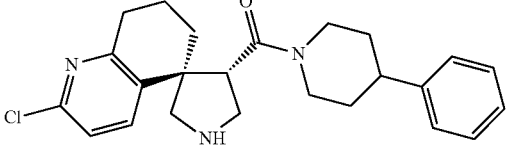 | [(3R,4S)-2'-chloro-7',8'-dihydro-6'H-spiro[pyrrolidine-3,5'-quinolin]-4-yl](4-phenylpiperidin-1-yl)methanone | 409.963 |
| 47 | 1 | 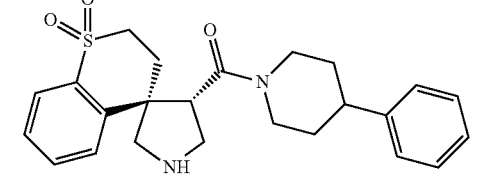 | [(3R,4S)-1',1'-dioxido-2',3'-dihydrospiro[pyrrolidine-3,4'-thiochromen]-4-yl](4-phenylpiperidin-1-yl)methanone | 424.566 |
| 48 | 2 | 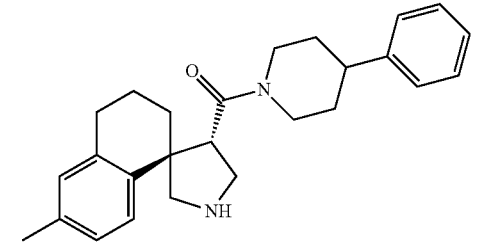 [SMILES: Cc1ccc2c(c1)CCC[C@]21CNC[C@H]1C(=O)N1CCC(c2ccccc2)CC1] | [(1R,4'S)-6-methyl-3,4-dihydro-2H-spiro[naphthalene-1,3'-pyrrolidin]-4'-yl](4-phenylpiperidin-1-yl)methanone | 388.558 |
| 49 | 2 | 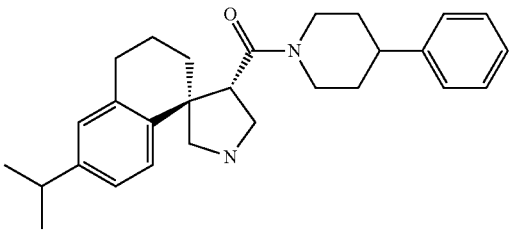 [SMILES: CC(C)c1ccc2c(c1)CCC[C@]21CNC[C@H]1C(=O)N1CCC(c2ccccc2)CC1] | (4-phenylpiperidin-1-yl)[(1R,4'S)-6-(propan-2-yl)-3,4-dihydro-2H-spiro[naphthalene-1,3'-pyrrolidin]-4'-yl]methanone | 416.612 |

TABLE 2-continued

| Ex | Scheme | Product | Name | Parent MW |
|---|---|---|---|---|
| 50 | 2 | | [(3R,4S)-2'-methyl-7',8'-dihydro-6'H-spiro[pyrrolidine-3,5'-quinolin]-4-yl](4-phenylpiperidin-1-yl)methanone | 389.545 |
| 51 | 2 | | [(3R,4S)-2'-chloro-7',8'-dihydro-6'H-spiro[pyrrolidine-3,5'-quinolin]-4-yl][(2R,4S)-2-cyclohexyl-4-phenylpiperidin-1-yl]methanone | 492.11 |
| 52 | 2 | | [(3R,4S)-2'-chloro-7',8'-dihydro-6'H-spiro[pyrrolidine-3,5'-quinolin]-4-yl][(2S,4R)-2-cyclohexyl-4-phenylpiperidin-1-yl]methanone | 492.11 |
| 53 | 2 | | [(3R,4S)-2'-chloro-7',8'-dihydro-6'H-spiro[pyrrolidine-3,5'-quinolin]-4-yl][(2R,4R)-2-cyclohexyl-4-phenylpiperidin-1-yl]methanone | 492.11 |
| 54 | 2 | | [(3R,4S)-2'-chloro-7',8'-dihydro-6'H-spiro[pyrrolidine-3,5'-quinolin]-4-yl][(2S,4S)-2-cyclohexyl-4-phenylpiperidin-1-yl]methanone | 492.11 |

TABLE 2-continued

| Ex | Scheme | Product | Name | Parent MW |
|---|---|---|---|---|
| 55 | 2 | | [(1R,4'S)-6-(morpholin-4-yl)-3,4-dihydro-2H-spiro[naphthalene-1,3'-pyrrolidin]-4'-yl](4-phenylpiperidin-1-yl)methanone | 459.637 |
| 56 | 2 | | [(1R,4'S)-6-tert-butyl-3,4-dihydro-2H-spiro[naphthalene-1,3'-pyrrolidin]-4'-yl](4-phenylpiperidin-1-yl)methanone | 430.639 |
| 57 | 2 | | [(2S,4R)-2-cyclohexyl-4-phenylpiperidin-1-yl][(3R,4S)-7',8'-dihydro-6'H-spiro[pyrrolidine-3,5'-quinolin]-4-yl]methanone | 457.665 |
| 58 | 2 | | [(1R,4'S)-6-cyclopropyl-3,4-dihydro-2H-spiro[naphthalene-1,3'-pyrrolidin]-4'-yl](4-phenylpiperidin-1-yl)methanone | 414.596 |
| 59 | 2 | | (4-phenylpiperidin-1-yl)[(1R,4'S)-6-(trifluoromethyl)-3,4-dihydro-2H-spiro[naphthalene-1,3'-pyrrolidin]-4'-yl]methanone | 442.529 |

TABLE 2-continued

| Ex | Scheme | Product | Name | Parent MW |
|---|---|---|---|---|
| 60 | 2 | | [(3R,4S)-2'-chloro-7',8'-dihydro-6'H-spiro[pyrrolidine-3,5'-quinolin]-4-yl][(2S,4R)-2,4-diphenylpiperidin-1-yl]methanone | 486.062 |
| 61 | 2 | | [(2S,4R)-2,4-diphenylpiperidin-1-yl][(3R,4S)-2'-methyl-7',8'-dihydro-6'H-spiro[pyrrolidine-3,5'-quinolin]-4-yl]methanone | 465.644 |
| 62 | 2 | | [(3R,4S)-2'-bromo-7',8'-dihydro-6'H-spiro[pyrrolidine-3,5'-quinolin]-4-yl][(2S,4R)-2-cyclohexyl-4-phenylpiperidin-1-yl]methanone | 536.561 |
| 63 | 2 | | [(2S,4R)-2-cyclohexyl-4-phenylpiperidin-1-yl][(3R,4S)-2'-methyl-7',8'-dihydro-6'H-spiro[pyrrolidine-3,5'-quinolin]-4-yl]methanone | 471.692 |
| 64 | 2 | | [(1R,4'S)-6-(difluoromethyl)-3,4-dihydro-2H-spiro[naphthalene-1,3'-pyrrolidin]-4'-yl](4-phenylpiperidin-1-yl)methanone | 424.539 |

TABLE 2-continued

| Ex | Scheme | Product | Name | Parent MW |
|---|---|---|---|---|
| 65 | 2 | | [(1R,4'S)-6-(hydroxymethyl)-3,4-dihydro-2H-spiro[naphthalene-1,3'-pyrrolidin]-4'-yl](4-phenylpiperidin-1-yl)methanone | 404.557 |
| 66 | 2 | | [(1R,4'S)-6-(aminomethyl)-3,4-dihydro-2H-spiro[naphthalene-1,3'-pyrrolidin]-4'-yl](4-phenylpiperidin-1-yl)methanone | 403.572 |
| 67 | 2 | | [(1R,4'S)-6-(fluoromethyl)-3,4-dihydro-2H-spiro[naphthalene-1,3'-pyrrolidin]-4'-yl](4-phenylpiperidin-1-yl)methanone | 406.548 |
| 68 | 1 | | [(2S,4R)-2-cyclohexyl-4-phenylpiperidin-1-yl][(4S,4'S)-2,3-dihydro-1H-spiro[isoquinoline-4,3'-pyrrolidin]-4'-yl]methanone | 457.665 |
| 69 | 1 | | [(2S,4R)-2-cyclohexyl-4-phenylpiperidin-1-yl][(4R,4'R)-2,3-dihydro-1H-spiro[isoquinoline-4,3'-pyrrolidin]-4'-yl]methanone | 457.665 |
| 70 | 2 | | [(2S,4R)-2-cyclohexyl-4-phenylpiperidin-1-yl][(3R,4S)-2'-(propan-2-yl)-7',8'-dihydro-6'H-spiro[pyrrolidine-3,5'-quinolin]-4-yl]methanone | 499.746 |

TABLE 2-continued

| Ex | Scheme | Product | Name | Parent MW |
|---|---|---|---|---|
| 71 | 2 | | (4-phenylpiperidin-1-yl)[(1R,4'S)-6-(2,2,2-trifluoro-1-hydroxyethyl)-3,4-dihydro-2H-spiro[naphthalene-1,3'-pyrrolidin]-4'-yl]methanone | 472.556 |
| 72 | 2 | | [(3R,4S)-2'-methyl-7',8'-dihydro-6'H-spiro[pyrrolidine-3,5'-quinolin]-4-yl][(2S,4R)-4-phenyl-2-(propan-2-yl)piperidin-1-yl]methanone | 431.627 |
| 73 | 2 | | [(2S,4R)-2-cyclohexyl-4-phenylpiperidin-1-yl][(3R,4S)-1'-oxido-7',8'-dihydro-6'H-spiro[pyrrolidine-3,5'-quinolin]-4-yl]methanone | 473.664 |
| 74 | 2 | | [(2S,4R)-2-tert-butyl-4-phenylpiperidin-1-yl][(3R,4S)-2'-methyl-7',8'-dihydro-6'H-spiro[pyrrolidine-3,5'-quinolin]-4-yl]methanone | 445.654 |
| 75 | 1 | | (4-phenylpiperidin-1-yl)[(4S,4'S)-1H-spiro[isochromene-4,3'-pyrrolidin]-4'-yl]methanone | 376.503 |

TABLE 2-continued

| Ex | Scheme | Name | Parent MW |
|---|---|---|---|
| 76 | 2 | [(3R,4S)-2'-chloro-7',8'-dihydro-6'H-spiro[pyrrolidine-3,5'-quinolin]-4-yl][(2S,4R)-2-(pentan-3-yl)-4-phenylpiperidin-1-yl]methanone | 480.099 |
| 77 | 2 | [(3R,4S)-2'-chloro-7',8'-dihydro-6'H-spiro[pyrrolidine-3,5'-quinolin]-4-yl](2'-phenyl-1'H-spiro[indene-1,4'-piperidin]-1'-yl)methanone | 510.084 |
| 78 | 2 | [(3R,4S)-2'-methyl-7',8'-dihydro-6'H-spiro[pyrrolidine-3,5'-quinolin]-4-yl][(2S,4R)-2-(pentan-3-yl)-4-phenylpiperidin-1-yl]methanone | 459.681 |
| 79 | 2 | [(2S,4R)-2-cyclohexyl-4-phenylpiperidin-1-yl][(1R,4'S)-6-(hydroxymethyl)-3,4-dihydro-2H-spiro[naphthalene-1,3'-pyrrolidin]-4'-yl]methanone | 486.704 |
| 80 | 2 | [(4S)-2'-chloro-7',8'-dihydro-6'H-spiro[pyrrolidine-3,5'-quinolin]-4-yl](4-phenyl-2-propylpiperidin-1-yl)methanone | 453.052 |

TABLE 2-continued

| Ex | Scheme | Product | Name | Parent MW |
|---|---|---|---|---|
| 81 | 2 | | [(4S)-2'-chloro-7',8'-dihydro-6'H-spiro[pyrrolidine-3,5'-quinolin]-4-yl][2-(2-methylpropyl)-4-phenylpiperidin-1-yl]methanone | 466.072 |
| 82 | 2 | | [(4S)-2'-chloro-7',8'-dihydro-6'H-spiro[pyrrolidine-3,5'-quinolin]-4-yl](4-phenyl-2-propylpiperidin-1-yl)methanone | 466.072 |
| 83 | 2 | | [(4S)-2'-chloro-7',8'-dihydro-6'H-spiro[pyrrolidine-3,5'-quinolin]-4-yl][2-(4-fluorophenyl)-4-phenylpiperidin-1-yl]methanone | 504.052 |
| 84 | 1 | | 2,3-dihydrospiro[chromene-4,3'-pyrrolidin]-4'-yl(2,4-diphenylpiperidin-1-yl)methanone | 452.602 |
| 85 | 2 | | (6-bromo-2,3-dihydrospiro[indene-1,3'-pyrrolidin]-4'-yl)[2-(4-fluorophenyl)-4-phenylpiperidin-1-yl]methanone | 533.489 |

TABLE 2-continued

| Ex | Scheme | Product | Name | Parent MW |
|---|---|---|---|---|
| 86 | 2 | 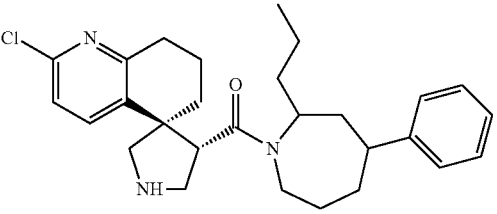 [SMILES: CCCC1CC(c2ccccc2)CCCN1C(=O)[C@@H]1CNC[C@]12CCCc1nc(Cl)ccc12] | [(3R,4S)-2'-chloro-7',8'-dihydro-6'H-spiro[pyrrolidine-3,5'-quinolin]-4-yl](4-phenyl-2-propylazepan-1-yl)methanone | 466.072 |
| 87 | 2 | 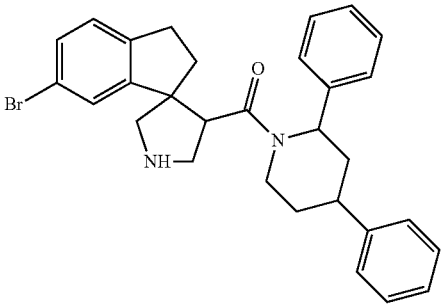 [SMILES: O=C(C1CNCC12CCc1ccc(Br)cc12)N1CCC(c2ccccc2)CC1c1ccccc1] | (6-bromo-2,3-dihydrospiro[indene-1,3'-pyrrolidin]-4'-yl)(2,4-diphenylpiperidin-1-yl)methanone | 515.498 |
| 88 | 2 | 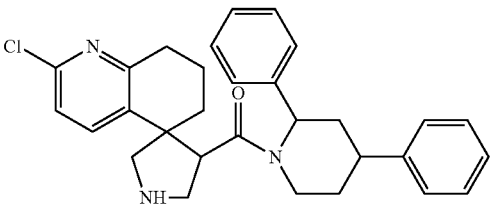 [SMILES: O=C(C1CNCC12CCCc1nc(Cl)ccc12)N1CCC(c2ccccc2)CC1c1ccccc1] | (2'-chloro-7',8'-dihydro-6'H-spiro[pyrrolidine-3,5'-quinolin]-4-yl)(2,4-diphenylpiperidin-1-yl)methanone | 486.062 |
| 89 | 1 | 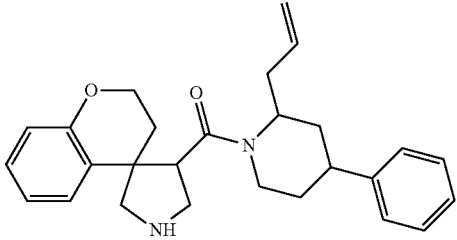 [SMILES: C=CCC1CC(c2ccccc2)CCN1C(=O)C1CNCC12CCOc1ccccc12] | 2,3-dihydrospiro[chromene-4,3'-pyrrolidin]-4'-yl[4-phenyl-2-(prop-2-en-1-yl)piperidin-1-yl]methanone | 416.568 |
| 90 | 1 | 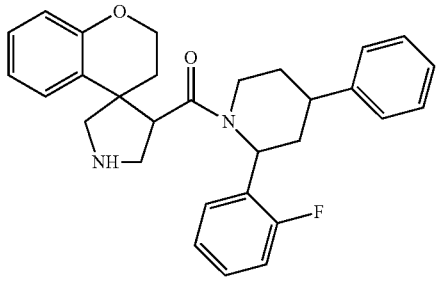 [SMILES: O=C(C1CNCC12CCOc1ccccc12)N1CCC(c2ccccc2)CC1c1ccccc1F] | 2,3-dihydrospiro[chromene-4,3'-pyrrolidin]-4'-yl[2-(2-fluorophenyl)-4-phenylpiperidin-1-yl]methanone | 470.592 |

TABLE 2-continued

| Ex | Scheme | Product | Name | Parent MW |
|---|---|---|---|---|
| 91 | 1 | | 2,3-dihydrospiro[chromene-4,3'-pyrrolidin]-4'-yl[2-(4-fluorophenyl)-4-phenylpiperidin-1-yl]methanone | 470.592 |
| 92 | 2 | | (2,4-diphenylpiperidin-1-yl)(6-ethyl-2,3-dihydrospiro[indene-1,3'-pyrrolidin]-4'-yl)methanone | 464.657 |
| 93 | 2 | | (3-benzylpiperidin-1-yl)[(3R,4S)-2'-chloro-7',8'-dihydro-6'H-spiro[pyrrolidine-3,5'-quinolin]-4-yl]methanone | 423.99 |
| 94 | 2 | | [(3R,4S)-2'-chloro-7',8'-dihydro-6'H-spiro[pyrrolidine-3,5'-quinolin]-4-yl](1'H-spiro[1-benzofuran-3,4'-piperidin]-1'-yl)methanone | 437.974 |
| 95 | 2 | | [(3R,4S)-2'-chloro-7',8'-dihydro-6'H-spiro[pyrrolidine-3,5'-quinolin]-4-yl](1,2-dihydro-1'H-spiro[indole-3,4'-piperidin]-1'-yl)methanone | 436.989 |
| 96 | 1 | | (2-butyl-2,3-dihydrospiro[chromene-4,3'-pyrrolidin]-4'-yl)(2,4-diphenylpiperidin-1-yl)methanone | 508.71 |

TABLE 2-continued

| Ex | Scheme | Product | Name | Parent MW |
|---|---|---|---|---|
| 97 | 2 | | (2'-chloro-7',8'-dihydro-6'H-spiro[pyrrolidine-3,5'-quinolin]-4-yl)(5-phenyl-2-propylazepan-1-yl)methanone | 466.072 |
| 98 | 2 | | (2'-chloro-7',8'-dihydro-6'H-spiro[pyrrolidine-3,5'-quinolin]-4-yl)[4-phenyl-2-(prop-2-en-1-yl)piperidin-1-yl]methanone | 450.029 |
| 99 | 2 | | (2'-chloro-7',8'-dihydro-6'H-spiro[pyrrolidine-3,5'-quinolin]-4-yl)[2-(2-fluorophenyl)-4-phenylpiperidin-1-yl]methanone | 504.052 |
| 100 | 2 | | [(3R,4S)-2'-chloro-7',8'-dihydro-6'H-spiro[pyrrolidine-3,5'-quinolin]-4-yl][2-(3-methylphenyl)-4-phenylpiperidin-1-yl]methanone | 500.089 |
| 101 | 1 | | (4R,4'S)-2,3-dihydrospiro[chromene-4,3'-pyrrolidin]-4'-yl[(2S,4R)-2,4-diphenylpiperidin-1-yl]methanone | 452.602 |

TABLE 2-continued

| Ex | Scheme | Product | Name | Parent MW |
|---|---|---|---|---|
| 102 | 1 | | [(2S,4R)-2,4-diphenylpiperidin-1-yl][(4R,4'S)-2-methyl-2,3-dihydrospiro[chromene-4,3'-pyrrolidin]-4'-yl]methanone | 466.629 |
| 103 | 1 | | [(4R,4'S)-2-butyl-2,3-dihydrospiro[chromene-4,3'-pyrrolidin]-4'-yl][(2S,4R)-2,4-diphenylpiperidin-1-yl]methanone | 508.71 |
| 104 | 2 | | [(4R,4'S)-6-chloro-2,3-dihydrospiro[chromene-4,3'-pyrrolidin]-4'-yl][(2S,4R)-2,4-diphenylpiperidin-1-yl]methanone | 487.047 |
| 105 | 2 | | [(4R,4'S)-6-chloro-7-methyl-2,3-dihydrospiro[chromene-4,3'-pyrrolidin]-4'-yl][(2S,4R)-2,4-diphenylpiperidin-1-yl]methanone | 501.074 |
| 106 | 2 | | [(3R,4S)-2'-chloro-1'-oxido-7',8'-dihydro-6'H-spiro[pyrrolidine-3,5'-quinolin]-4-yl][(2R,4S)-2,4-diphenylpiperidin-1-yl]methanone | 502.061 |

TABLE 2-continued

| Ex | Scheme | Product | Name | Parent MW |
|---|---|---|---|---|
| 107 | 2 | | [(2R,4S)-2,4-diphenylpiperidin-1-yl][(3R,4S)-2'-ethyl-7',8'-dihydro-6'H-spiro[pyrrolidine-3,5'-quinolin]-4-yl]methanone | 479.671 |
| 108 | 2 | | [(3R,4S)-2'-chloro-7',8'-dihydro-6'H-spiro[pyrrolidine-3,5'-quinolin]-4-yl][2'-(4-fluorophenyl)-1'H-spiro[indene-1,4'-piperidin]-1'-yl]methanone | 528.075 |
| 109 | 2 | | [(3R,4S)-2'-chloro-7',8'-dihydro-6'H-spiro[pyrrolidine-3,5'-quinolin]-4-yl](2'-phenyl-1'H-spiro[indene-1,4'-piperidin]-1'-yl)methanone | 510.084 |
| 110 | 1 | | (4R,4'S)-4'-{[(2S,4R)-2,4-diphenylpiperidin-1-yl]carbonyl}-1,5,6,7-tetrahydrospiro[indole-4,3'-pyrrolidine] | 439.59 |
| 111 | 1 | | (4R,4'S)-4'-{[(2S,4R)-2,4-diphenylpiperidin-1-yl]carbonyl}-6,7-dihydro-5H-spiro[1-benzothiophene-4,3'-pyrrolidine] | 456.64 |

TABLE 2-continued

| Ex | Scheme | Name | Parent MW |
|---|---|---|---|
| 112 | 1 | (4R,4'S)-4'-{[(2S,4R)-2,4-diphenylpiperidin-1-yl]carbonyl}-6,7-dihydro-5H-spiro[1-benzofuran-4,3'-pyrrolidine] | 440.58 |
| 113 | 1 | (4'S,7S)-4'-{[(2S,4R)-2,4-diphenylpiperidin-1-yl]carbonyl}-2-methyl-5,6-dihydro-4H-spiro[1,3-benzothiazole-7,3'-pyrrolidine] | 471.66 |
| 114 | 1 | (4'S,7S)-4'-{[(2S,4R)-2,4-diphenylpiperidin-1-yl]carbonyl}-5,6-dihydro-4H-spiro[1-benzothiophene-7,3'-pyrrolidine] | 456.64 |
| 115 | 1 | (4'S,7S)-4'-{[(2S,4R)-2,4-diphenylpiperidin-1-yl]carbonyl}-5,6-dihydro-4H-spiro[1-benzofuran-7,3'-pyrrolidine] | 440.58 |
| 116 | 1 | (3R,4S)-4-{[(2S,4R)-2,4-diphenylpiperidin-1-yl]carbonyl}-7'-methyl-2',3'-dihydrospiro[pyrrolidine-3,4'-thiopyrano[2,3-b]pyridine] | 483.67 |
| 117 | 2 | (3S,4S)-2'-chloro-4-{[(2S,4R)-2,4-diphenylpiperidin-1-yl]carbonyl}-6',7'-dihydro-5'H-spiro[pyrrolidine-3,8'-quinoline] | 486.05 |

TABLE 2-continued

| Ex | Scheme | Product | Name | Parent MW |
|---|---|---|---|---|
| 118 | 2 | | (3R,4S)-3'-chloro-4-{[(2S,4R)-2,4-diphenylpiperidin-1-yl]carbonyl}-7',8'-dihydro-6'H-spiro[pyrrolidine-3,5'-quinoline] | 486.05 |
| 119 | 1 | | (3S,4S)-4-{[(2S,4R)-2,4-diphenylpiperidin-1-yl]carbonyl}-2'-phenyl-6',7'-dihydro-5'H-spiro[pyrrolidine-3,8'-quinoline] | 527.7 |
| 120 | 1 | | (3R,4S)-4-{[(2S,4R)-2,4-diphenylpiperidin-1-yl]carbonyl}-3'-methyl-7',8'-dihydro-6'H-spiro[pyrrolidine-3,5'-quinoline] | 464.64 |
| 121 | 1 | | (3R,4S)-4-{[(2S,4R)-2,4-diphenylpiperidin-1-yl]carbonyl}-4'-methyl-7',8'-dihydro-6'H-spiro[pyrrolidine-3,5'-quinoline] | 464.64 |
| 122 | 1 | | (3S,4S)-4-{[(2S,4R)-2,4-diphenylpiperidin-1-yl]carbonyl}-3'-methyl-6',7'-dihydro-5'H-spiro[pyrrolidine-3,8'-quinoline] | 464.64 |
| 123 | 1 | | (3R,4S)-4-{[(2S,4R)-2,4-diphenylpiperidin-1-yl]carbonyl}-2'-methyl-7',8'-dihydro-6'H-spiro[pyrrolidine-3,5'-quinazoline] | 465.63 |

TABLE 2-continued

| Ex | Scheme | Product | Name | Parent MW |
|---|---|---|---|---|
| 124 | 1 | | (3R,4S)-4-{[(2S,4R)-2,4-diphenylpiperidin-1-yl]carbonyl}-2'-phenyl-7',8'-dihydro-6'H-spiro[pyrrolidine-3,5'-quinazoline] | 527.7 |
| 125 | 1 | | (3S,4S)-4-{[(2S,4R)-2,4-diphenylpiperidin-1-yl]carbonyl}-7',8'-dihydro-6'H-spiro[pyrrolidine-3,5'-quinoxaline] | 451.6 |
| 126 | 1 | | (3R,4S)-4-{[(2S,4R)-2,4-diphenylpiperidin-1-yl]carbonyl}-4'-(trifluoromethyl)-7',8'-dihydro-6'H-spiro[pyrrolidine-3,5'-quinoline] | 518.61 |
| 127 | 1 | | (4'S,8R)-4'-{[(2S,4R)-2,4-diphenylpiperidin-1-yl]carbonyl}-1,3-dimethyl-6,7-dihydro-5H-spiro[isoquinoline-8,3'-pyrrolidine] | 478.67 |
| 128 | 1 | | (1R,4'S)-4'-{[(2S,4R)-2,4-diphenylpiperidin-1-yl]carbonyl}-6,8-dimethyl-3,4-dihydro-2H-spiro[naphthalene-1,3'-pyrrolidine] | 478.67 |
| 129 | 1 | | (1R,4'S)-4'-{[(2S,4R)-2,4-diphenylpiperidin-1-yl]carbonyl}-3,4,5,6,7,8-hexahydro-2H-spiro[acridine-1,3'-pyrrolidine] | 504.7 |

TABLE 2-continued

| Ex | Scheme | Product | Name | Parent MW |
|---|---|---|---|---|
| 130 | 1 | | (4'S,9R)-4'-{[(2S,4R)-2,4-diphenylpiperidin-1-yl]carbonyl}-1,2,3,6,7,8-hexahydrospiro[cyclopenta[c]quinoline-9,3'-pyrrolidine] | 520.75 |
| 131 | 1 | | (4R,4'S)-4'-{[(2S,4R)-2,4-diphenylpiperidin-1-yl]carbonyl}-2,2-dimethyl-2,3-dihydrospiro[chromene-4,3'-pyrrolidine] | 479.65 |
| 132 | 2 | | (4R,4'S)-7-bromo-4'-{[(2S,4R)-2,4-diphenylpiperidin-1-yl]carbonyl}-2,3-dihydrospiro[chromene-4,3'-pyrrolidine] | 530.5 |
| 133 | 2 | | (3S,4'S)-6-bromo-4'-{[(2S,4R)-2,4-diphenylpiperidin-1-yl]carbonyl}spiro[1-benzofuran-3,3'-pyrrolidine] | 516.47 |
| 134 | 2 | | (1R,4'S)-5-bromo-4'-{[(2S,4R)-2,4-diphenylpiperidin-1-yl]carbonyl}-2,3-dihydrospiro[indene-1,3'-pyrrolidine] | 514.5 |

TABLE 2-continued

| Ex | Scheme | Product | Name | Parent MW |
|---|---|---|---|---|
| 135 | 1 | | (1S,4'S)-7-bromo-4'-{[(2S,4R)-2,4-diphenylpiperidin-1-yl]carbonyl}-4,5-dihydrospiro[3-benzoxepine-1,3'-pyrrolidine] | 465.63 |

Compounds in Table 2 having a basic group or acidic group are depicted and named as the free base acid. Depending on the reaction and purification conditions, various compounds in Table 1 having a basic group were isolated in either the free base form, or as a salt (such as HCl salt), or in both free base and salt forms.

The following compounds were prepared similar to Examples 1 to 3 using the starting materials and methods described herein, and applying the knowledge of one of skilled in the art.

TABLE 3

| Ex. No. | Scheme | Structure | Parent MW |
|---|---|---|---|
| 136 | 2 | 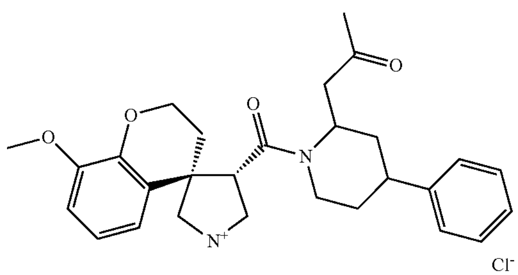 [SMILES: COc1cccc2c1OCC[C@]21C[NH2+]C[C@H]1C(=O)N1CCC(c2ccccc2)CC1CC(C)=O ; [Cl-]] | 462.594 |
| 137 | 2 | 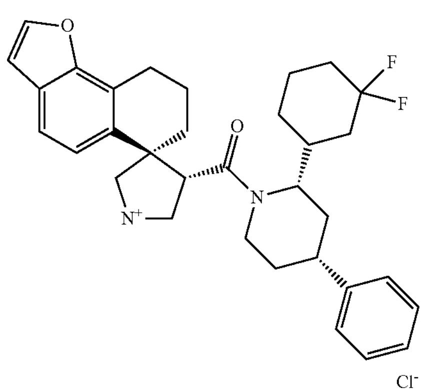 [SMILES: O=C([C@@H]1C[NH2+]C[C@]12CCCc1c2ccc2ccoc12)N1CC[C@@H](c2ccccc2)C[C@H]1C1CCCC(F)(F)C1 ; [Cl-]] | 532.68 |

TABLE 3-continued
| Ex. No. | Scheme | Structure | Parent MW |
|---|---|---|---|
| 138 | 2 | 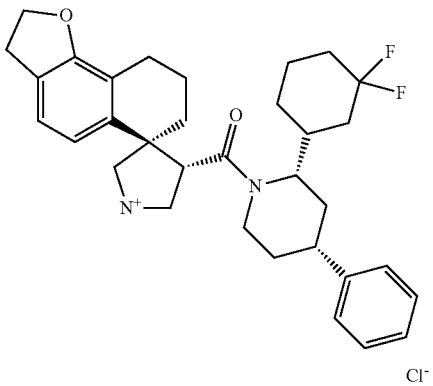 [SMILES: O=C([C@@H]1C[NH2+]C[C@]12CCCc1c2ccc2c1OCC2)N1CC[C@@H](c2ccccc2)C[C@H]1C1CCCC(F)(F)C1 ; [Cl-]] | 534.696 |
| 139 | 2 | 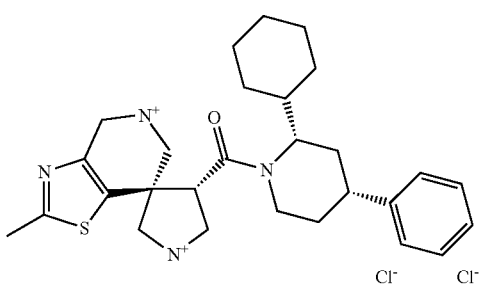 [SMILES: Cc1nc2c(s1)[C@]1(C[NH2+]C2)C[NH2+]C[C@H]1C(=O)N1CC[C@@H](c2ccccc2)C[C@H]1C1CCCCC1 ; [Cl-] ; [Cl-]] | 478.705 |
| 140 | 2 | 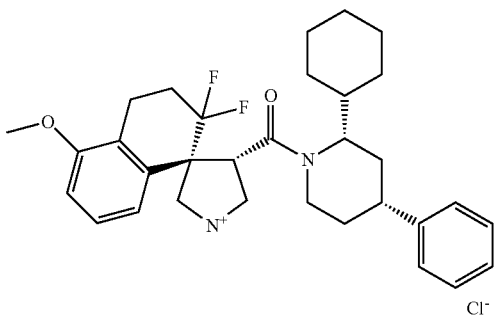 [SMILES: COc1cccc2c1CCC(F)(F)[C@]21C[NH2+]C[C@H]1C(=O)N1CC[C@@H](c2ccccc2)C[C@H]1C1CCCCC1 ; [Cl-]] | 522.685 |
| 141 | 2 | 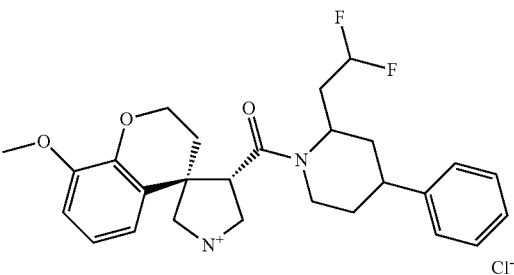 [SMILES: COc1cccc2c1OCC[C@]21C[NH2+]C[C@H]1C(=O)N1CCC(c2ccccc2)CC1CC(F)F ; [Cl-]] | 470.564 |

TABLE 3-continued

| Ex. No. | Scheme | Structure | Parent MW |
|---|---|---|---|
| 142 | 2 | 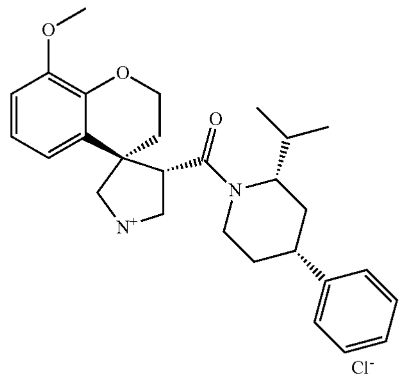 [SMILES: COc1cccc2c1OCC[C@]21C[NH2+]C[C@H]1C(=O)N1CC[C@@H](c2ccccc2)C[C@H]1C(C)C ; [Cl-]] | 448.611 |
| 143 | 2 | 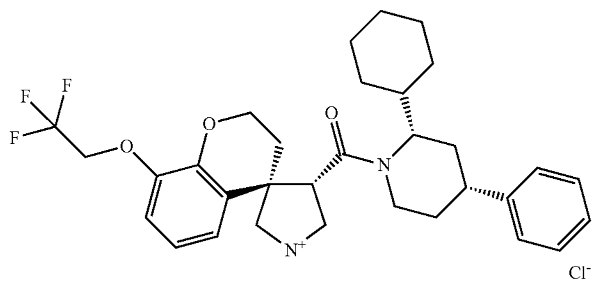 [SMILES: O=C([C@@H]1C[NH2+]C[C@]12CCOc1c(OCC(F)(F)F)cccc12)N1CC[C@@H](c2ccccc2)C[C@H]1C1CCCCC1 ; [Cl-]] | 556.674 |
| 144 | 2 | 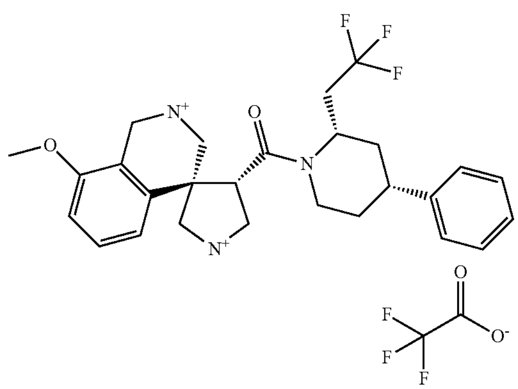 [SMILES: COc1cccc2c1C[NH2+]C[C@]21C[NH2+]C[C@H]1C(=O)N1CC[C@@H](c2ccccc2)C[C@H]1CC(F)(F)F ; O=C([O-])C(F)(F)F] | 487.57 |
| 145 | 2 | 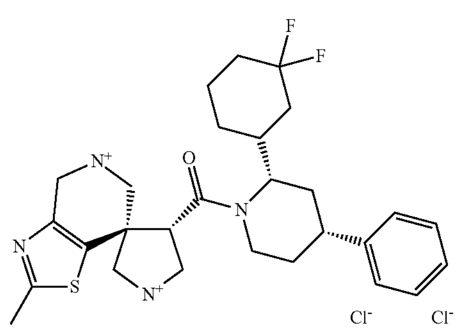 [SMILES: Cc1nc2c(s1)[C@]1(C[NH2+]C2)C[NH2+]C[C@H]1C(=O)N1CC[C@@H](c2ccccc2)C[C@H]1C1CCCC(F)(F)C1 ; [Cl-] ; [Cl-]] | 514.686 |

TABLE 3-continued
| Ex. No. | Scheme | Structure | Parent MW |
|---|---|---|---|
| 146 | 2 | 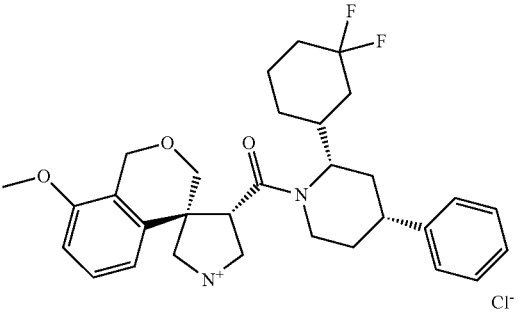 [SMILES: COc1cccc2c1COC[C@]21C[NH2+]C[C@H]1C(=O)N1CC[C@@H](c2ccccc2)C[C@H]1C1CCCC(F)(F)C1 ; [Cl-]] | 524.657 |
| 147 | 2 | 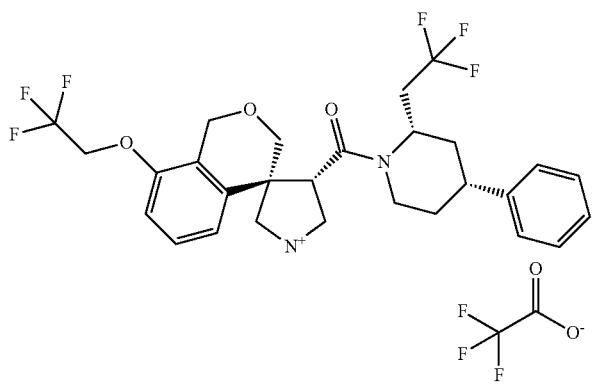 [SMILES: O=C([C@@H]1C[NH2+]C[C@]12COCc1c(OCC(F)(F)F)cccc12)N1CC[C@@H](c2ccccc2)C[C@H]1CC(F)(F)F ; O=C([O-])C(F)(F)F] | 556.553 |
| 148 | 2 | 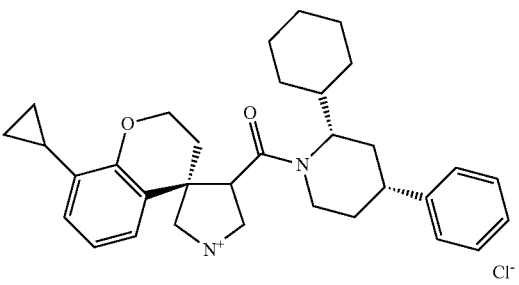 [SMILES: O=C(C1C[NH2+]C[C@]12CCOc1c(C3CC3)cccc12)N1CC[C@@H](c2ccccc2)C[C@H]1C1CCCCC1 ; [Cl-]] | 498.715 |
| 149 | 2 | 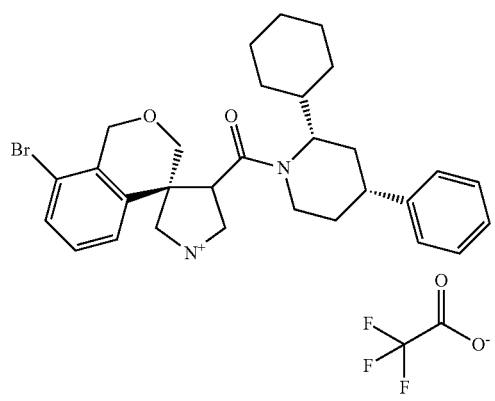 [SMILES: O=C(C1C[NH2+]C[C@]12COCc1c(Br)cccc12)N1CC[C@@H](c2ccccc2)C[C@H]1C1CCCCC1 ; O=C([O-])C(F)(F)F] | 537.546 |

TABLE 3-continued

| Ex. No. | Scheme | Structure | Parent MW |
|---|---|---|---|
| 150 | 2 | 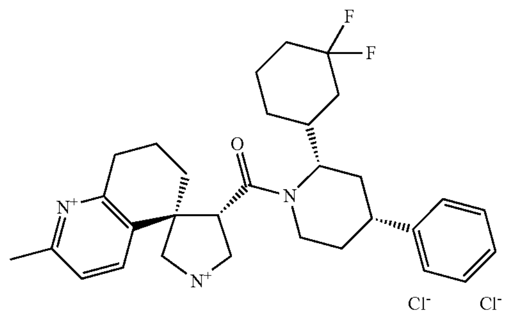 [SMILES: Cc1ccc2c([nH+]1)CCC[C@]21C[NH2+]C[C@H]1C(=O)N1CC[C@@H](c2ccccc2)C[C@H]1C1CCCC(F)(F)C1 ; [Cl-] ; [Cl-]] | 507.673 |
| 151 | 2 | 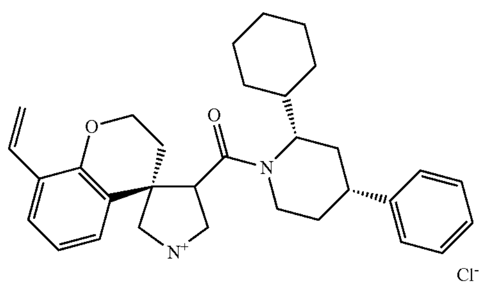 [SMILES: C=Cc1cccc2c1OCC[C@]21C[NH2+]CC1C(=O)N1CC[C@@H](c2ccccc2)C[C@H]1C1CCCCC1 ; [Cl-]] | 484.668 |
| 152 | 2 | 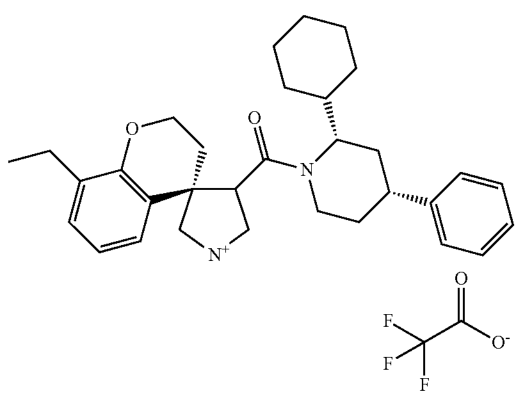 [SMILES: CCc1cccc2c1OCC[C@]21C[NH2+]CC1C(=O)N1CC[C@@H](c2ccccc2)C[C@H]1C1CCCCC1 ; O=C([O-])C(F)(F)F] | 486.704 |
| 153 | 2 | 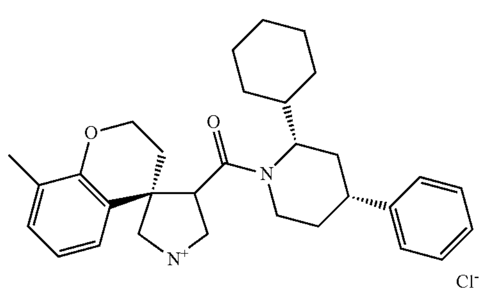 [SMILES: Cc1cccc2c1OCC[C@]21C[NH2+]CC1C(=O)N1CC[C@@H](c2ccccc2)C[C@H]1C1CCCCC1 ; [Cl-]] | 471.677 |

TABLE 3-continued
| Ex. No. | Scheme | Structure | Parent MW |
|---|---|---|---|
| 154 | 2 | 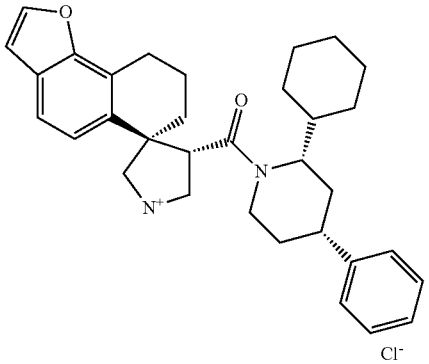 [SMILES: O=C([C@@H]1C[NH2+]C[C@]12CCCc1c2ccc2ccoc12)N1CC[C@@H](c2ccccc2)C[C@H]1C1CCCCC1 ; [Cl-]] | 496.699 |
| 155 | 2 | 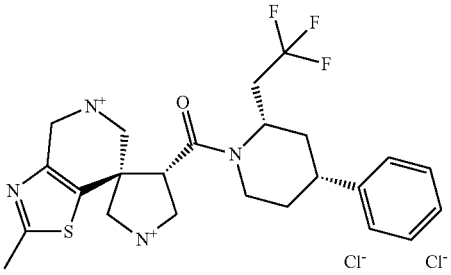 [SMILES: Cc1nc2c(s1)[C@]1(C[NH2+]C2)C[NH2+]C[C@H]1C(=O)N1CC[C@@H](c2ccccc2)C[C@H]1CC(F)(F)F ; [Cl-] ; [Cl-]] | 478.554 |
| 156 | 2 | 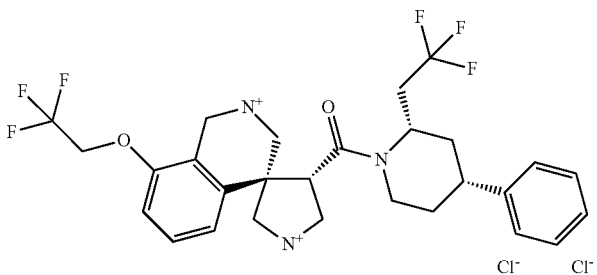 [SMILES: O=C([C@@H]1C[NH2+]C[C@]12C[NH2+]Cc1c(OCC(F)(F)F)cccc12)N1CC[C@@H](c2ccccc2)C[C@H]1CC(F)(F)F ; [Cl-] ; [Cl-]] | 555.569 |
| 157 | 2 | 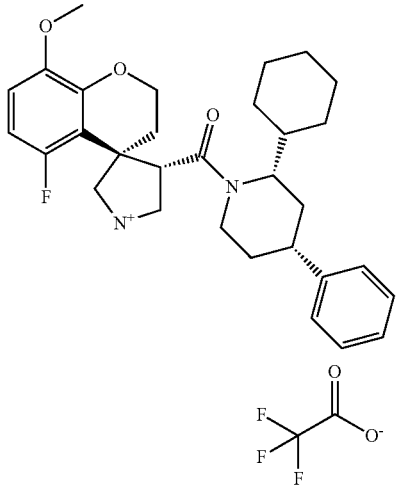 [SMILES: COc1ccc(F)c2c1OCC[C@]21C[NH2+]C[C@H]1C(=O)N1CC[C@@H](c2ccccc2)C[C@H]1C1CCCCC1 ; O=C([O-])C(F)(F)F] | 506.666 |

TABLE 3-continued

| Ex. No. | Scheme | Structure | Parent MW |
|---|---|---|---|
| 158 | 2 | 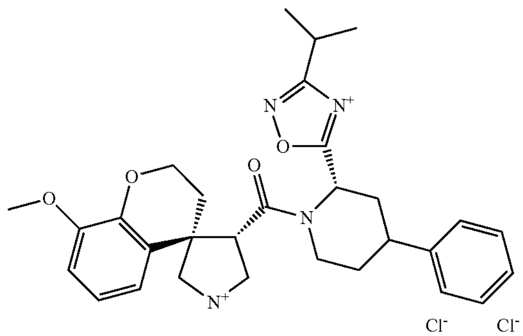 [SMILES: COc1cccc2c1OCC[C@]21C[NH2+]C[C@H]1C(=O)N1CCC(c2ccccc2)C[C@H]1c1[nH+]c(C(C)C)no1 ; [Cl-] ; [Cl-]] | 576.646 |
| 159 | 2 | 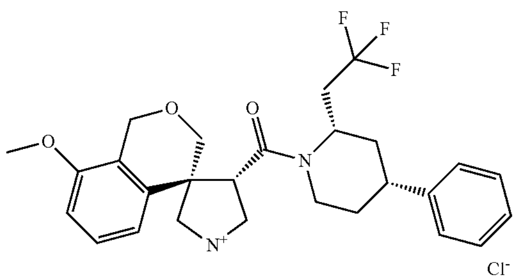 [SMILES: COc1cccc2c1COC[C@]21C[NH2+]C[C@H]1C(=O)N1CC[C@@H](c2ccccc2)C[C@H]1CC(F)(F)F ; [Cl-]] | 488.555 |
| 160 | 2 | 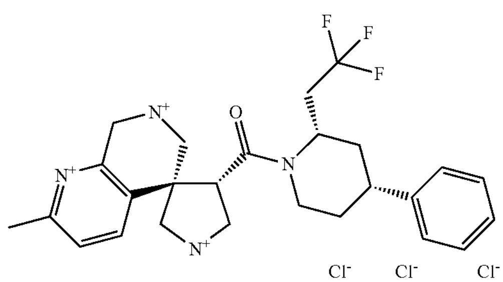 [SMILES: Cc1ccc2c([nH+]1)C[NH2+]C[C@]21C[NH2+]C[C@H]1C(=O)N1CC[C@@H](c2ccccc2)C[C@H]1CC(F)(F)F ; [Cl-] ; [Cl-] ; [Cl-]] | 472.558 |
| 161 | 2 | 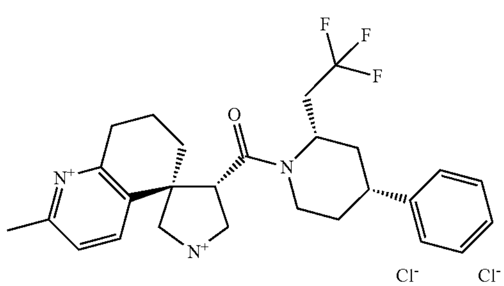 [SMILES: Cc1ccc2c([nH+]1)CCC[C@]21C[NH2+]C[C@H]1C(=O)N1CC[C@@H](c2ccccc2)C[C@H]1CC(F)(F)F ; [Cl-] ; [Cl-]] | 471.571 |
| 162 | 2 | 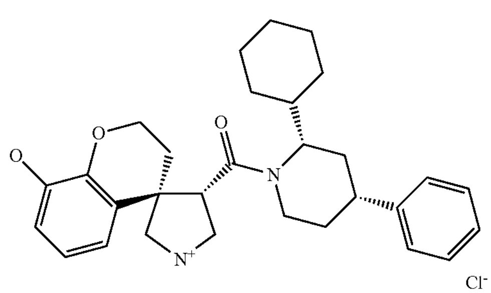 [SMILES: O=C([C@@H]1C[NH2+]C[C@]12CCOc1c(O)cccc12)N1CC[C@@H](c2ccccc2)C[C@H]1C1CCCCC1 ; [Cl-]] | 476.649 |

TABLE 3-continued
| Ex. No. | Scheme | Structure | Parent MW |
|---|---|---|---|
| 163 | 2 | 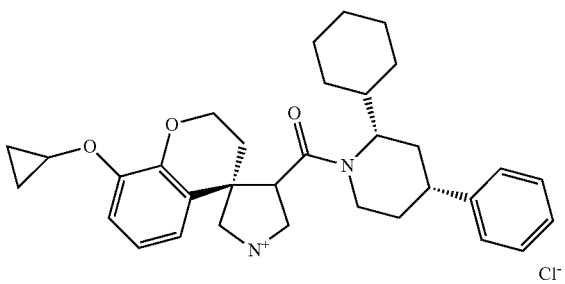 [SMILES: O=C(C1C[NH2+]C[C@]12CCOc1c(OC3CC3)cccc12)N1CC[C@@H](c2ccccc2)C[C@H]1C1CCCCC1 ; [Cl-]] | 514.714 |
| 164 | 2 | 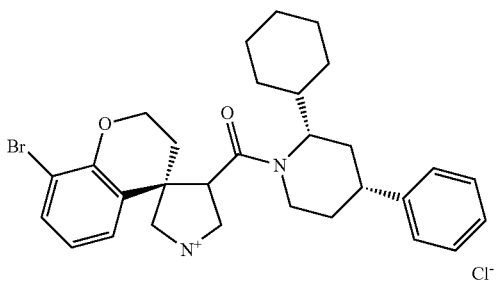 [SMILES: O=C(C1C[NH2+]C[C@]12CCOc1c(Br)cccc12)N1CC[C@@H](c2ccccc2)C[C@H]1C1CCCCC1 ; [Cl-]] | 537.546 |
| 165 | 2 | Chiral 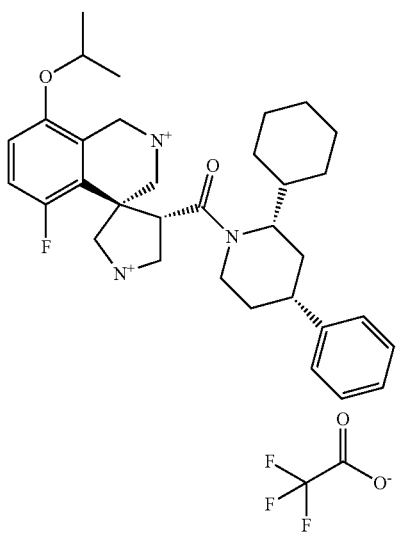 | 533.736 |
| 166 | 2 | 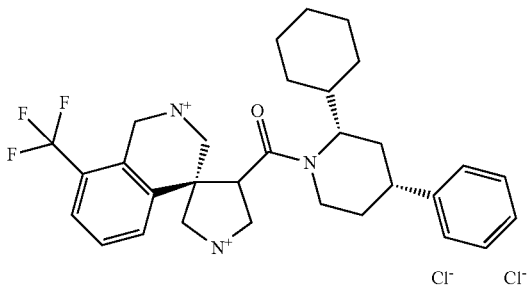 [SMILES: O=C(C1C[NH2+]C[C@]12C[NH2+]Cc1c(C(F)(F)F)cccc12)N1CC[C@@H](c2ccccc2)C[C@H]1C1CCCCC1 ; [Cl-] ; [Cl-]] | 525.663 |

TABLE 3-continued

| Ex. No. | Scheme | Structure | Parent MW |
|---|---|---|---|
| 167 | 2 | 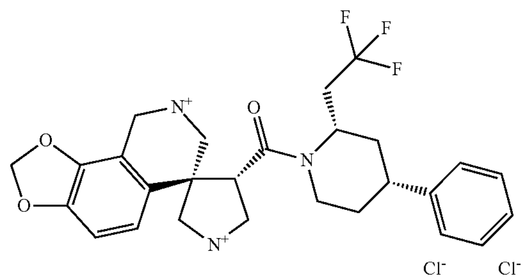 [SMILES: O=C([C@@H]1C[NH2+]C[C@]12C[NH2+]Cc1c2ccc2c1OCO2)N1CC[C@@H](c2ccccc2)C[C@H]1CC(F)(F)F ; [Cl-] ; [Cl-]] | 501.554 |
| 168 | 2 | 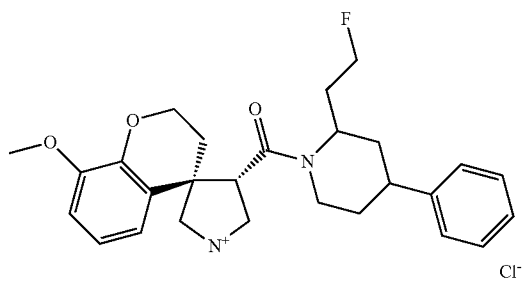 [SMILES: COc1cccc2c1OCC[C@]21C[NH2+]C[C@H]1C(=O)N1CCC(c2ccccc2)CC1CCF ; [Cl-]] | 452.574 |
| 169 | 2 | 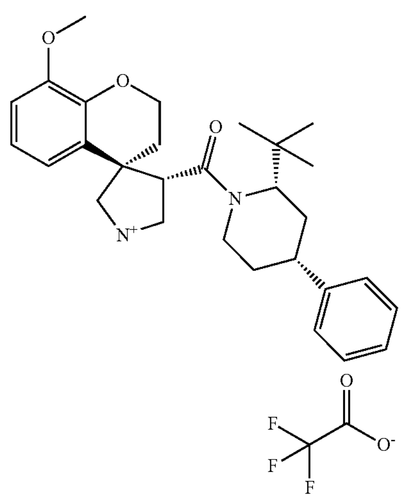 [SMILES: COc1cccc2c1OCC[C@]21C[NH2+]C[C@H]1C(=O)N1CC[C@@H](c2ccccc2)C[C@H]1C(C)(C)C ; O=C([O-])C(F)(F)F] | 462.638 |
| 170 | 2 | 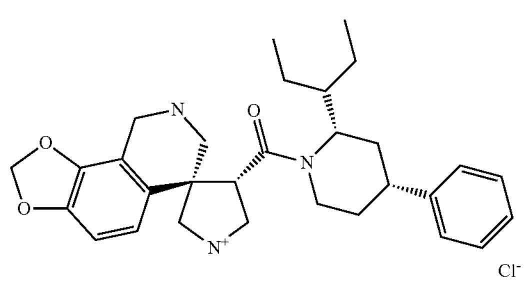 [SMILES: CCC(CC)[C@@H]1C[C@H](c2ccccc2)CCN1C(=O)[C@@H]1C[NH2+]C[C@]12CNCc1c2ccc2c1OCO2 ; [Cl-]] | 489.664 |

TABLE 3-continued

| Ex. No. | Scheme | Structure | Parent MW |
|---|---|---|---|
| 171 | 2 | 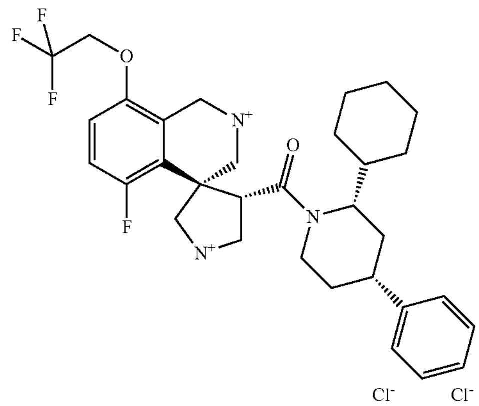 [SMILES: O=C([C@@H]1C[NH2+]C[C@]12C[NH2+]Cc1c(OCC(F)(F)F)ccc(F)c12)N1CC[C@@H](c2ccccc2)C[C@H]1C1CCCCC1 ; [Cl-] ; [Cl-]] | 573.68 |
| 172 | 2 | 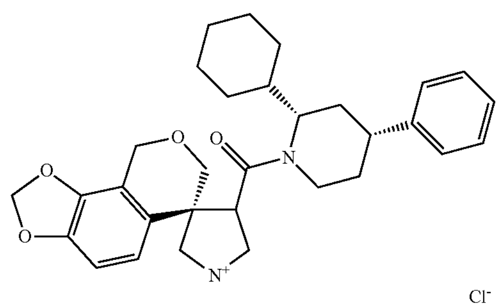 [SMILES: O=C(C1C[NH2+]C[C@]12COCc1c2ccc2c1OCO2)N1CC[C@@H](c2ccccc2)C[C@H]1C1CCCCC1 ; [Cl-]] | 502.66 |
| 173 | 2 | 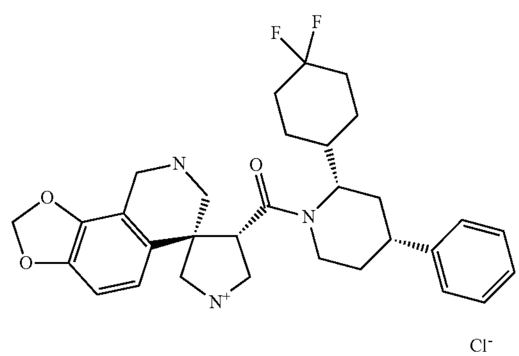 [SMILES: O=C([C@@H]1C[NH2+]C[C@]12CNCc1c2ccc2c1OCO2)N1CC[C@@H](c2ccccc2)C[C@H]1C1CCC(F)(F)CC1 ; [Cl-]] | 537.656 |
| 174 | 2 | 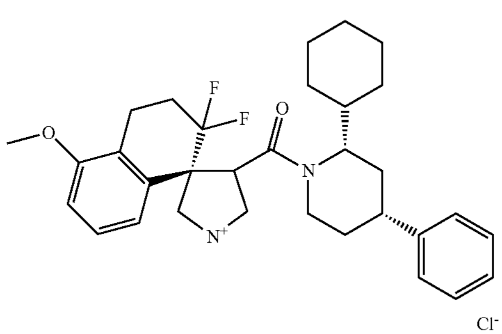 [SMILES: COc1cccc2c1CCC(F)(F)[C@]21C[NH2+]CC1C(=O)N1CC[C@@H](c2ccccc2)C[C@H]1C1CCCCC1 ; [Cl-]] | 522.685 |

TABLE 3-continued

| Ex. No. | Scheme | Structure | Parent MW |
|---|---|---|---|
| 175 | 2 | 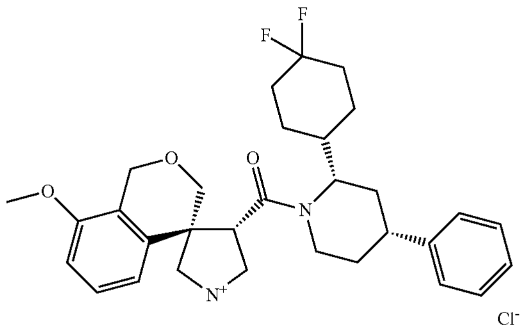 [SMILES: COc1cccc2c1COC[C@]21C[NH2+]C[C@H]1C(=O)N1CC[C@@H](c2ccccc2)C[C@H]1C1CCC(F)(F)CC1 ; [Cl-]] | 524.657 |
| 176 | 2 | 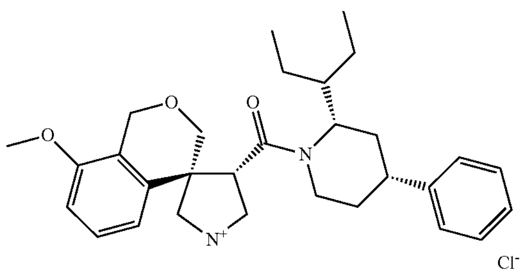 [SMILES: CCC(CC)[C@@H]1C[C@H](c2ccccc2)CCN1C(=O)[C@@H]1C[NH2+]C[C@]12COCc1c(OC)cccc12 ; [Cl-]] | 476.665 |
| 177 | 2 | 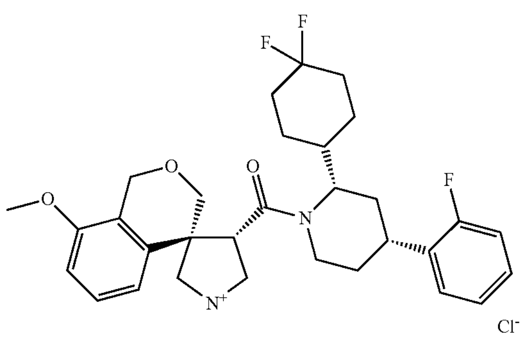 [SMILES: COc1cccc2c1COC[C@]21C[NH2+]C[C@H]1C(=O)N1CC[C@@H](c2ccccc2F)C[C@H]1C1CCC(F)(F)CC1 ; [Cl-]] | 542.647 |
| 178 | 2 | 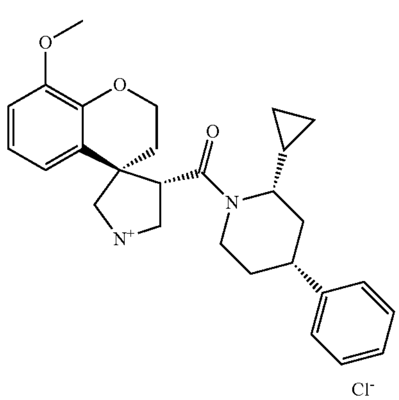 [SMILES: COc1cccc2c1OCC[C@]21C[NH2+]C[C@H]1C(=O)N1CC[C@@H](c2ccccc2)C[C@H]1C1CC1 ; [Cl-]] | 445.595 |

TABLE 3-continued

| Ex. No. | Scheme | Structure | Parent MW |
|---|---|---|---|
| 179 | 2 | 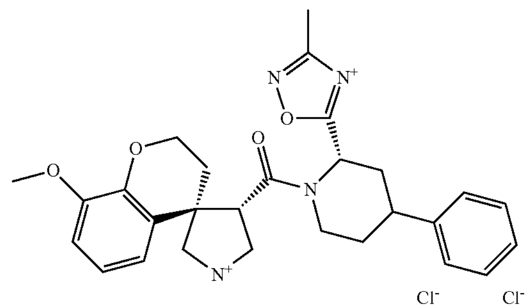 [SMILES: COc1cccc2c1OCC[C@]21C[NH2+]C[C@H]1C(=O)N1CCC(c2ccccc2)C[C@H]1c1[nH+]c(C)no1 ; [Cl-] ; [Cl-]] | 488.592 |
| 180 | 2 | 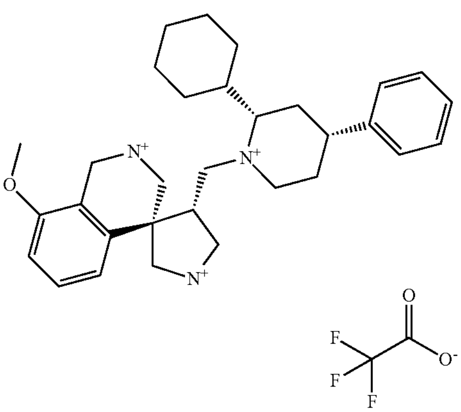 [SMILES: COc1cccc2c1C[NH2+]C[C@]21C[NH2+]C[C@H]1C[NH+]1CC[C@@H](c2ccccc2)C[C@H]1C1CCCCC1 ; O=C([O-])C(F)(F)F] | 473.708 |
| 181 | 2 | 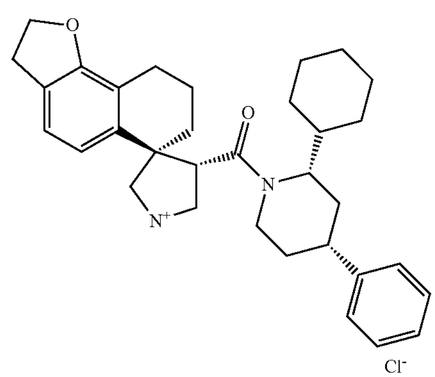 [SMILES: O=C([C@@H]1C[NH2+]C[C@]12CCCc1c2ccc2c1OCC2)N1CC[C@@H](c2ccccc2)C[C@H]1C1CCCCC1 ; [Cl-]] | 498.715 |
| 182 | 2 | 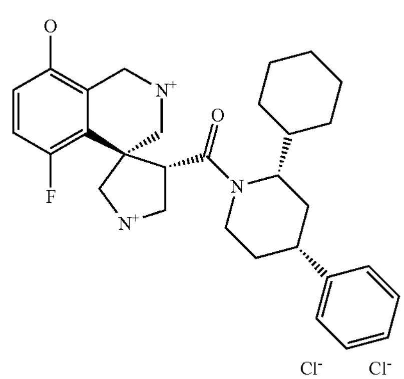 [SMILES: O=C([C@@H]1C[NH2+]C[C@]12C[NH2+]Cc1c(O)ccc(F)c12)N1CC[C@@H](c2ccccc2)C[C@H]1C1CCCCC1 ; [Cl-] ; [Cl-]] | 491.655 |

TABLE 3-continued

| Ex. No. | Scheme | Structure | Parent MW |
|---|---|---|---|
| 183 | 2 | 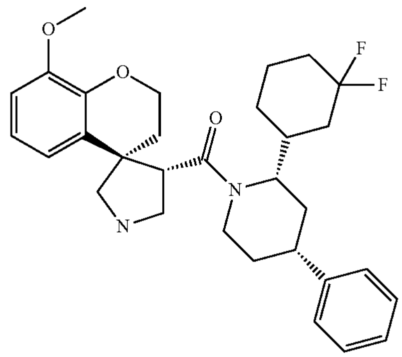 [SMILES: COc1cccc2c1OCC[C@]21CNC[C@H]1C(=O)N1CC[C@@H](c2ccccc2)C[C@H]1C1CCCC(F)(F)C1] | 524.657 |
| 184 | 2 | 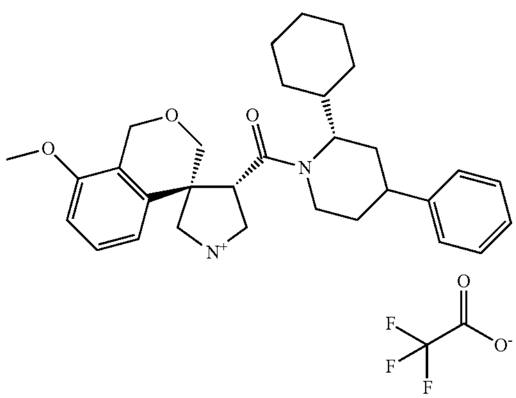 [SMILES: COc1cccc2c1COC[C@]21C[NH2+]C[C@H]1C(=O)N1CCC(c2ccccc2)C[C@H]1C1CCCCC1 ; O=C([O-])C(F)(F)F] | 488.676 |
| 185 | 2 | 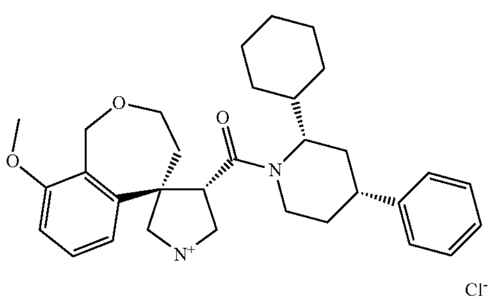 [SMILES: COc1cccc2c1COCC[C@]21C[NH2+]C[C@H]1C(=O)N1CC[C@@H](c2ccccc2)C[C@H]1C1CCCCC1 ; [Cl-]] | 502.703 |
| 186 | 2 | 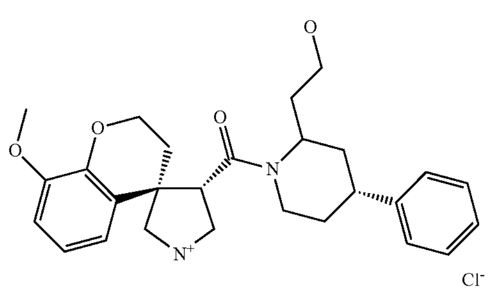 [SMILES: COc1cccc2c1OCC[C@]21C[NH2+]C[C@H]1C(=O)N1CC[C@@H](c2ccccc2)CC1CCO ; [Cl-]] | 450.583 |

TABLE 3-continued

| Ex. No. | Scheme | Structure | Parent MW |
|---|---|---|---|
| 187 | 2 | 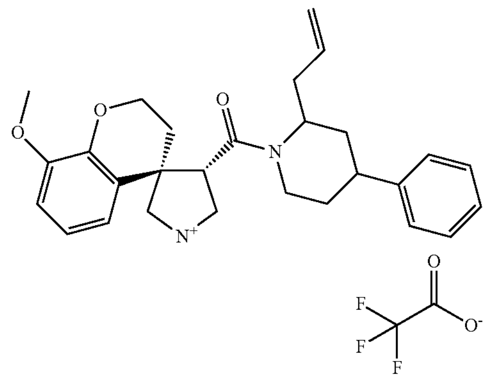 [SMILES: C=CCC1CC(c2ccccc2)CCN1C(=O)[C@@H]1C[NH2+]C[C@]12CCOc1c(OC)cccc12 ; O=C([O-])C(F)(F)F] | 446.595 |
| 188 | 2 | 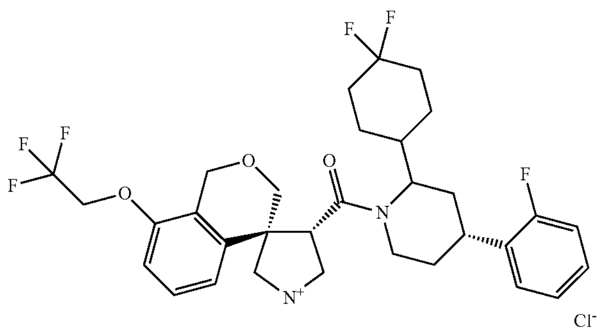 [SMILES: O=C([C@@H]1C[NH2+]C[C@]12COCc1c(OCC(F)(F)F)cccc12)N1CC[C@@H](c2ccccc2F)CC1C1CCC(F)(F)CC1 ; [Cl-]] | 610.646 |
| 189 | 2 | 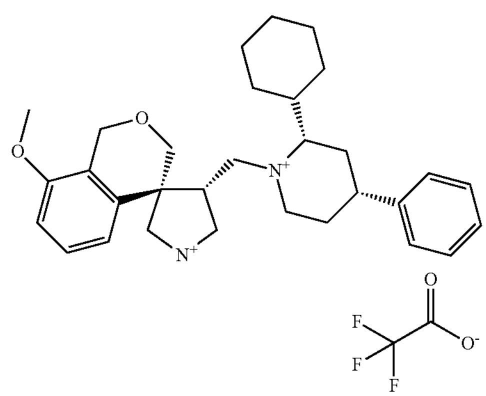 | 474.693 |
| 190 | 2 | 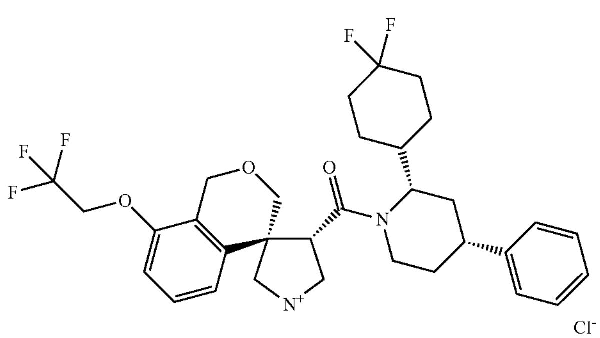 [SMILES: O=C([C@@H]1C[NH2+]C[C@]12COCc1c(OCC(F)(F)F)cccc12)N1CC[C@@H](c2ccccc2)C[C@H]1C1CCC(F)(F)CC1 ; [Cl-]] | 592.655 |

TABLE 3-continued

| Ex. No. | Scheme | Structure | Parent MW |
|---|---|---|---|
| 191 | 2 | 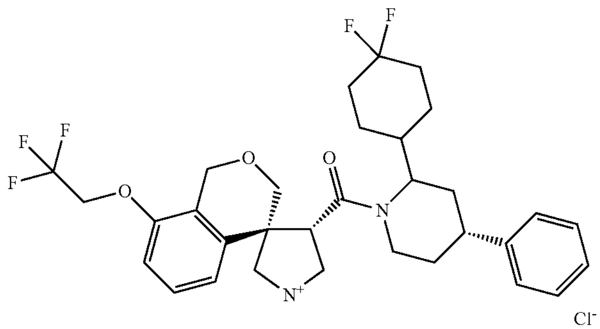 [SMILES: O=C([C@@H]1C[NH2+]C[C@]12COCc1c(OCC(F)(F)F)cccc12)N1CC[C@@H](c2ccccc2)CC1C1CCC(F)(F)CC1 ; [Cl-]] | 544.663 |
| 192 | 2 | 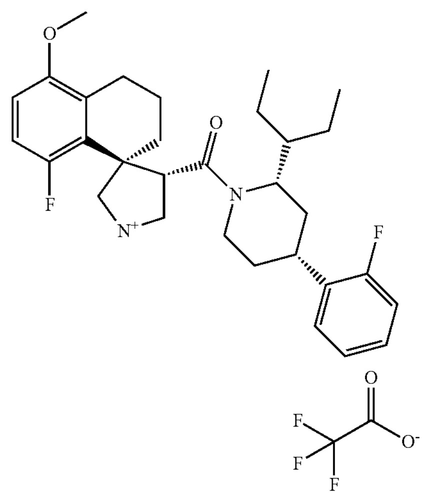 [SMILES: CCC(CC)[C@@H]1C[C@H](c2ccccc2F)CCN1C(=O)[C@@H]1C[NH2+]C[C@]12CCCc1c(OC)ccc(F)c12 ; O=C([O-])C(F)(F)F] | 570.673 |
| 193 | 2 | 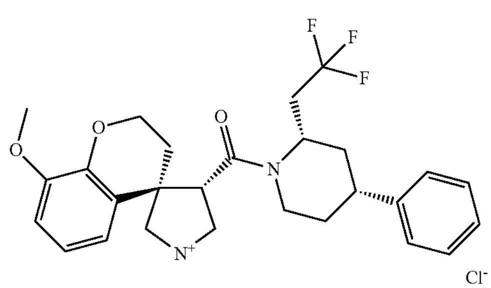 [SMILES: COc1cccc2c1OCC[C@]21C[NH2+]C[C@H]1C(=O)N1CC[C@@H](c2ccccc2)C[C@H]1CC(F)(F)F ; [Cl-]] | 488.555 |
| 194 | 2 | 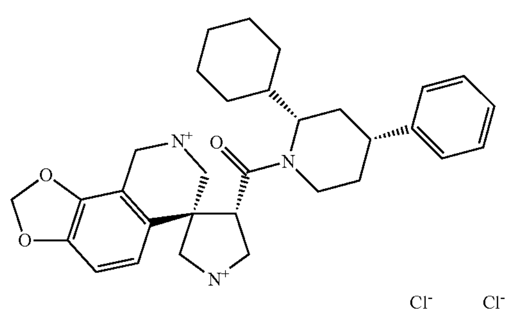 [SMILES: O=C([C@@H]1C[NH2+]C[C@]12C[NH2+]Cc1c2ccc2c1OCO2)N1CC[C@@H](c2ccccc2)C[C@H]1C1CCCCC1 ; [Cl-] ; [Cl-]] | 501.675 |

TABLE 3-continued
| Ex. No. | Scheme | Structure | Parent MW |
|---|---|---|---|
| 195 | 2 | 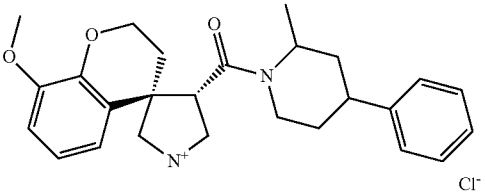 [SMILES: COc1cccc2c1OCC[C@]21C[NH2+]C[C@H]1C(=O)N1CCC(c2ccccc2)CC1C ; [Cl-]] | 420.557 |
| 196 | 2 | 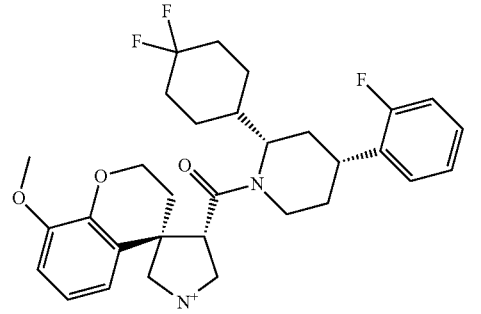 | 542.647 |
| 197 | 2 | 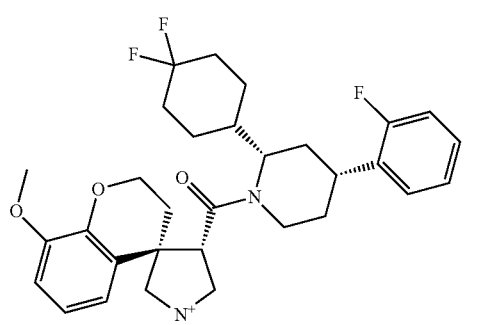 | 420.557 |
| 198 | 2 | 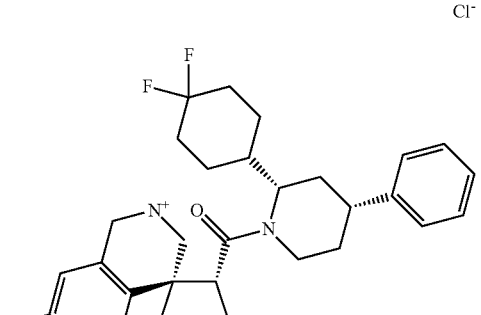 | 507.673 |
| 199 | 2 | 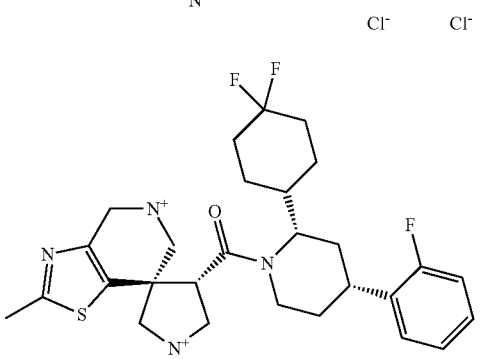 | 532.677 |

TABLE 3-continued
| Ex. No. | Scheme | Structure | Parent MW |
|---|---|---|---|
| 200 | 2 | 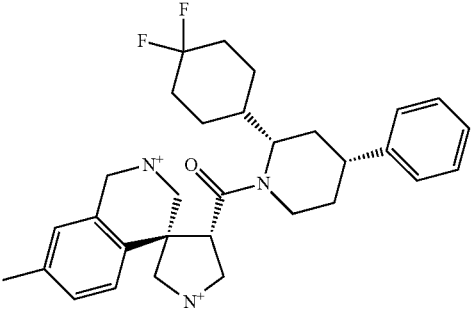 | 525.663 |
| 201 | 2 | 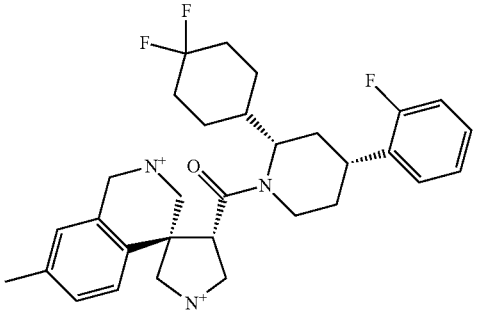 | 507.673 |
| 202 | 2 | 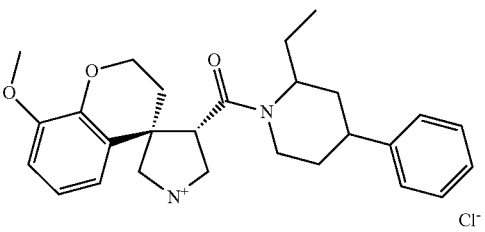 [SMILES: CCC1CC(c2ccccc2)CCN1C(=O)[C@@H]1C[NH2+]C[C@]12CCOc1c(OC)cccc12 ; [Cl-]] | 434.584 |
| 203 | 2 | 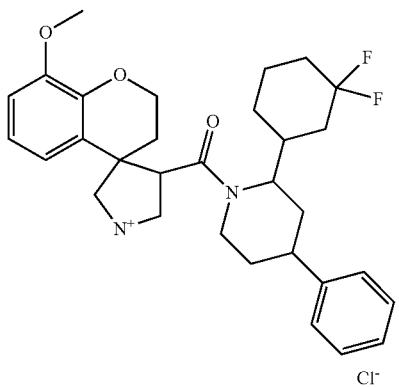 [SMILES: COc1cccc2c1OCCC21C[NH2+]CC1C(=O)N1CCC(c2ccccc2)CC1C1CCCC(F)(F)C1 ; [Cl-]] | 522.685 |

TABLE 3-continued

| Ex. No. | Scheme | Structure | Parent MW |
|---|---|---|---|
| 204 | 2 | 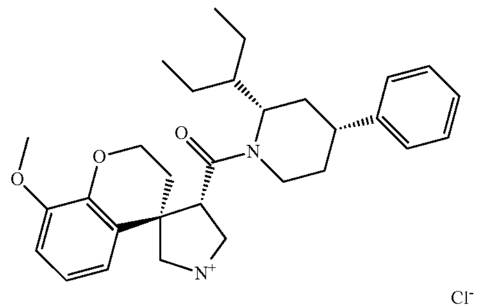 [SMILES: CCC(CC)[C@@H]1C[C@H](c2ccccc2)CCN1C(=O)[C@@H]1C[NH2+]C[C@]12CCOc1c(OC)cccc12 ; [Cl-]] | 476.665 |
| 205 | 2 | 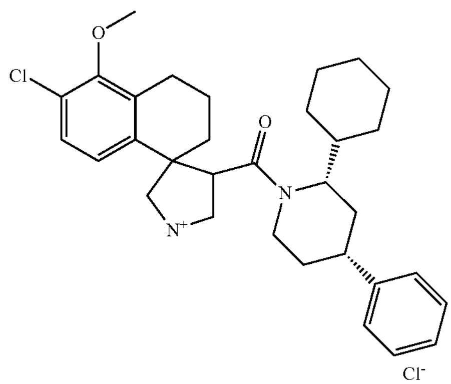 [SMILES: COc1c(Cl)ccc2c1CCCC21C[NH2+]CC1C(=O)N1CC[C@@H](c2ccccc2)C[C@H]1C1CCCCC1 ; [Cl-]] | 521.149 |
| 206 | 2 | 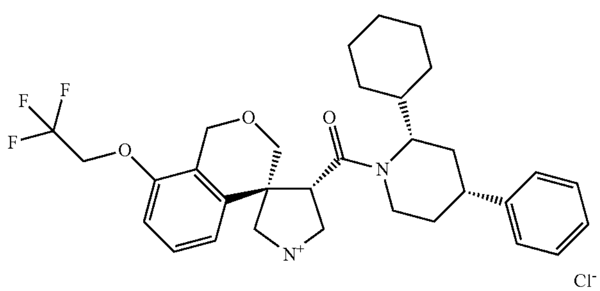 [SMILES: O=C([C@@H]1C[NH2+]C[C@]12COCc1c(OCC(F)(F)F)cccc12)N1CC[C@@H](c2ccccc2)C[C@H]1C1CCCCC1 ; [Cl-]] | 556.674 |
| 207 | 2 | 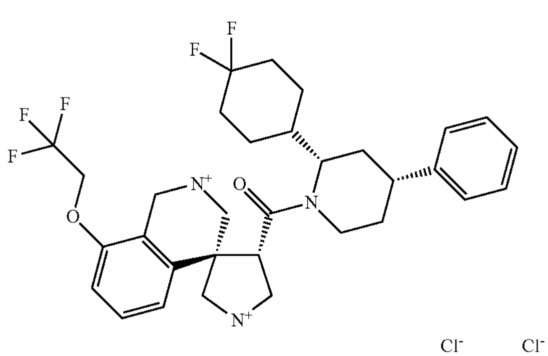 | 591.671 |

TABLE 3-continued
| Ex. No. | Scheme | Structure | Parent MW |
|---|---|---|---|
| 208 | 2 | 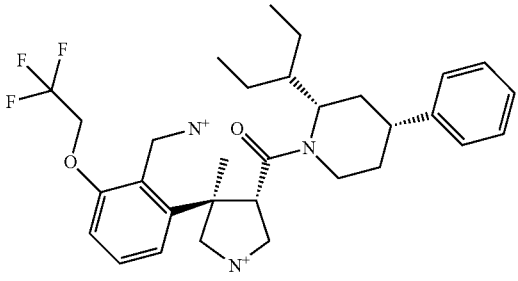 | 543.679 |
| 209 | 2 | 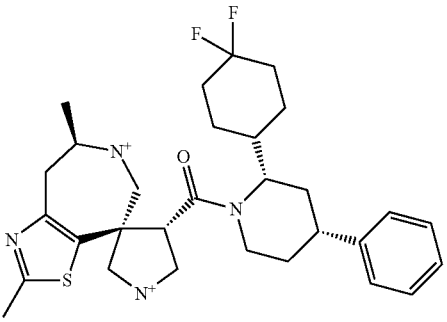 | 542.74 |
| 210 | 2 | 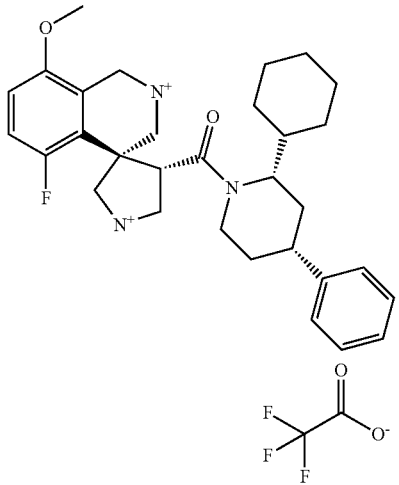 [SMILES: COc1ccc(F)c2c1C[NH2+]C[C@]21C[NH2+]C[C@H]1C(=O)N1CC[C@@H](c2ccccc2)C[C@H]1C1CCCCC1 ; O=C([O-])C(F)(F)F] | 505.682 |
| 211 | 2 | 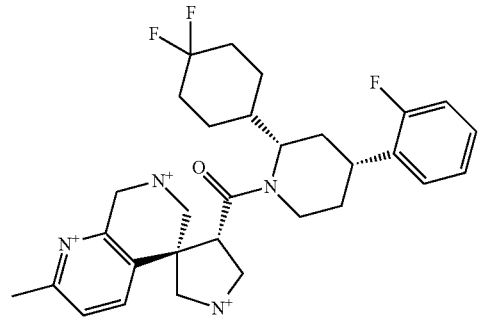 | 526.651 |

TABLE 3-continued

| Ex. No. | Scheme | Structure | Parent MW |
|---|---|---|---|
| 212 | 2 | 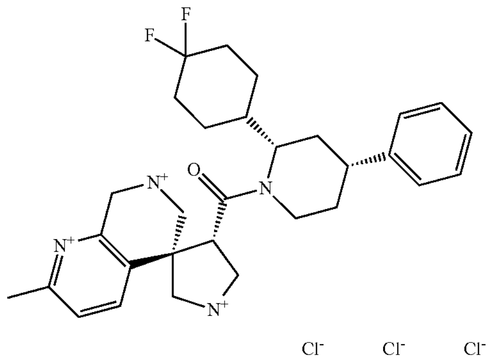 [SMILES: Cc1ccc2c([nH+]1)C[NH2+]C[C@]21C[NH2+]C[C@H]1C(=O)N1CC[C@@H](c2ccccc2)C[C@H]1C1CCC(F)(F)CC1 ; [Cl-] ; [Cl-] ; [Cl-]] | 508.66 |
| 213 | 2 | 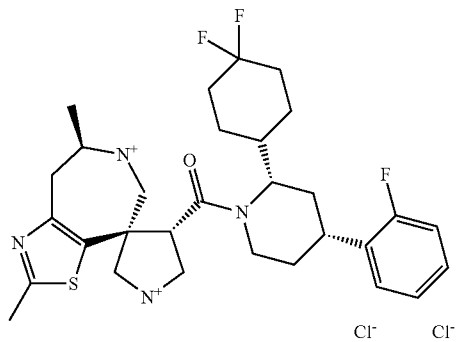 [SMILES: Cc1nc2c(s1)[C@@]1(C[NH2+]C[C@H]1C(=O)N1CC[C@@H](c3ccccc3F)C[C@H]1C1CCC(F)(F)CC1)C[NH2+][C@H](C)C2 ; [Cl-] ; [Cl-]] | 560.731 |
| 214 | 2 | 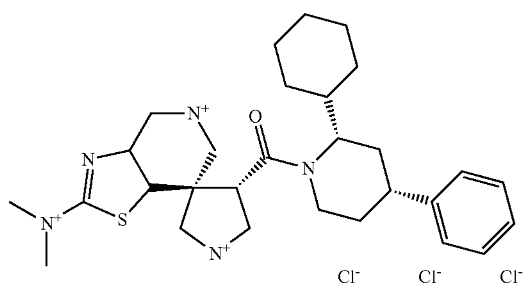 | 509.763 |
| 215 | 2 | 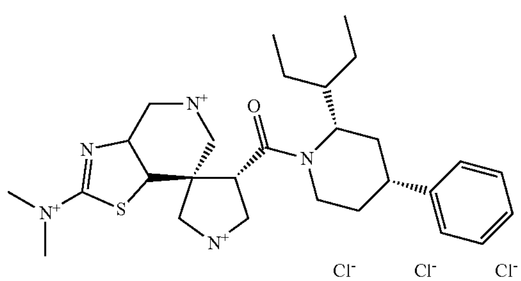 | 497.752 |
| 216 | 2 | 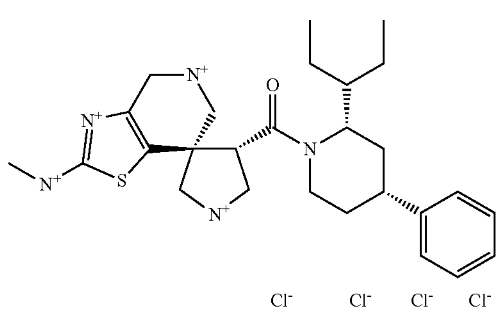 [SMILES: CCC(CC)[C@@H]1C[C@H](c2ccccc2)CCN1C(=O)[C@@H]1C[NH2+]C[C@]12C[NH2+]Cc1[nH+]c([NH2+]C)sc12 ; [Cl-] ; [Cl-] ; [Cl-] ; [Cl-]] | 481.709 |

TABLE 3-continued
| Ex. No. | Scheme | Structure | Parent MW |
|---|---|---|---|
| 217 | 2 | 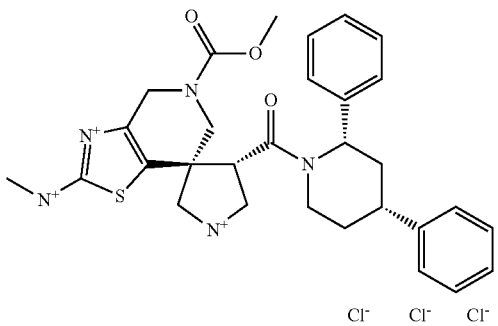 [SMILES: C[NH2+]c1[nH+]c2c(s1)[C@@]1(C[NH2+]C[C@H]1C(=O)N1CC[C@@H](c3ccccc3)C[C@H]1c1ccccc1)CN(C(=O)OC)C2 ; [Cl-] ; [Cl-] ; [Cl-]] | 545.709 |
| 218 | 2 | 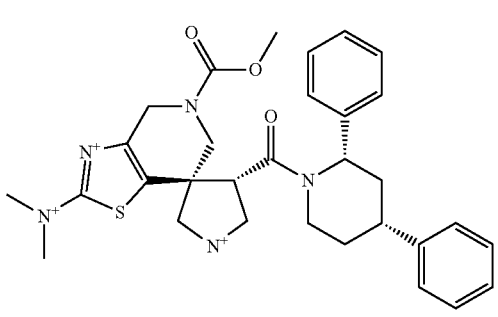 | 559.736 |
| 219 | 2 | 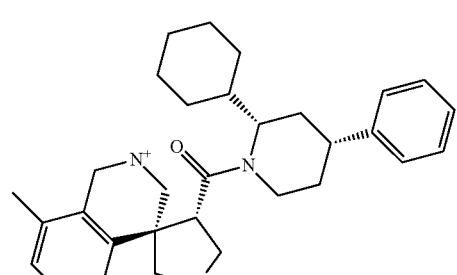 | 471.692 |
| 220 | 2 | 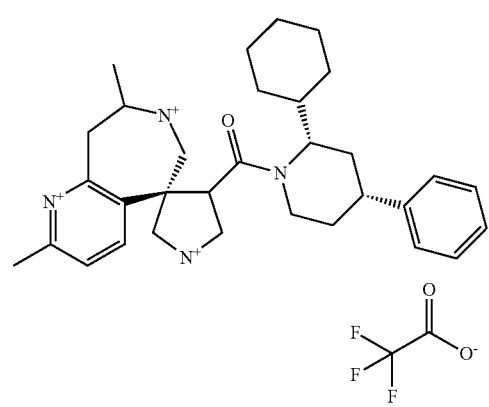 | 500.734 |

TABLE 3-continued

| Ex. No. | Scheme | Structure | Parent MW |
|---|---|---|---|
| 221 | 2 | 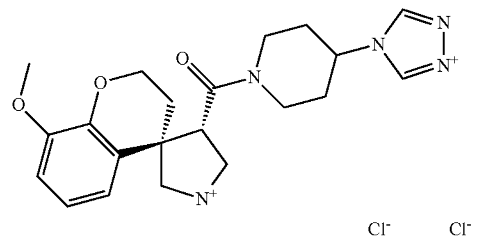 [SMILES: COc1cccc2c1OCC[C@]21C[NH2+]C[C@H]1C(=O)N1CCC(n2cn[nH+]c2)CC1 ; [Cl-] ; [Cl-]] | 397.481 |
| 222 | 2 | 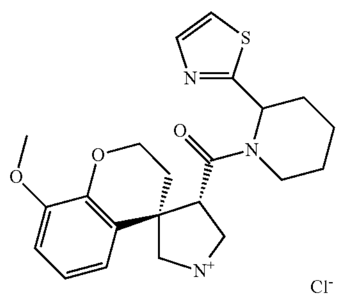 [SMILES: COc1cccc2c1OCC[C@]21C[NH2+]C[C@H]1C(=O)N1CCCCC1c1nccs1 ; [Cl-]] | 413.543 |
| 223 | 2 | 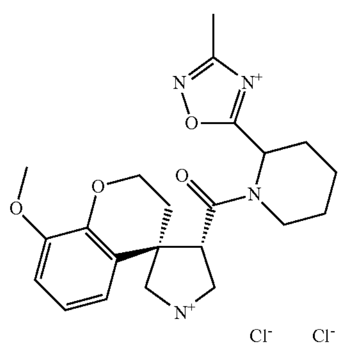 [SMILES: COc1cccc2c1OCC[C@]21C[NH2+]C[C@H]1C(=O)N1CCCCC1c1[nH+]c(C)no1 ; [Cl-] ; [Cl-]] | 412.493 |
| 224 | 2 | 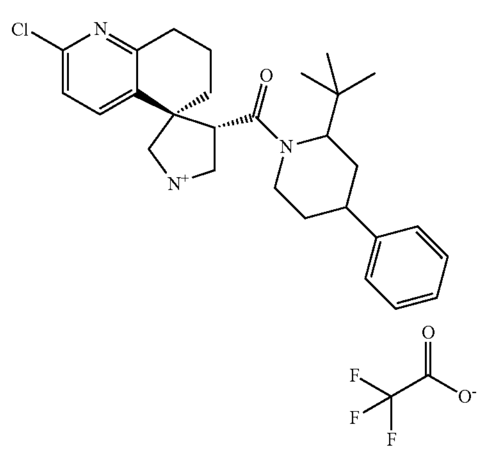 [SMILES: CC(C)(C)C1CC(c2ccccc2)CCN1C(=O)[C@@H]1C[NH2+]C[C@]12CCCc1nc(Cl)ccc12 ; O=C([O-])C(F)(F)F] | 466.072 |

TABLE 3-continued

| Ex. No. | Scheme | Structure | Parent MW |
|---|---|---|---|
| 225 | 2 | 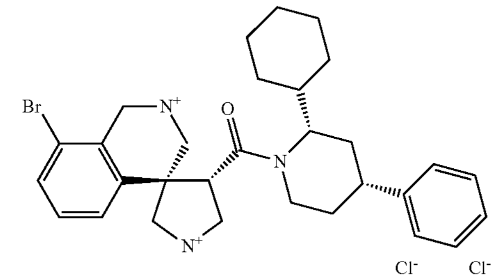 [SMILES: O=C([C@@H]1C[NH2+]C[C@]12C[NH2+]Cc1c(Br)cccc12)N1CC[C@@H](c2ccccc2)C[C@H]1C1CCCCC1 ; [Cl-] ; [Cl-]] | 536.561 |
| 226 | 2 | 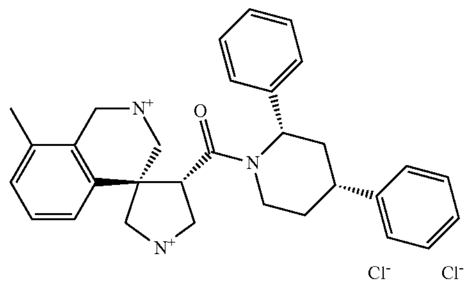 [SMILES: Cc1cccc2c1C[NH2+]C[C@]21C[NH2+]C[C@H]1C(=O)N1CC[C@@H](c2ccccc2)C[C@H]1c1ccccc1 ; [Cl-] ; [Cl-]] | 465.644 |
| 227 | 2 | 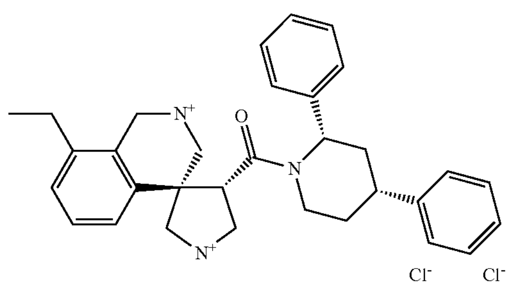 [SMILES: CCc1cccc2c1C[NH2+]C[C@]21C[NH2+]C[C@H]1C(=O)N1CC[C@@H](c2ccccc2)C[C@H]1c1ccccc1 ; [Cl-] ; [Cl-]] | 479.671 |
| 228 | 2 | 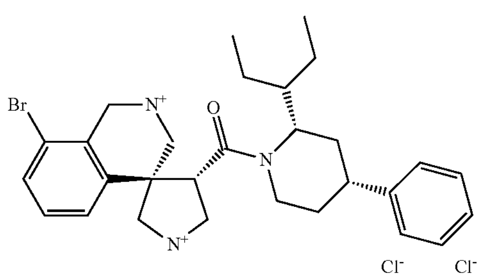 [SMILES: CCC(CC)[C@@H]1C[C@H](c2ccccc2)CCN1C(=O)[C@@H]1C[NH2+]C[C@]12C[NH2+]Cc1c(Br)cccc12 ; [Cl-] ; [Cl-]] | 524.55 |
| 229 | 2 | 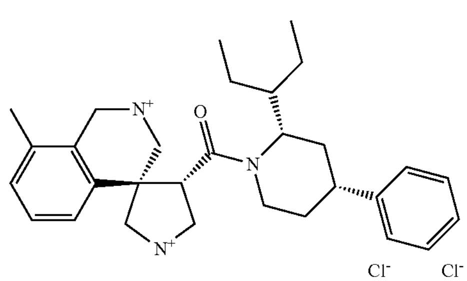 [SMILES: CCC(CC)[C@@H]1C[C@H](c2ccccc2)CCN1C(=O)[C@@H]1C[NH2+]C[C@]12C[NH2+]Cc1c(C)cccc12 ; [Cl-] ; [Cl-]] | 459.681 |

TABLE 3-continued

| Ex. No. | Scheme | Structure | Parent MW |
|---|---|---|---|
| 230 | 2 | 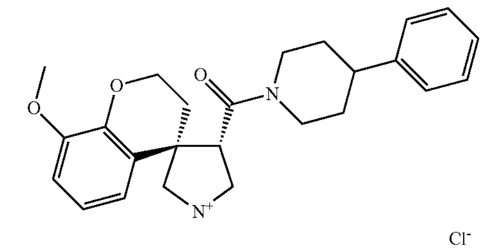 [SMILES: COc1cccc2c1OCC[C@]21C[NH2+]C[C@H]1C(=O)N1CCC(c2ccccc2)CC1 ; [Cl-]] | 406.529 |
| 231 | 2 | 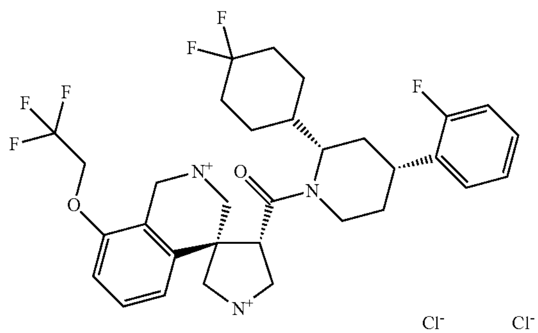 [SMILES: O=C([C@@H]1C[NH2+]C[C@]12C[NH2+]Cc1c(OCC(F)(F)F)cccc12)N1CC[C@@H](c2ccccc2F)C[C@H]1C1CCC(F)(F)CC1 ; [Cl-] ; [Cl-]] | 609.661 |
| 232 | 2 | 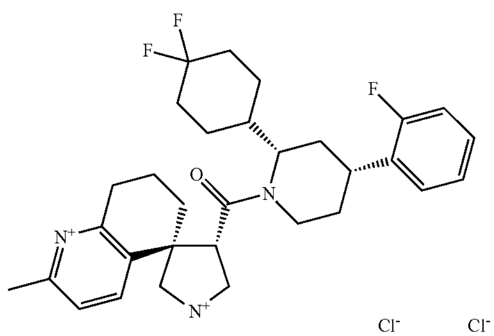 [SMILES: Cc1ccc2c([nH+]1)CCC[C@]21C[NH2+]C[C@H]1C(=O)N1CC[C@@H](c2ccccc2F)C[C@H]1C1CCC(F)(F)CC1 ; [Cl-] ; [Cl-]] | 525.663 |
| 233 | 2 | 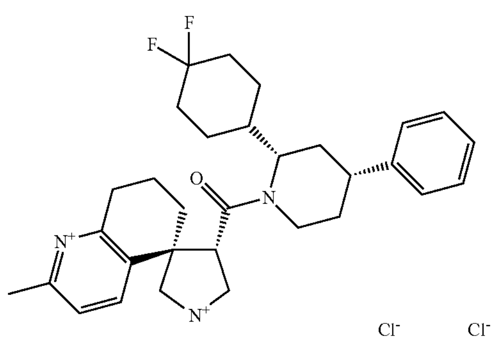 [SMILES: Cc1ccc2c([nH+]1)CCC[C@]21C[NH2+]C[C@H]1C(=O)N1CC[C@@H](c2ccccc2)C[C@H]1C1CCC(F)(F)CC1 ; [Cl-] ; [Cl-]] | 507.673 |
| 234 | 2 | 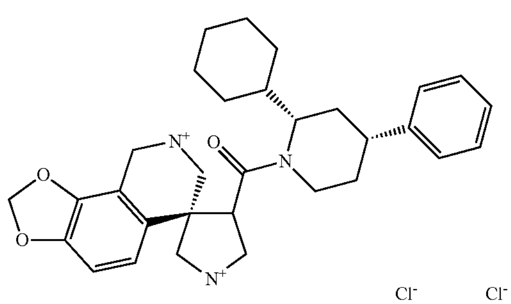 [SMILES: O=C(C1C[NH2+]C[C@]12C[NH2+]Cc1c2ccc2c1OCO2)N1CC[C@@H](c2ccccc2)C[C@H]1C1CCCCC1 ; [Cl-] ; [Cl-]] | 501.675 |

TABLE 3-continued

| Ex. No. | Scheme | Structure | Parent MW |
|---|---|---|---|
| 235 | 2 | 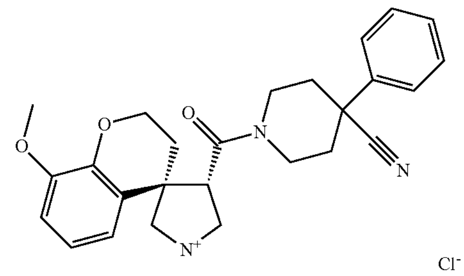 [SMILES: COc1cccc2c1OCC[C@]21C[NH2+]C[C@H]1C(=O)N1CCC(C#N)(c2ccccc2)CC1 ; [Cl-]] | 431.539 |
| 236 | 2 | 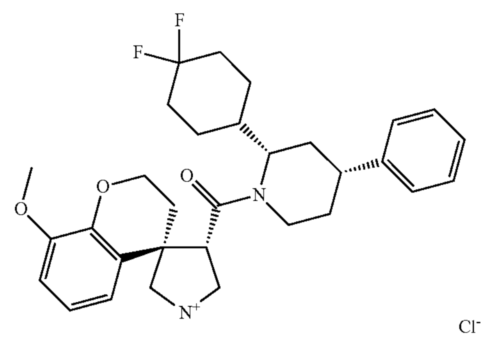 [SMILES: COc1cccc2c1OCC[C@]21C[NH2+]C[C@H]1C(=O)N1CC[C@@H](c2ccccc2)C[C@H]1C1CCC(F)(F)CC1 ; [Cl-]] | 524.657 |
| 237 | 2 | 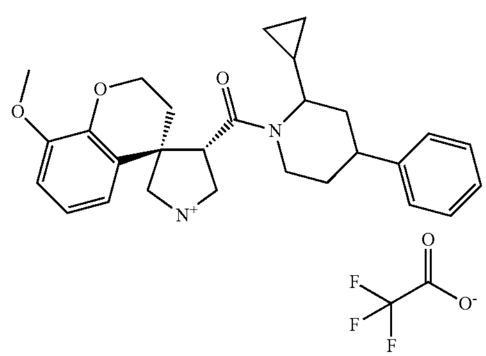 [SMILES: COc1cccc2c1OCC[C@]21C[NH2+]C[C@H]1C(=O)N1CCC(c2ccccc2)CC1C1CC1 ; O=C([O-])C(F)(F)F] | 446.595 |
| 238 | 2 | 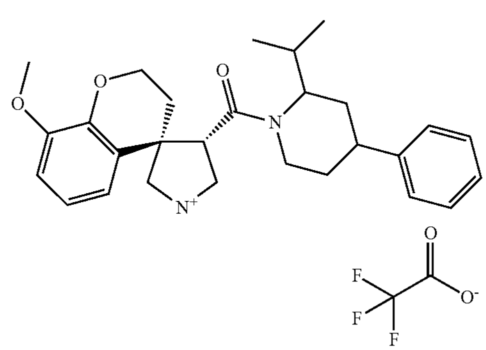 [SMILES: COc1cccc2c1OCC[C@]21C[NH2+]C[C@H]1C(=O)N1CCC(c2ccccc2)CC1C(C)C ; O=C([O-])C(F)(F)F] | 448.611 |

TABLE 3-continued

| Ex. No. | Scheme | Structure | Parent MW |
|---|---|---|---|
| 239 | 2 | 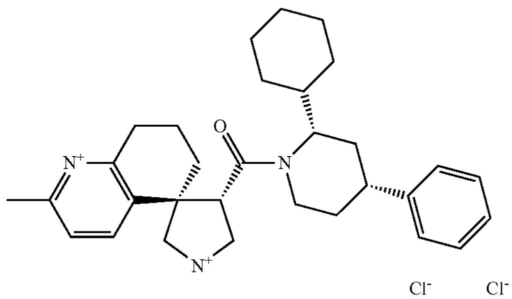 [SMILES: Cc1ccc2c([nH+]1)CCC[C@]21C[NH2+]C[C@H]1C(=O)N1CC[C@@H](c2ccccc2)C[C@H]1C1CCCCC1 ; [Cl-] ; [Cl-]] | 471.692 |
| 240 | 2 | 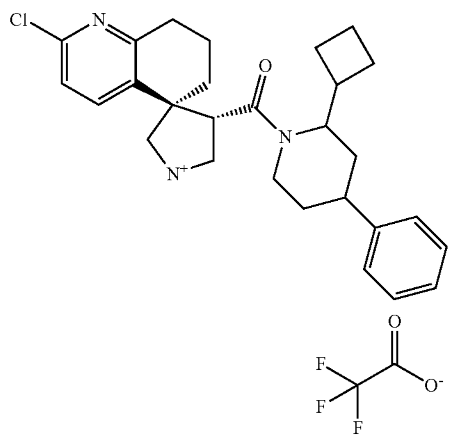 [SMILES: O=C([C@@H]1C[NH2+]C[C@]12CCCc1nc(Cl)ccc12)N1CCC(c2ccccc2)CC1C1CCC1 ; O=C([O-])C(F)(F)F] | 464.056 |
| 241 | 2 | 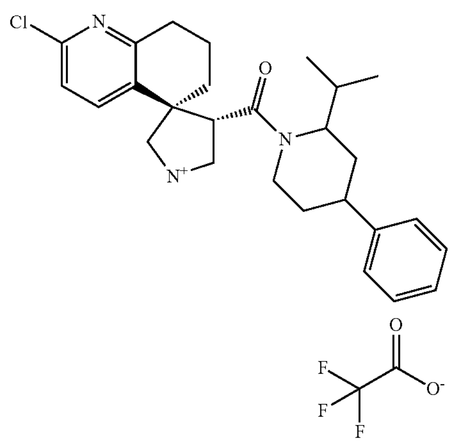 [SMILES: CC(C)C1CC(c2ccccc2)CCN1C(=O)[C@@H]1C[NH2+]C[C@]12CCCc1nc(Cl)ccc12 ; O=C([O-])C(F)(F)F] | 452.045 |
| 242 | 2 | 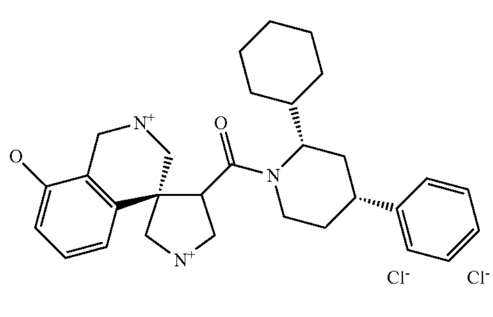 [SMILES: O=C(C1C[NH2+]C[C@]12C[NH2+]Cc1c(O)cccc12)N1CC[C@@H](c2ccccc2)C[C@H]1C1CCCCC1 ; [Cl-] ; [Cl-]] | 473.664 |

TABLE 3-continued
| Ex. No. | Scheme | Structure | Parent MW |
|---|---|---|---|
| 243 | 2 | 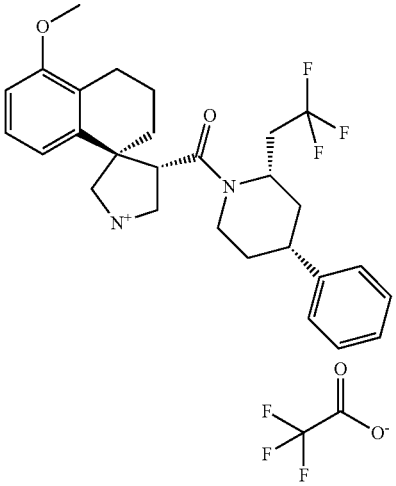 [SMILES: COc1cccc2c1CCC[C@]21C[NH2+]C[C@H]1C(=O)N1CC[C@@H](c2ccccc2)C[C@H]1CC(F)(F)F ; O=C([O-])C(F)(F)F] | 486.583 |
| 244 | 2 | 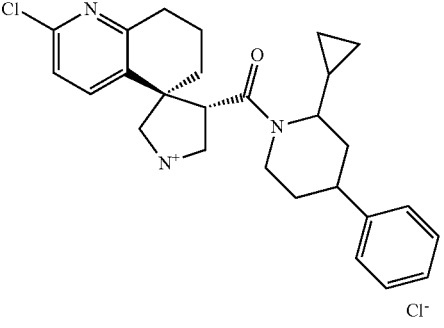 [SMILES: O=C([C@@H]1C[NH2+]C[C@]12CCCc1nc(Cl)ccc12)N1CCC(c2ccccc2)CC1C1CC1 ; [Cl-]] | 450.029 |
| 245 | 2 | 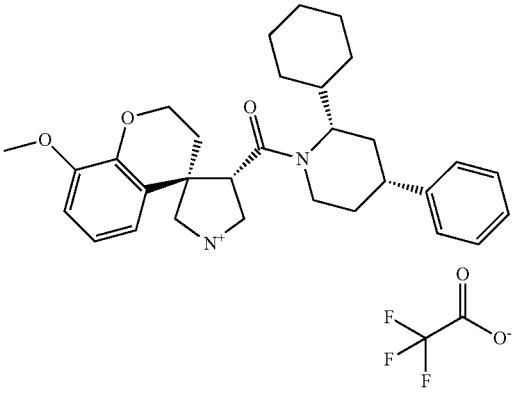 [SMILES: COc1cccc2c1OCC[C@]21C[NH2+]C[C@H]1C(=O)N1CC[C@@H](c2ccccc2)C[C@H]1C1CCCCC1 ; O=C([O-])C(F)(F)F] | 488.676 |
| 246 | 2 | 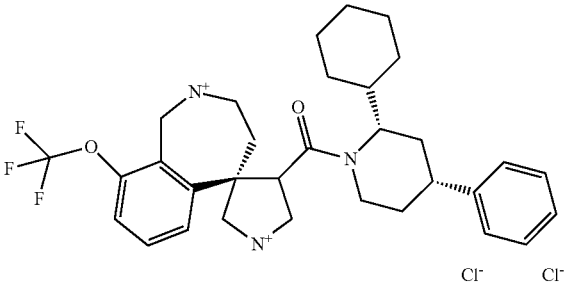 [SMILES: O=C(C1C[NH2+]C[C@]12CC[NH2+]Cc1c(OC(F)(F)F)cccc12)N1CC[C@@H](c2ccccc2)C[C@H]1C1CCCCC1 ; [Cl-] ; [Cl-]] | 555.69 |

TABLE 3-continued

| Ex. No. | Scheme | Structure | Parent MW |
|---|---|---|---|
| 247 | 2 | 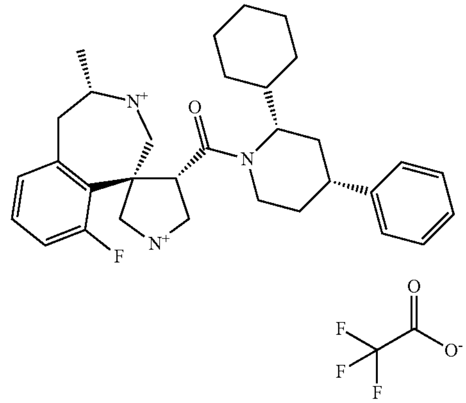 [SMILES: C[C@H]1Cc2cccc(F)c2[C@@]2(C[NH2+]C[C@H]2C(=O)N2CC[C@@H](c3ccccc3)C[C@H]2C2CCCCC2)C[NH2+]1 ; O=C([O-])C(F)(F)F] | 503.709 |
| 248 | 2 | 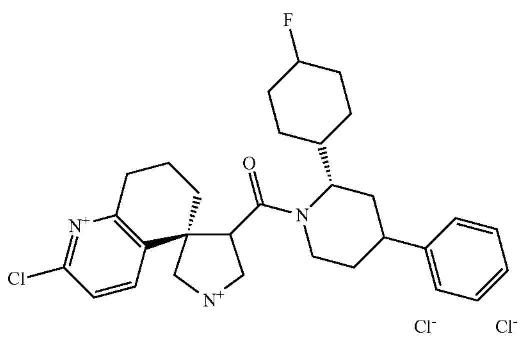 [SMILES: O=C(C1C[NH2+]C[C@]12CCCc1[nH+]c(Cl)ccc12)N1CCC(c2ccccc2)C[C@H]1C1CCC(F)CC1 ; [Cl-] ; [Cl-]] | 510.1 |
| 249 | 2 | 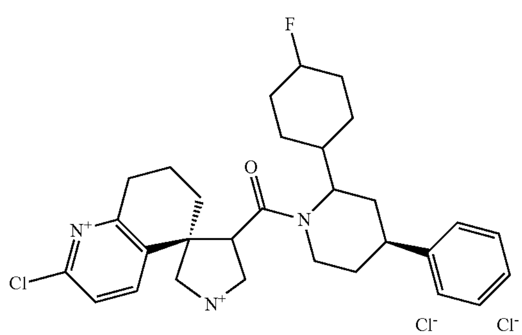 [SMILES: O=C(C1C[NH2+]C[C@]12CCCc1[nH+]c(Cl)ccc12)N1CC[C@H](c2ccccc2)CC1C1CCC(F)CC1 ; [Cl-] ; [Cl-]] | 510.1 |
| 250 | 2 | 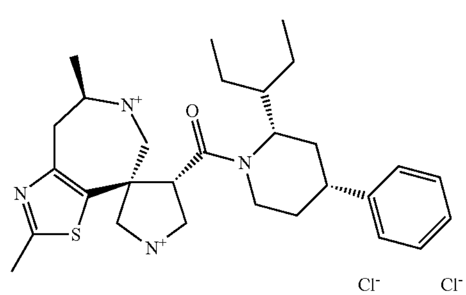 [SMILES: CCC(CC)[C@@H]1C[C@H](c2ccccc2)CCN1C(=O)[C@@H]1C[NH2+]C[C@]12C[NH2+][C@H](C)Cc1nc(C)sc12 ; [Cl-] ; [Cl-]] | 494.748 |

TABLE 3-continued
| Ex. No. | Scheme | Structure | Parent MW |
|---|---|---|---|
| 251 | 2 | 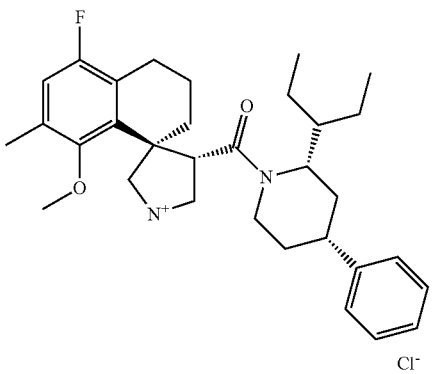 [SMILES: CCC(CC)[C@@H]1C[C@H](c2ccccc2)CCN1C(=O)[C@@H]1C[NH2+]C[C@]12CCCc1c(F)cc(C)c(OC)c12 ; [Cl-]] | 506.71 |
| 252 | 2 | 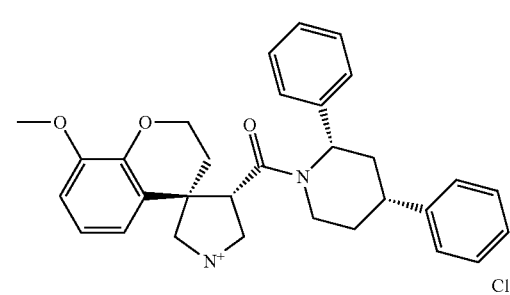 [SMILES: COc1cccc2c1OCC[C@]21C[NH2+]C[C@H]1C(=O)N1CC[C@@H](c2ccccc2)C[C@H]1c1ccccc1 ; [Cl-]] | 482.628 |
| 253 | 2 | 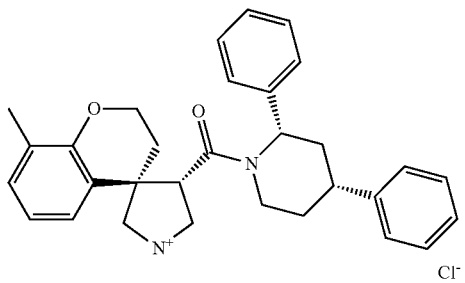 | 466.629 |
| 254 | 2 | 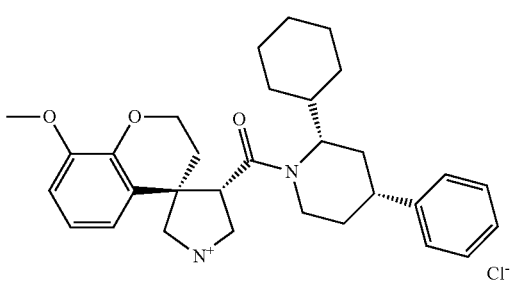 [SMILES: COc1cccc2c1OCC[C@]21C[NH2+]C[C@H]1C(=O)N1CC[C@@H](c2ccccc2)C[C@H]1C1CCCCC1 ; [Cl-]] | 488.676 |
| 255 | 2 | 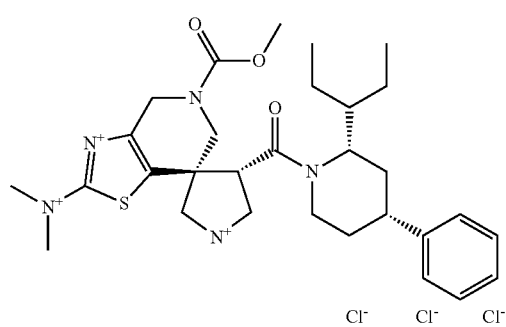 [SMILES: CCC(CC)[C@@H]1C[C@H](c2ccccc2)CCN1C(=O)[C@@H]1C[NH2+]C[C@]12CN(C(=O)OC)Cc1[nH+]c([NH+](C)C)sc12 ; [Cl-] ; [Cl-] ; [Cl-]] | 553.773 |

TABLE 3-continued

| Ex. No. | Scheme | Structure | Parent MW |
|---|---|---|---|
| 256 | 2 | 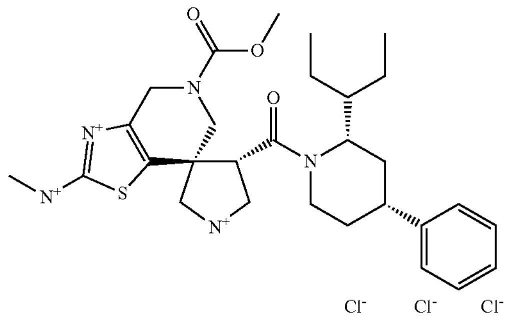 [SMILES: CCC(CC)[C@@H]1C[C@H](c2ccccc2)CCN1C(=O)[C@@H]1C[NH2+]C[C@]12CN(C(=O)OC)Cc1[nH+]c([NH2+]C)sc12 ; [Cl-] ; [Cl-] ; [Cl-]] | 539.746 |
| 257 | 2 | 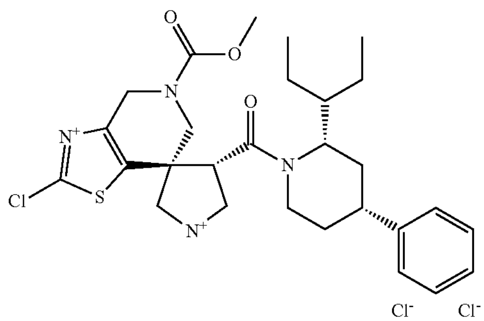 [SMILES: CCC(CC)[C@@H]1C[C@H](c2ccccc2)CCN1C(=O)[C@@H]1C[NH2+]C[C@]12CN(C(=O)OC)Cc1[nH+]c(Cl)sc12 ; [Cl-] ; [Cl-]] | 545.149 |
| 258 | 2 | 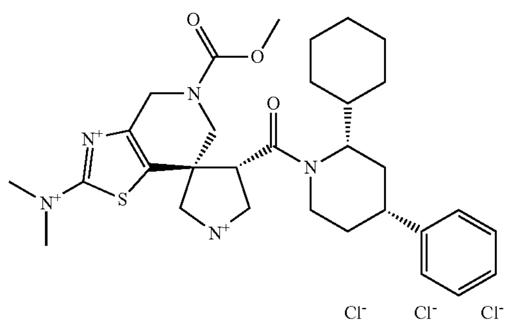 [SMILES: COC(=O)N1Cc2[nH+]c([NH+](C)C)sc2[C@@]2(C[NH2+]C[C@H]2C(=O)N2CC[C@@H](c3ccccc3)C[C@H]2C2CCCCC2)C1 ; [Cl-] ; [Cl-] ; [Cl-]] | 565.784 |
| 259 | 2 | 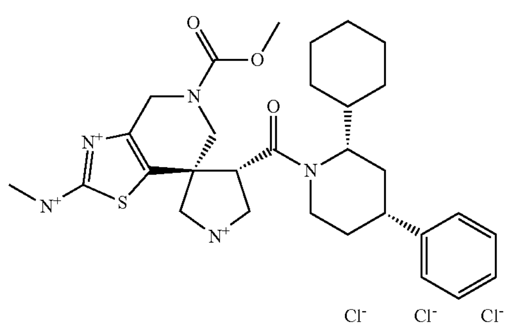 [SMILES: C[NH2+]c1[nH+]c2c(s1)[C@@]1(C[NH2+]C[C@H]1C(=O)N1CC[C@@H](c3ccccc3)C[C@H]1C1CCCCC1)CN(C(=O)OC)C2 ; [Cl-] ; [Cl-] ; [Cl-]] | 551.757 |
| 260 | 2 | 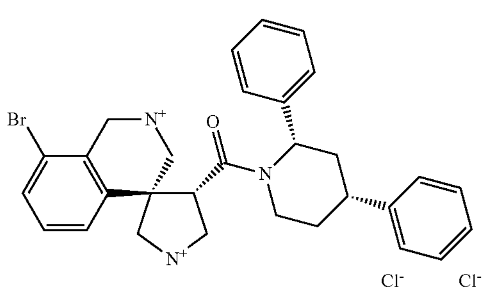 [SMILES: O=C([C@@H]1C[NH2+]C[C@]12C[NH2+]Cc1c(Br)cccc12)N1CC[C@@H](c2ccccc2)C[C@H]1c1ccccc1 ; [Cl-] ; [Cl-]] | 530.513 |

TABLE 3-continued
| Ex. No. | Scheme | Structure | Parent MW |
|---|---|---|---|
| 261 | 2 | 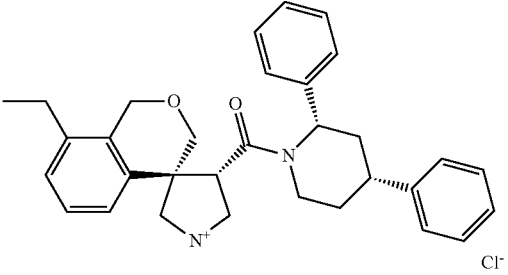 [SMILES: CCc1cccc2c1COC[C@]21C[NH2+]C[C@H]1C(=O)N1CC[C@@H](c2ccccc2)C[C@H]1c1ccccc1 ; [Cl-]] | 480.656 |
| 262 | 2 | 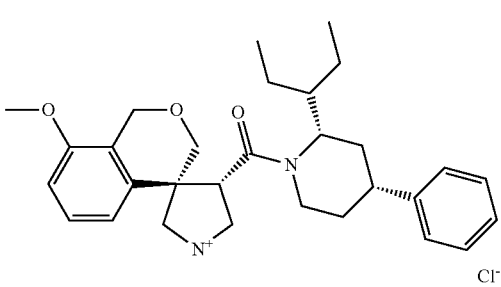 [SMILES: CCC(CC)[C@@H]1C[C@H](c2ccccc2)CCN1C(=O)[C@@H]1C[NH2+]C[C@]12COCc1c(OC)cccc12 ; [Cl-]] | 476.665 |
| 264 | 2 | 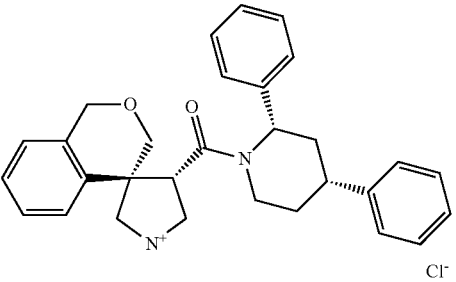 [SMILES: O=C([C@@H]1C[NH2+]C[C@]12COCc1ccccc12)N1CC[C@@H](c2ccccc2)C[C@H]1c1ccccc1 ; [Cl-]] | 452.602 |
| 265 | 2 | 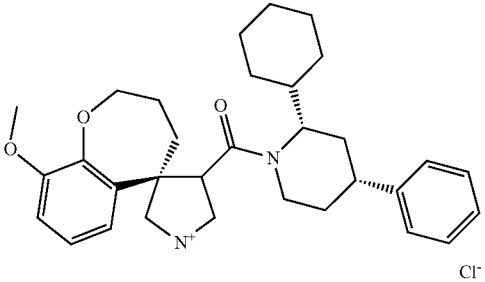 [SMILES: COc1cccc2c1OCCC[C@]21C[NH2+]CC1C(=O)N1CC[C@@H](c2ccccc2)C[C@H]1C1CCCCC1 ; [Cl-]] | 502.703 |
| 266 | 2 | 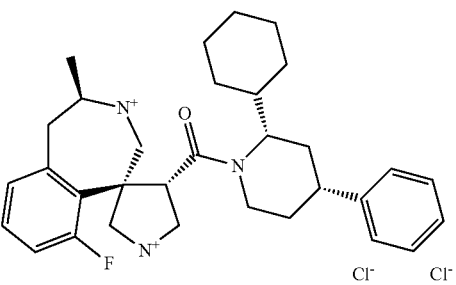 [SMILES: C[C@@H]1Cc2cccc(F)c2[C@@]2(C[NH2+]C[C@H]2C(=O)N2CC[C@@H](c3ccccc3)C[C@H]2C2CCCCC2)C[NH2+]1 ; [Cl-] ; [Cl-]] | 503.709 |

TABLE 3-continued

| Ex. No. | Scheme | Structure | Parent MW |
|---|---|---|---|
| 267 | 2 | 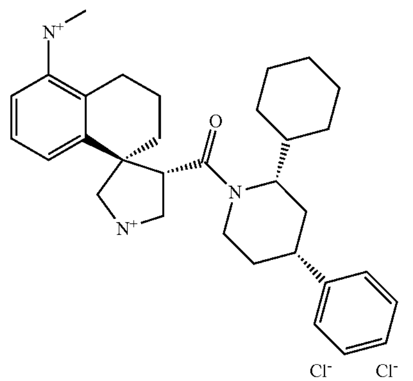 [SMILES: C[NH2+]c1cccc2c1CCC[C@]21C[NH2+]C[C@H]1C(=O)N1CC[C@@H](c2ccccc2)C[C@H]1C1CCCCC1 ; [Cl-] ; [Cl-]] | 485.719 |
| 268 | 2 | 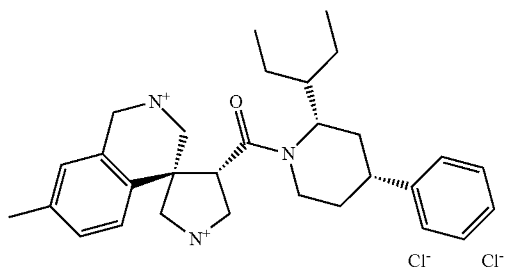 [SMILES: CCC(CC)[C@@H]1C[C@H](c2ccccc2)CCN1C(=O)[C@@H]1C[NH2+]C[C@]12C[NH2+]Cc1cc(C)ccc12 ; [Cl-] ; [Cl-]] | 459.681 |
| 269 | 2 | 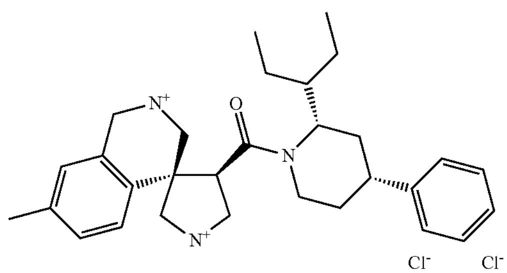 [SMILES: CCC(CC)[C@@H]1C[C@H](c2ccccc2)CCN1C(=O)[C@H]1C[NH2+]C[C@@]12C[NH2+]Cc1cc(C)ccc12 ; [Cl-] ; [Cl-]] | 459.681 |
| 270 | 2 | 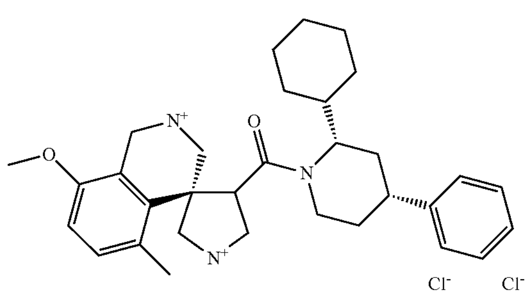 [SMILES: COc1ccc(C)c2c1C[NH2+]C[C@]21C[NH2+]CC1C(=O)N1CC[C@@H](c2ccccc2)C[C@H]1C1CCCCC1 ; [Cl-] ; [Cl-]] | 501.718 |
| 271 | 2 | 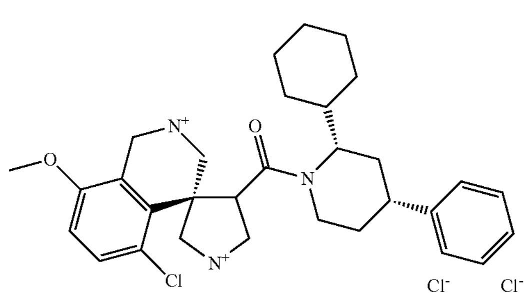 [SMILES: COc1ccc(Cl)c2c1C[NH2+]C[C@]21C[NH2+]CC1C(=O)N1CC[C@@H](c2ccccc2)C[C@H]1C1CCCCC1 ; [Cl-] ; [Cl-]] | 522.136 |

TABLE 3-continued

| Ex. No. | Scheme | Structure | Parent MW |
|---|---|---|---|
| 272 | 2 | 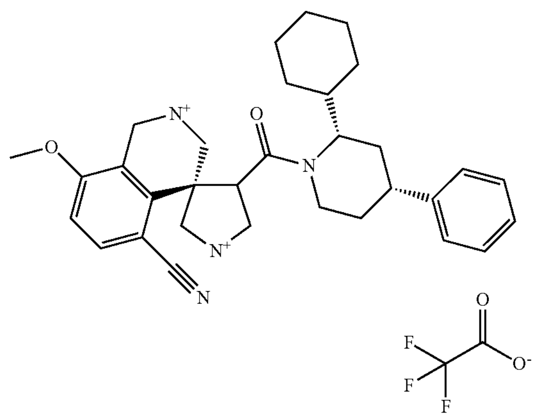 [SMILES: COc1ccc(C#N)c2c1C[NH2+]C[C@]21C[NH2+]CC1C(=O)N1CC[C@@H](c2ccccc2)C[C@H]1C1CCCCC1 ; O=C([O-])C(F)(F)F] | 512.701 |
| 273 | 2 | 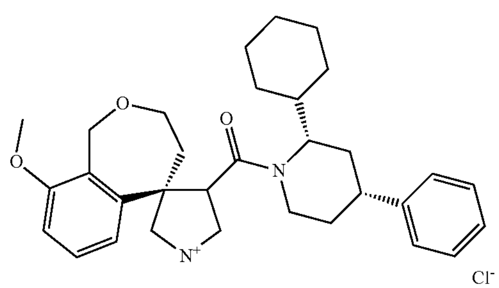 [SMILES: COc1cccc2c1COCC[C@]21C[NH2+]CC1C(=O)N1CC[C@@H](c2ccccc2)C[C@H]1C1CCCCC1 ; [Cl-]] | 502.703 |
| 274 | 2 | 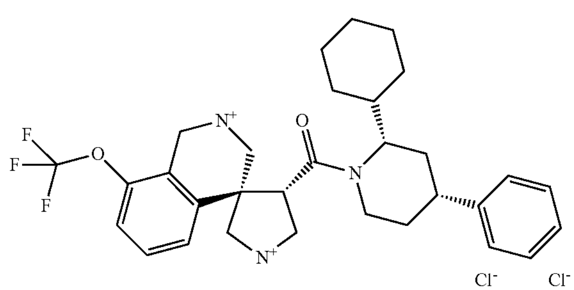 [SMILES: O=C([C@@H]1C[NH2+]C[C@]12C[NH2+]Cc1c(OC(F)(F)F)cccc12)N1CC[C@@H](c2ccccc2)C[C@H]1C1CCCCC1 ; [Cl-] ; [Cl-]] | 541.663 |
| 275 | 2 | 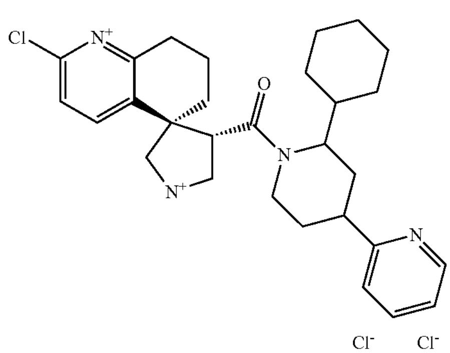 [SMILES: O=C([C@@H]1C[NH2+]C[C@]12CCCc1[nH+]c(Cl)ccc12)N1CCC(c2ccccn2)CC1C1CCCCC1 ; [Cl-] ; [Cl-]] | 493.097 |

TABLE 3-continued
| Ex. No. | Scheme | Structure | Parent MW |
|---|---|---|---|
| 276 | 2 | 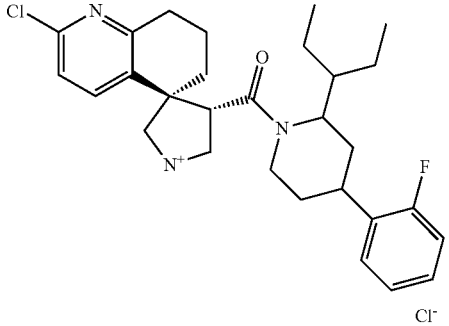 [SMILES: CCC(CC)C1CC(c2ccccc2F)CCN1C(=O)[C@@H]1C[NH2+]C[C@]12CCCc1nc(Cl)ccc12 ; [Cl-]] | 498.089 |
| 277 | 2 | 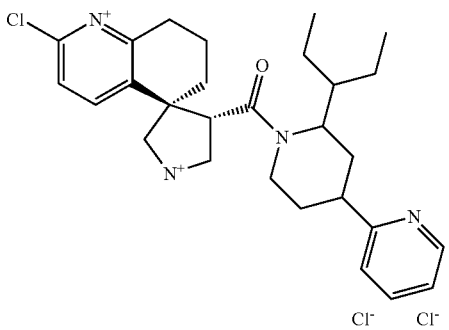 [SMILES: CCC(CC)C1CC(c2ccccn2)CCN1C(=O)[C@@H]1C[NH2+]C[C@]12CCCc1[nH+]c(Cl)ccc12 ; [Cl-] ; [Cl-]] | 481.086 |
| 278 | 2 | 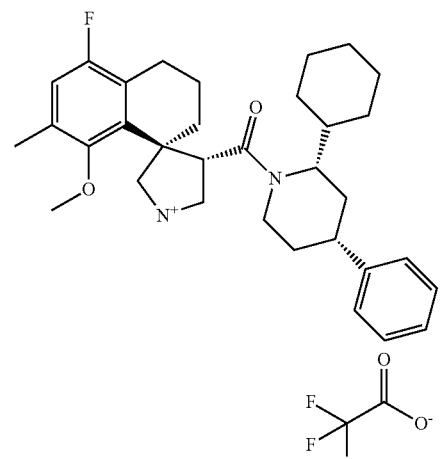 | 518.721 |
| 279 | 2 | 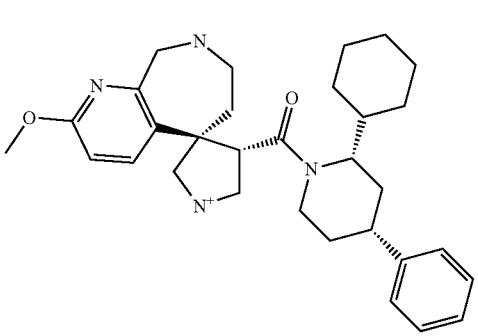 | 502.706 |

TABLE 3-continued
| Ex. No. | Scheme | Structure | Parent MW |
|---|---|---|---|
| 280 | 2 | 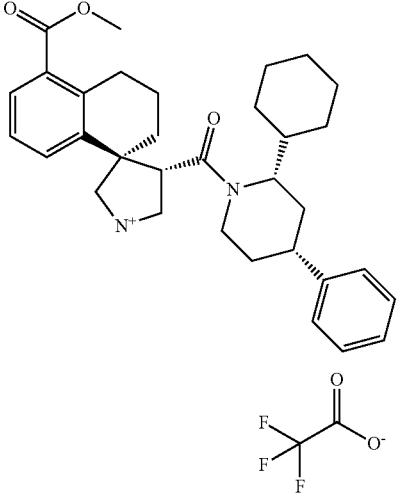 [SMILES: COC(=O)c1cccc2c1CCC[C@]21C[NH2+]C[C@H]1C(=O)N1CC[C@@H](c2ccccc2)C[C@H]1C1CCCCC1 ; O=C([O-])C(F)(F)F] | 514.714 |
| 281 | 2 | 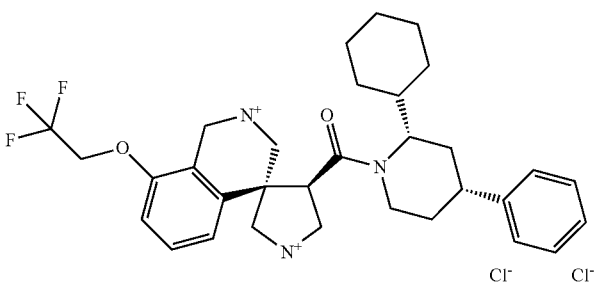 [SMILES: O=C([C@H]1C[NH2+]C[C@]12C[NH2+]Cc1c(OCC(F)(F)F)cccc12)N1CC[C@@H](c2ccccc2)C[C@H]1C1CCCCC1 ; [Cl-] ; [Cl-]] | 555.69 |
| 282 | 2 | 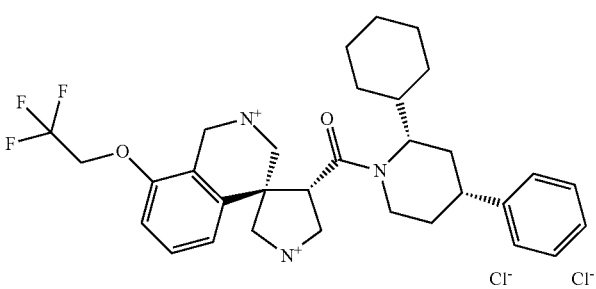 [SMILES: O=C([C@@H]1C[NH2+]C[C@]12C[NH2+]Cc1c(OCC(F)(F)F)cccc12)N1CC[C@@H](c2ccccc2)C[C@H]1C1CCCCC1 ; [Cl-] ; [Cl-]] | 555.69 |
| 283 | 2 | 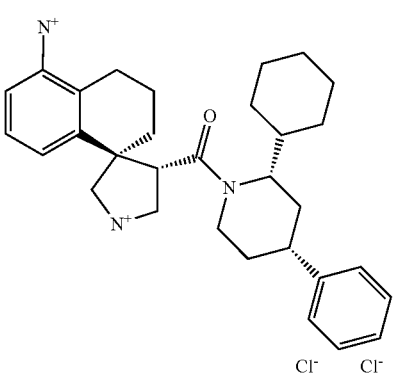 [SMILES: [NH3+]c1cccc2c1CCC[C@]21C[NH2+]C[C@H]1C(=O)N1CC[C@@H](c2ccccc2)C[C@H]1C1CCCCC1 ; [Cl-] ; [Cl-]] | 471.692 |

TABLE 3-continued
| Ex. No. | Scheme | Structure | Parent MW |
|---|---|---|---|
| 284 | 2 | 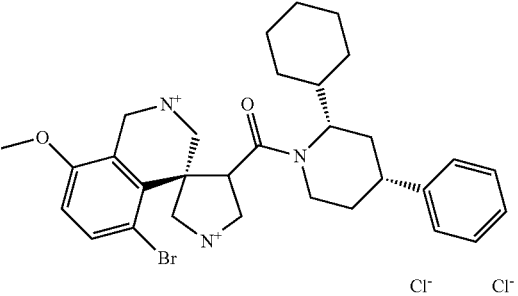 [SMILES: COc1ccc(Br)c2c1C[NH2+]C[C@]21C[NH2+]CC1C(=O)N1CC[C@@H](c2ccccc2)C[C@H]1C1CCCCC1 ; [Cl-] ; [Cl-]] | 566.587 |
| 285 | 2 | 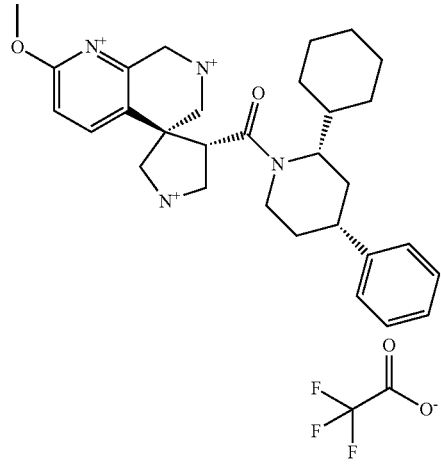 [SMILES: COc1ccc2c([nH+]1)C[NH2+]C[C@]21C[NH2+]C[C@H]1C(=O)N1CC[C@@H](c2ccccc2)C[C@H]1C1CCCCC1 ; O=C([O-])C(F)(F)F] | 488.679 |
| 286 | 2 | 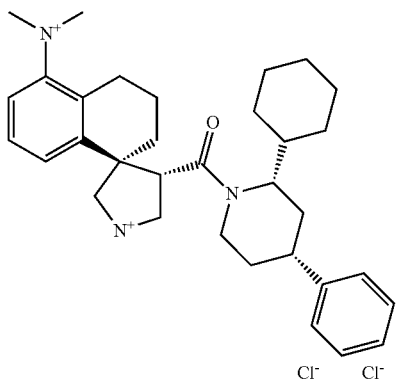 [SMILES: C[NH+](C)c1cccc2c1CCC[C@]21C[NH2+]C[C@H]1C(=O)N1CC[C@@H](c2ccccc2)C[C@H]1C1CCCCC1 ; [Cl-] ; [Cl-]] | 499.746 |

TABLE 3-continued
| Ex. No. | Scheme | Structure | Parent MW |
|---|---|---|---|
| 287 | 2 | 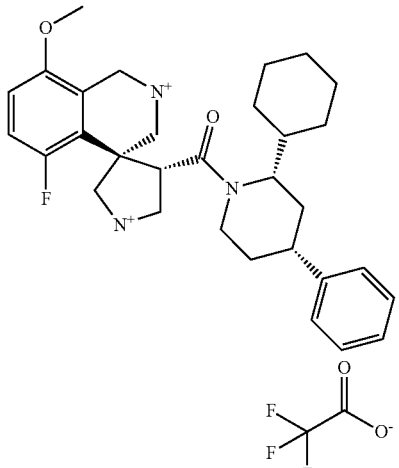 | 505.682 |
| 288 | 2 | 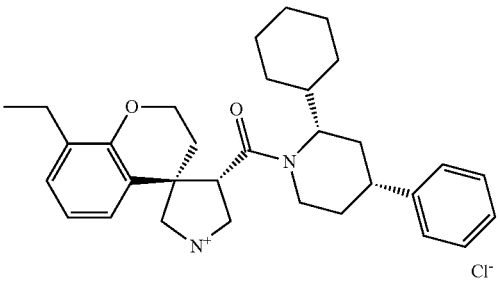 [SMILES: CCc1cccc2c1OCC[C@]21C[NH2+]C[C@H]1C(=O)N1CC[C@@H](c2ccccc2)C[C@H]1C1CCCCC1 ; [Cl-]] | 486.704 |
| 289 | 2 | 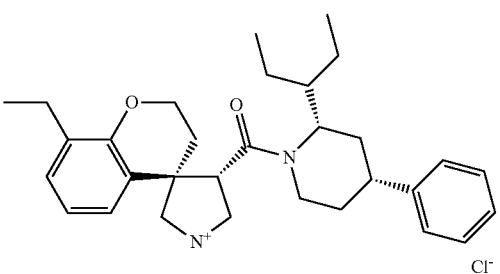 [SMILES: CCc1cccc2c1OCC[C@]21C[NH2+]C[C@H]1C(=O)N1CC[C@@H](c2ccccc2)C[C@H]1C(CC)CC ; [Cl-]] | 474.693 |
| 290 | 2 | 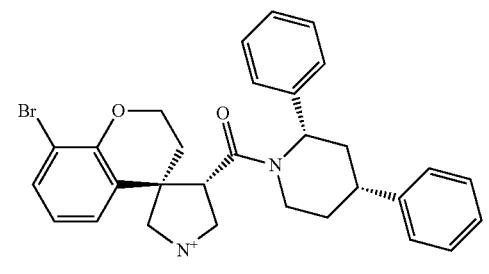 | 531.498 |

TABLE 3-continued
| Ex. No. | Scheme | Structure | Parent MW |
|---|---|---|---|
| 291 | 2 | 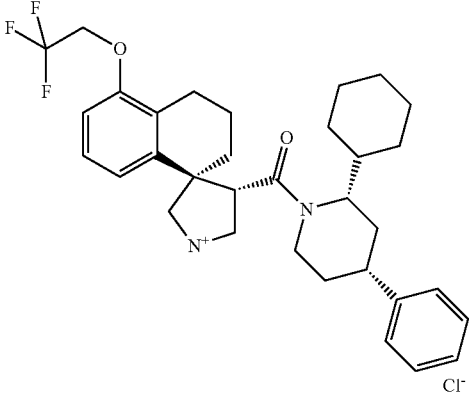 [SMILES: O=C([C@@H]1C[NH2+]C[C@]12CCCc1c(OCC(F)(F)F)cccc12)N1CC[C@@H](c2ccccc2)C[C@H]1C1CCCCC1 ; [Cl-]] | 554.702 |
| 292 | 2 | 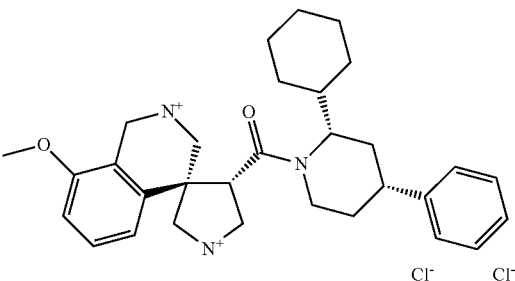 [SMILES: COc1cccc2c1C[NH2+]C[C@]21C[NH2+]C[C@H]1C(=O)N1CC[C@@H](c2ccccc2)C[C@H]1C1CCCCC1 ; [Cl-] ; [Cl-]] | 487.691 |
| 293 | 2 | 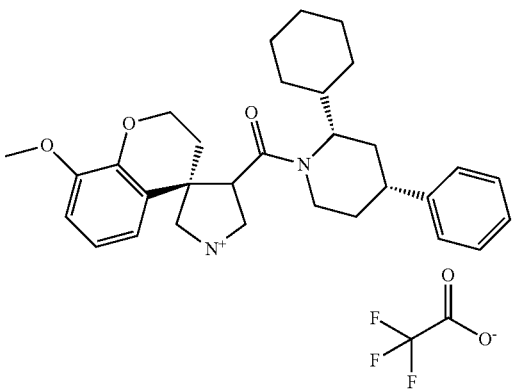 [SMILES: COc1cccc2c1OCC[C@]21C[NH2+]CC1C(=O)N1CC[C@@H](c2ccccc2)C[C@H]1C1CCCCC1 ; O=C([O-])C(F)(F)F] | 488.676 |
| 294 | 2 | 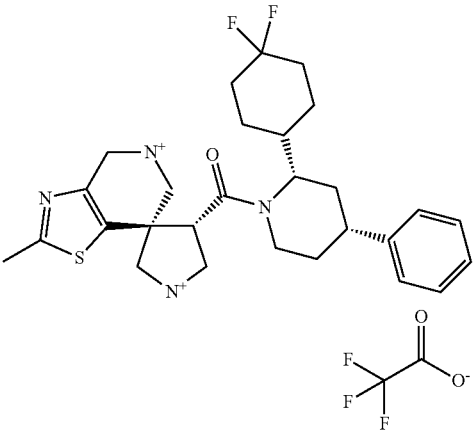 [SMILES: Cc1nc2c(s1)[C@]1(C[NH2+]C2)C[NH2+]C[C@H]1C(=O)N1CC[C@@H](c2ccccc2)C[C@H]1C1CCC(F)(F)CC1 ; O=C([O-])C(F)(F)F] | 514.686 |

TABLE 3-continued

| Ex. No. | Scheme | Structure | Parent MW |
|---|---|---|---|
| 295 | 2 | 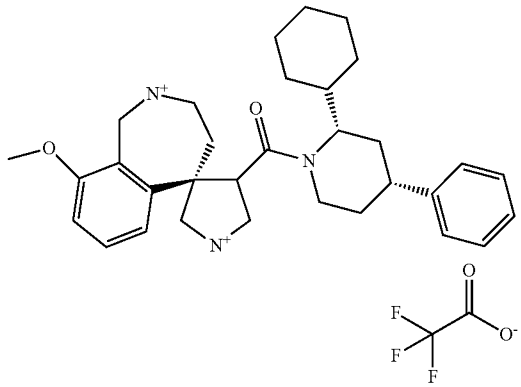 [SMILES: COc1cccc2c1C[NH2+]CC[C@]21C[NH2+]CC1C(=O)N1CC[C@@H](c2ccccc2)C[C@H]1C1CCCCC1 ; O=C([O-])C(F)(F)F] | 501.718 |
| 296 | 2 | 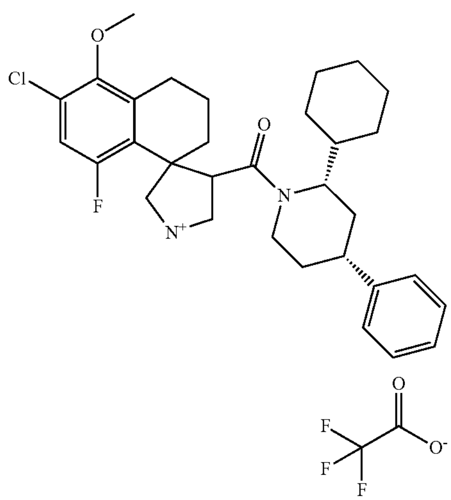 [SMILES: COc1c(Cl)cc(F)c2c1CCCC21C[NH2+]CC1C(=O)N1CC[C@@H](c2ccccc2)C[C@H]1C1CCCCC1 ; O=C([O-])C(F)(F)F] | 539.139 |
| 297 | 2 | 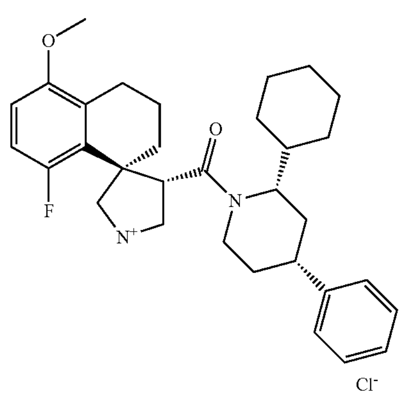 [SMILES: COc1ccc(F)c2c1CCC[C@]21C[NH2+]C[C@H]1C(=O)N1CC[C@@H](c2ccccc2)C[C@H]1C1CCCCC1 ; [Cl-]] | 504.694 |

TABLE 3-continued
| Ex. No. | Scheme | Structure | Parent MW |
|---|---|---|---|
| 298 | 2 | 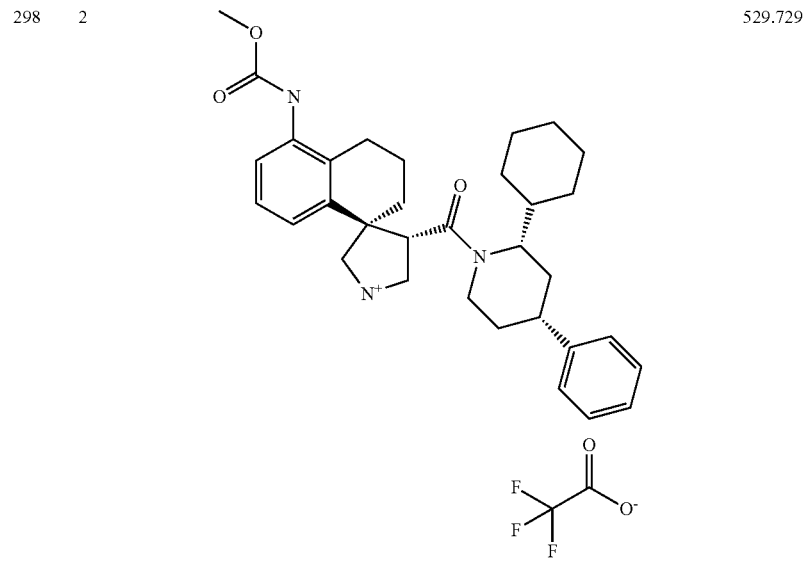 | 529.729 |
| 299 | 2 | 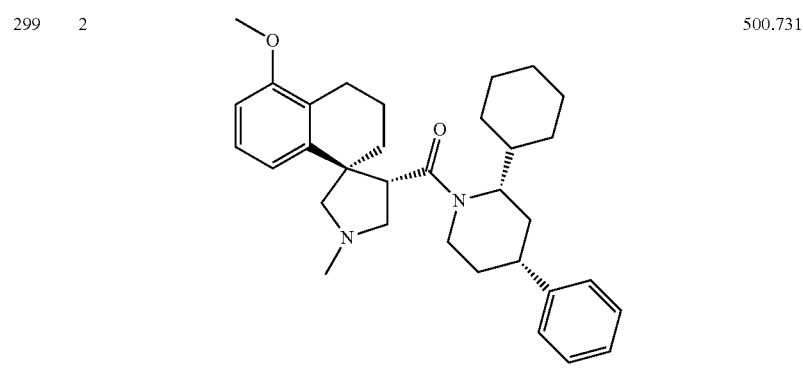 | 500.731 |
| 300 | 2 | 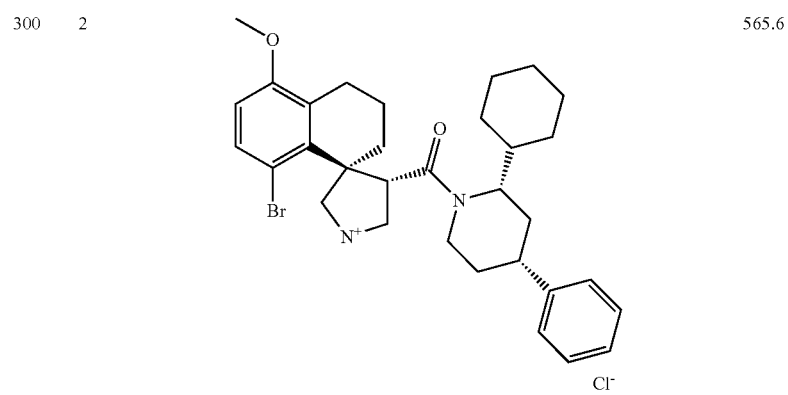 | 565.6 |

TABLE 3-continued

| Ex. No. | Scheme | Structure | Parent MW |
|---|---|---|---|
| 301 | 2 | 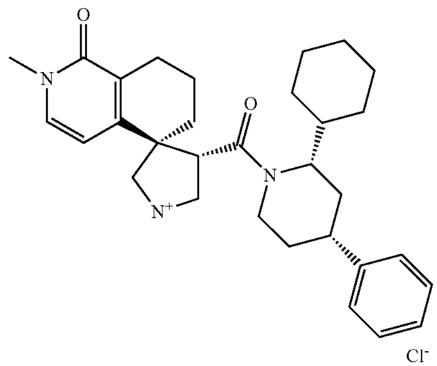 [SMILES: Cn1ccc2c(c1=O)CCC[C@]21C[NH2+]C[C@H]1C(=O)N1CC[C@@H](c2ccccc2)C[C@H]1C1CCCCC1 ; [Cl-]] | 487.691 |
| 302 | 2 | 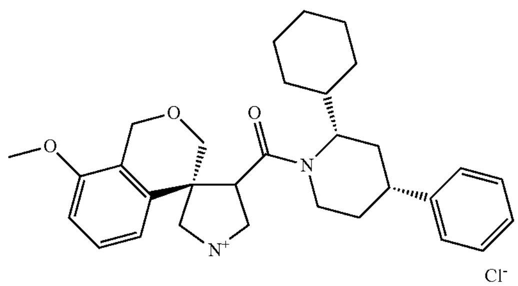 [SMILES: COc1cccc2c1COC[C@]21C[NH2+]CC1C(=O)N1CC[C@@H](c2ccccc2)C[C@H]1C1CCCCC1 ; [Cl-]] | 488.676 |
| 303 | 2 | 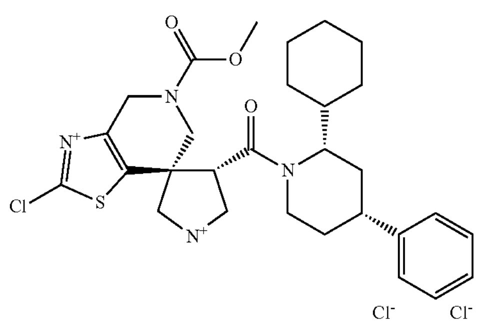 [SMILES: COC(=O)N1Cc2[nH+]c(Cl)sc2[C@@]2(C[NH2+]C[C@H]2C(=O)N2CC[C@@H](c3ccccc3)C[C@H]2C2CCCCC2)C1 ; [Cl-] ; [Cl-]] | 557.16 |
| 304 | 2 | 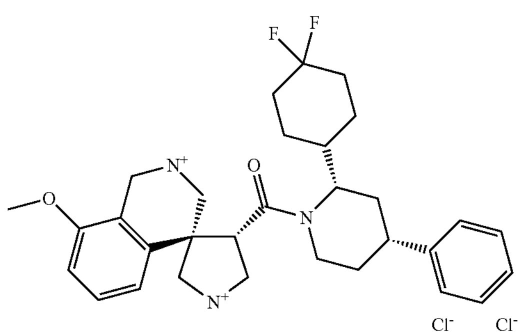 [SMILES: COc1cccc2c1C[NH2+]C[C@]21C[NH2+]C[C@H]1C(=O)N1CC[C@@H](c2ccccc2)C[C@H]1C1CCC(F)(F)CC1 ; [Cl-] ; [Cl-]] | 523.672 |
| 305 | 2 | 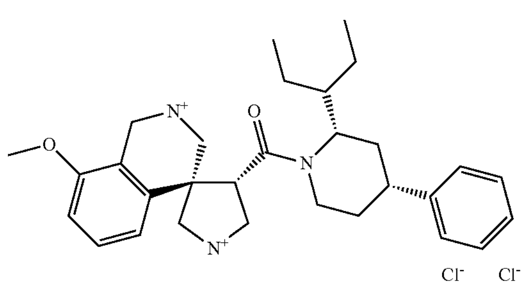 [SMILES: CCC(CC)[C@@H]1C[C@H](c2ccccc2)CCN1C(=O)[C@@H]1C[NH2+]C[C@]12C[NH2+]Cc1c(OC)cccc12 ; [Cl-] ; [Cl-]] | 475.68 |

TABLE 3-continued

| Ex. No. | Scheme | Structure | Parent MW |
|---|---|---|---|
| 306 | 2 | 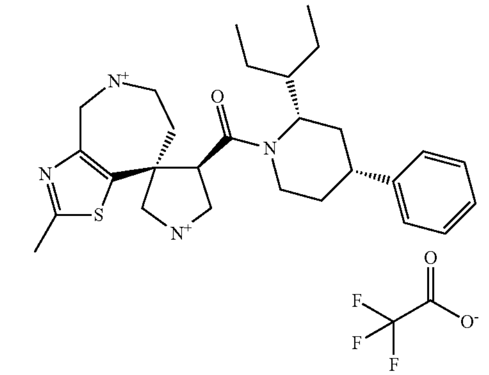 [SMILES: CCC(CC)[C@@H]1C[C@H](c2ccccc2)CCN1C(=O)[C@H]1C[NH2+]C[C@]12CC[NH2+]Cc1nc(C)sc12 ; O=C([O-])C(F)(F)F] | 480.721 |
| 307 | 2 | 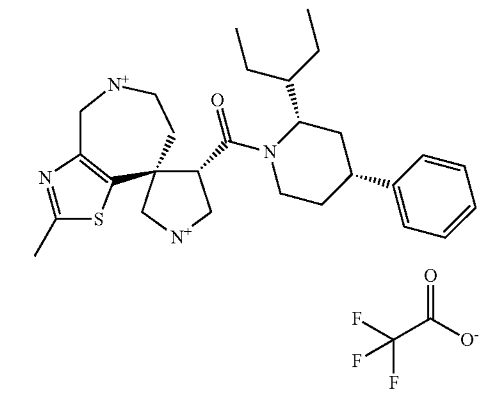 [SMILES: CCC(CC)[C@@H]1C[C@H](c2ccccc2)CCN1C(=O)[C@@H]1C[NH2+]C[C@]12CC[NH2+]Cc1nc(C)sc12 ; O=C([O-])C(F)(F)F] | 480.721 |
| 308 | 2 | 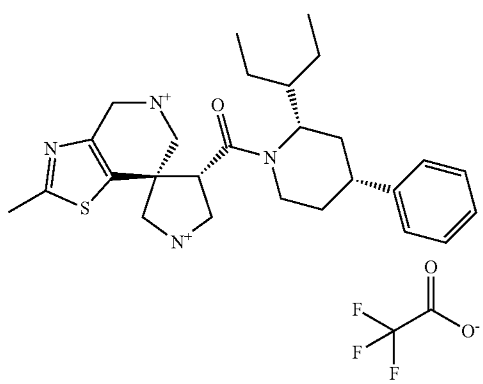 [SMILES: CCC(CC)[C@@H]1C[C@H](c2ccccc2)CCN1C(=O)[C@@H]1C[NH2+]C[C@]12C[NH2+]Cc1nc(C)sc12 ; O=C([O-])C(F)(F)F] | 466.694 |
| 309 | 2 | 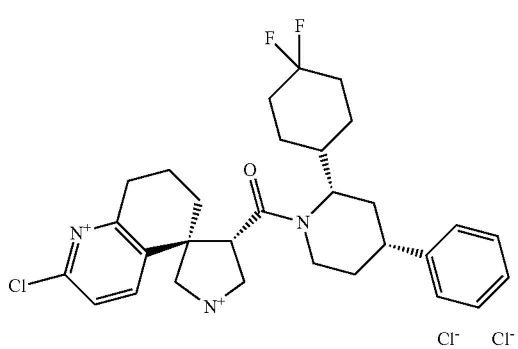 [SMILES: O=C([C@@H]1C[NH2+]C[C@]12CCCc1[nH+]c(Cl)ccc12)N1CC[C@@H](c2ccccc2)C[C@H]1C1CCC(F)(F)CC1 ; [Cl-] ; [Cl-]] | 528.091 |

TABLE 3-continued

| Ex. No. | Scheme | Structure | Parent MW |
|---|---|---|---|
| 310 | 2 | 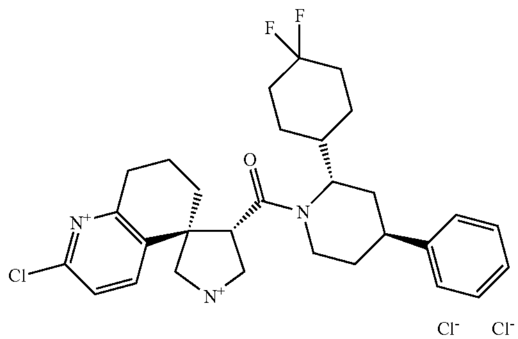 [SMILES: O=C([C@@H]1C[NH2+]C[C@]12CCCc1[nH+]c(Cl)ccc12)N1CC[C@H](c2ccccc2)C[C@H]1C1CCC(F)(F)CC1 ; [Cl-] ; [Cl-]] | 528.091 |
| 311 | 2 | 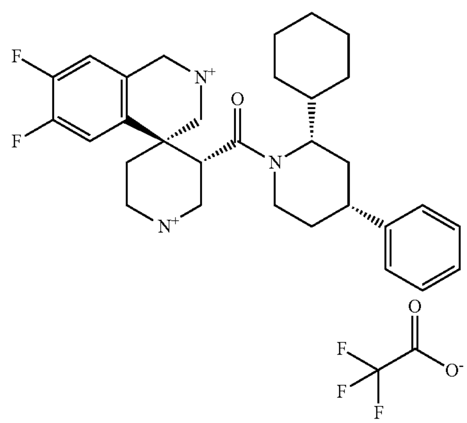 [SMILES: O=C([C@@H]1C[NH2+]CC[C@]12C[NH2+]Cc1cc(F)c(F)cc12)N1CC[C@@H](c2ccccc2)C[C@H]1C1CCCCC1 ; O=C([O-])C(F)(F)F] | 507.673 |
| 312 | 2 | 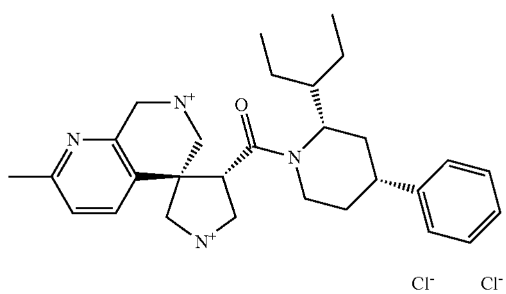 [SMILES: CCC(CC)[C@@H]1C[C@H](c2ccccc2)CCN1C(=O)[C@@H]1C[NH2+]C[C@]12C[NH2+]Cc1nc(C)ccc12 ; [Cl-] ; [Cl-]] | 460.668 |
| 313 | 2 | 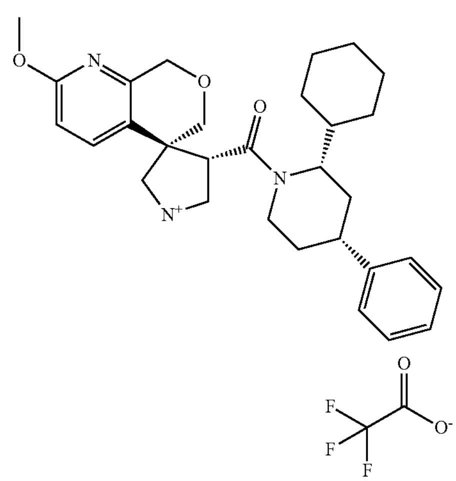 [SMILES: COc1ccc2c(n1)COC[C@]21C[NH2+]C[C@H]1C(=O)N1CC[C@@H](c2ccccc2)C[C@H]1C1CCCCC1 ; O=C([O-])C(F)(F)F] | 489.664 |

TABLE 3-continued
| Ex. No. | Scheme | Structure | Parent MW |
|---|---|---|---|
| 314 | 2 | 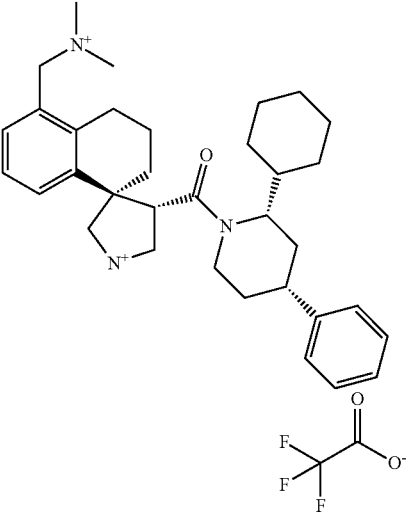 [SMILES: C[NH+](C)Cc1cccc2c1CCC[C@]21C[NH2+]C[C@H]1C(=O)N1CC[C@@H](c2ccccc2)C[C@H]1C1CCCCC1 ; O=C([O-])C(F)(F)F] | 573.773 |
| 315 | 2 | 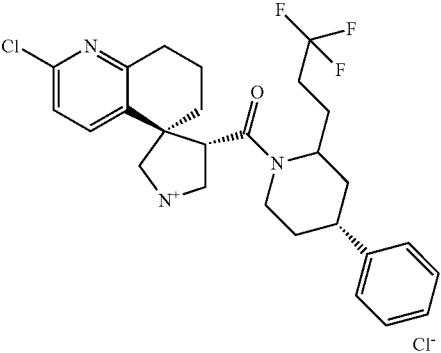 [SMILES: O=C([C@@H]1C[NH2+]C[C@]12CCCc1nc(Cl)ccc12)N1CC[C@@H](c2ccccc2)CC1CCC(F)(F)F ; [Cl-]] | 506.016 |
| 316 | 2 | 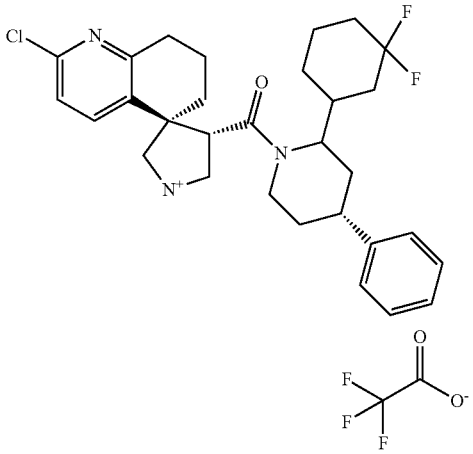 [SMILES: O=C([C@@H]1C[NH2+]C[C@]12CCCc1nc(Cl)ccc12)N1CC[C@@H](c2ccccc2)CC1C1CCCC(F)(F)C1 ; O=C([O-])C(F)(F)F] | 528.091 |

TABLE 3-continued

| Ex. No. | Scheme | Structure | Parent MW |
|---|---|---|---|
| 317 | 2 | 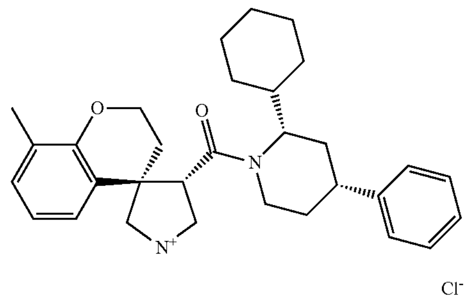 [SMILES: Cc1cccc2c1OCC[C@]21C[NH2+]C[C@H]1C(=O)N1CC[C@@H](c2ccccc2)C[C@H]1C1CCCCC1 ; [Cl-]] | 472.677 |
| 318 | 2 | 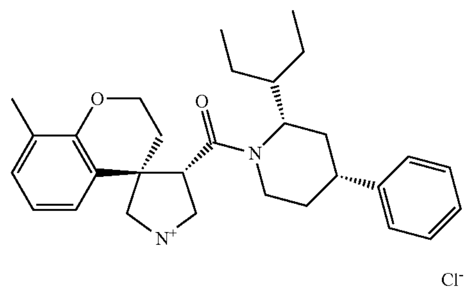 [SMILES: CCC(CC)[C@@H]1C[C@H](c2ccccc2)CCN1C(=O)[C@@H]1C[NH2+]C[C@]12CCOc1c(C)cccc12 ; [Cl-]] | 460.665 |
| 319 | 2 | 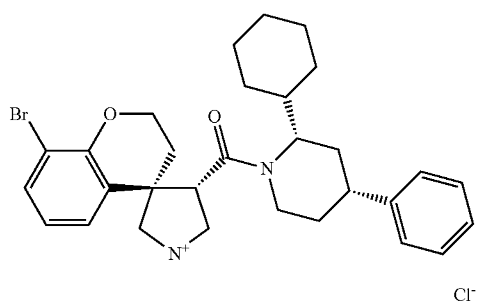 [SMILES: O=C([C@@H]1C[NH2+]C[C@]12CCOc1c(Br)cccc12)N1CC[C@@H](c2ccccc2)C[C@H]1C1CCCCC1 ; [Cl-]] | 537.546 |
| 320 | 2 | 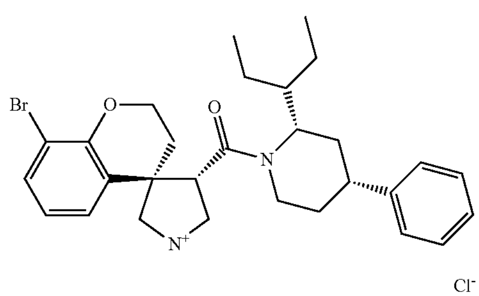 [SMILES: CCC(CC)[C@@H]1C[C@H](c2ccccc2)CCN1C(=O)[C@@H]1C[NH2+]C[C@]12CCOc1c(Br)cccc12 ; [Cl-]] | 525.534 |
| 321 | 2 | 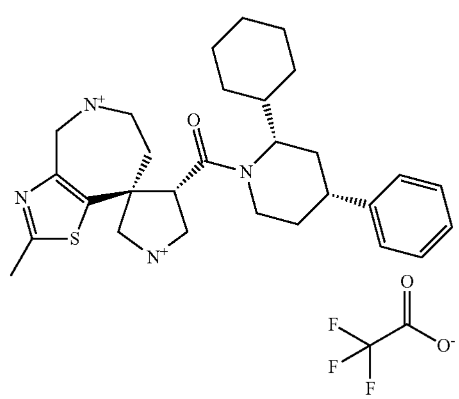 [SMILES: Cc1nc2c(s1)[C@]1(CC[NH2+]C2)C[NH2+]C[C@H]1C(=O)N1CC[C@@H](c2ccccc2)C[C@H]1C1CCCCC1 ; O=C([O-])C(F)(F)F] | 492.732 |

TABLE 3-continued
| Ex. No. | Scheme | Structure | Parent MW |
|---|---|---|---|
| 322 | 2 | 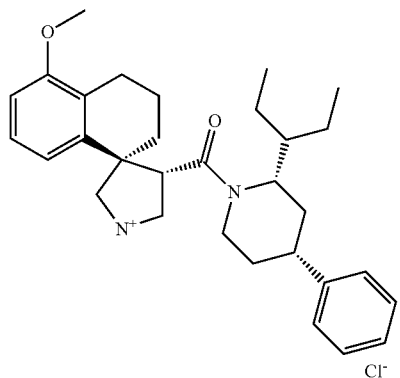 [SMILES: CCC(CC)[C@@H]1C[C@H](c2ccccc2)CCN1C(=O)[C@@H]1C[NH2+]C[C@]12CCCc1c(OC)cccc12 ; [Cl-]] | 474.693 |
| 323 | 2 | 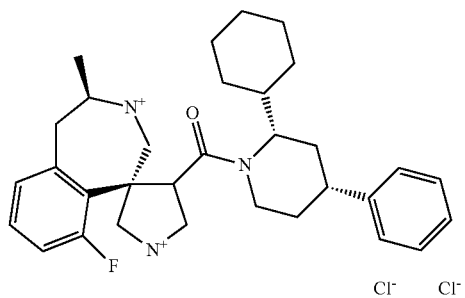 [SMILES: C[C@@H]1Cc2cccc(F)c2[C@@]2(C[NH2+]CC2C(=O)N2CC[C@@H](c3ccccc3)C[C@H]2C2CCCCC2)C[NH2+]1 ; [Cl-] ; [Cl-]] | 503.709 |
| 324 | 2 | 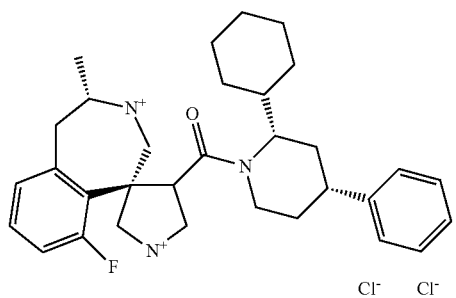 [SMILES: C[C@H]1Cc2cccc(F)c2[C@@]2(C[NH2+]CC2C(=O)N2CC[C@@H](c3ccccc3)C[C@H]2C2CCCCC2)C[NH2+]1 ; [Cl-] ; [Cl-]] | 503.709 |
| 325 | 2 | 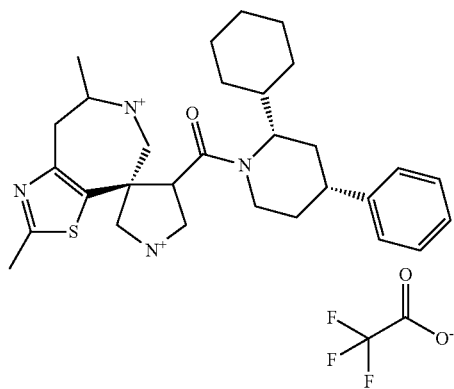 | 506.759 |

TABLE 3-continued
| Ex. No. | Scheme | Structure | Parent MW |
|---|---|---|---|
| 326 | 2 | 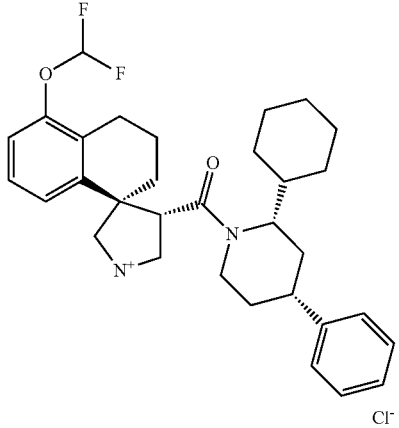 [SMILES: O=C([C@@H]1C[NH2+]C[C@]12CCCc1c(OC(F)F)cccc12)N1CC[C@@H](c2ccccc2)C[C@H]1C1CCCCC1 ; [Cl-]] | 522.685 |
| 327 | 2 | 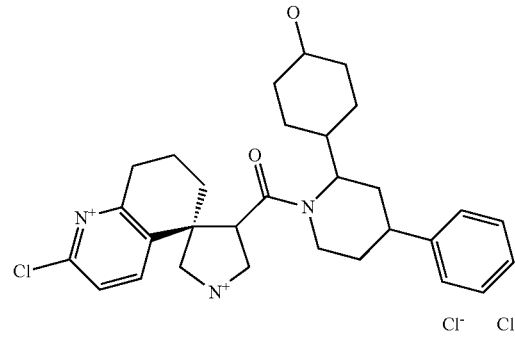 [SMILES: O=C(C1C[NH2+]C[C@]12CCCc1[nH+]c(Cl)ccc12)N1CCC(c2ccccc2)CC1C1CCC(O)CC1 ; [Cl-] ; [Cl-]] | 508.109 |
| 328 | 2 | 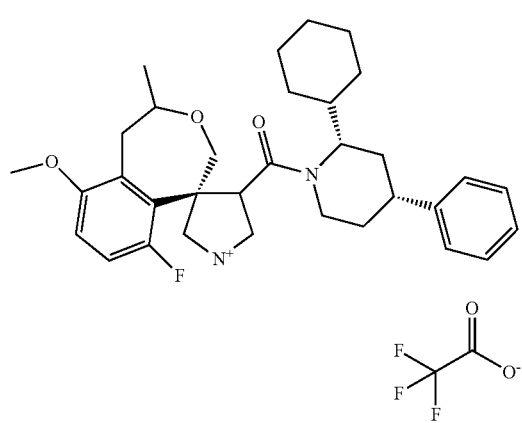 | 534.721 |
| 329 | 2 | 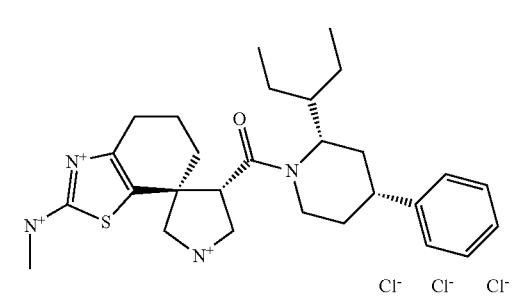 [SMILES: CCC(CC)[C@@H]1C[C@H](c2ccccc2)CCN1C(=O)[C@@H]1C[NH2+]C[C@]12CCCc1[nH+]c([NH2+]C)sc12 ; [Cl-] ; [Cl-] ; [Cl-]] | 590.104 |

TABLE 3-continued

| Ex. No. | Scheme | Structure | Parent MW |
|---|---|---|---|
| 330 | 2 | 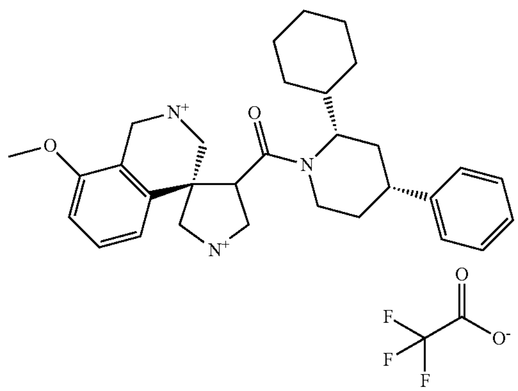 [SMILES: COc1cccc2c1C[NH2+]C[C@]21C[NH2+]CC1C(=O)N1CC[C@@H](c2ccccc2)C[C@H]1C1CCCCC1 ; O=C([O-])C(F)(F)F] | 487.691 |
| 331 | 2 | 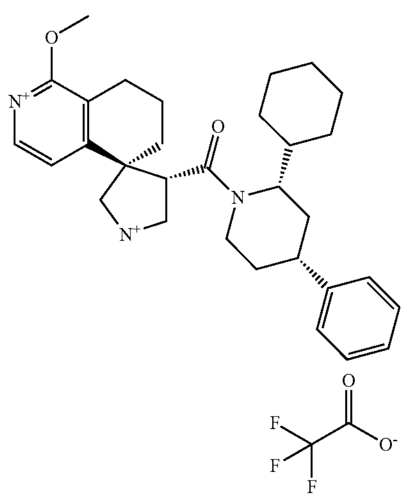 [SMILES: COc1[nH+]ccc2c1CCC[C@]21C[NH2+]C[C@H]1C(=O)N1CC[C@@H](c2ccccc2)C[C@H]1C1CCCCC1 ; O=C([O-])C(F)(F)F] | 487.691 |
| 332 | 2 | 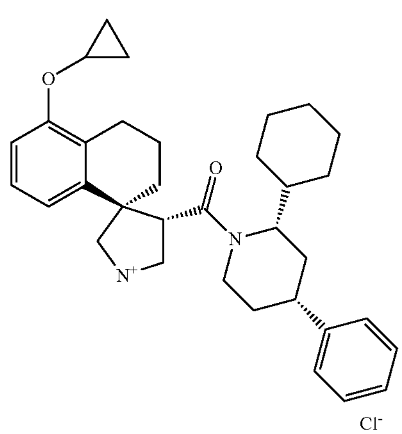 [SMILES: O=C([C@@H]1C[NH2+]C[C@]12CCCc1c(OC3CC3)cccc12)N1CC[C@@H](c2ccccc2)C[C@H]1C1CCCCC1 ; [Cl-]] | 517.742 |

TABLE 3-continued

| Ex. No. | Scheme | Structure | Parent MW |
|---|---|---|---|
| 333 | 2 | 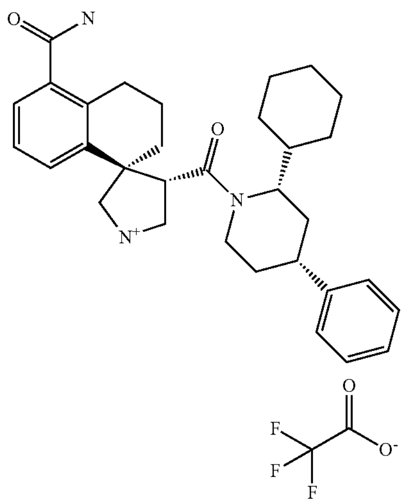 [SMILES: NC(=O)c1cccc2c1CCC[C@]21C[NH2+]C[C@H]1C(=O)N1CC[C@@H](c2ccccc2)C[C@H]1C1CCCCC1 ; O=C([O-])C(F)(F)F] | 499.702 |
| 334 | 2 | 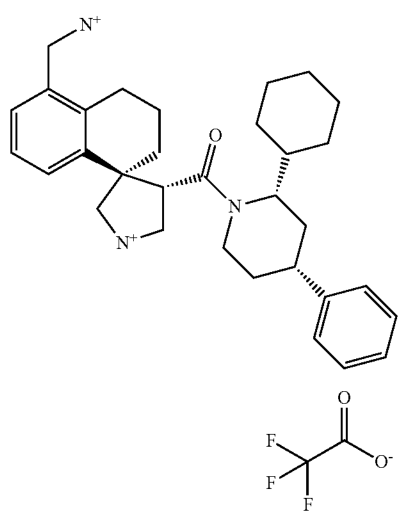 [SMILES: [NH3+]Cc1cccc2c1CCC[C@]21C[NH2+]C[C@H]1C(=O)N1CC[C@@H](c2ccccc2)C[C@H]1C1CCCCC1 ; O=C([O-])C(F)(F)F] | 485.719 |
| 335 | 2 | 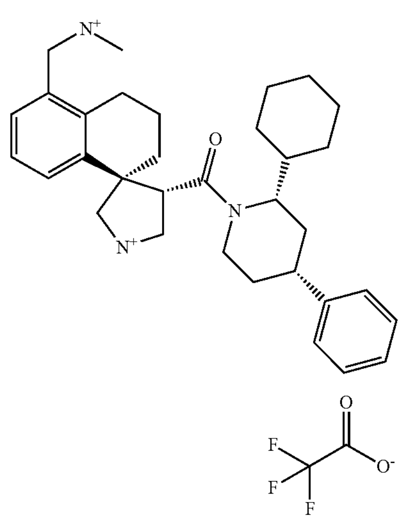 [SMILES: C[NH2+]Cc1cccc2c1CCC[C@]21C[NH2+]C[C@H]1C(=O)N1CC[C@@H](c2ccccc2)C[C@H]1C1CCCCC1 ; O=C([O-])C(F)(F)F] | 499.746 |

TABLE 3-continued
| Ex. No. | Scheme | Structure | Parent MW |
|---|---|---|---|
| 336 | 2 | 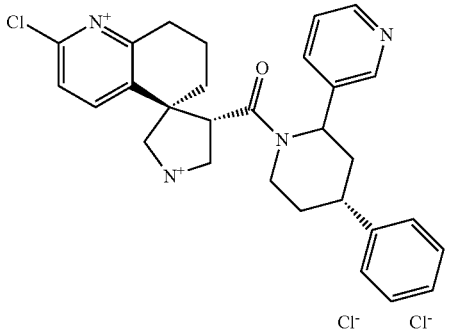 [SMILES: O=C([C@@H]1C[NH2+]C[C@]12CCCc1[nH+]c(Cl)ccc12)N1CC[C@@H](c2ccccc2)CC1c1cccnc1 ; [Cl-] ; [Cl-]] | 487.05 |
| 337 | 2 | 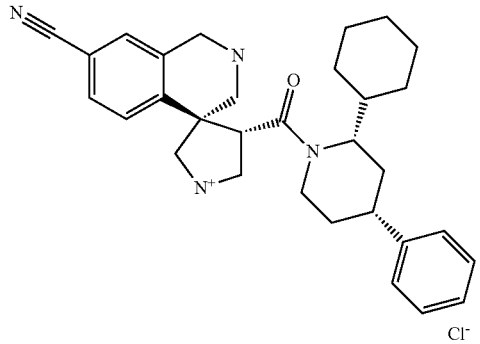 [SMILES: N#Cc1ccc2c(c1)CNC[C@]21C[NH2+]C[C@H]1C(=O)N1CC[C@@H](c2ccccc2)C[C@H]1C1CCCCC1 ; [Cl-]] | 482.675 |
| 338 | 2 | 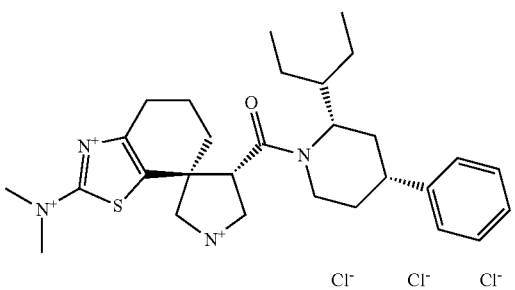 [SMILES: CCC(CC)[C@@H]1C[C@H](c2ccccc2)CCN1C(=O)[C@@H]1C[NH2+]C[C@]12CCCc1[nH+]c([NH+](C)C)sc12 ; [Cl-] ; [Cl-] ; [Cl-]] | 494.748 |
| 339 | 2 | 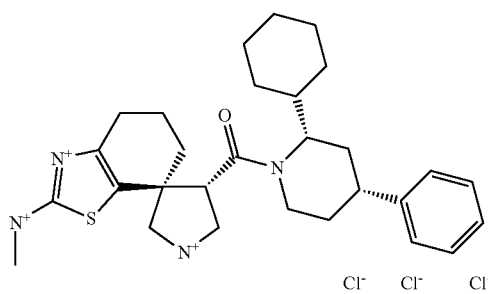 | 492.732 |
| 340 | 2 | 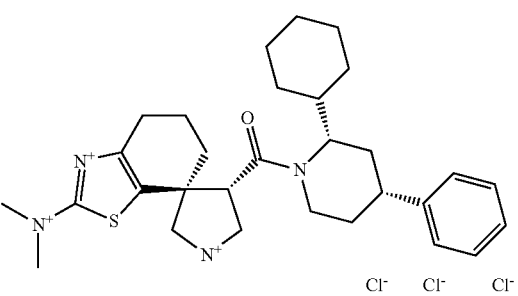 [SMILES: C[NH+](C)c1[nH+]c2c(s1)[C@]1(CCC2)C[NH2+]C[C@H]1C(=O)N1CC[C@@H](c2ccccc2)C[C@H]1C1CCCCC1 ; [Cl-] ; [Cl-] ; [Cl-]] | 506.759 |

TABLE 3-continued
| Ex. No. | Scheme | Structure | Parent MW |
|---|---|---|---|
| 341 | 2 | 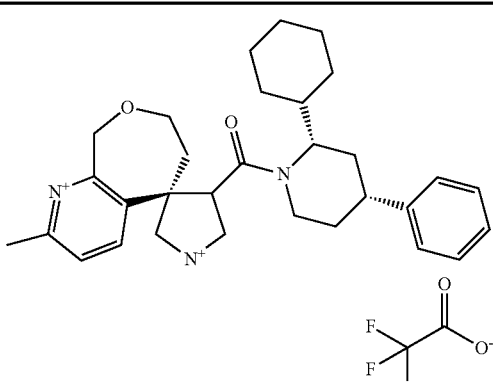 | 487.691 |
| 342 | 2 | 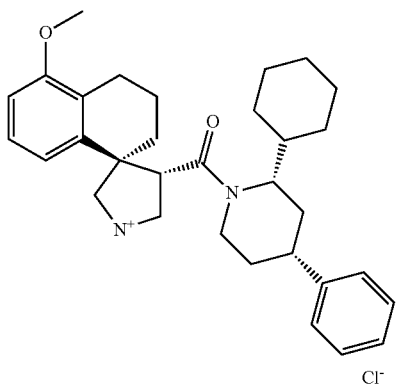 [SMILES: COc1cccc2c1CCC[C@]21C[NH2+]C[C@H]1C(=O)N1CC[C@@H](c2ccccc2)C[C@H]1C1CCCCC1 ; [Cl-]] | 486.704 |
| 343 | 2 | 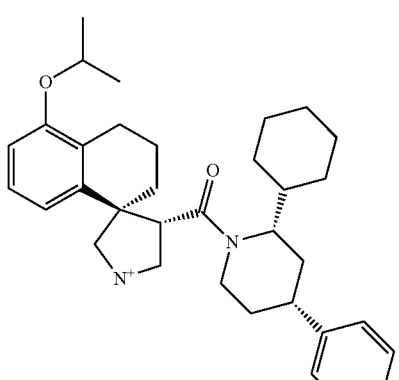 | 514.758 |
| 344 | 2 | 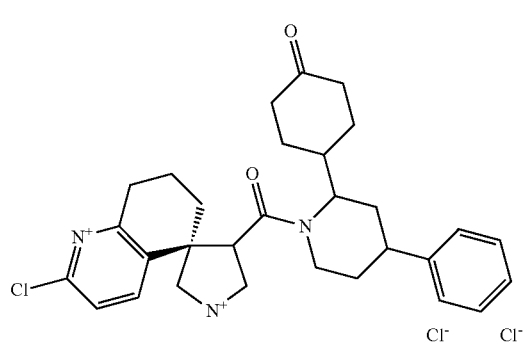 [SMILES: O=C1CCC(C2CC(c3ccccc3)CCN2C(=O)C2C[NH2+]C[C@]23CCCc2[nH+]c(Cl)ccc23)CC1 ; [Cl-] ; [Cl-]] | 506.093 |

TABLE 3-continued

| Ex. No. | Scheme | Structure | Parent MW |
|---|---|---|---|
| 345 | 2 | 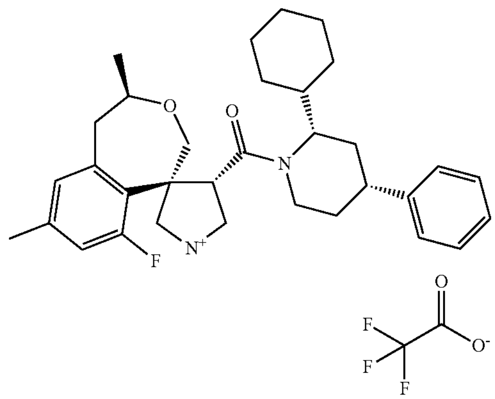 [SMILES: Cc1cc(F)c2c(c1)C[C@@H](C)OC[C@]21C[NH2+]C[C@H]1C(=O)N1CC[C@@H](c2ccccc2)C[C@H]1C1CCCCC1 ; O=C([O-])C(F)(F)F] | 518.721 |
| 346 | 2 | 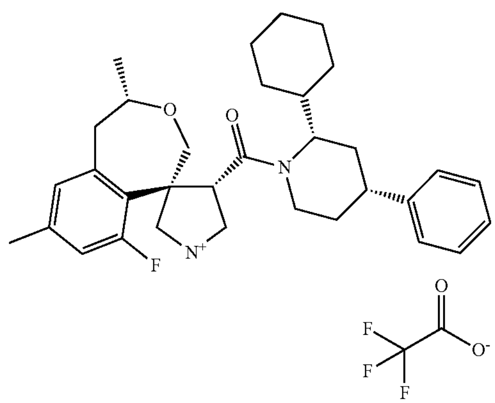 [SMILES: Cc1cc(F)c2c(c1)C[C@H](C)OC[C@]21C[NH2+]C[C@H]1C(=O)N1CC[C@@H](c2ccccc2)C[C@H]1C1CCCCC1 ; O=C([O-])C(F)(F)F] | 518.721 |
| 347 | 2 | 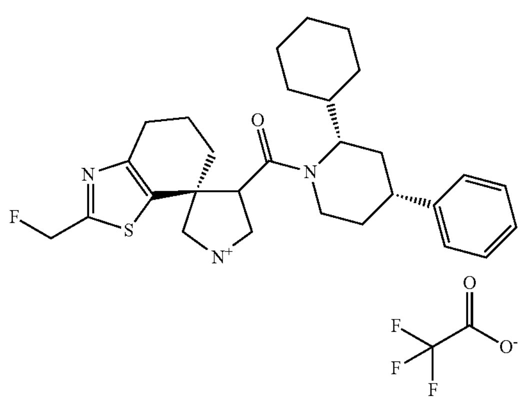 [SMILES: O=C(C1C[NH2+]C[C@]12CCCc1nc(CF)sc12)N1CC[C@@H](c2ccccc2)C[C@H]1C1CCCCC1 ; O=C([O-])C(F)(F)F] | 495.708 |
| 348 | 2 | 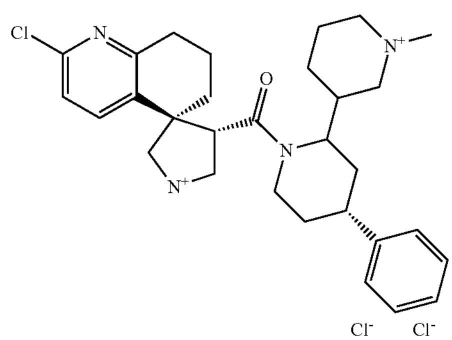 [SMILES: C[NH+]1CCCC(C2C[C@H](c3ccccc3)CCN2C(=O)[C@@H]2C[NH2+]C[C@]23CCCc2nc(Cl)ccc23)C1 ; [Cl-] ; [Cl-]] | 507.125 |

211
212
TABLE 3-continued
| Ex. No. | Scheme | Structure | Parent MW |
|---|---|---|---|
| 349 | 2 | 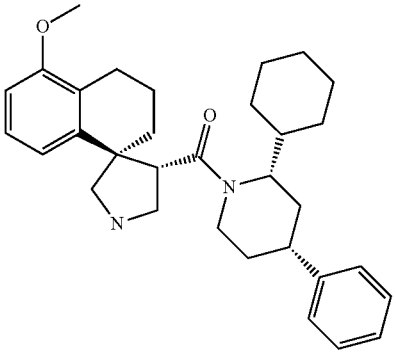 [SMILES: COc1cccc2c1CCC[C@]21CNC[C@H]1C(=O)N1CC[C@@H](c2ccccc2)C[C@H]1C1CCCCC1] | 486.704 |
| 350 | 2 | 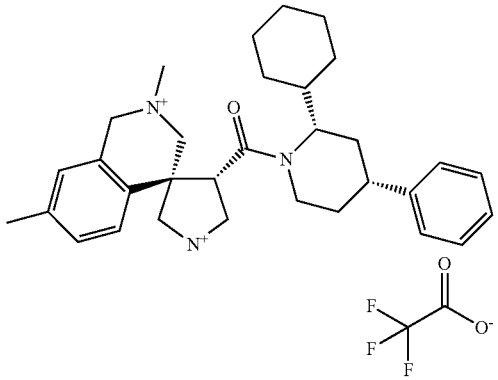 | 485.719 |
| 351 | 2 | 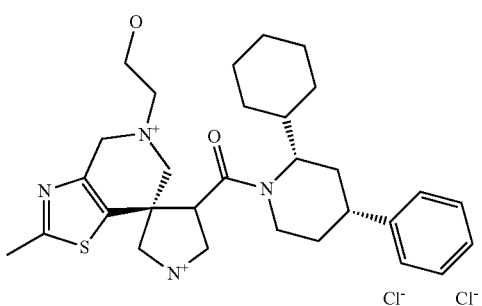 | 522.759 |
| 352 | 2 | 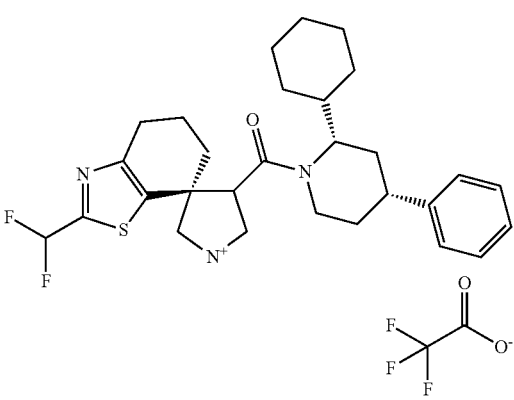 [SMILES: O=C(C1C[NH2+]C[C@]12CCCc1nc(C(F)F)sc12)N1CC[C@@H](c2ccccc2)C[C@H]1C1CCCCC1 ; O=C([O-])C(F)(F)F] | 513.699 |

TABLE 3-continued

| Ex. No. | Scheme | Structure | Parent MW |
|---|---|---|---|
| 353 | 2 | 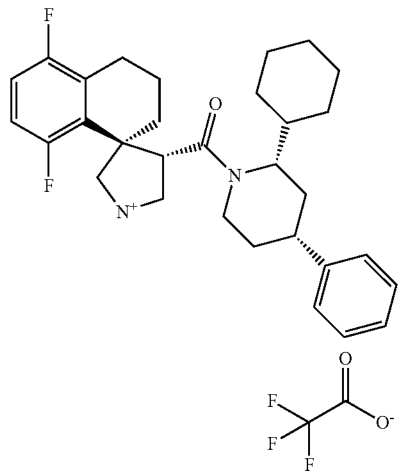 [SMILES: O=C([C@@H]1C[NH2+]C[C@]12CCCc1c(F)ccc(F)c12)N1CC[C@@H](c2ccccc2)C[C@H]1C1CCCCC1 ; O=C([O-])C(F)(F)F] | 492.658 |
| 354 | 2 | 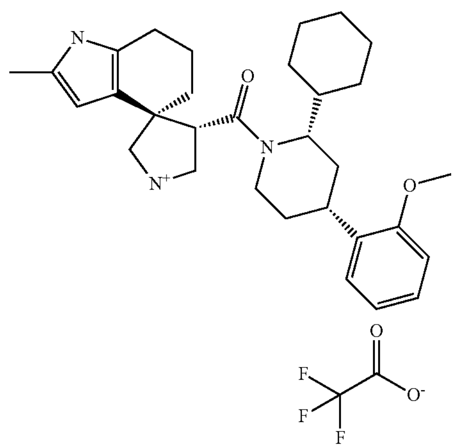 | 489.707 |
| 355 | 2 | 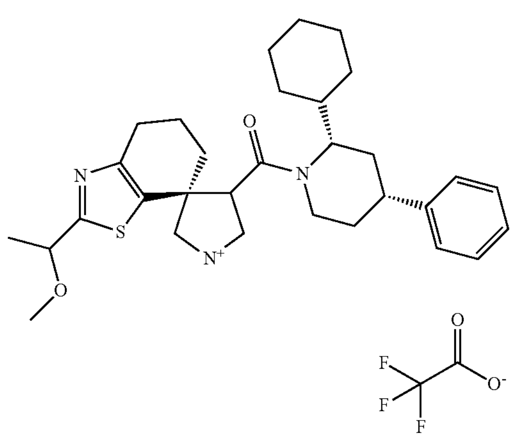 [SMILES: COC(C)c1nc2c(s1)[C@]1(CCC2)C[NH2+]CC1C(=O)N1CC[C@@H](c2ccccc2)C[C@H]1C1CCCCC1 ; O=C([O-])C(F)(F)F] | 521.771 |

TABLE 3-continued
| Ex. No. | Scheme | Structure | Parent MW |
|---|---|---|---|
| 356 | 2 | 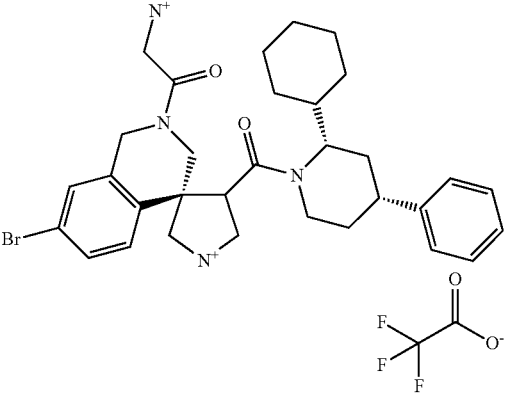 [SMILES: [NH3+]CC(=O)N1Cc2cc(Br)ccc2[C@@]2(C[NH2+]CC2C(=O)N2CC[C@@H](c3ccccc3)C[C@H]2C2CCCCC2)C1 ; O=C([O-])C(F)(F)F] | 593.613 |
| 357 | 2 | 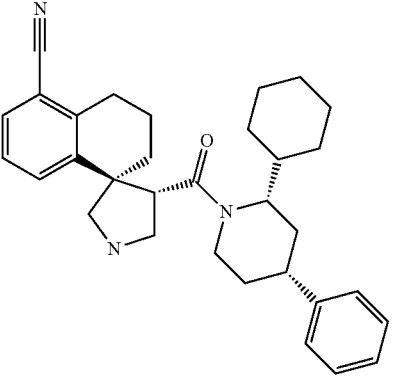 [SMILES: N#Cc1cccc2c1CCC[C@]21CNC[C@H]1C(=O)N1CC[C@@H](c2ccccc2)C[C@H]1C1CCCCC1] | 481.687 |
| 358 | 2 | 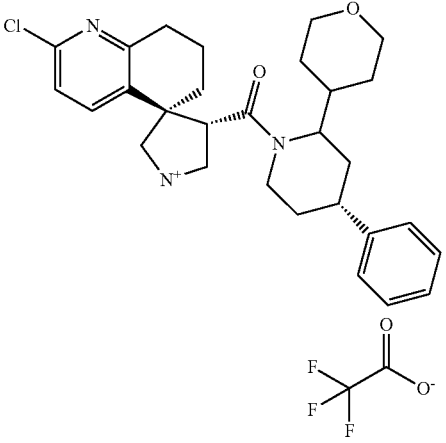 | 494.082 |
| 359 | 2 | 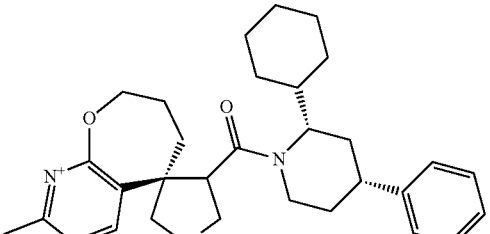 | 487.691 |

TABLE 3-continued
| Ex. No. | Scheme | Structure | Parent MW |
|---|---|---|---|
| 360 | 2 | 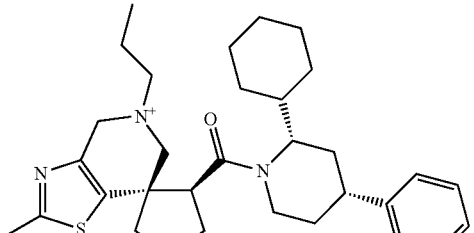 | 520.787 |
| 361 | 2 | 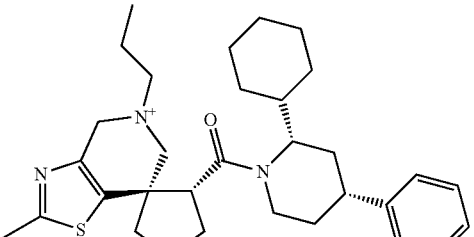 | 520.787 |
| 362 | 2 | 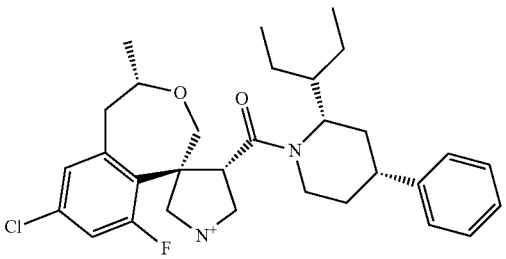 | 527.128 |
| 363 | 2 | 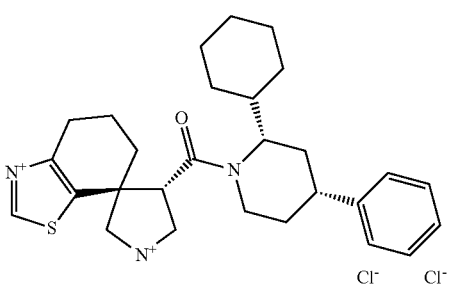 [SMILES: O=C([C@@H]1C[NH2+]C[C@]12CCCc1[nH+]csc12)N1CC[C@@H](c2ccccc2)C[C@H]1C1CCCCC1 ; [Cl-] ; [Cl-]] | 463.691 |

TABLE 3-continued
| Ex. No. | Scheme | Structure | Parent MW |
|---|---|---|---|
| 364 | 2 | 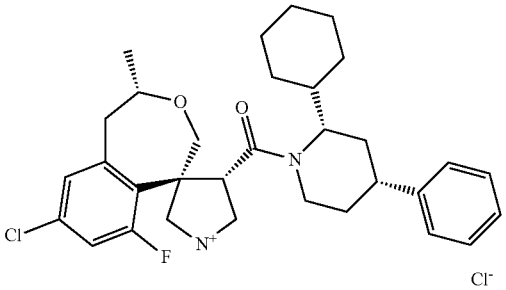 [SMILES: C[C@H]1Cc2cc(Cl)cc(F)c2[C@@]2(C[NH2+]C[C@H]2C(=O)N2CC[C@@H](c3ccccc3)C[C@H]2C2CCCCC2)CO1 ; [Cl-]] | 539.139 |
| 365 | 2 | 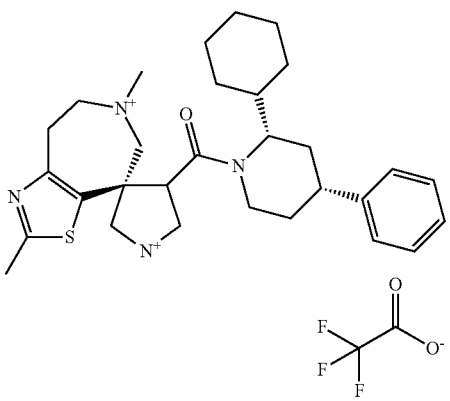 | 506.759 |
| 366 | 2 | 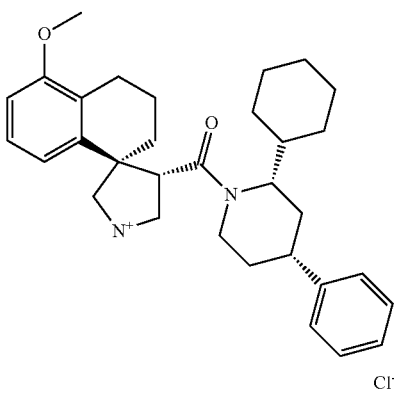 [SMILES: COc1cccc2c1CCC[C@]21C[NH2+]C[C@H]1C(=O)N1CC[C@@H](c2ccccc2)C[C@H]1C1CCCCC1 ; [Cl-]] | 486.704 |
| 367 | 2 | 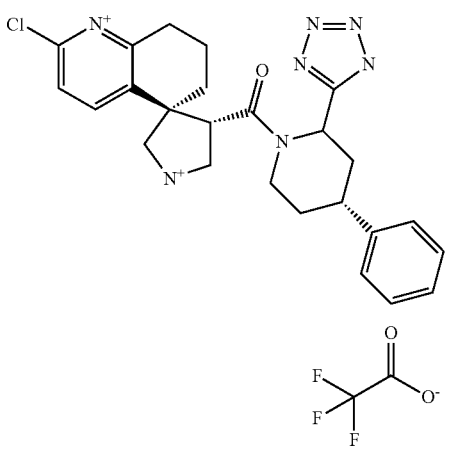 [SMILES: O=C([C@@H]1C[NH2+]C[C@]12CCCc1[nH+]c(Cl)ccc12)N1CC[C@@H](c2ccccc2)CC1c1nnn[nH]1 ; O=C([O-])C(F)(F)F] | 478.001 |

TABLE 3-continued

| Ex. No. | Scheme | Structure | Parent MW |
|---|---|---|---|
| 368 | 2 | 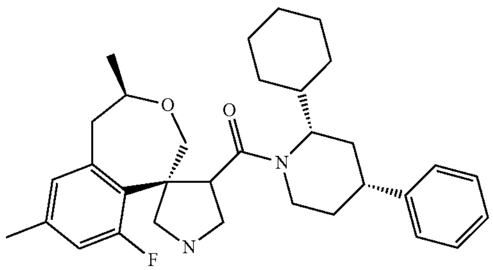 [SMILES: Cc1cc(F)c2c(c1)C[C@@H](C)OC[C@]21CNCC1C(=O)N1CC[C@@H](c2ccccc2)C[C@H]1C1CCCCC1] | 578.721 |
| 369 | 2 | 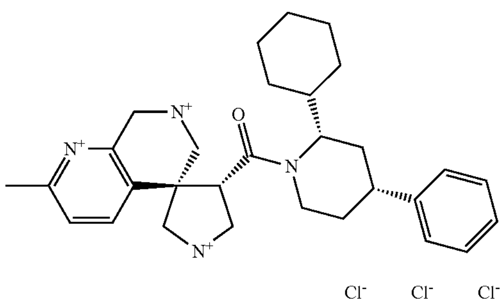 [SMILES: Cc1ccc2c([nH+]1)C[NH2+]C[C@]21C[NH2+]C[C@H]1C(=O)N1CC[C@@H](c2ccccc2)C[C@H]1C1CCCCC1 ; [Cl-] ; [Cl-] ; [Cl-]] | 472.679 |
| 370 | 2 | 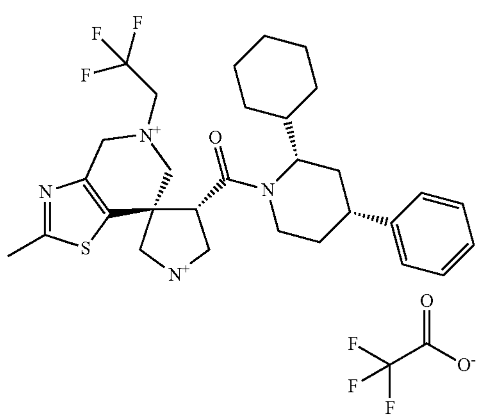 | 560.731 |
| 371 | 2 | 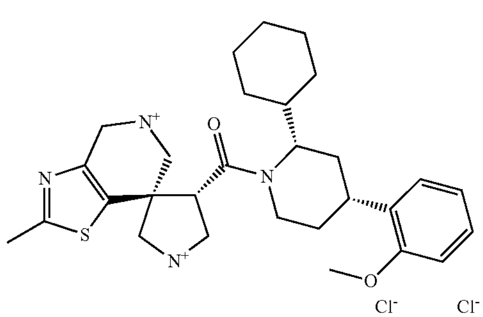 [SMILES: COc1ccccc1[C@@H]1CCN(C(=O)[C@@H]2C[NH2+]C[C@]23C[NH2+]Cc2nc(C)sc23)[C@H](C2CCCCC2)C1 ; [Cl-] ; [Cl-]] | 508.732 |

TABLE 3-continued

| Ex. No. | Scheme | Structure | Parent MW |
|---|---|---|---|
| 372 | 2 | 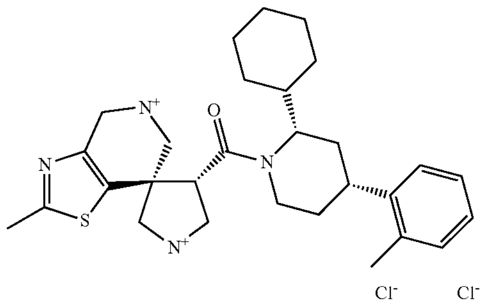 [SMILES: Cc1nc2c(s1)[C@]1(C[NH2+]C2)C[NH2+]C[C@H]1C(=O)N1CC[C@@H](c2ccccc2C)C[C@H]1C1CCCCC1 ; [Cl-] ; [Cl-]] | 492.732 |
| 373 | 2 | 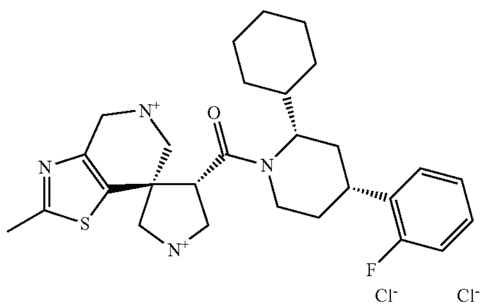 [SMILES: Cc1nc2c(s1)[C@]1(C[NH2+]C2)C[NH2+]C[C@H]1C(=O)N1CC[C@@H](c2ccccc2F)C[C@H]1C1CCCCC1 ; [Cl-] ; [Cl-]] | 496.696 |
| 374 | 2 | 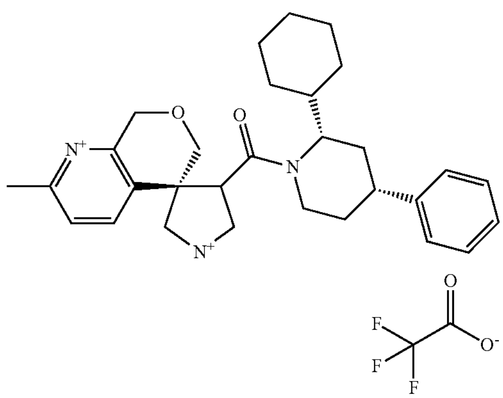 [SMILES: Cc1ccc2c([nH+]1)COC[C@]21C[NH2+]CC1C(=O)N1CC[C@@H](c2ccccc2)C[C@H]1C1CCCCC1 ; O=C([O-])C(F)(F)F] | 473.664 |
| 375 | 2 | 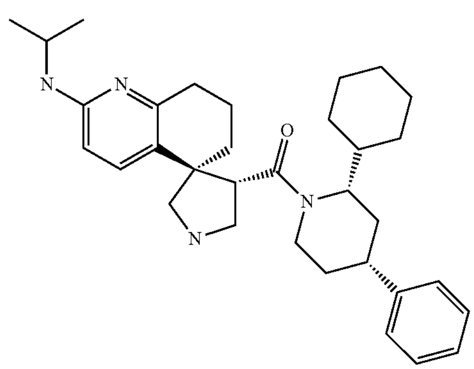 [SMILES: CC(C)Nc1ccc2c(n1)CCC[C@]21CNC[C@H]1C(=O)N1CC[C@@H](c2ccccc2)C[C@H]1C1CCCCC1] | 514.761 |

TABLE 3-continued

| Ex. No. | Scheme | Structure | Parent MW |
|---|---|---|---|
| 376 | 2 | 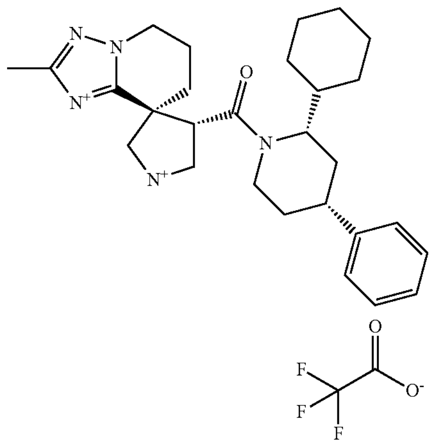 [SMILES: Cc1nn2c([nH+]1)[C@]1(CCC2)C[NH2+]C[C@H]1C(=O)N1CC[C@@H](c2ccccc2)C[C@H]1C1CCCCC1 ; O=C([O-])C(F)(F)F] | 461.656 |
| 377 | 2 | 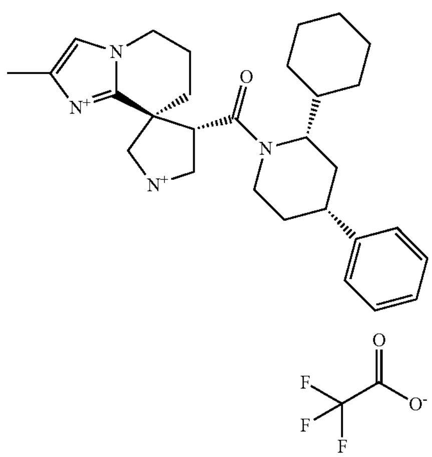 [SMILES: Cc1cn2c([nH+]1)[C@]1(CCC2)C[NH2+]C[C@H]1C(=O)N1CC[C@@H](c2ccccc2)C[C@H]1C1CCCCC1 ; O=C([O-])C(F)(F)F] | 460.668 |
| 378 | 2 | 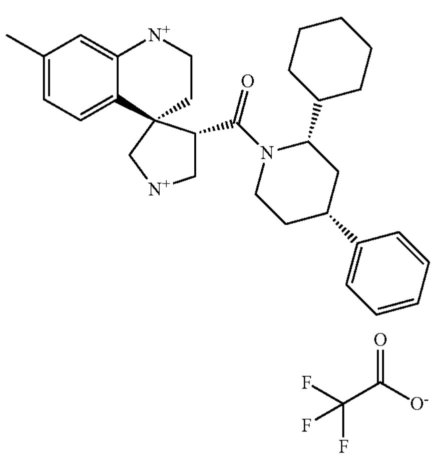 [SMILES: Cc1ccc2c(c1)[NH2+]CC[C@]21C[NH2+]C[C@H]1C(=O)N1CC[C@@H](c2ccccc2)C[C@H]1C1CCCCC1 ; O=C([O-])C(F)(F)F] | 471.692 |

TABLE 3-continued
| Ex. No. | Scheme | Structure | Parent MW |
|---|---|---|---|
| 379 | 2 | 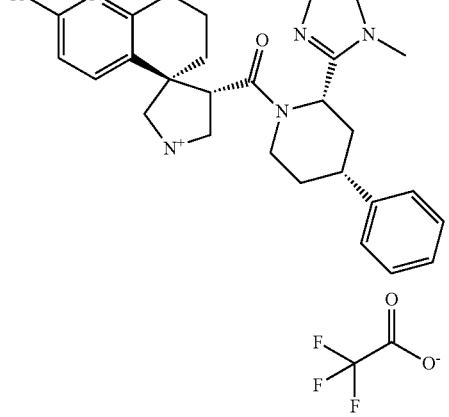 | 490.053 |
| 380 | 2 | 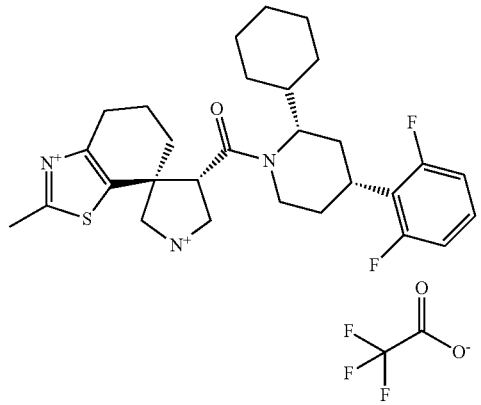 [SMILES: Cc1[nH+]c2c(s1)[C@]1(CCC2)C[NH2+]C[C@H]1C(=O)N1CC[C@@H](c2c(F)cccc2F)C[C@H]1C1CCCCC1 ; O=C([O-])C(F)(F)F] | 627.723 |
| 381 | 2 | 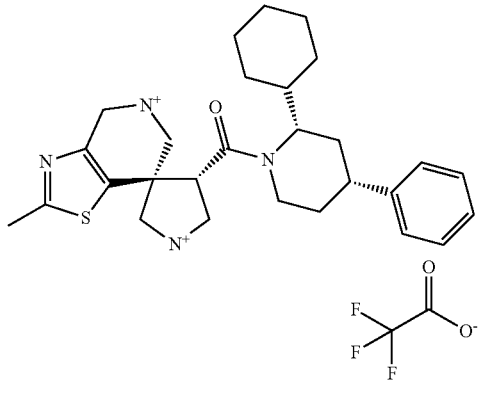 [SMILES: Cc1nc2c(s1)[C@]1(C[NH2+]C2)C[NH2+]C[C@H]1C(=O)N1CC[C@@H](c2ccccc2)C[C@H]1C1CCCCC1 ; O=C([O-])C(F)(F)F] | 478.705 |
| 382 | 2 | 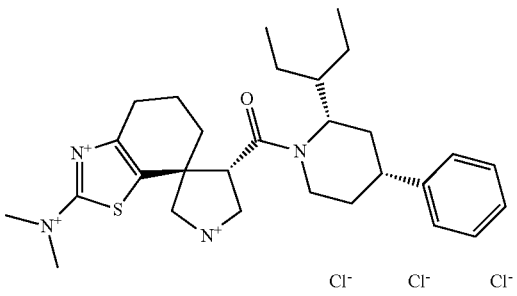 [SMILES: CCC(CC)[C@@H]1C[C@H](c2ccccc2)CCN1C(=O)[C@@H]1C[NH2+]C[C@]12CCCc1[nH+]c([NH+](C)C)sc12 ; [Cl-] ; [Cl-] ; [Cl-]] | 494.748 |

TABLE 3-continued

| Ex. No. | Scheme | Structure | Parent MW |
|---|---|---|---|
| 383 | 2 | 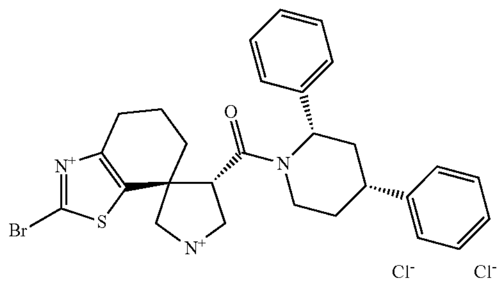 [SMILES: O=C([C@@H]1C[NH2+]C[C@]12CCCc1[nH+]c(Br)sc12)N1CC[C@@H](c2ccccc2)C[C@H]1c1ccccc1 ; [Cl-] ; [Cl-]] | 536.539 |
| 384 | 2 | 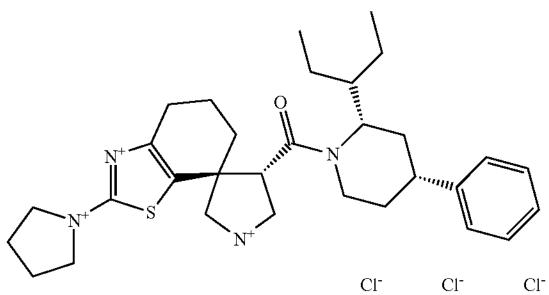 [SMILES: CCC(CC)[C@@H]1C[C@H](c2ccccc2)CCN1C(=O)[C@@H]1C[NH2+]C[C@]12CCCc1[nH+]c([NH+]3CCCC3)sc12 ; [Cl-] ; [Cl-] ; [Cl-]] | 520.787 |
| 385 | 2 | 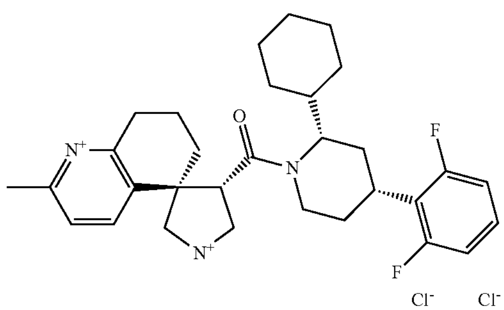 [SMILES: Cc1ccc2c([nH+]1)CCC[C@]21C[NH2+]C[C@H]1C(=O)N1CC[C@@H](c2c(F)cccc2F)C[C@H]1C1CCCCC1 ; [Cl-] ; [Cl-]] | 507.673 |
| 386 | 2 | 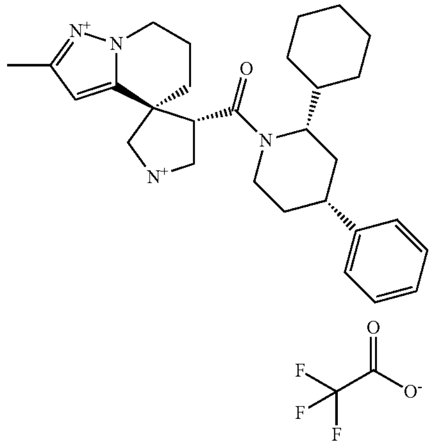 [SMILES: Cc1cc2n([nH+]1)CCC[C@]21C[NH2+]C[C@H]1C(=O)N1CC[C@@H](c2ccccc2)C[C@H]1C1CCCCC1 ; O=C([O-])C(F)(F)F] | 460.688 |

TABLE 3-continued

| Ex. No. | Scheme | Structure | Parent MW |
|---|---|---|---|
| 387 | 2 | 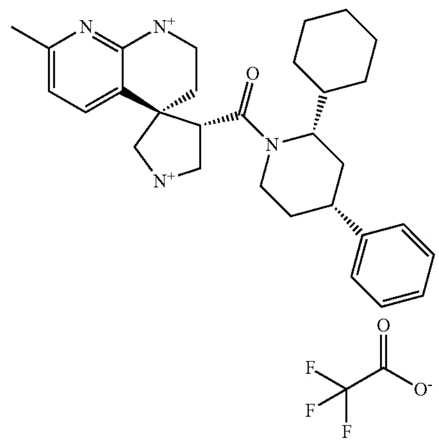 [SMILES: Cc1ccc2c(n1)[NH2+]CC[C@]21C[NH2+]C[C@H]1C(=O)N1CC[C@@H](c2ccccc2)C[C@H]1C1CCCCC1 ; O=C([O-])C(F)(F)F] | 472.679 |
| 388 | 2 | 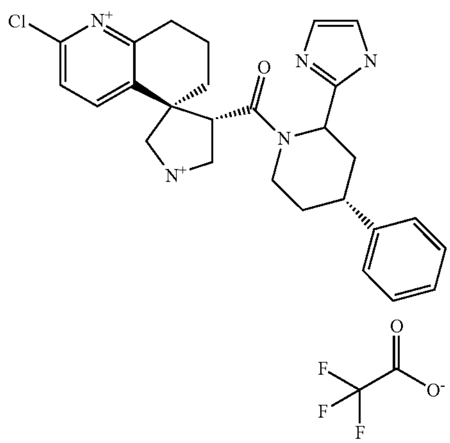 [SMILES: O=C([C@@H]1C[NH2+]C[C@]12CCCc1[nH+]c(Cl)ccc12)N1CC[C@@H](c2ccccc2)CC1c1ncc[nH]1 ; O=C([O-])C(F)(F)F] | 476.026 |
| 389 | 2 | 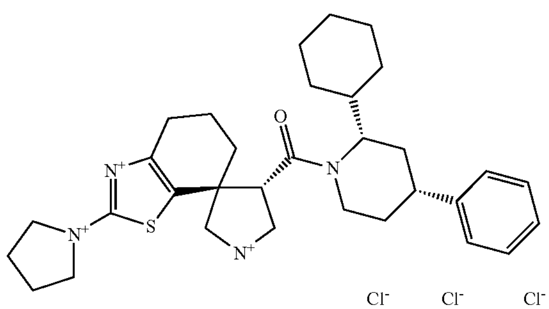 [SMILES: O=C([C@@H]1C[NH2+]C[C@]12CCCc1[nH+]c([NH+]3CCCC3)sc12)N1CC[C@@H](c2ccccc2)C[C@H]1C1CCCCC1 ; [Cl-] ; [Cl-] ; [Cl-]] | 532.798 |
| 390 | 2 | 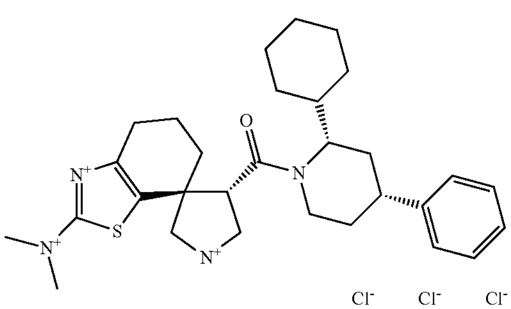 [SMILES: C[NH+](C)c1[nH+]c2c(s1)[C@]1(CCC2)C[NH2+]C[C@H]1C(=O)N1CC[C@@H](c2ccccc2)C[C@H]1C1CCCCC1 ; [Cl-] ; [Cl-] ; [Cl-]] | 506.759 |

TABLE 3-continued
| Ex. No. | Scheme | Structure | Parent MW |
|---|---|---|---|
| 391 | 2 | 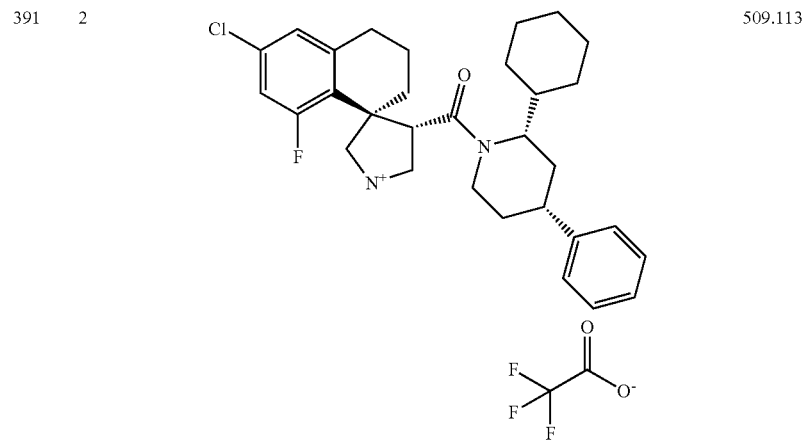 | 509.113 |
| 392 | 2 | 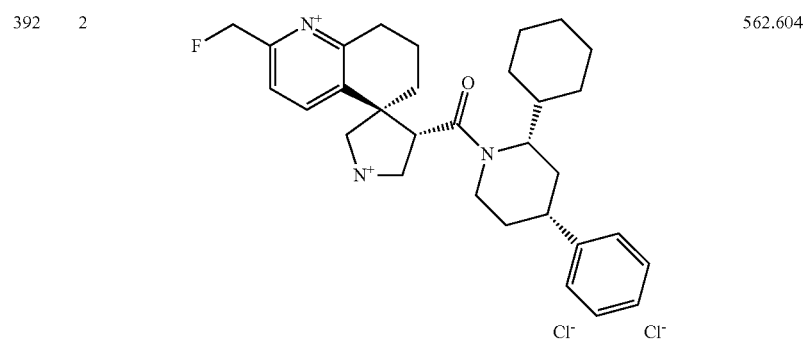 | 562.604 |
| 393 | 2 | 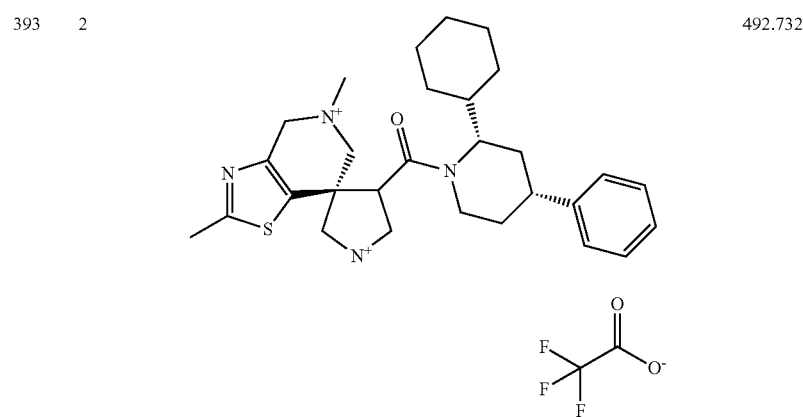 | 492.732 |

TABLE 3-continued
| Ex. No. | Scheme | Structure | Parent MW |
|---|---|---|---|
| 394 | 2 | 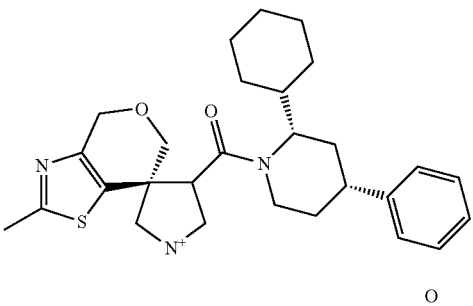 | 479.69 |
| 395 | 2 | 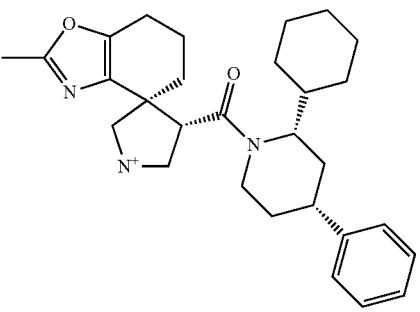 | 461.653 |
| 396 | 2 | 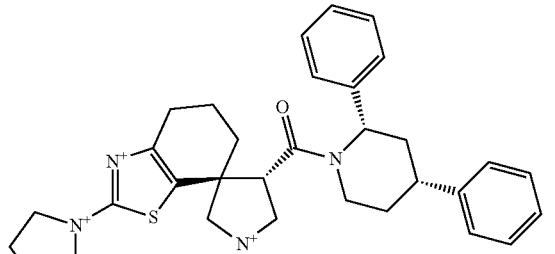 | 526.75 |
| 397 | 2 | 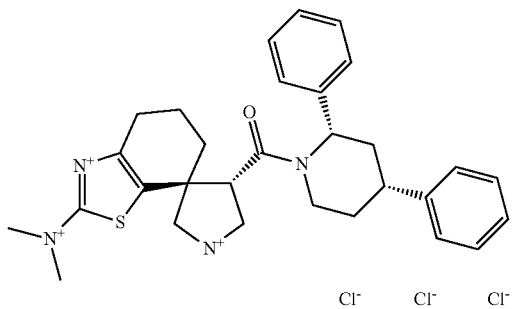 [SMILES: C[NH+](C)c1[nH+]c2c(s1)[C@]1(CCC2)C[NH2+]C[C@H]1C(=O)N1CC[C@@H](c2ccccc2)C[C@H]1c1ccccc1 ; [Cl-] ; [Cl-] ; [Cl-]] | 500.712 |

TABLE 3-continued
| Ex. No. | Scheme | Structure | Parent MW |
|---|---|---|---|
| 398 | 2 | 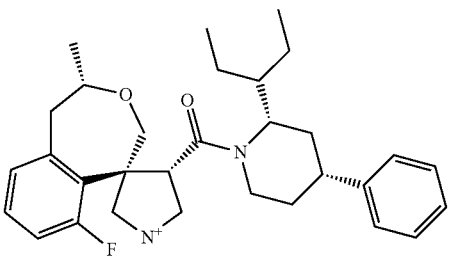 | 492.683 |
| 399 | 2 | 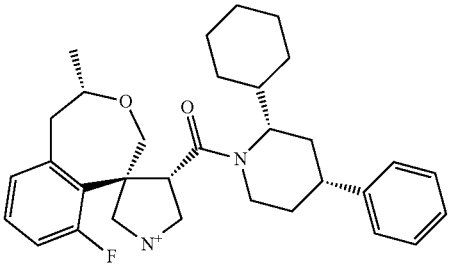 | 504.694 |
| 400 | 2 | 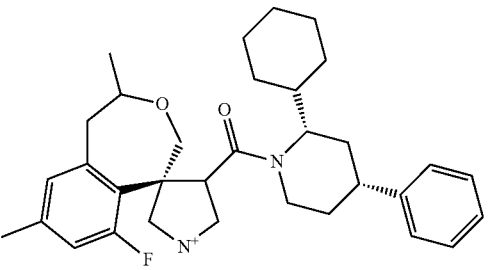 | 518.721 |
| 401 | 2 | 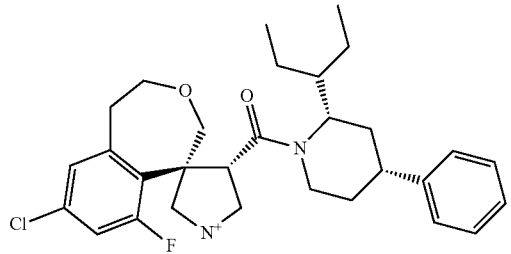 | 513.101 |

TABLE 3-continued

| Ex. No. | Scheme | Structure | Parent MW |
|---|---|---|---|
| 402 | 2 | | 460.665 |
| 402 | 2 | | 528.091 |
| 404 | 2 | 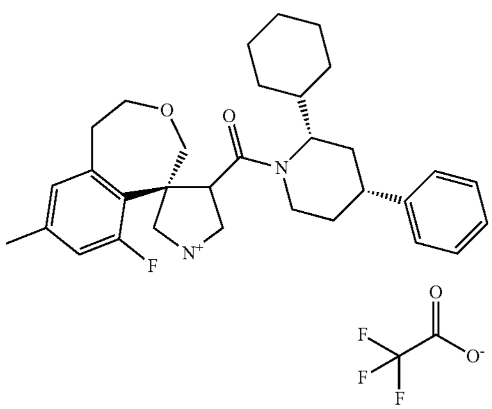 [SMILES: Cc1cc(F)c2c(c1)CCOC[C@]21C[NH2+]CC1C(=O)N1CC[C@@H](c2ccccc2)C[C@H]1C1CCCCC1 ; O=C([O-])C(F)(F)F] | 504.694 |
| 405 | 2 | 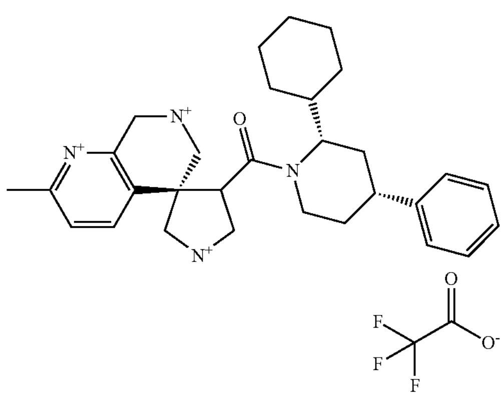 [SMILES: Cc1ccc2c([nH+]1)C[NH2+]C[C@]21C[NH2+]CC1C(=O)N1CC[C@@H](c2ccccc2)C[C@H]1C1CCCCC1 ; O=C([O-])C(F)(F)F] | 472.679 |

TABLE 3-continued

| Ex. No. | Scheme | Structure | Parent MW |
|---|---|---|---|
| 406 | 2 | 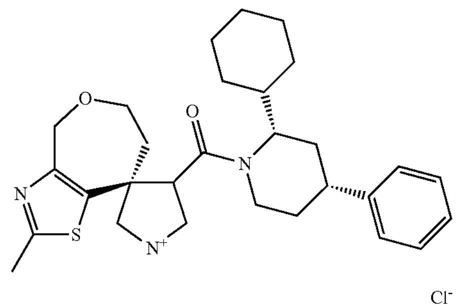 [SMILES: Cc1nc2c(s1)[C@]1(CCOC2)C[NH2+]CC1C(=O)N1CC[C@@H](c2ccccc2)C[C@H]1C1CCCCC1 ; [Cl-]] | 493.717 |
| 407 | 2 | 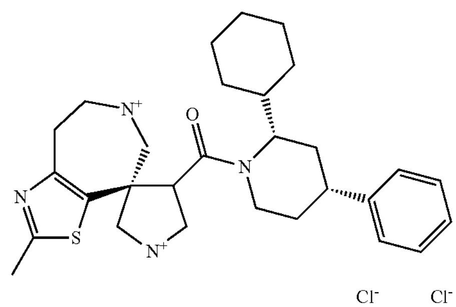 [SMILES: Cc1nc2c(s1)[C@]1(C[NH2+]CC2)C[NH2+]CC1C(=O)N1CC[C@@H](c2ccccc2)C[C@H]1C1CCCCC1 ; [Cl-] ; [Cl-]] | 493.732 |
| 408 | 2 | 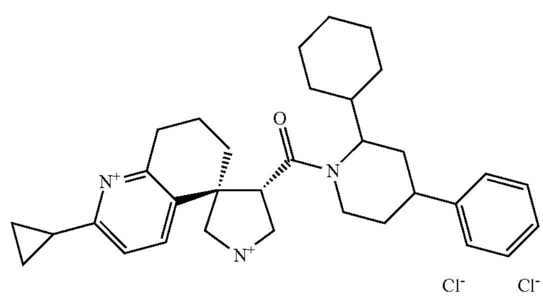 [SMILES: O=C([C@@H]1C[NH2+]C[C@]12CCCc1[nH+]c(C3CC3)ccc12)N1CCC(c2ccccc2)CC1C1CCCCC1 ; [Cl-] ; [Cl-]] | 497.93 |
| 409 | 2 | 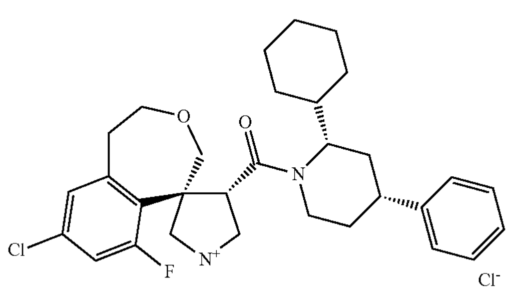 [SMILES: O=C([C@@H]1C[NH2+]C[C@]12COCCc1cc(Cl)cc(F)c12)N1CC[C@@H](c2ccccc2)C[C@H]1C1CCCCC1 ; [Cl-]] | 525.112 |

TABLE 3-continued
| Ex. No. | Scheme | Structure | Parent MW |
|---|---|---|---|
| 410 | 2 | 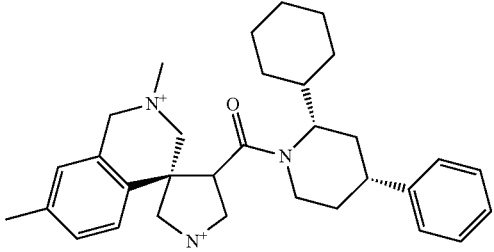 | 485.719 |
| 411 | 2 | 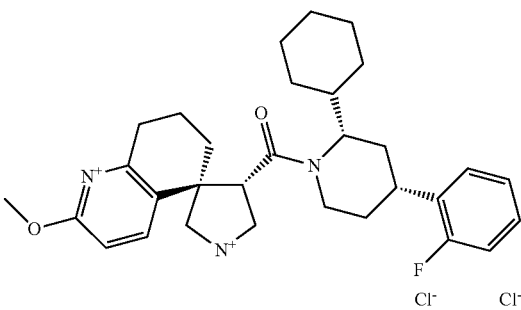 | 505.682 |
| 412 | 2 | 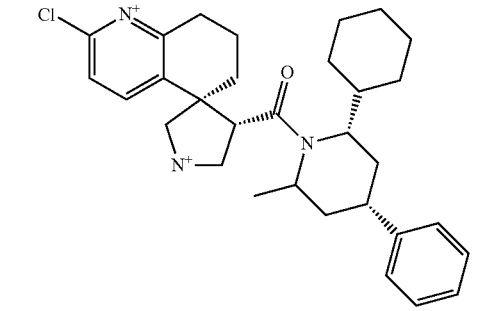 | 506.137 |
| 413 | 2 | 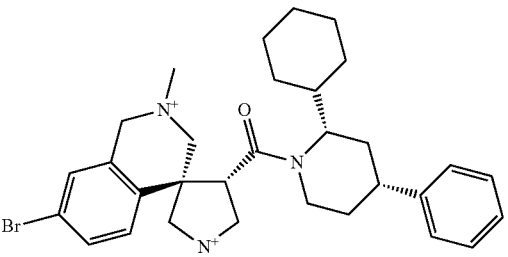 | 550.588 |

TABLE 3-continued
| Ex. No. | Scheme | Structure | Parent MW |
|---|---|---|---|
| 414 | 2 | 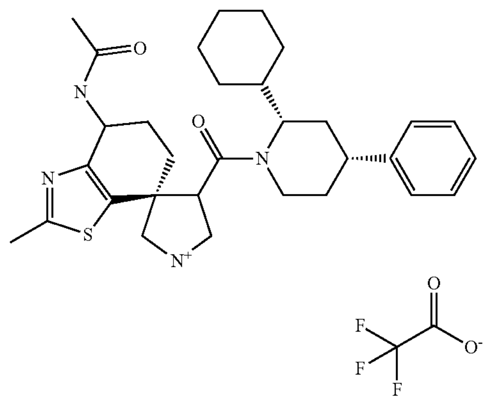 | 534.77 |
| 415 | 2 | 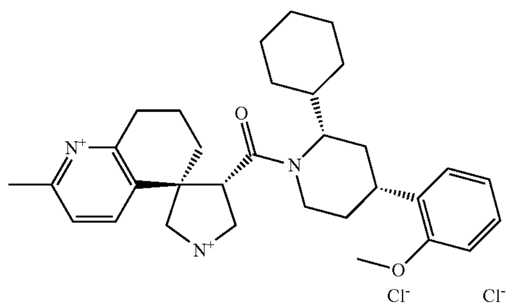 [SMILES: COc1ccccc1[C@@H]1CCN(C(=O)[C@@H]2C[NH2+]C[C@]23CCCc2[nH+]c(C)ccc23)[C@H](C2CCCCC2)C1 ; [Cl-] ; [Cl-]] | 501.718 |
| 416 | 2 | 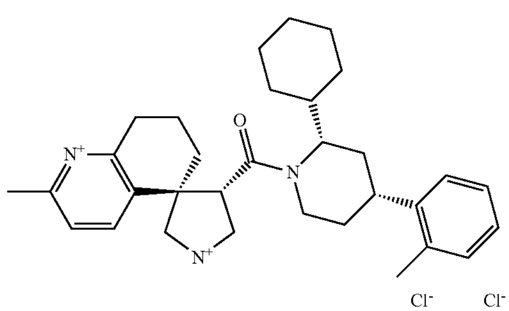 [SMILES: Cc1ccc2c([nH+]1)CCC[C@]21C[NH2+]C[C@H]1C(=O)N1CC[C@@H](c2ccccc2C)C[C@H]1C1CCCCC1 ; [Cl-] ; [Cl-]] | 485.719 |
| 417 | 2 | 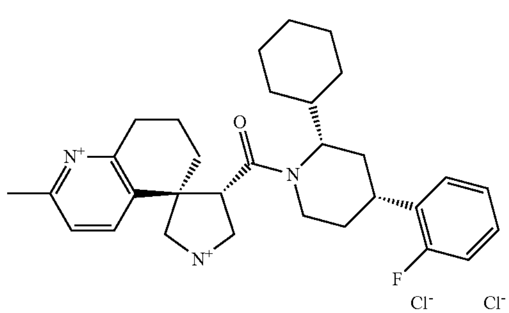 | 489.682 |
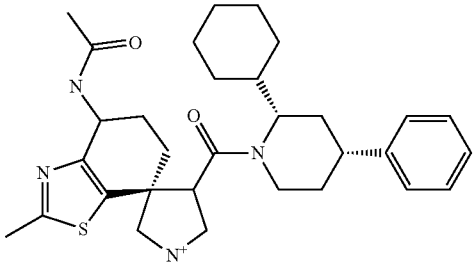

TABLE 3-continued

| Ex. No. | Scheme | Structure | Parent MW |
|---|---|---|---|
| 418 | 2 | 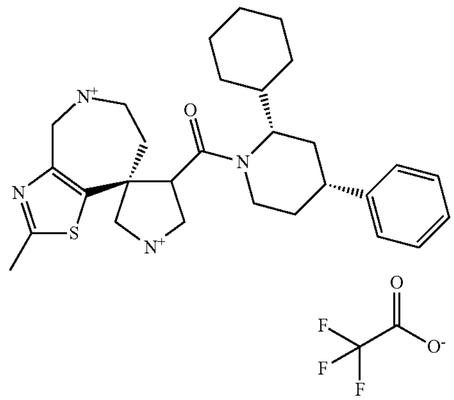 [SMILES: Cc1nc2c(s1)[C@]1(CC[NH2+]C2)C[NH2+]CC1C(=O)N1CC[C@@H](c2ccccc2)C[C@H]1C1CCCCC1 ; O=C([O-])C(F)(F)F] | 492.732 |
| 419 | 2 | 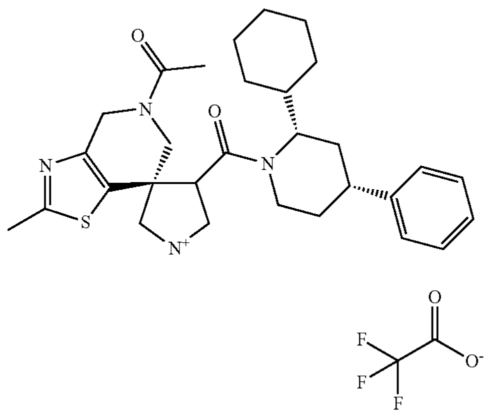 [SMILES: CC(=O)N1Cc2nc(C)sc2[C@@]2(C[NH2+]CC2C(=O)N2CC[C@@H](c3ccccc3)C[C@H]2C2CCCCC2)C1 ; O=C([O-])C(F)(F)F] | 520.743 |
| 420 | 2 | 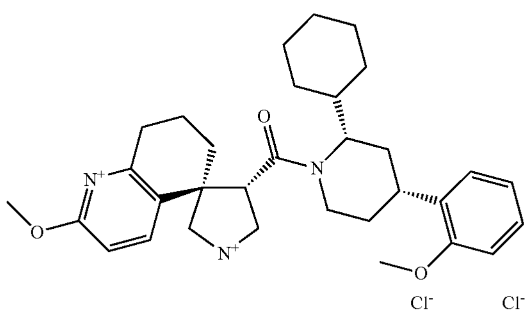 [SMILES: COc1ccc2c([nH+]1)CCC[C@]21C[NH2+]C[C@H]1C(=O)N1CC[C@@H](c2ccccc2OC)C[C@H]1C1CCCCC1 ; [Cl-] ; [Cl-]] | 517.718 |
| 421 | 2 | 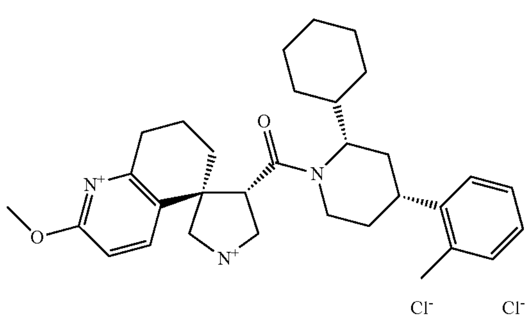 [SMILES: COc1ccc2c([nH+]1)CCC[C@]21C[NH2+]C[C@H]1C(=O)N1CC[C@@H](c2ccccc2C)C[C@H]1C1CCCCC1 ; [Cl-] ; [Cl-]] | 501.718 |

TABLE 3-continued

| Ex. No. | Scheme | Structure | Parent MW |
|---|---|---|---|
| 422 | 2 | 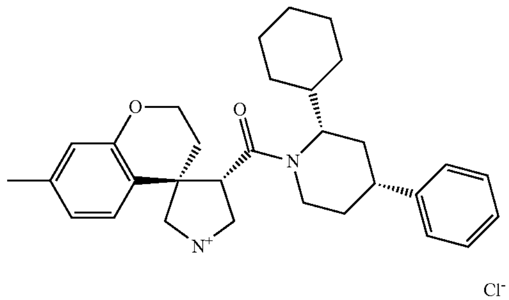 [SMILES: Cc1ccc2c(c1)OCC[C@]21C[NH2+]C[C@H]1C(=O)N1CC[C@@H](c2ccccc2)C[C@H]1C1CCCCC1 ; [Cl-]] | 472.677 |
| 423 | 2 | 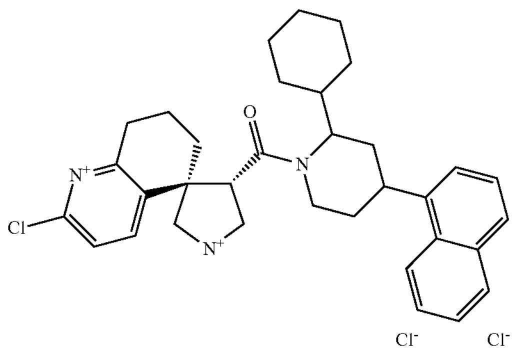 [SMILES: O=C([C@@H]1C[NH2+]C[C@]12CCCc1[nH+]c(Cl)ccc12)N1CCC(c2cccc3ccccc23)CC1C1CCCCC1 ; [Cl-] ; [Cl-]] | 542.17 |
| 424 | 2 | 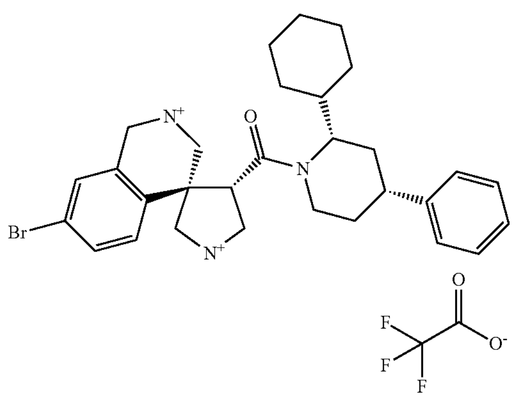 [SMILES: O=C([C@@H]1C[NH2+]C[C@]12C[NH2+]Cc1cc(Br)ccc12)N1CC[C@@H](c2ccccc2)C[C@H]1C1CCCCC1 ; O=C([O-])C(F)(F)F] | 536.561 |
| 425 | 2 | 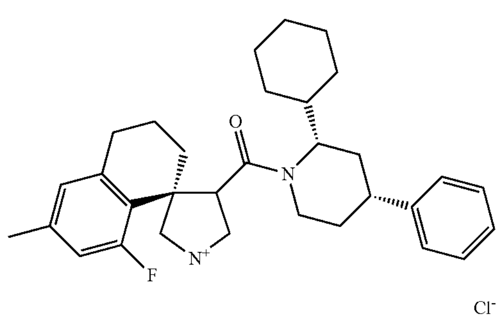 [SMILES: Cc1cc(F)c2c(c1)CCC[C@]21C[NH2+]CC1C(=O)N1CC[C@@H](c2ccccc2)C[C@H]1C1CCCCC1 ; [Cl-]] | 488.695 |

TABLE 3-continued
| Ex. No. | Scheme | Structure | Parent MW |
|---|---|---|---|
| 426 | 2 | 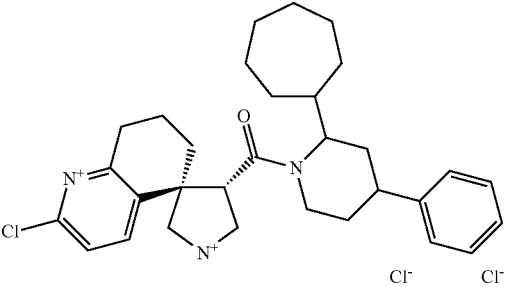 [SMILES: O=C([C@@H]1C[NH2+]C[C@]12CCCc1[nH+]c(Cl)ccc12)N1CCC(c2ccccc2)CC1C1CCCCCC1 ; [Cl-] ; [Cl-]] | 506.137 |
| 427 | 2 | 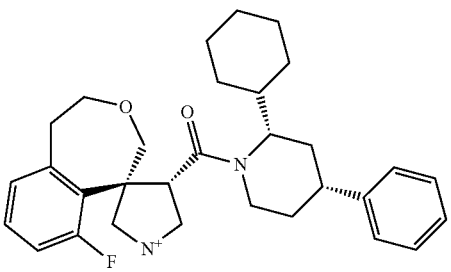 | 490.667 |
| 428 | 2 | 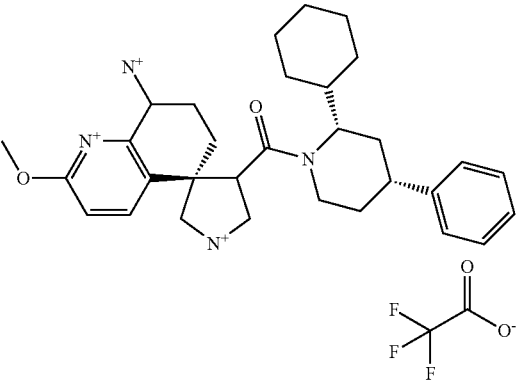 | 844.778 |
| 429 | 2 | 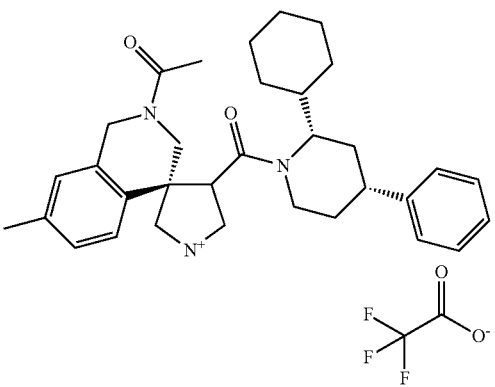 [SMILES: CC(=O)N1Cc2cc(C)ccc2[C@@]2(C[NH2+]CC2C(=O)N2CC[C@@H](c3ccccc3)C[C@H]2C2CCCCC2)C1 ; O=C([O-])C(F)(F)F] | 513.73 |

TABLE 3-continued

| Ex. No. | Scheme | Structure | Parent MW |
|---|---|---|---|
| 430 | 2 | 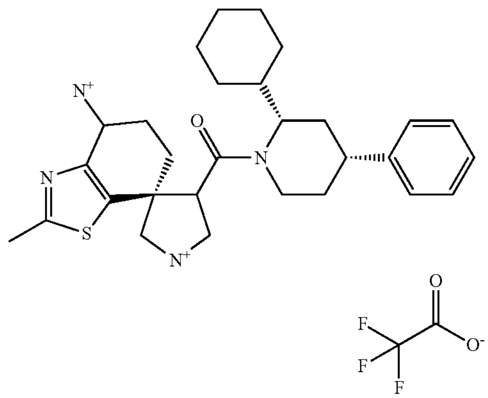 | 492.732 |
| 431 | 2 | 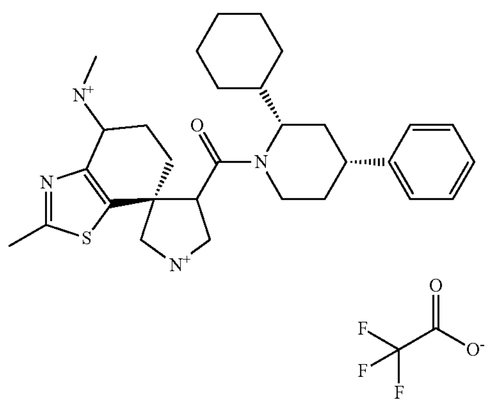 | 506.759 |
| 432 | 2 | 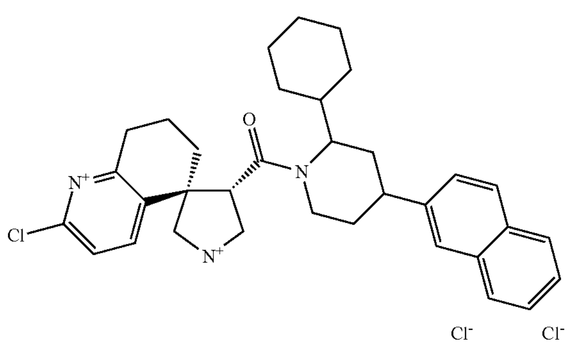 [SMILES: O=C([C@@H]1C[NH2+]C[C@]12CCCc1[nH+]c(Cl)ccc12)N1CCC(c2ccc3ccccc3c2)CC1C1CCCCC1 ; [Cl-] ; [Cl-]] | 542.17 |
| 433 | 2 | 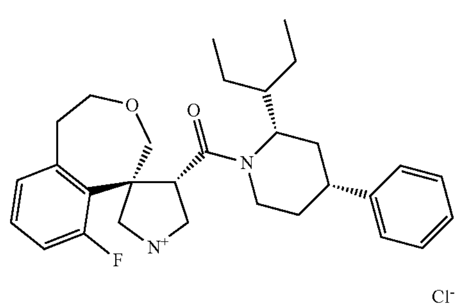 [SMILES: CCC(CC)[C@@H]1C[C@H](c2ccccc2)CCN1C(=O)[C@@H]1C[NH2+]C[C@]12COCCc1cccc(F)c12 ; [Cl-]] | 478.656 |

TABLE 3-continued

| Ex. No. | Scheme | Structure | Parent MW |
|---|---|---|---|
| 434 | 2 | 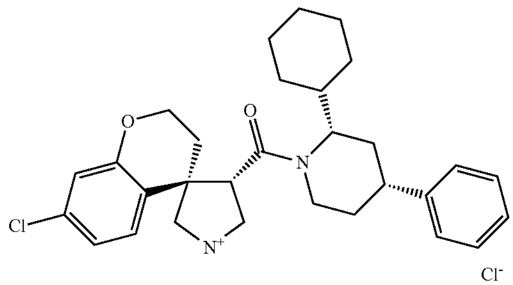 [SMILES: O=C([C@@H]1C[NH2+]C[C@]12CCOc1cc(Cl)ccc12)N1CC[C@@H](c2ccccc2)C[C@H]1C1CCCCC1 ; [Cl-]] | 493.095 |
| 435 | 2 | 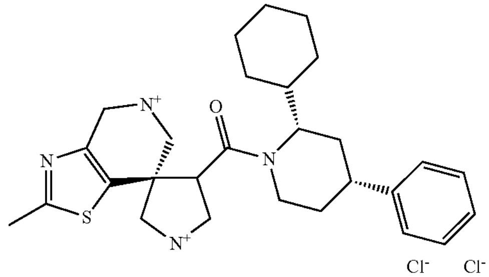 [SMILES: Cc1nc2c(s1)[C@]1(C[NH2+]C2)C[NH2+]CC1C(=O)N1CC[C@@H](c2ccccc2)C[C@H]1C1CCCCC1 ; [Cl-] ; [Cl-]] | 478.705 |
| 436 | 2 | 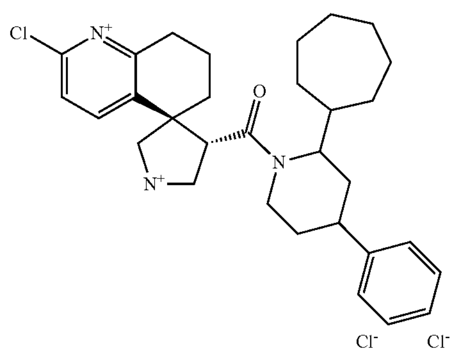 [SMILES: O=C([C@@H]1C[NH2+]C[C@]12CCCc1[nH+]c(Cl)ccc12)N1CCC(c2ccccc2)CC1C1CCCCCC1 ; [Cl-] ; [Cl-]] | 506.137 |
| 437 | 2 | 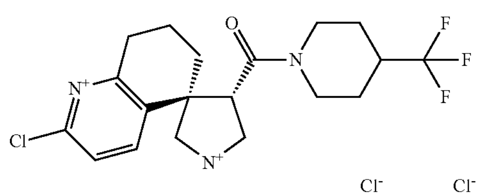 [SMILES: O=C([C@@H]1C[NH2+]C[C@]12CCCc1[nH+]c(Cl)ccc12)N1CCC(C(F)(F)F)CC1 ; [Cl-] ; [Cl-]] | 401.863 |
| 438 | 2 | 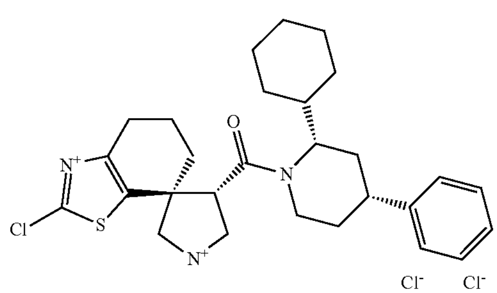 [SMILES: O=C([C@@H]1C[NH2+]C[C@]12CCCc1[nH+]c(Cl)sc12)N1CC[C@@H](c2ccccc2)C[C@H]1C1CCCCC1 ; [Cl-] ; [Cl-]] | 498.136 |

TABLE 3-continued

| Ex. No. | Scheme | Structure | Parent MW |
|---|---|---|---|
| 439 | 2 | 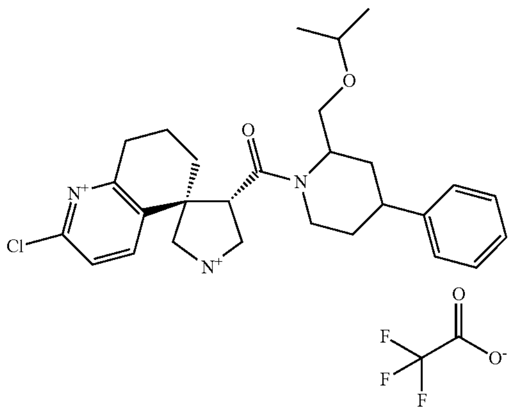 [SMILES: CC(C)OCC1CC(c2ccccc2)CCN1C(=O)[C@@H]1C[NH2+]C[C@]12CCCc1[nH+]c(Cl)ccc12 ; O=C([O-])C(F)(F)F] | 482.071 |
| 440 | 2 | 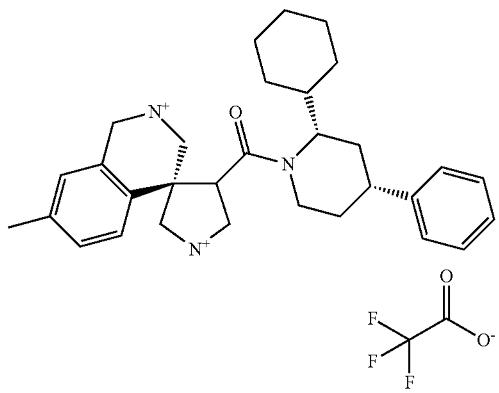 [SMILES: Cc1ccc2c(c1)C[NH2+]C[C@]21C[NH2+]CC1C(=O)N1CC[C@@H](c2ccccc2)C[C@H]1C1CCCCC1 ; O=C([O-])C(F)(F)F] | 491.692 |
| 441 | 2 | 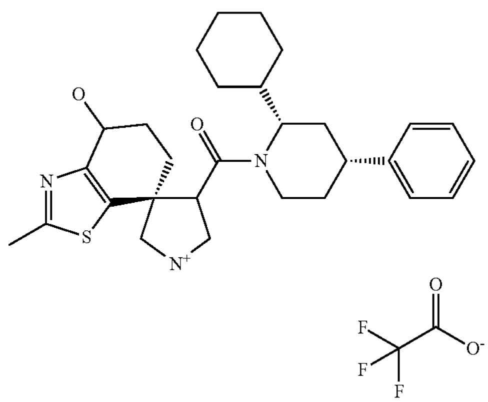 | 493.717 |
| 442 | 2 | 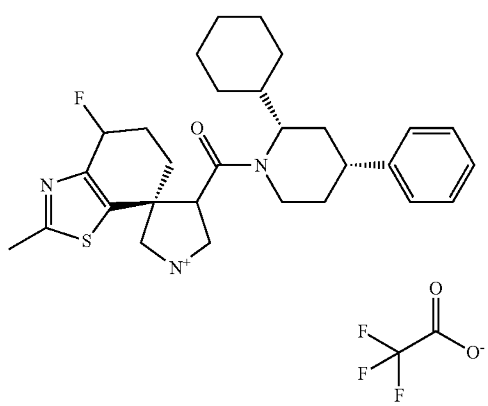 | 495.708 |

TABLE 3-continued
| Ex. No. | Scheme | Structure | Parent MW |
|---|---|---|---|
| 443 | 2 | 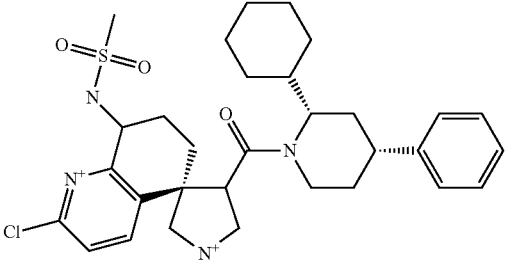 | 585.214 |
| 444 | 2 | 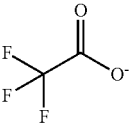 | 544.186 |
| 445 | 2 | 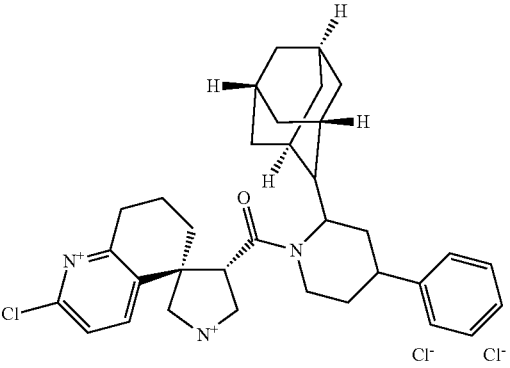 [SMILES: O=C([C@@H]1C[NH2+]C[C@]12CCCc1[nH+]c(Cl)ccc12)N1CCC(c2ccccc2)CC1C1[C@H]2C[C@@H]3C[C@@H](C[C@H]1C3)C2 ; [Cl-] ; [Cl-]] | 549.162 |

TABLE 3-continued

| Ex. No. | Scheme | Structure | Parent MW |
|---|---|---|---|
| 446 | 2 | 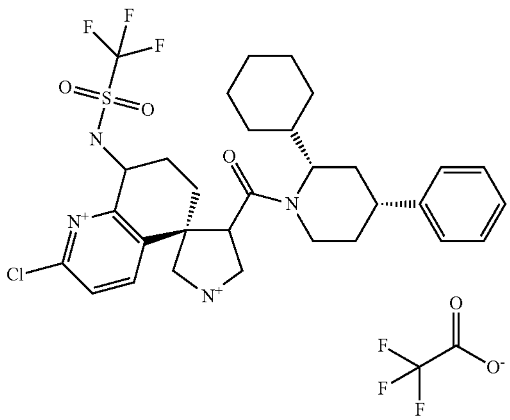 | 639.186 |
| 447 | 2 | 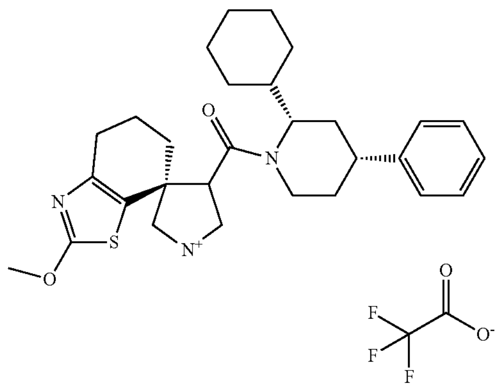 [SMILES: COc1nc2c(s1)[C@]1(CCC2)C[NH2+]CC1C(=O)N1CC[C@@H](c2ccccc2)C[C@H]1C1CCCCC1 ; O=C([O-])C(F)(F)F] | 493.717 |
| 448 | 2 | 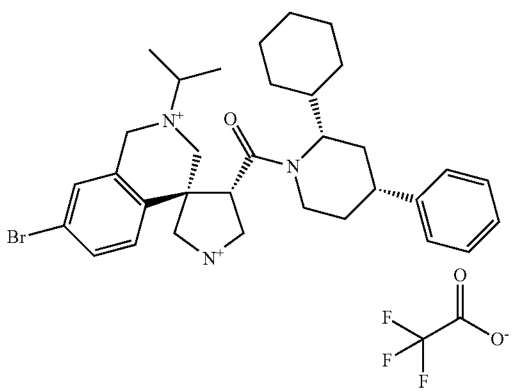 | 578.642 |
| 449 | 2 | 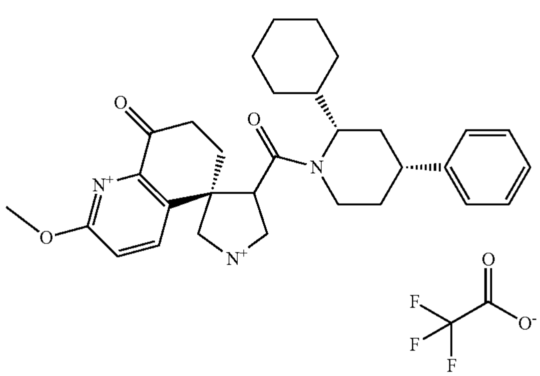 [SMILES: COc1ccc2c([nH+]1)C(=O)CC[C@]21C[NH2+]CC1C(=O)N1CC[C@@H](c2ccccc2)C[C@H]1C1CCCCC1 ; O=C([O-])C(F)(F)F] | 501.675 |

TABLE 3-continued

| Ex. No. | Scheme | Structure | Parent MW |
|---|---|---|---|
| 450 | 2 | 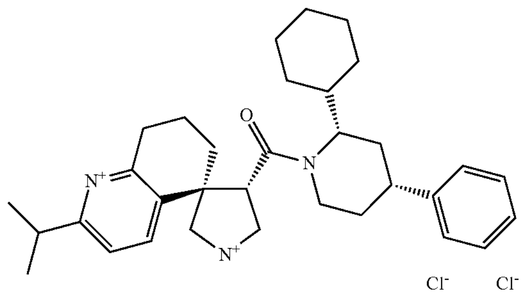 [SMILES: CC(C)c1ccc2c([nH+]1)CCC[C@]21C[NH2+]C[C@H]1C(=O)N1CC[C@@H](c2ccccc2)C[C@H]1C1CCCCC1 ; [Cl-] ; [Cl-]] | 499.746 |
| 451 | 2 | 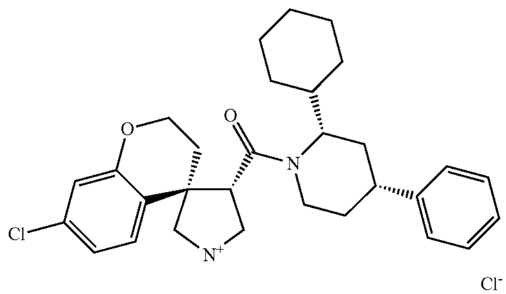 | 493.095 |
| 452 | 2 | 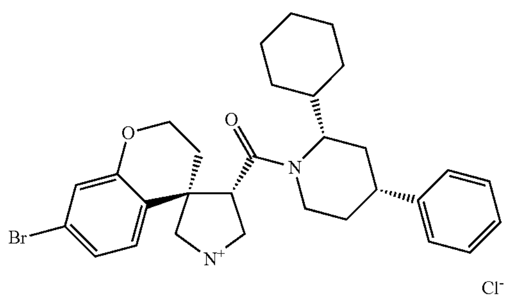 [SMILES: O=C([C@@H]1C[NH2+]C[C@]12CCOc1cc(Cl)ccc12)N1CC[C@@H](c2ccccc2)C[C@H]1C1CCCCC1 ; [Cl-]] | 537.546 |
| 453 | 2 | 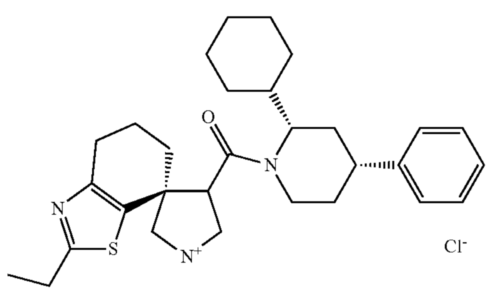 [SMILES: CCc1nc2c(s1)[C@]1(CCC2)C[NH2+]CC1C(=O)N1CC[C@@H](c2ccccc2)C[C@H]1C1CCCCC1 ; [Cl-]] | 491.745 |
| 454 | 2 | 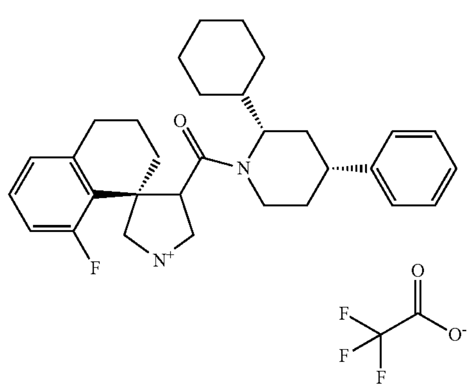 [SMILES: O=C(C1C[NH2+]C[C@]12CCCc1cccc(F)c12)N1CC[C@@H](c2ccccc2)C[C@H]1C1CCCCC1 ; O=C([O-])C(F)(F)F] | 474.668 |

TABLE 3-continued

| Ex. No. | Scheme | Structure | Parent MW |
|---|---|---|---|
| 455 | 2 | 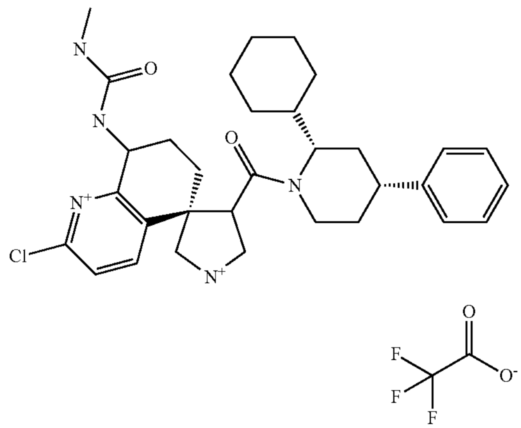 | 564.177 |
| 456 | 2 | 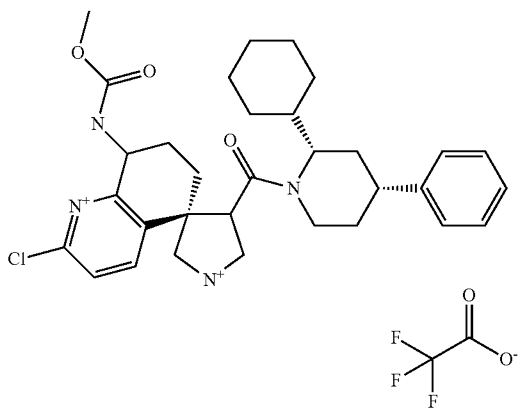 | 585.162 |
| 457 | 2 | 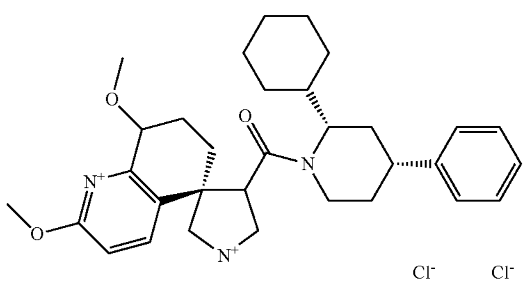 | 517.718 |
| 458 | 2 | 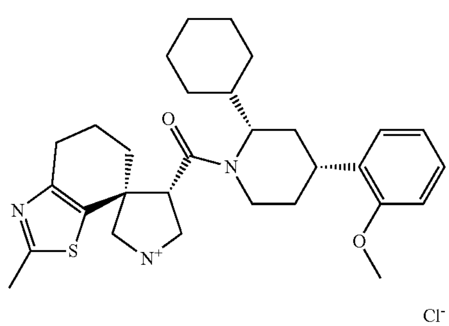 [SMILES: COc1ccccc1[C@@H]1CCN(C(=O)[C@@H]2C[NH2+]C[C@]23CCCc2nc(C)sc23)[C@H](C2CCCCC2)C1 ; [Cl-]] | 507.744 |

TABLE 3-continued
| Ex. No. | Scheme | Structure | Parent MW |
|---|---|---|---|
| 459 | 2 | 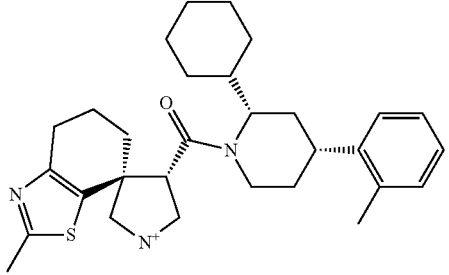 | 491.745 |
| 460 | 2 | 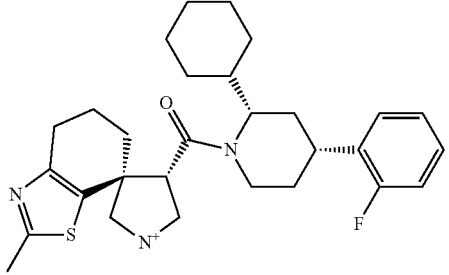 | 495.708 |
| 461 | 2 | 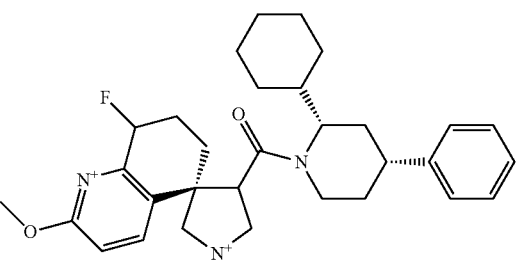 | 505.682 |
| 462 | 2 | 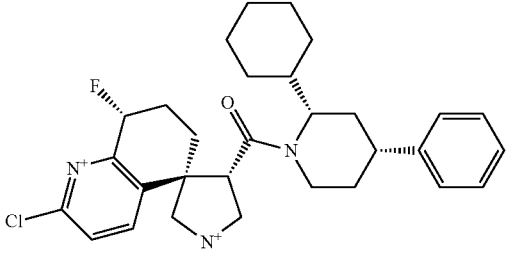 | 510.1 |

TABLE 3-continued

| Ex. No. | Scheme | Structure | Parent MW |
|---|---|---|---|
| 463 | 2 | 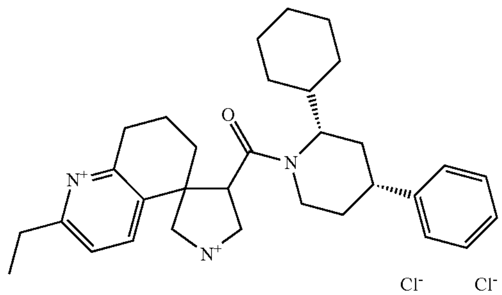 [SMILES: CCc1ccc2c([nH+]1)CCCC21C[NH2+]CC1C(=O)N1CC[C@@H](c2ccccc2)C[C@H]1C1CCCCC1 ; [Cl-] ; [Cl-]] | 485.719 |
| 464 | 2 | 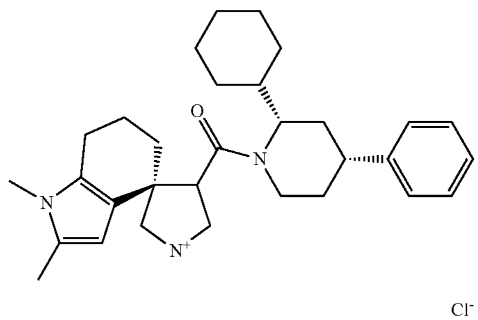 [SMILES: Cc1cc2c(n1C)CCC[C@]21C[NH2+]CC1C(=O)N1CC[C@@H](c2ccccc2)C[C@H]1C1CCCCC1 ; [Cl-]] | 473.708 |
| 465 | 2 | 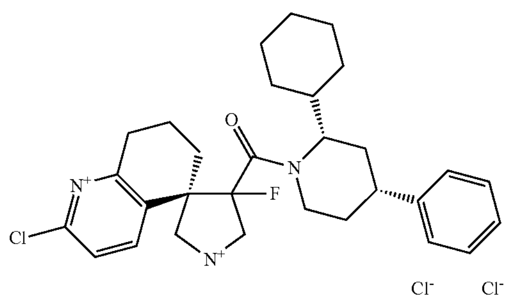 [SMILES: O=C(N1CC[C@@H](c2ccccc2)C[C@H]1C1CCCCC1)C1(F)C[NH2+]C[C@]12CCCc1[nH+]c(Cl)ccc12 ; [Cl-] ; [Cl-]] | 510.1 |
| 466 | 2 | 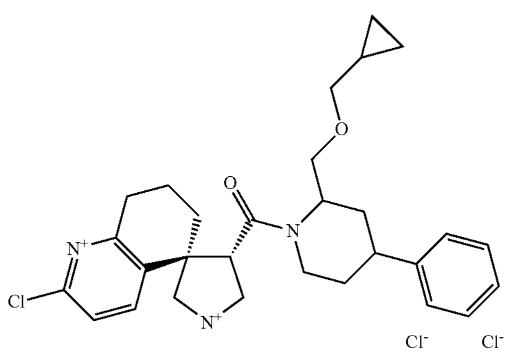 [SMILES: O=C([C@@H]1C[NH2+]C[C@]12CCCc1[nH+]c(Cl)ccc12)N1CCC(c2ccccc2)CC1COCC1CC1 ; [Cl-] ; [Cl-]] | 494.082 |
| 467 | 2 | 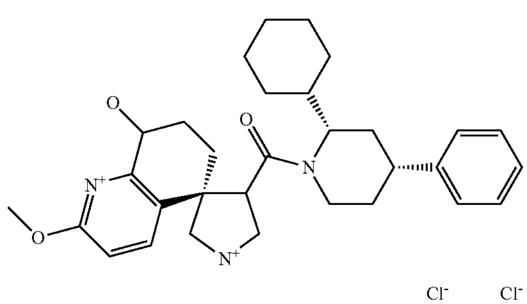 | 503.691 |

TABLE 3-continued

| Ex. No. | Scheme | Structure | Parent MW |
|---|---|---|---|
| 468 | 2 | 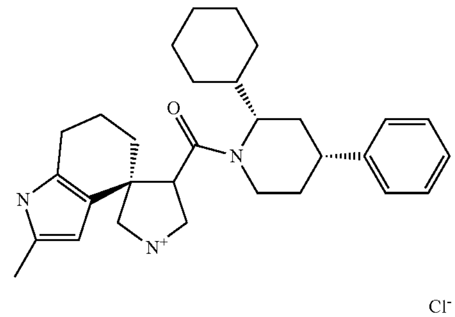 [SMILES: Cc1cc2c([nH]1)CCC[C@]21C[NH2+]CC1C(=O)N1CC[C@@H](c2ccccc2)C[C@H]1C1CCCCC1 ; [Cl-]] | 495.681 |
| 469 | 2 | 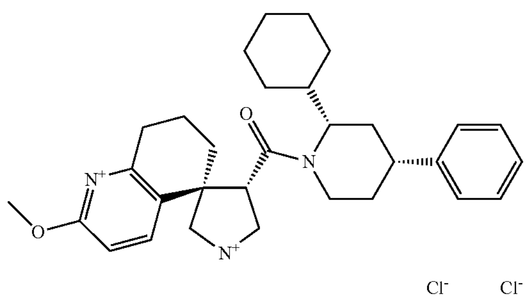 [SMILES: COc1ccc2c([nH+]1)CCC[C@]21C[NH2+]C[C@H]1C(=O)N1CC[C@@H](c2ccccc2)C[C@H]1C1CCCCC1 ; [Cl-] ; [Cl-]] | 487.691 |
| 470 | 2 | 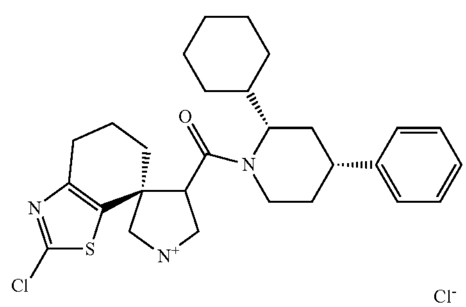 [SMILES: O=C(C1C[NH2+]C[C@]12CCCc1nc(Cl)sc12)N1CC[C@@H](c2ccccc2)C[C@H]1C1CCCCC1 ; [Cl-]] | 498.136 |
| 471 | 2 | 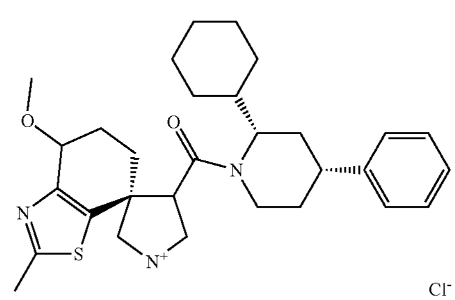 | 507.744 |

TABLE 3-continued
| Ex. No. | Scheme | Structure | Parent MW |
|---|---|---|---|
| 472 | 2 | 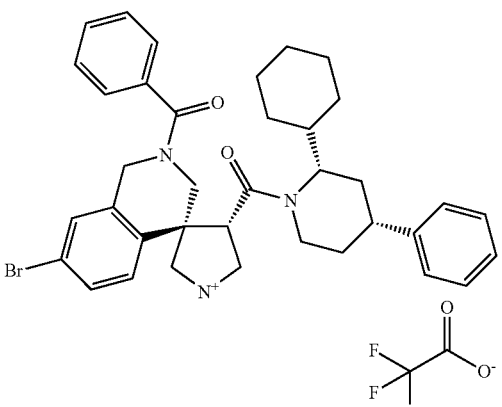 | 640.67 |
| 473 | 2 | 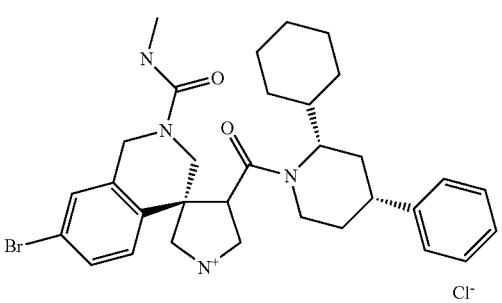 [SMILES: CNC(=O)N1Cc2cc(Br)ccc2[C@@]2(C[NH2+]CC2C(=O)N2CC[C@@H](c3ccccc3)C[C@H]2C2CCCCC2)C1 ; [Cl-]] | 593.613 |
| 474 | 2 | 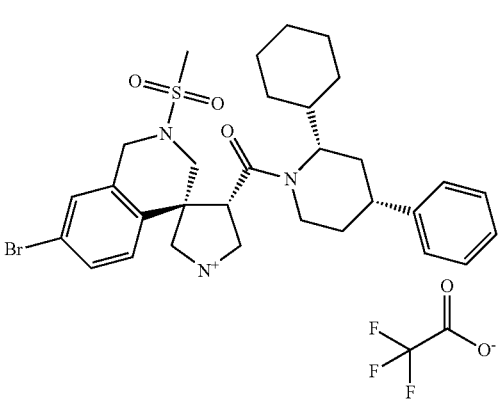 [SMILES: CS(=O)(=O)N1Cc2cc(Br)ccc2[C@@]2(C[NH2+]C[C@H]2C(=O)N2CC[C@@H](c3ccccc3)C[C@H]2C2CCCCC2)C1 ; O=C([O-])C(F)(F)F] | 614.651 |
| 475 | 2 | 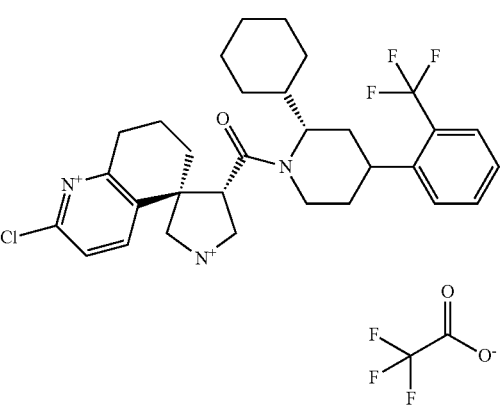 [SMILES: O=C([C@@H]1C[NH2+]C[C@]12CCCc1[nH+]c(Cl)ccc12)N1CCC(c2ccccc2C(F)(F)F)C[C@H]1C1CCCCC1 ; O=C([O-])C(F)(F)F] | 560.108 |

TABLE 3-continued
| Ex. No. | Scheme | Structure | Parent MW |
|---|---|---|---|
| 476 | 2 | 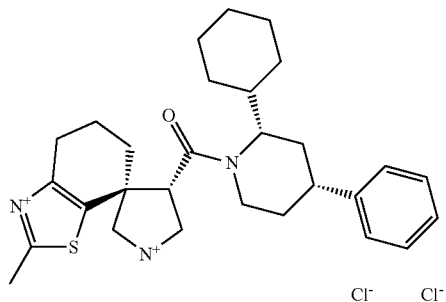 [SMILES: Cc1[nH+]c2c(s1)[C@]1(CCC2)C[NH2+]C[C@H]1C(=O)N1CC[C@@H](c2ccccc2)C[C@H]1C1CCCCC1 ; [Cl-] ; [Cl-]] | 477.718 |
| 477 | 2 | 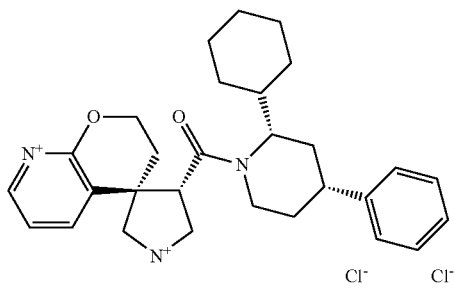 [SMILES: O=C([C@@H]1C[NH2+]C[C@]12CCOc1[nH+]cccc12)N1CC[C@@H](c2ccccc2)C[C@H]1C1CCCCC1 ; [Cl-] ; [Cl-]] | 459.637 |
| 478 | 2 | 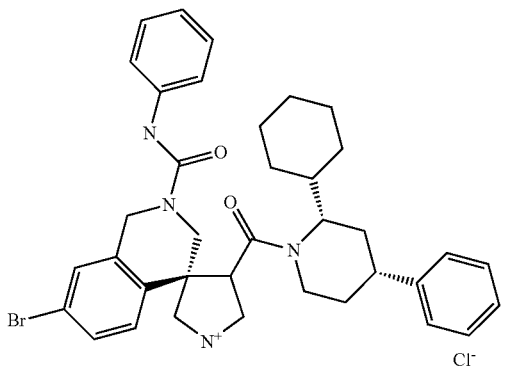 [SMILES: O=C(Nc1ccccc1)N1Cc2cc(Br)ccc2[C@@]2(C[NH2+]CC2C(=O)N2CC[C@@H](c3ccccc3)C[C@H]2C2CCCCC2)C1 ; [Cl-]] | 655.685 |
| 479 | 2 | 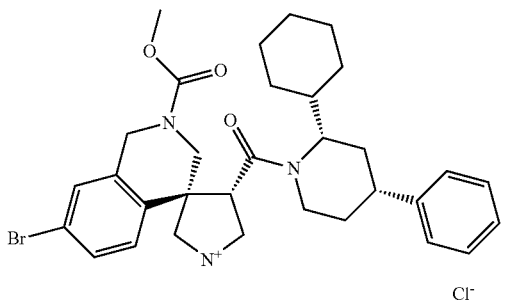 [SMILES: COC(=O)N1Cc2cc(Br)ccc2[C@@]2(C[NH2+]C[C@H]2C(=O)N2CC[C@@H](c3ccccc3)C[C@H]2C2CCCCC2)C1 ; [Cl-]] | 594.598 |

TABLE 3-continued

| Ex. No. | Scheme | Structure | Parent MW |
|---|---|---|---|
| 480 | 2 | 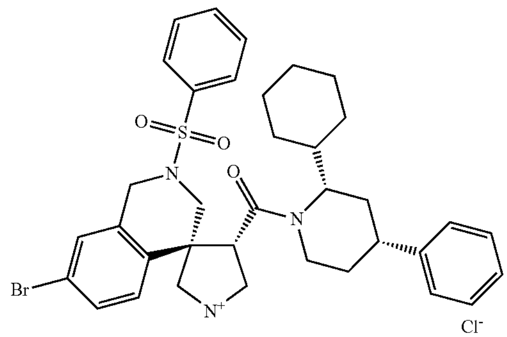 [SMILES: O=C([C@@H]1C[NH2+]C[C@]12CN(S(=O)(=O)c1ccccc1)Cc1cc(Br)ccc12)N1CC[C@@H](c2ccccc2)C[C@H]1C1CCCCC1 ; [Cl-]] | 676.722 |
| 481 | 2 | 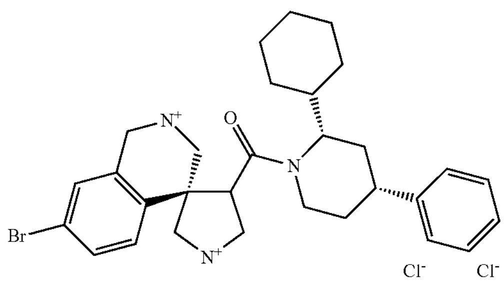 [SMILES: O=C(C1C[NH2+]C[C@]12C[NH2+]Cc1cc(Br)ccc12)N1CC[C@@H](c2ccccc2)C[C@H]1C1CCCCC1 ; [Cl-] ; [Cl-]] | 536.561 |
| 482 | 2 | 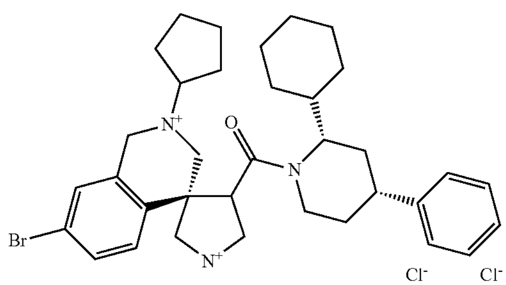 | 604.68 |
| 483 | 2 | 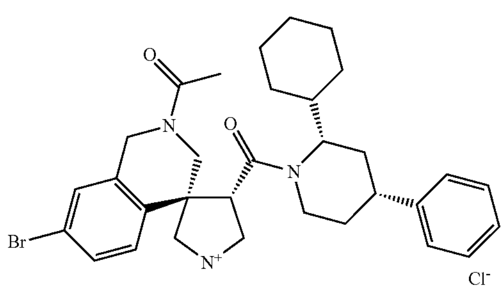 [SMILES: CC(=O)N1Cc2cc(Br)ccc2[C@@]2(C[NH2+]C[C@H]2C(=O)N2CC[C@@H](c3ccccc3)C[C@H]2C2CCCCC2)C1 ; [Cl-]] | 578.598 |
| 484 | 2 | 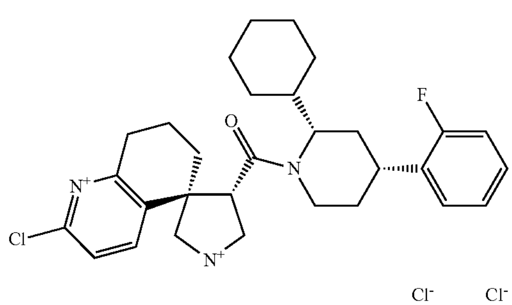 | 510.1 |

TABLE 3-continued

| Ex. No. | Scheme | Structure | Parent MW |
|---|---|---|---|
| 485 | 2 | 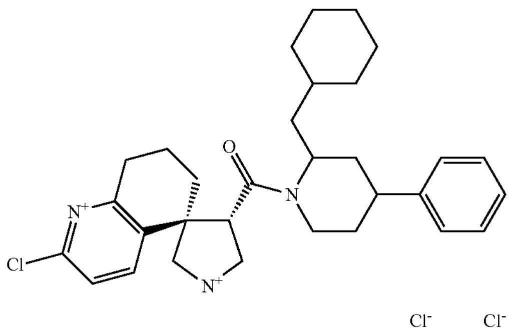 [SMILES: O=C([C@@H]1C[NH2+]C[C@]12CCCc1[nH+]c(Cl)ccc12)N1CCC(c2ccccc2)CC1CC1CCCCC1 ; [Cl-] ; [Cl-]] | 506.137 |
| 486 | 2 | 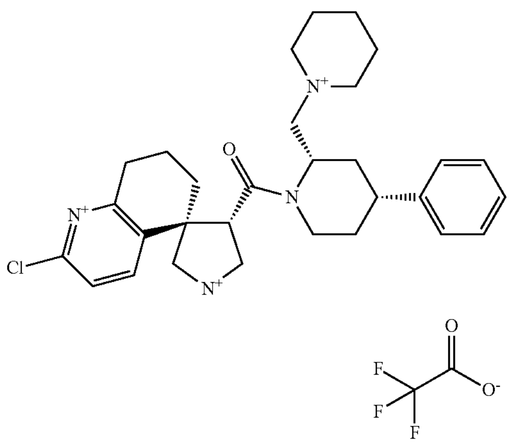 [SMILES: O=C([C@@H]1C[NH2+]C[C@]12CCCc1[nH+]c(Cl)ccc12)N1CC[C@@H](c2ccccc2)C[C@H]1C[NH+]1CCCCC1 ; O=C([O-])C(F)(F)F] | 507.125 |
| 487 | 2 | 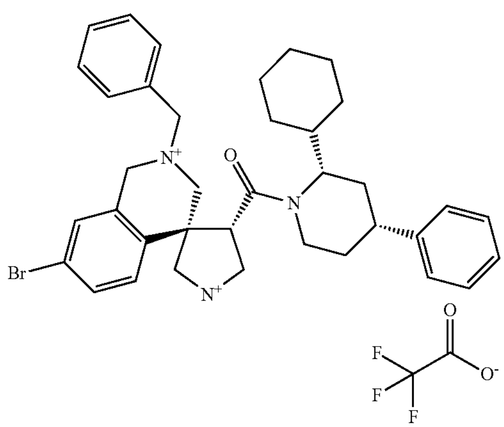 | 626.687 |
| 488 | 2 | 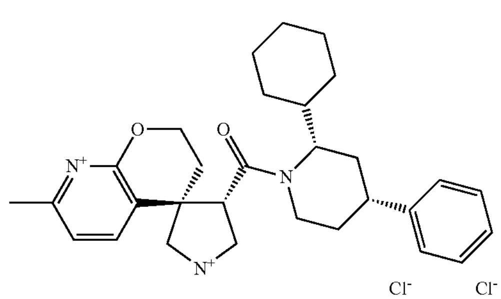 [SMILES: Cc1ccc2c([nH+]1)OCC[C@]21C[NH2+]C[C@H]1C(=O)N1CC[C@@H](c2ccccc2)C[C@H]1C1CCCCC1 ; [Cl-] ; [Cl-]] | 473.664 |

TABLE 3-continued

| Ex. No. | Scheme | Structure | Parent MW |
|---|---|---|---|
| 489 | 2 | 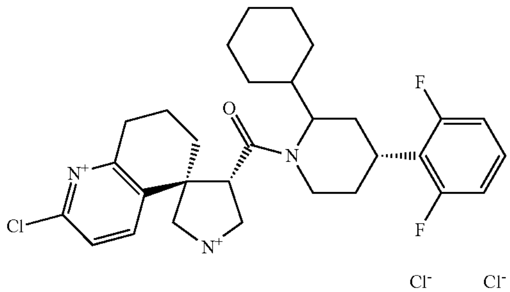 [SMILES: O=C([C@@H]1C[NH2+]C[C@]12CCCc1[nH+]c(Cl)ccc12)N1CC[C@@H](c2c(F)cccc2F)CC1C1CCCCC1 ; [Cl-] ; [Cl-]] | 528.091 |
| 490 | 2 | 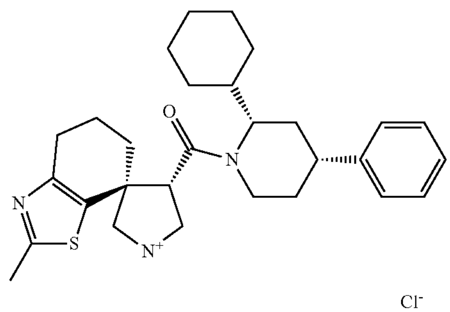 [SMILES: Cc1nc2c(s1)[C@]1(CCC2)C[NH2+]C[C@H]1C(=O)N1CC[C@@H](c2ccccc2)C[C@H]1C1CCCCC1 ; [Cl-]] | 477.718 |
| 491 | 2 | 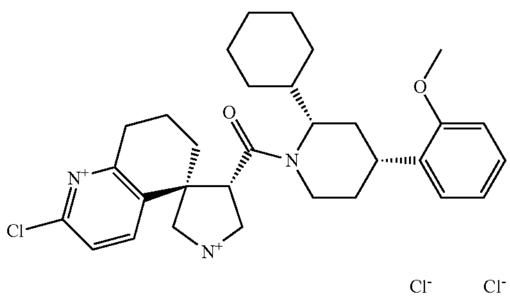 [SMILES: COc1ccccc1[C@@H]1CCN(C(=O)[C@@H]2C[NH2+]C[C@]23CCCc2[nH+]c(Cl)ccc23)[C@H](C2CCCCC2)C1 ; [Cl-] ; [Cl-]] | 522.136 |
| 492 | 2 | 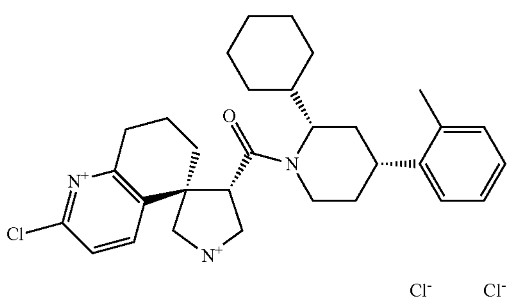 | 506.137 |
| 493 | 2 | 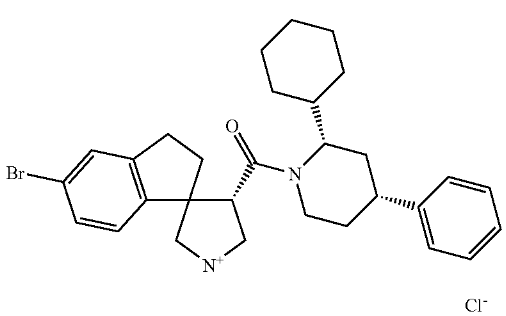 [SMILES: O=C([C@@H]1C[NH2+]CC12CCc1cc(Br)ccc12)N1CC[C@@H](c2ccccc2)C[C@H]1C1CCCCC1 ; [Cl-]] | 521.546 |

TABLE 3-continued

| Ex. No. | Scheme | Structure | Parent MW |
|---|---|---|---|
| 494 | 2 | 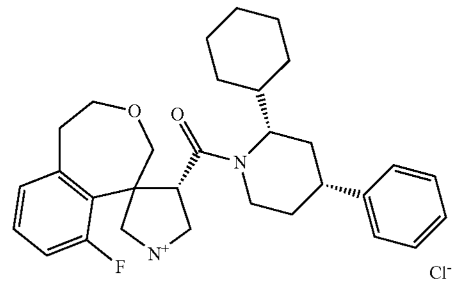 [SMILES: O=C([C@@H]1C[NH2+]CC12COCCc1cccc(F)c12)N1CC[C@@H](c2ccccc2)C[C@H]1C1CCCCC1 ; [Cl-]] | 490.667 |
| 495 | 2 | 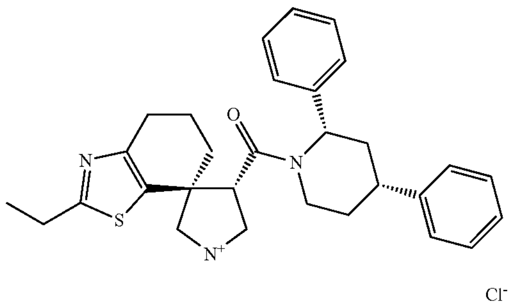 [SMILES: CCc1nc2c(s1)[C@]1(CCC2)C[NH2+]C[C@H]1C(=O)N1CC[C@@H](c2ccccc2)C[C@H]1c1ccccc1 ; [Cl-]] | 485.697 |
| 496 | 2 | 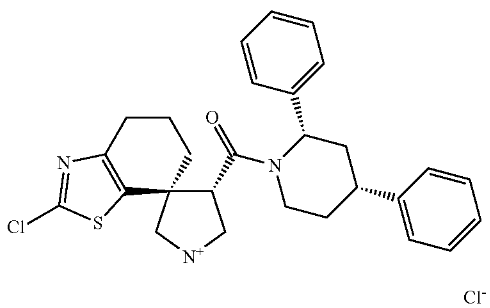 [SMILES: O=C([C@@H]1C[NH2+]C[C@]12CCCc1nc(Cl)sc12)N1CC[C@@H](c2ccccc2)C[C@H]1c1ccccc1 ; [Cl-]] | 492.008 |
| 497 | 2 | 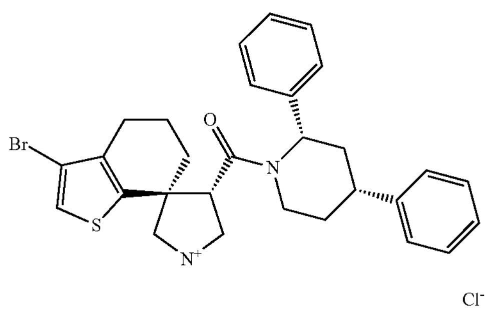 [SMILES: O=C([C@@H]1C[NH2+]C[C@]12CCCc1c(Br)csc12)N1CC[C@@H](c2ccccc2)C[C@H]1c1ccccc1 ; [Cl-]] | 535.551 |
| 498 | 2 | 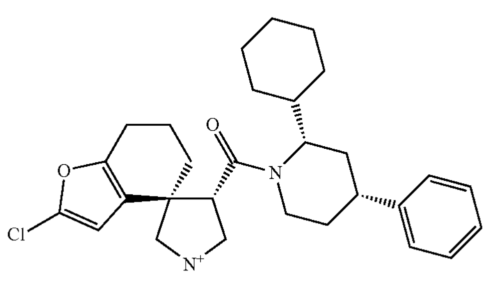 | 481.083 |

TABLE 3-continued
| Ex. No. | Scheme | Structure | Parent MW |
|---|---|---|---|
| 499 | 2 | 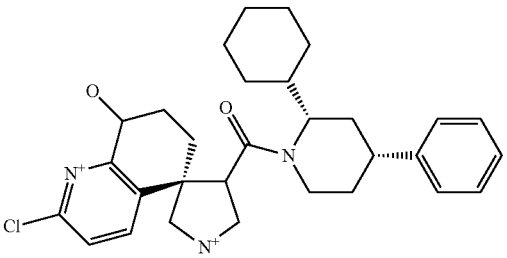 | 508.109 |
| 500 | 2 | 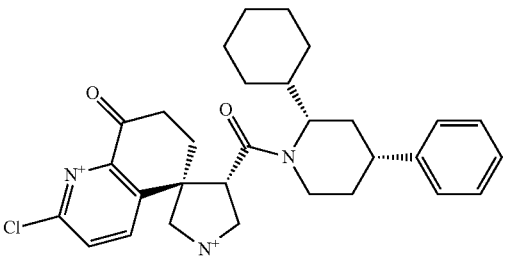 | 506.093 |
| 501 | 2 | 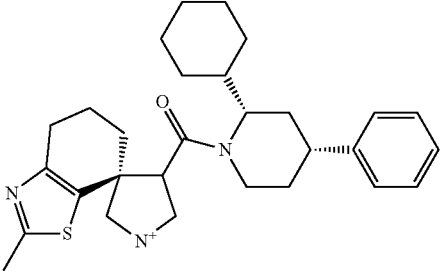 | 477.718 |
| 502 | 2 | 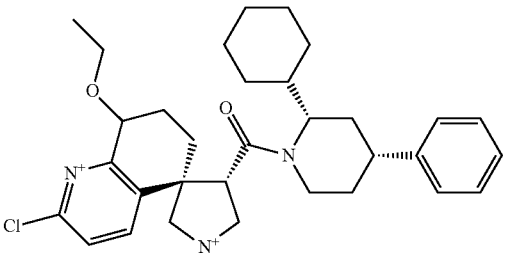 | 536.163 |

TABLE 3-continued

| Ex. No. | Scheme | Structure | Parent MW |
|---|---|---|---|
| 503 | 2 | 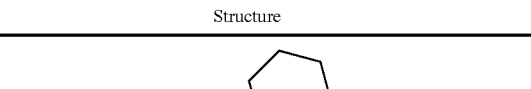 | 525.112 |

Compounds in Table 3 having a basic group or acidic group are depicted and named either as the free base acid or as the salt thereof. Depending on the reaction and purification conditions, the compounds of Table 1 may be isolated in either the free base form, or as a salt (such as HCl salt), or in both free base and salt forms.

The utility of the compounds in accordance with the present invention as inhibitors of β-secretase enzyme activity may be demonstrated by methodology known in the art. Enzyme inhibition is determined as follows.

ECL Assay: A homogeneous end point electrochemiluminescence (ECL) assay is performed using a biotinylated BACE substrate. The Km of the substrate is approximated at 50 μM. A typical reaction contains approximately 0.6 nM enzyme, 0.25 μM of the substrate, and buffer (50 mM Pipes, pH 6.5, 0.1 mg/ml BSA, 0.2% CHAPS, 15 mM EDTA and 1 mM deferoxamine) in a total reaction volume of 100 μl. The reaction proceeds for 1-2 hrs and is then stopped by the addition of 150 μL of a quench cocktail solution (25 μl M Tris-HCl, pH 8.0, 50 μl INC buffer (2% BSA, 0.2% Tween-20 and 0.05% sodium azide diluted in Phosphate buffered saline (PBS) plus 75 μL PBS), containing Streptavidin coated magnetic beads and ruthenylated antibody which specifically recognizes the C-terminal residue of the product. The samples are subjected to M-384 (Igen Inc., Gaithersburg, Md.) analysis. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency for compounds, 10 concentrations of inhibitors are prepared starting from 200 μM with three fold series dilution. Solutions of the inhibitor in DMSO are included in the reaction mixture (final DMSO concentration is 10%). All experiments are conducted at rt using the standard reaction conditions described above. To determine the $IC_{50}$ of the compound, a four parameter equation is used for curve fitting. The errors in reproducing the dissociation constants are typically less than two-fold.

In particular, the compounds of the following examples had activity in inhibiting the beta-secretase enzyme in the aforementioned assay, generally with an $IC_{50}$ from about 1 nM to 200 μM. Such a result is indicative of the intrinsic activity of the compounds in use as inhibitors of beta-secretase enzyme activity.

Several methods for preparing the compounds of this invention are illustrated in the Schemes and Examples herein. Starting materials are made according to procedures known in the art or as illustrated herein. The following examples are provided so that the invention might be more fully understood. These examples are illustrative only and should not be construed as limiting the invention in any way.

Exemplary $IC_{50}$ values for representative compounds of the invention (as described in the following Examples) are provided below in Table 3.

TABLE 3

| Example | $IC_{50}(\mu M)$ |
|---|---|
| 3 | 2.19 |
| 7 | 22 |
| 10 | 20 |
| 19 | 0.92 |
| 21 | 0.071 |
| 30 | 14 |
| 31 | 0.024 |
| 38 | 12 |
| 44 | 19 |
| 77 | 0.2 |
| 100 | 0.45 |

The following abbreviations are used throughout the text:

Me: methyl

Et: ethyl

Bu: butyl t-Bu: tert-butyl i-Bu: iso-butyl

Pr: propyl i-Pr: iso-propyl

Ar: aryl

Ph: phenyl

Bn: benzyl

BOP: benzotriazolyl-N-oxy-tris(dimethylamino)phosphonium hexafluorophosphate

Boc: tert butyloxycarbonyl

TFA: trifluoro acetic acid

THF: tetrahydrofuran

Ac: acetyl aq: aqueous rt: room temperature h: hours min: minutes

What is claimed is:

1. A compound of formula (I)

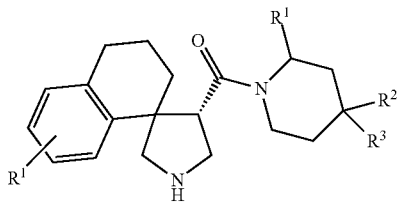

wherein:
R¹ is selected from the group consisting of
  (1) hydrogen
  (2) $C_{1-6}$alkyl,
  (3) $C_{3-9}$ cycloalkyl, and
  (4) phenyl,
  wherein said alkyl, cycloalkyl or phenyl R¹ moiety is optionally substituted with one or more
    (a) halo,
    (b) —OH,
    (c) —CN,
    (d) —$C_{1-6}$ alkyl
    (e) —$C_{3-6}$ cycloalkyl, or
    (f) —O—$C_{1-6}$ alkyl;
R² is hydrogen;
R³ is selected from the group consisting of:
  (1) hydrogen,
  (2) $C_{6-10}$aryl (for example, phenyl), and
  (3) heteroaryl,
  wherein said aryl or heteroaryl R³ moiety is optionally substituted with one or more
    (a) halo,
    (b) —$C_{1-6}$ alkyl, wherein said alkyl is optionally substituted with one or more halogen, and
    (c) —O—$C_{1-6}$ alkyl;
R¹¹ is selected from the group consisting of
  (1) hydrogen
  (2) $C_{1-6}$alkyl,
  (3) $C_{3-6}$ cycloalkyl, and
  (4) phenyl,
  wherein said alkyl, cycloalkyl or phenyl R¹¹ moiety is optionally substituted with one or more
    (a) halo,
    (b) —OH,
    (c) —CN,
    (d) —$C_{1-6}$ alkyl
    (e) —$C_{3-6}$ cycloalkyl, or
    (f) —O—$C_{1-6}$ alkyl.

2. A compound of claim 1, wherein R¹ is selected from the group consisting of: hydrogen, phenyl (optionally substituted with halogen), and cyclohexyl.

3. A compound of claim 2, wherein R³ is hydrogen or unsubstituted phenyl.

4. A compound, or a pharmaceutically acceptable salt thereof, said compound having a structure:

| Structure |
|---|
| 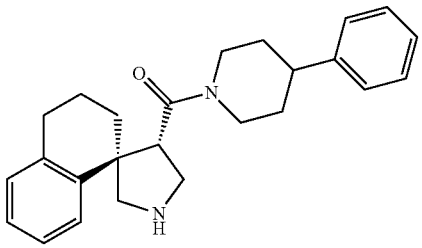 [SMILES: O=C([C@@H]1CNC[C@]12CCCc1ccccc12)N1CCC(c2ccccc2)CC1] |
| 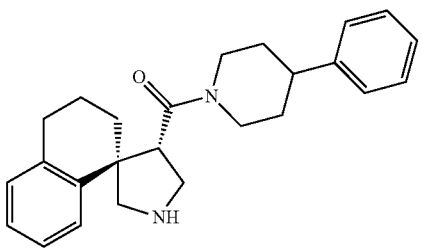 [SMILES: O=C([C@@H]1CNC[C@]12CCCc1ccccc12)N1CCC(c2ccccc2)CC1] |
| 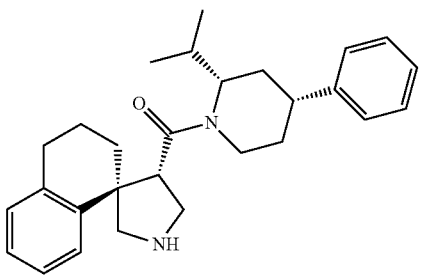 [SMILES: CC(C)[C@@H]1C[C@H](c2ccccc2)CCN1C(=O)[C@@H]1CNC[C@]12CCCc1ccccc12] |
| 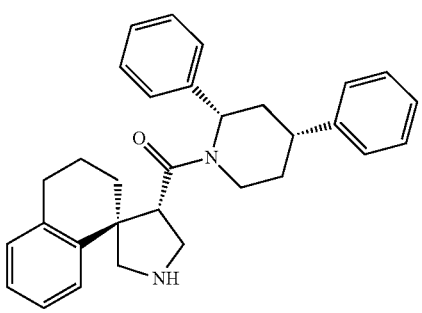 [SMILES: O=C([C@@H]1CNC[C@]12CCCc1ccccc12)N1CC[C@@H](c2ccccc2)C[C@H]1c1ccccc1] |
| 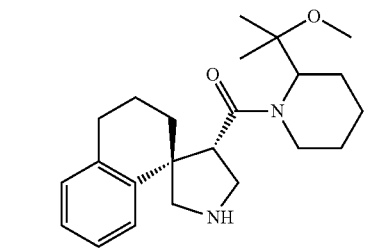 [SMILES: COC(C)(C)C1CCCCN1C(=O)[C@@H]1CNC[C@@]12CCCc1ccccc12] |
| 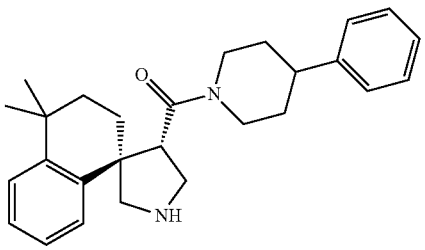 [SMILES: CC1(C)CC[C@]2(CNC[C@H]2C(=O)N2CCC(c3ccccc3)CC2)c2ccccc21] |

| 291 -continued | 292 -continued |
|---|---|
| Structure | Structure |
| 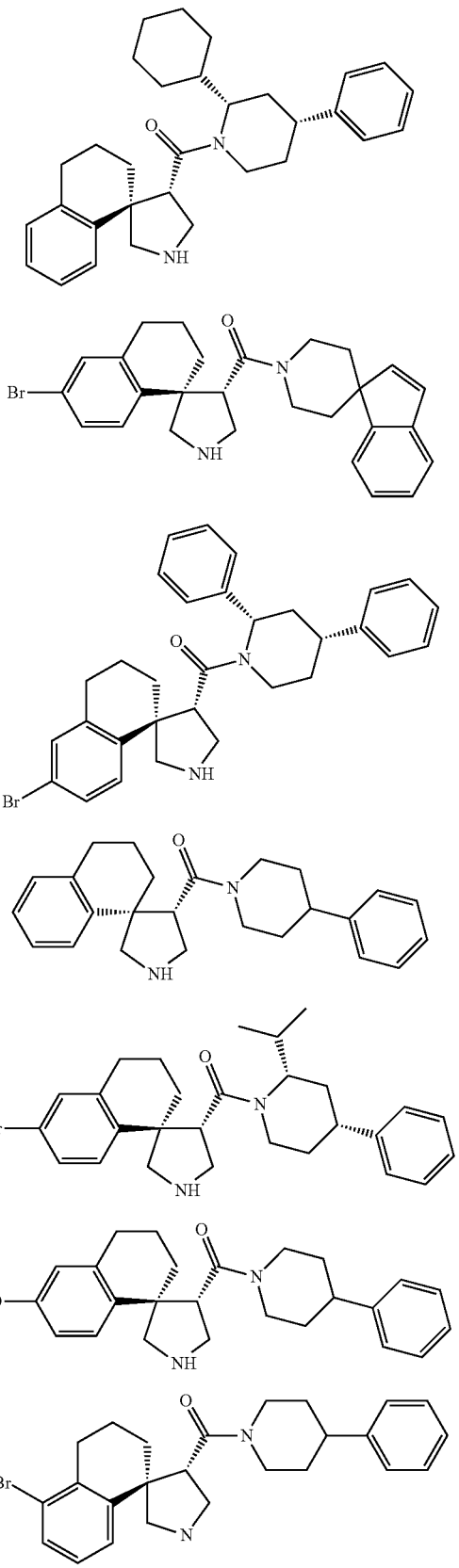 | 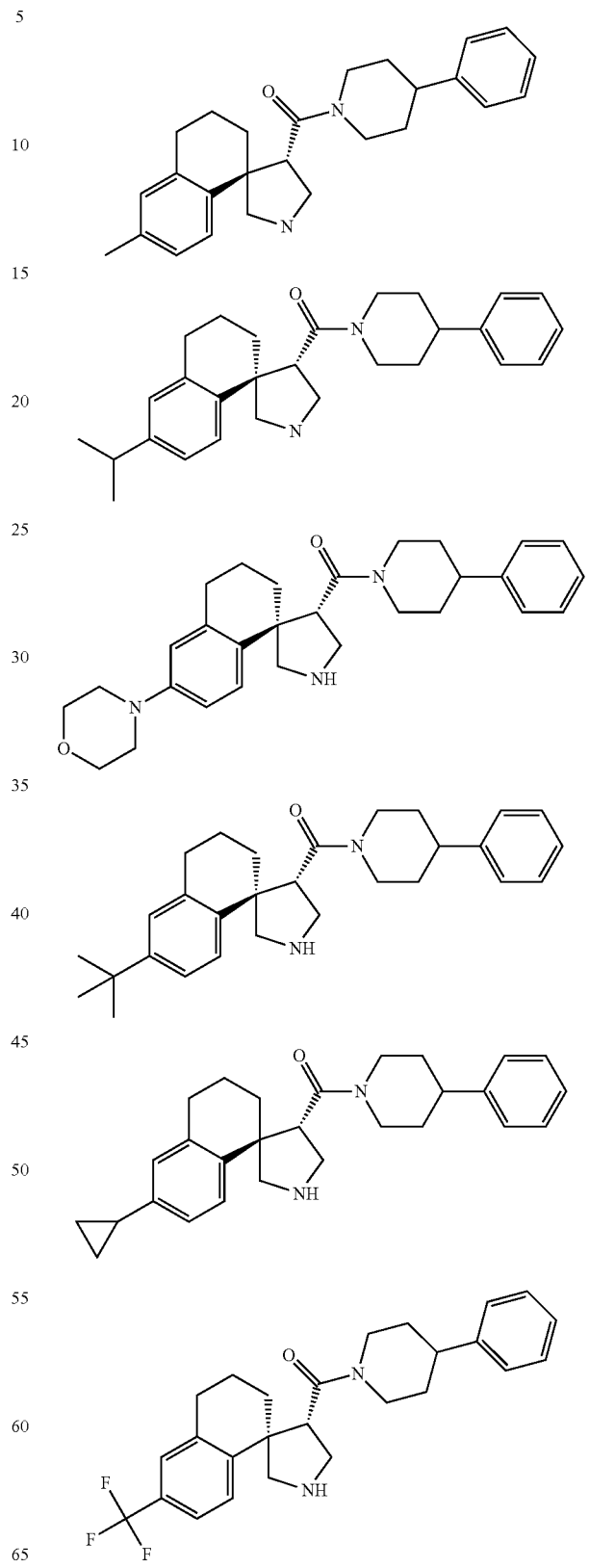 |

| 293 -continued | 294 -continued |
|---|---|
| Structure | Structure |
| 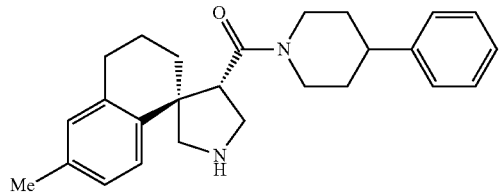 [SMILES: Cc1ccc2c(c1)CCC[C@]21CNC[C@H]1C(=O)N1CCC(c2ccccc2)CC1] | 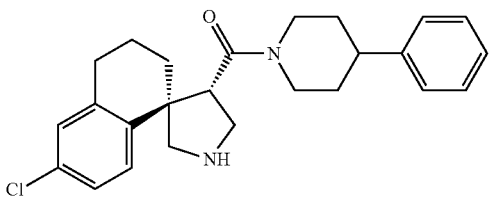 |
| 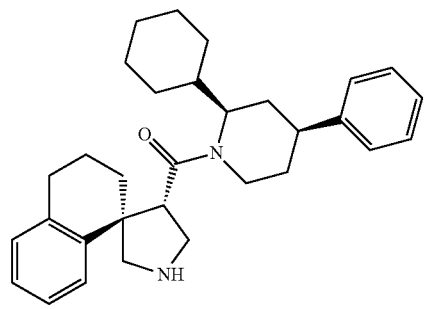 [SMILES: O=C([C@@H]1CNC[C@]12CCCc1ccccc12)N1CC[C@H](c2ccccc2)C[C@@H]1C1CCCCC1] | 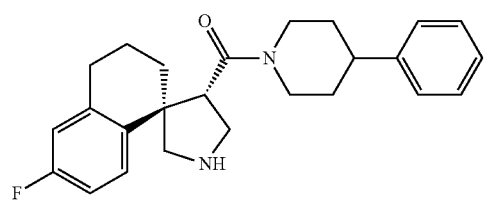 |
| 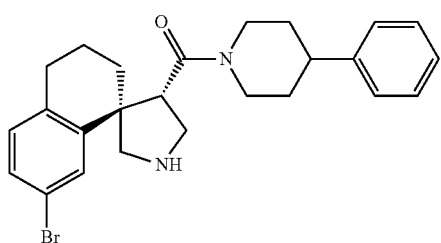 [SMILES: O=C([C@@H]1CNC[C@]12CCCc1ccc(Br)cc12)N1CCC(c2ccccc2)CC1] | 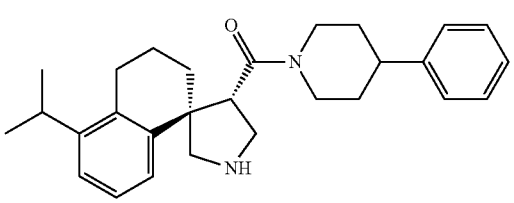 |
| 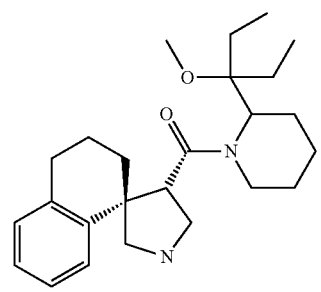 | 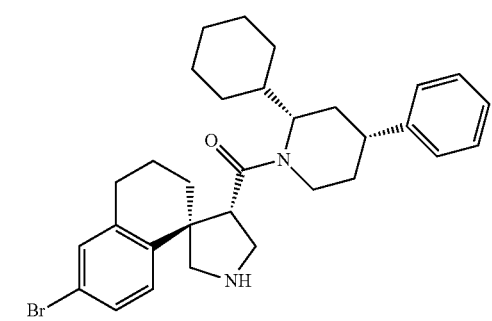 |
| 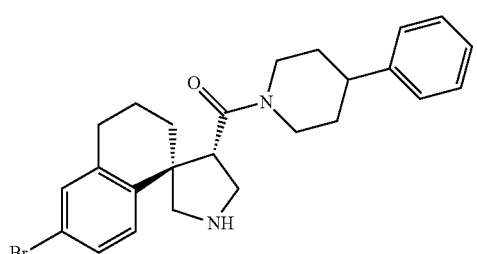 | 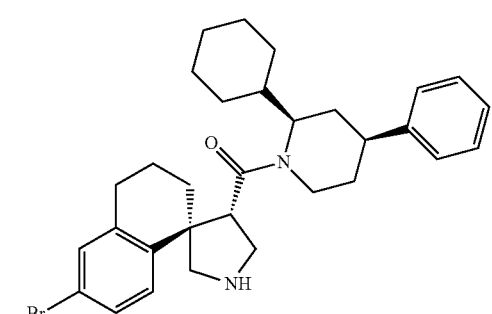 |
| 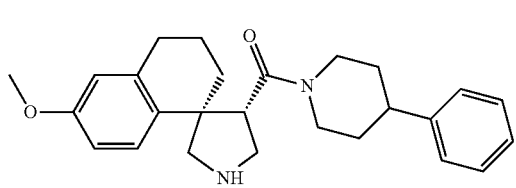 [SMILES: COc1ccc2c(c1)CCC[C@]21CNC[C@H]1C(=O)N1CCC(c2ccccc2)CC1] | 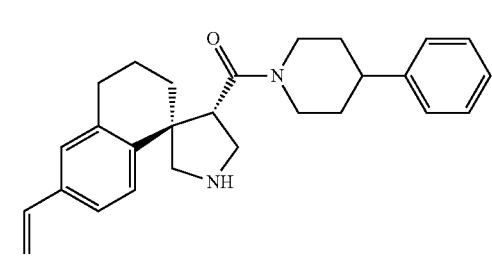 [SMILES: C=Cc1ccc2c(c1)CCC[C@]21CNC[C@H]1C(=O)N1CCC(c2ccccc2)CC1] |

| Structure |
|---|
| 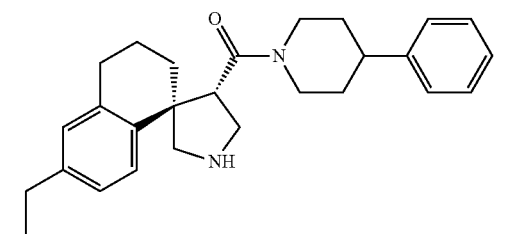 [SMILES: CCc1ccc2c(c1)CCC[C@]21CNC[C@H]1C(=O)N1CCC(c2ccccc2)CC1] |
| 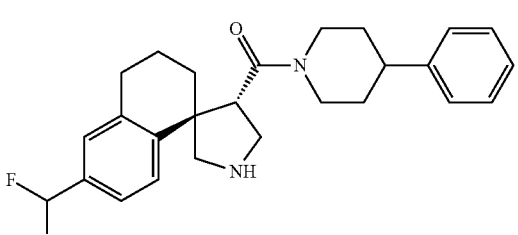 |
| 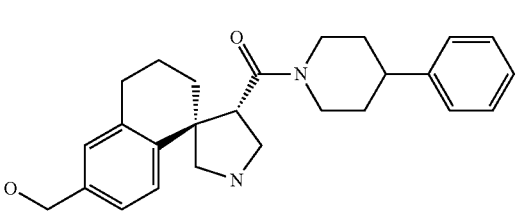 [SMILES: O=C([C@@H]1CNC[C@]12CCCc1cc(CO)ccc12)N1CCC(c2ccccc2)CC1] |
| 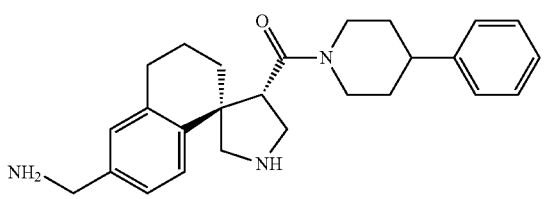 [SMILES: NCc1ccc2c(c1)CCC[C@]21CNC[C@H]1C(=O)N1CCC(c2ccccc2)CC1] |
| 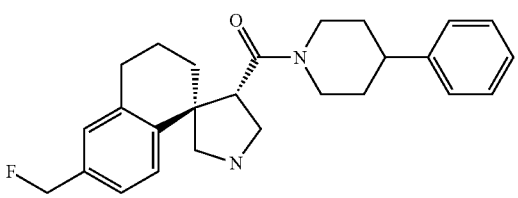 [SMILES: O=C([C@@H]1CNC[C@]12CCCc1cc(CF)ccc12)N1CCC(c2ccccc2)CC1] |
| 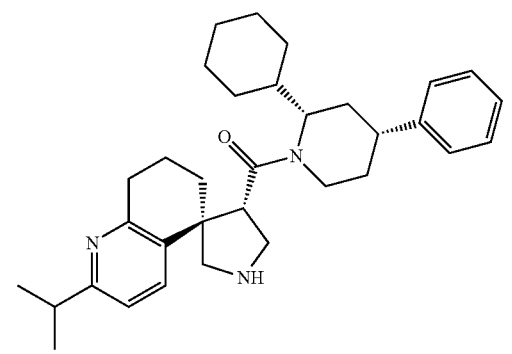 [SMILES: CC(C)c1ccc2c(n1)CCC[C@]21CNC[C@H]1C(=O)N1CC[C@@H](c2ccccc2)C[C@H]1C1CCCCC1] |
| Structure |
|---|
| 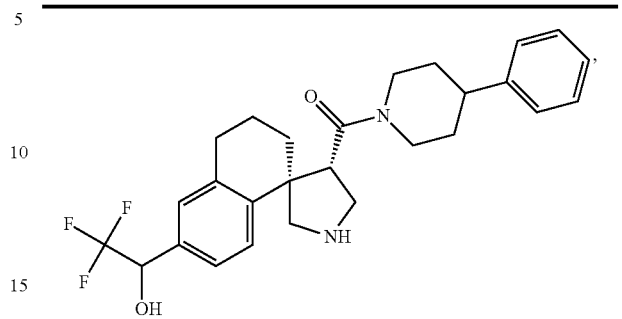 |
| and |
| 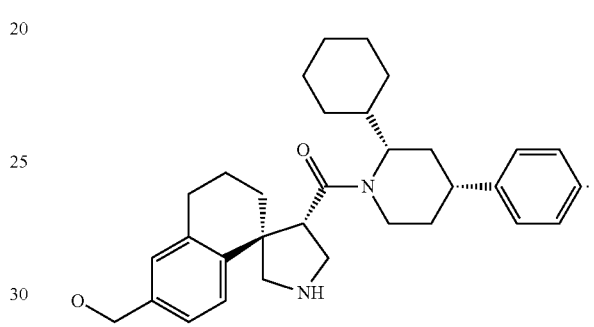 |
5. A compound, or a pharmaceutically acceptable salt thereof, said compound having a structure:
| Structure |
|---|
| 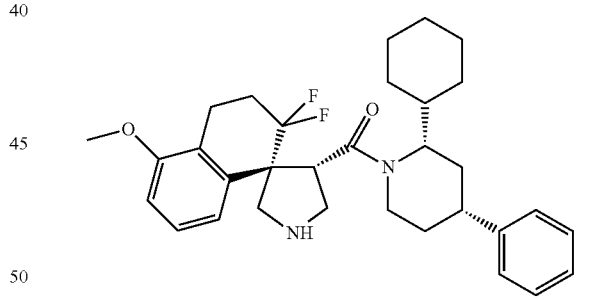 |
| 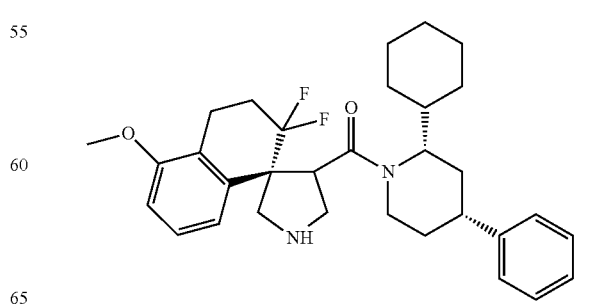 |

| 297 -continued | 298 -continued |
|---|---|
| Structure | Structure |
| 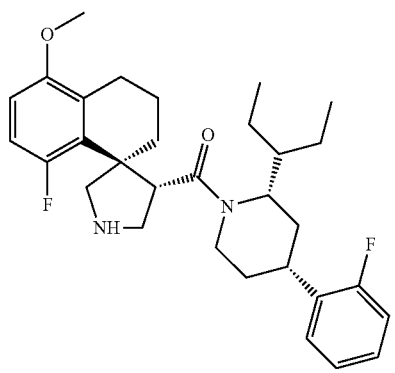 [SMILES: CCC(CC)[C@@H]1C[C@H](c2ccccc2F)CCN1C(=O)[C@@H]1CNC[C@]12CCCc1c(OC)ccc(F)c12] | 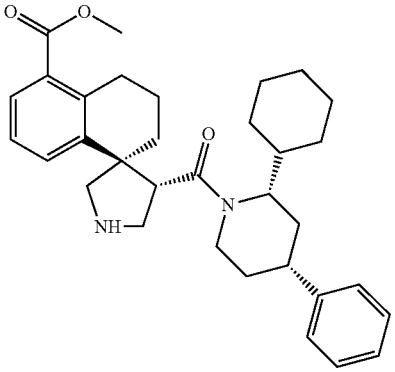 |
| 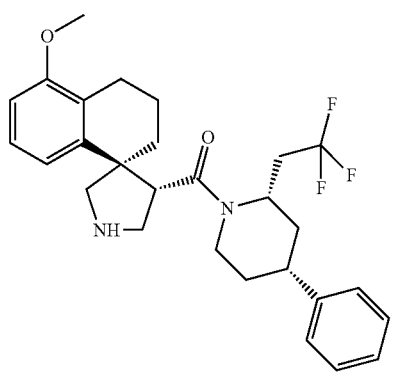 [SMILES: COc1cccc2c1CCC[C@]21CNC[C@H]1C(=O)N1CC[C@@H](c2ccccc2)C[C@H]1CC(F)(F)F] | 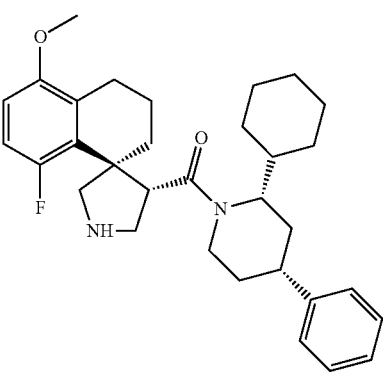 |
| 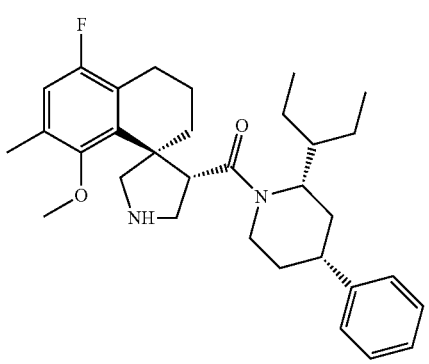 [SMILES: CCC(CC)[C@@H]1C[C@H](c2ccccc2)CCN1C(=O)[C@@H]1CNC[C@]12CCCc1c(F)cc(C)c(OC)c12] | 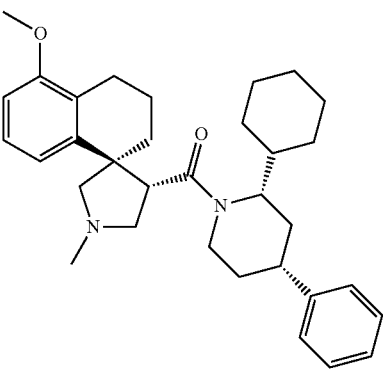 [SMILES: COc1cccc2c1CCC[C@]21CN(C)C[C@H]1C(=O)N1CC[C@@H](c2ccccc2)C[C@H]1C1CCCCC1] |
| 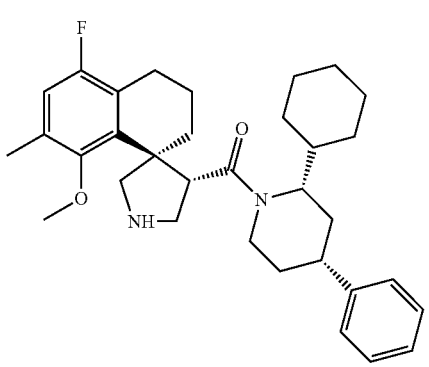 [SMILES: COc1c(C)cc(F)c2c1[C@]1(CCC2)CNC[C@H]1C(=O)N1CC[C@@H](c2ccccc2)C[C@H]1C1CCCCC1] | 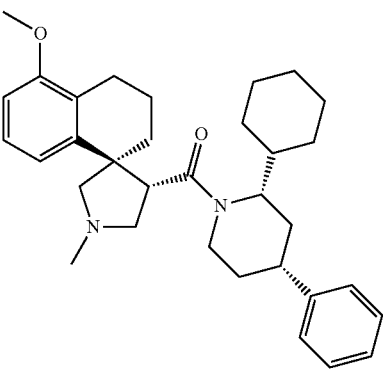 [SMILES: COc1cccc2c1CCC[C@]21CN(C)C[C@H]1C(=O)N1CC[C@@H](c2ccccc2)C[C@H]1C1CCCCC1] |

| 299 -continued | 300 -continued |
| --- | --- |
| Structure | Structure |
| 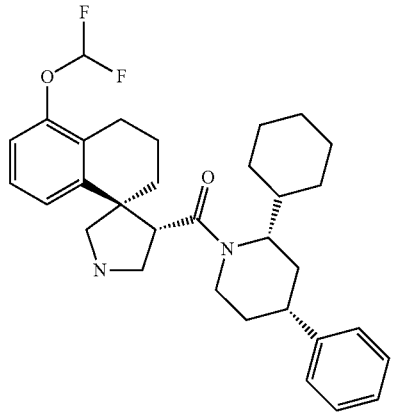 [SMILES: O=C([C@@H]1CNC[C@]12CCCc1c(OC(F)F)cccc12)N1CC[C@@H](c2ccccc2)C[C@H]1C1CCCCC1] | 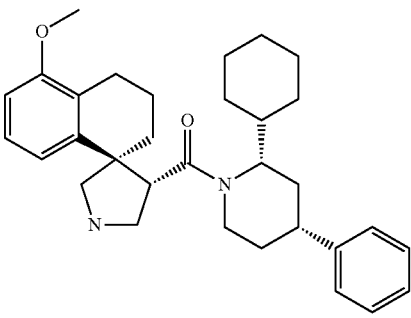 |
| 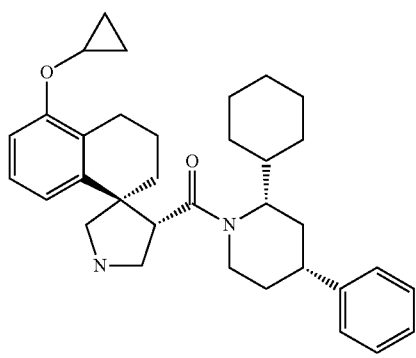 [SMILES: O=C([C@@H]1CNC[C@]12CCCc1c(OC3CC3)cccc12)N1CC[C@@H](c2ccccc2)C[C@H]1C1CCCCC1] | 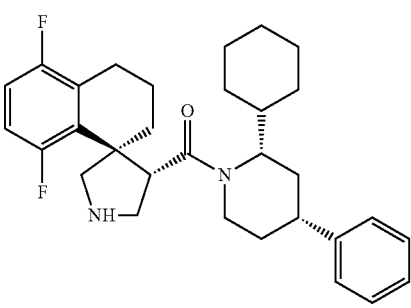 |
| 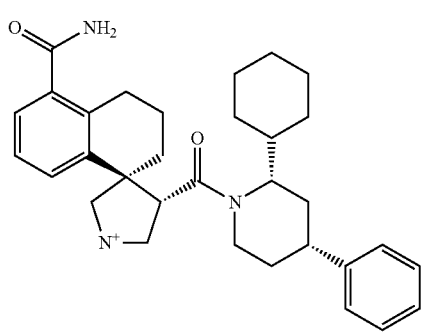 [SMILES: NC(=O)c1cccc2c1CCC[C@]21C[NH2+]C[C@H]1C(=O)N1CC[C@@H](c2ccccc2)C[C@H]1C1CCCCC1] | 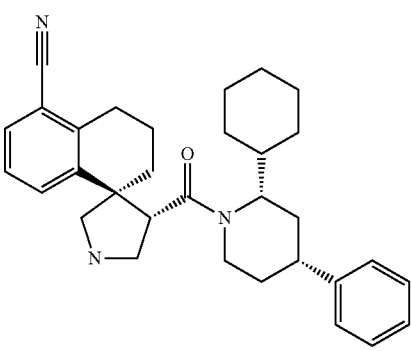 |
| 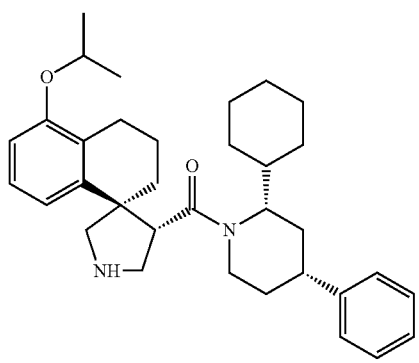 [SMILES: CC(C)Oc1cccc2c1CCC[C@]21CNC[C@H]1C(=O)N1CC[C@@H](c2ccccc2)C[C@H]1C1CCCCC1] | 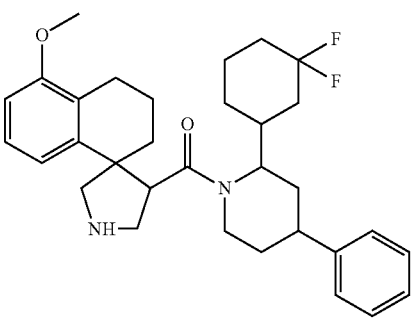 [SMILES: COc1cccc2c1CCCC21CNCC1C(=O)N1CCC(c2ccccc2)CC1C1CCCC(F)(F)C1] |

| 301 -continued | 302 -continued |
|---|---|
| Structure | Structure |
| 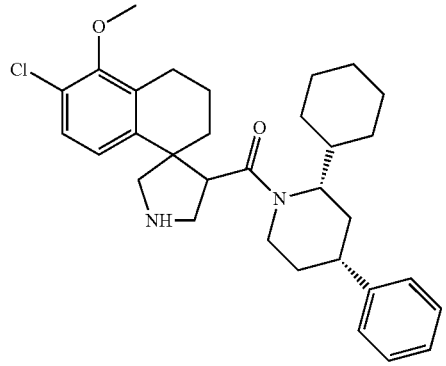 [SMILES: COc1c(Cl)ccc2c1CCCC21CNCC1C(=O)N1CC[C@@H](c2ccccc2)C[C@H]1C1CCCCC1] | 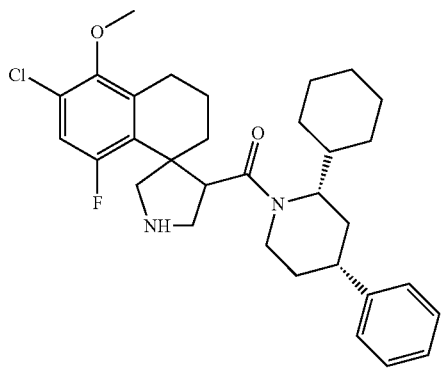 |
| 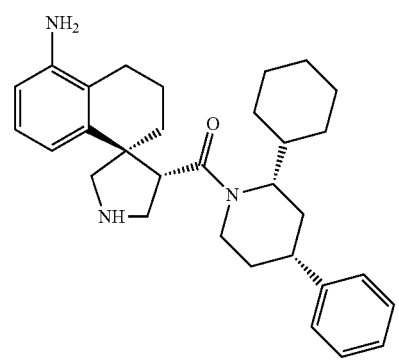 [SMILES: Nc1cccc2c1CCC[C@]21CNC[C@H]1C(=O)N1CC[C@@H](c2ccccc2)C[C@H]1C1CCCCC1] | 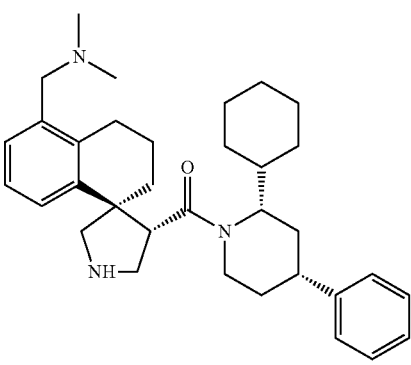 |
| 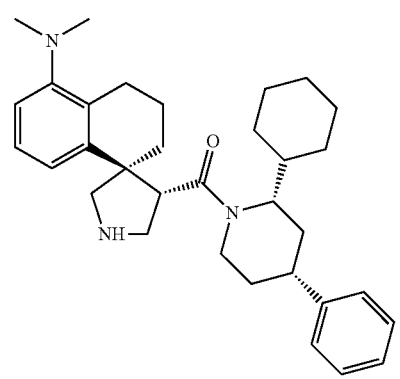 [SMILES: CN(C)c1cccc2c1CCC[C@]21CNC[C@H]1C(=O)N1CC[C@@H](c2ccccc2)C[C@H]1C1CCCCC1] | 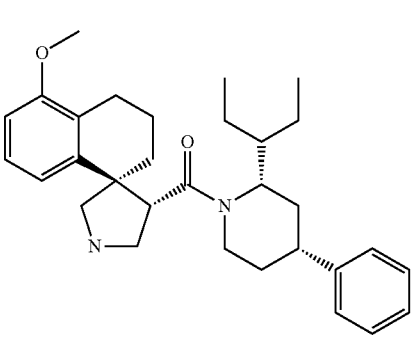 |
| 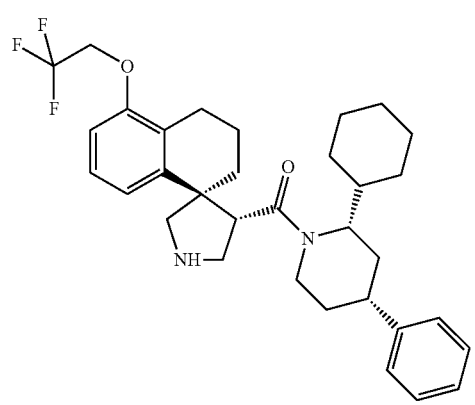 [SMILES: O=C([C@@H]1CNC[C@]12CCCc1c(OCC(F)(F)F)cccc12)N1CC[C@@H](c2ccccc2)C[C@H]1C1CCCCC1] | 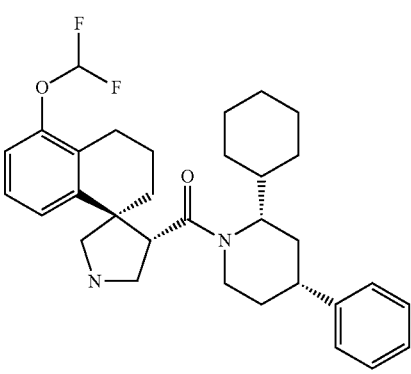 [SMILES: O=C([C@@H]1CNC[C@]12CCCc1c(OC(F)F)cccc12)N1CC[C@@H](c2ccccc2)C[C@H]1C1CCCCC1] |

| 303 -continued | 304 -continued |
|---|---|
| Structure | Structure |
| 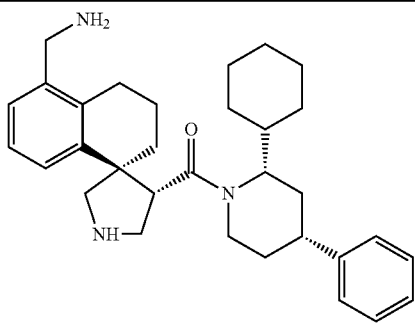 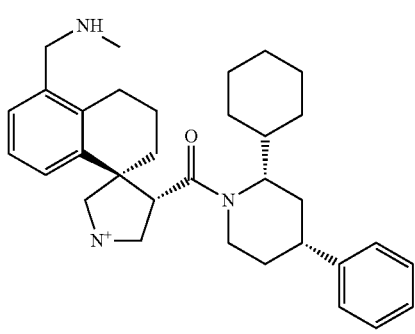 [SMILES: CNCc1cccc2c1CCC[C@]21C[NH2+]C[C@H]1C(=O)N1CC[C@@H](c2ccccc2)C[C@H]1C1CCCCC1] 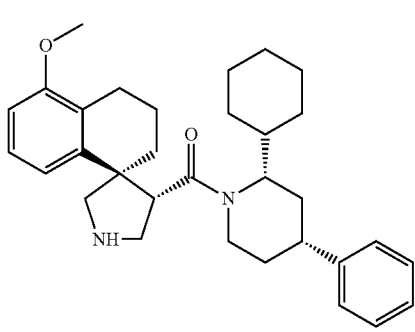 [SMILES: COc1cccc2c1CCC[C@]21CNC[C@H]1C(=O)N1CC[C@@H](c2ccccc2)C[C@H]1C1CCCCC1] 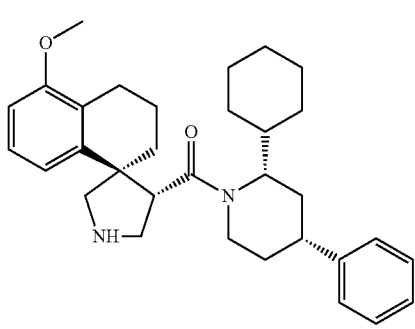 [SMILES: COc1cccc2c1CCC[C@]21CNC[C@H]1C(=O)N1CC[C@@H](c2ccccc2)C[C@H]1C1CCCCC1] | 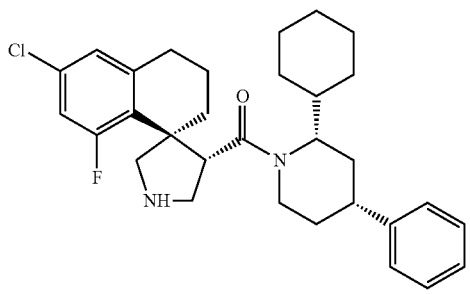 [SMILES: O=C([C@@H]1CNC[C@]12CCCc1cc(Cl)cc(F)c12)N1CC[C@@H](c2ccccc2)C[C@H]1C1CCCCC1] and 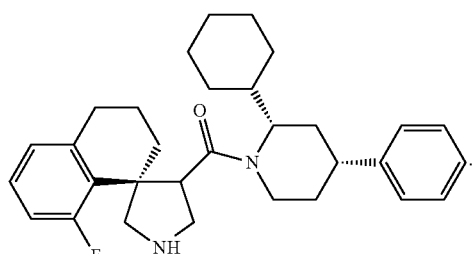 |

6. A pharmaceutical composition, comprising a compound of claim 1, or a pharmaceutically acceptable salt thereof, and a pharmaceutically acceptable carrier.

7. A pharmaceutical composition, comprising a compound of claim 5, or a pharmaceutically acceptable salt thereof, and a pharmaceutically acceptable carrier.

8. A pharmaceutical composition, comprising a compound of claim 4, or a pharmaceutically acceptable salt thereof, and a pharmaceutically acceptable carrier.

* * * * *